US011746359B2

(12) United States Patent
Ruan et al.

(10) Patent No.: US 11,746,359 B2

(45) Date of Patent: Sep. 5, 2023

(54) HELPER-DEPENDENT ADENOVIRAL GENE THERAPY DELIVERY AND EXPRESSION SYSTEM

(71) Applicant: Baylor College of Medicine, Houston, TX (US)

(72) Inventors: Merry Ruan, South San Francisco, CA (US); Kilian Guse, Berlin (DE); Brendan Lee, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 17/711,647

(22) Filed: Apr. 1, 2022

(65) Prior Publication Data

US 2022/0282280 A1 Sep. 8, 2022

Related U.S. Application Data

(63) Continuation of application No. 17/358,904, filed on Jun. 25, 2021, which is a continuation of application No. 14/763,326, filed as application No. PCT/IB2014/000071 on Jan. 27, 2014, now abandoned.

(60) Provisional application No. 61/756,516, filed on Jan. 25, 2013.

(51) Int. Cl.

*C12N 15/861* (2006.01)
*A61K 48/00* (2006.01)
*C07K 14/545* (2006.01)
*C12N 15/86* (2006.01)

(52) U.S. Cl.

CPC .......... *C12N 15/86* (2013.01); *A61K 48/0058* (2013.01); *C12N 2710/10043* (2013.01); *C12N 2710/10343* (2013.01); *C12N 2800/24* (2013.01)

(58) Field of Classification Search

None

See application file for complete search history.

(56) References Cited

U.S. PATENT DOCUMENTS

| | | | | |
|---|---|---|---|---|
| 5,747,072 | A * | 5/1998 | Davidson | C07K 14/54 435/320.1 |
| 6,743,774 | B1 | 6/2004 | Jay | |
| 2004/0072741 | A1 | 4/2004 | Jay | |
| 2009/0104148 | A1 | 4/2009 | Jay et al. | |
| 2009/0274688 | A1 | 11/2009 | Boyle et al. | |
| 2010/0215731 | A1 | 8/2010 | Emans et al. | |
| 2010/0254937 | A1 | 10/2010 | Han et al. | |
| 2010/0255572 | A1 | 10/2010 | Schmidt et al. | |
| 2016/0304572 | A1* | 10/2016 | Schmidt | C07K 14/4725 |

FOREIGN PATENT DOCUMENTS

| | | |
|---|---|---|
| WO | WO02082908 | 10/2002 |
| WO | WO2005016130 | 2/2005 |
| WO | WO2013114199 | 8/2013 |

OTHER PUBLICATIONS

Schmidt et al., Disulfide-bonded multimers of proteoglycan 4 (PRG4) are present in normal synovial fluids, Biochimica et Biophysica Acta 1790 (2009) 375-384.*

Roessler et al., Inhibition o f Interleukin-1-Induced Effects in Synoviocytes T r a n s d u c e d with the H u m a n IL-1 Receptor Antagonist cDNA Using an Adenoviral Vector, Human Gene Therapy, 1995, pp. 307-316.*

R. Borzi et al., "Matrix metalloproteinase 13 loss associated with impaired extracellular matrix remodeling disrupts Chondrocyte differentiation by concerted effects on multiple regulatory factors", Arthritis & Rheumatism, 62(8):2370-2381 (2010).

N. Brunetti-Pierri et al, "Transgene expression up to 7 years in nonhuman primates following hepatic transduction with helper-dependent adenoviral vectors", Human Gene Therapy, 24:1-5 (Aug. 2013).

J. Caron et al., "Chondroprotective effect of Intraarticular injections of interleukin-1 receptor antagonist in experimental osteoarthritis", Arthritis & Rheumatism, 39(9):1535-1544 (Sep. 1996).

J. Coles et al., "Loss of cartilage structure, stiffness, and frictional properties in mice lacking PRG4", Arthritis & Rheumatism, 62(6):1666-1674 (Jun. 2010).

M. Daheshia et al, "The interleukin 1-beta pathway in the pathogenesis of osteoarthritis", The Journal of Rheumatology, 35(12):2306-2312 (2008).

F. Echtermeyer et al, "Syndecan-4 regulates ADAMTS-5 activation and cartilage breakdown in osteoarthritis", Nature Medicine, 15(9):1072-1077, (Sep. 2009).

C. Evans et al., "Osteoarthritis gene therapy", Gene Therapy, vol. 11, pp. 379-389, http://www.nature.com/gt, (2004).

G. Jay et al, "The role of lubricin in the mechanical behavior of synovial fluid", PNAS, 104(15):6194-6199, (Apr. 10, 2007).

K. Johnson et al, "A stem cell-based approach to cartilage repair", Scienceexpress, Internet article: http://www.sciencemag.org/content/early/recent, p. 1/10.1126/science.1215157 (Apr. 5, 2012).

J. Kay et al., "Intra-articular gene delivery and expression of interleukin-1Ra mediated by self-complementary adeno-associated virus", The Journal of Gene Medicine, vol. 11, pp. 605-614, (2009).

(Continued)

*Primary Examiner* — Maria Marvich

(74) *Attorney, Agent, or Firm* — Cooley LLP

(57) ABSTRACT

The present invention relates to gene therapy delivery and expression systems comprising at least one helper-dependent adenoviral vector containing a nucleic acid sequence encoding for proteoglycan 4 (PRG4) or a biologically active fragment thereof. The invention further relates to a pharmaceutical composition comprising a therapeutically effective amount of at least one helper-dependent adenoviral vector containing said nucleic acid sequence encoding for proteoglycan 4 (PRG4), or a homolog thereof from any other species, or a biologically active fragment thereof. The invention also relates to the use of the novel gene therapy delivery and expression system according to the invention for use in the prevention and/or treatment of camptodactyly-arthropathy-coxa vara-pericarditis (CACP), or a musculoskeletal disorder such as a joint disorder or joint disease.

6 Claims, 8 Drawing Sheets

Specification includes a Sequence Listing.

(56) References Cited

OTHER PUBLICATIONS

G. Matthews et al., "Emerging drugs for osteoarthritis", Expert Opin. Emerging Drugs [Early Online], pp. 1-13, (10.1517/14728214.2011.576670 Informa UK, Ltd. ISSN 1472-8214) (2011).
K. Mitani et al., "Rescue, propagation, and partial purification of a helper virus-dependent adenovirus vector", Proc. Natl. Acad. Sci., 92:3854-3858 (Apr. 1995).
D. Palmer et al, "Improved system for helper-dependent adenoviral vector production", Molecular Therapy, 8 (5):846-852 (Nov. 2003).
R. Parks et al, "A help-dependent adenovirus vector system: Removal of helper virus by Cre-mediated excision of the viral packaging signal", Proc. Natl. Acad. Sci., 93:13565-13570 (Nov. 1996).
R. Parks et al, "Improvements in adenoviral vector technology: overcoming barriers for gene therapy", Clinical Genetics, 58:1-11 (2000).
D. Rhee et al,"The secreted glycoprotein lubricin protects cartilage surfaces and inhibits synovial cell overgowth", The Journal of Clinical Investigation, 115(3):622-631 (Mar. 2005).
T. Saito et al., "Transcriptional regulation of endochondral ossification by HIF-2alpha during skeletal growth and osteoarthrtis development", Nature Medicine, 16(6):678-687 (Jun. 2010).
A. Nobuhiro et al, "Enhancement of bone repair with a helper-dependent adenoviral transfer of bone morphogenetic protein-2", Biochemical and Biophysical Research Communications, 297(3):523-527 (Sep. 2002).
N. Horwood et al, "High-efficiency gene transfer into nontransformed cells: utility for studying gene regulation and analysis of potential therapeutic targets", Arthritis Research, Current Science, London, UK, 4(3):S215-S225 (May 9, 2002).
A. Bakker et al, "C3-Tat/HIV-regulated intraarticular human interleukin-1 receptor antagonist gene therapy results in efficient inhibition of collagen-induced arthritis superior to cytomegalovirus-regulated expression of the same transgene", Arthritis & Rheumatism, 46(6):1661-1670 (Jun. 2006).
C. Flannery et al., "Prevention of cartilage degeneration in a rat model of osteoarthritis by inreaarticular treatment with recombinant lubricin", Arthritis & Rheumatism, 60(3):840-847 (Mar. 2009).
M. Ruan et al, "Protoglycan 4 expression protects against the development of osteoarthritis", Science Translational Medicine, 5(176):1-16 (Mar. 13, 2013).
A. Nathwani et al, "Adenovirus-associated virus vector-mediated gene transfer in Hemophilia B", N. Engl. J. Med., pp. 1-9 (Dec. 10, 2011).
D. Muruve et al, "Helper-dependent adenovirus vectors elicit intact innate but attenuated adaptive host immune responses in vivo", J. Virol., 78(11):5966-5972 (Jun. 2004).
N. Morral et al, "Lethal toxicity, severe endothelial injury, and a threshold effect with high doses of an adenoviral vector in baboons", Human Gene Therapy, 13:143-154 (Jan. 1, 2002).
C. Manno et al., "AAV-mediated factor IX gene transfer to skeletal muscle in patients with severe hemophilia B", Blood, 101(8):2963-2972 (Apr. 15, 2003).
A. Ishihara et al, "Inflammation and immune response of intra-articular serotype 2 adeno-associated virus or adenovirus vectors in a large animal model", Arthritis, pp. 1-8 (2012).
P. Goossens et al, "The influence of synovial fluid on adenovirus-mediated gene transfer to the synovial tissue", Arthritis & Rheumatism, 44(1):48-52 (Jan. 2001) (Goossens II).
P. Goossens et al, "Infection efficiency of Type 5 adenoviral vectors in synovial tissue can be enhanced with a Type 16 fiber", Arthritis & Rheumatism, 44(3):570-577 (Mar. 2001) (Goossens I).
L.R. Goodrich et al, "ScAAVIL-1ra dosing trial in a large animal model and validation of long-term expression with repeat administration for osteoarthritis therapy", Gene Therapy, pp. 1-10 (2015) (Goodrich IV).
L.R. Goodrich et al., "Ex vivo serotype-specific transduction of equine joint tissue by self-complementary adeno-associated viral vectors", Human Gene Therapy, 20:1697-1702 (Dec. 2009) (Goodrich II).
L.R. Goodrich et al, "Direct adenovirus-mediated IGF-I gene transduction of synovium induces persisting synovial fluid IGF-I ligand elevations", Gene Therapy, 13:1253-1262 (2006) (Goodrich I).
D.D. Frisbie et al, "Treatment of experimental equine osteoarthritis by in vivo delivery of the equine interleukin-1 receptor antagonist gene", Gene Therapy, 9:12-20 (2002).
R. Castello et al, "Helper-dependent adenoviral vectors for liver-directed gene therapy of primary hyperoxaluria type 1", Gene Therapy, pp. 1-6 (2015).
N. Brunetti-Pierri et al, "Acute toxicity after high-dose systemic injection of helper-dependent adenoviral vectors into nonhuman primates", Human Gene Therapy, 15:35-46 (Jan. 2004).
J. Bergelson et al, "Isolation of a common receptor for coxsackie B viruses and adenoviruses 2 and 5", Science, 275:1320-1323 (Feb. 28, 1997).
A.C. Bakker et al, "A tropism-modified adenoviral vector increased the effectiveness of gene therapy for arthritis", Gene Therapy, 8:1785-1793 (2001) (Bakker I).
G. White II et al, "Gene therapy for hemophilia A", Textbook of Hemophilia, Chapter 39, pp. 226-228, Blackwell Publishing Ltd. (2007).
K. Willett et al, "Immunology of AAV-mediated gene transfer in the eye", Frontiers in Immunology, 4(261):1-8 (Aug. 2013).
H-H Chen et al., "Persistence in muscle of an adenoviral vector that lacks all viral genes", Proc. Natl. Acad. Sci. USA, 94:1645-1650 (Mar. 1997).
S. Kochanek, "High-capacity adenoviral vectors for gene transfer and somatic gene therapy", Human Gene Therapy, 10:2451-2459 (Oct. 10, 1999).
A. Castel et al, "Repeat instability as the basis for human diseases and as a potential target for therapy", Mol. Cell Biol., 11:165-170 (Mar. 2010).
M. Oren et al, "Short tandem repeats, segmental duplications, gene deletion, and genomic instability in a rapidly diversified immune gene family", BMC Genomics, 17:900-919 (2016).
C. Pearson et al, "Repeat instability: mechanisms of dynamic mutations", Genetics, 6:729-742 (Oct. 2005).
Adriaansen J et al. "Gene therapy as a therapeutic approach for the treatment of rheumatoid arthritis: innovative vectors and therapeutic genes", Rheumatology 45:656-668 (2006).
Dinser et al. "Comparison of long-term transgene expression after non-viral and adenoviral gene transfer into primary articular chondrocytes", Histochemistry and Cell Biology 116:69-77 (2001).
Evans et al. "Gene Therapy for Rheumatic Diseases", Arthritis & Rheumatism, vol. 42, No. 1, p. 1-16 (1999).
Ghivizzani et al. "Direct adenovirus-mediated gene transfer of interleukin 1 and tumor necrosis factor α soluble receptors to rabbit knees with experimental arthritis has local and distal anti-arthritic effects", Proc. Natl. Acad. Sci. USA, vol. 95, pp. 4613-4618, (1998).
Harui et al. "Frequency and Stability of Chromosomal Integration of Adenovirus Vectors", Journal of Virology, Jul. 1999, vol. 73, No. 7, p. 6141-6146.
Ogawa et al. "Mechanical motion promotes expression of Prg4 in articular cartilage via multiple CREB-dependent, fluid flow shear stress-induced signaling pathways", Genes & Development, 2013, 28:127-139.
Smith et al. "Secretory lnterleukin-1 Receptor Antagonist Gene Expression Requires both a PU.1 and a Novel Composite NF-kB/PU.1/GA-binding Protein Binding Site", JBC, p. 24272-24279 (1998).
Vetrini et al. "Gene Therapy with Helper-Dependent Adenoviral Vectors: Current Advances and Future Perspectives", Viruses, p. 1886-1917 (2010).
Yeh and Perricaudet, "Advances in adenoviral vectors: from genetic engineering to their biology", FASEB Journal 11 (8):615-23 (1997).

* cited by examiner

HELPER-DEPENDENT ADENOVIRAL GENE THERAPY DELIVERY AND EXPRESSION SYSTEM

CROSS REFERENCE TO RELATED APPLICATIONS

In accordance with 37 C.F.R. § 176, a claim of priority is included in an Application Data Sheet filed concurrently herewith. The present application is a continuation application of U.S. patent application Ser. No. 17/358,904, filed Jun. 25, 2021, which is a continuation application of U.S. patent application Ser. No. 14/763,326, filed Jul. 24, 2015, which is a national stage filing in accordance with 35 U.S.C. § of International Patent Application No. PCT/IB2014/000071, filed Jan. 27, 2014, which claims the benefit of U.S. Provisional Patent Application No. 61/756,516, filed Jan. 25, 2013, the entire contents of each of which are incorporated herein by reference.

REFERENCE TO SEQUENCE LISTING SUBMITTED ELECTRONICALLY

The contents of the file named "GEQB-001_03US_SeqList_ST25", which was created on Jan. 13, 2023, and is 241,968 bytes, are hereby incorporated by reference in its entirety.

FIELD OF THE INVENTION

The present invention relates to gene therapy delivery and expression systems comprising at least one helper-dependent adenoviral vector containing a nucleic acid sequence encoding for proteoglycan 4 (PRG4) or a biologically active fragment thereof. The invention further relates to a pharmaceutical composition comprising a therapeutically effective amount of at least one helper-dependent adenoviral vector containing said nucleic acid sequence encoding for proteoglycan 4 (PRG4), or a homolog thereof from any other species, or a biologically active fragment thereof. The invention also relates to the use of the novel gene therapy delivery and expression system according to the invention for use in the prevention and/or treatment of camptodactyly-arthropathy-coxa vara-pericarditis (CACP), or a musculoskeletal disorder such as a joint disorder or joint disease.

BACKGROUND OF THE INVENTION

Musculoskeletal conditions are the most common chronic conditions, affecting nearly one third of the human population. Musculoskeletal conditions are defined as conditions of the bones, muscles and their attachments such as joints, tendons and ligaments. They consist of a variety of different diseases that cause pain or discomfort in the bones, joints, tendons, ligaments, muscles or surrounding structures. Musculoskeletal disorders range from back pain to rheumatoid arthritis, and gout, and include different types of arthritis, tendinitis and musculoskeletal pain. Furthermore, musculoskeletal diseases or disorders include, but are not limited to arthropathies, all types of arthritis, including arthritis-related disorders, osteoarthritis, rheumatoid arthritis, gout and pseudo-gout, septic arthritis, psoriatic arthritis, ankylosing spondylitis, juvenile idiopathic arthritis. Still's disease, Reiter's syndrome, or tendinopathies including tendonitis, tendinosis, tenosynovitis; synovial disorders including synovitis; Bursa disorders including bursitis; equine musculoskeletal disorders including bone spavin, navicular syndrome, osselet.

In addition, there are heritable disorders such as CAPC (camptodactyly-arthropathy-coxa vara-pericarditis) syndrome that have their origin in a non-functional PRG4 gene. The disorder results in synoviocyte hyperplasia and early onset osteoarthritis, the principal pathological features of the CAPC syndrome.

Osteoarthritis (OA) is an age-related or post-traumatic degenerative disease of the joint that is characterized by loss of articular cartilage, chondrocyte proliferation and hypertrophic differentiation, subchondral bone remodelling, inflammation, and finally, osteophyte formation (K. Johnson et al., A Stem Cell-Based Approach to Cartilage Repair. Science (New York, N.Y.) 336, 717 (Jun. 10, 2012)). It is among the leading causes of chronic disability (Matthews, G. L., and Hunter, D. J. (2011), Emerging drugs for osteoarthritis. Expert Opin. Emerging Drugs 1-13). Surprisingly, given the impact of OA, relatively few genetic mouse models have been developed to provide insights into potential protective mechanisms that can modify the development of osteoarthritis. To date, most have been loss-of-function genetic models of cartilage degrading enzymes such as ADAMTS5 and MMP13 (F. Echtermeyer et al., Syndecan-4 regulates ADAMTS-5 activation and cartilage breakdown in osteoarthritis. *Nature Medicine,* 1 (Mar. 30, 2102); T. Saito et al., Transcriptional regulation of endochondral ossification by HIF-2α during skeletal growth and osteoarthritis development. *Nature Medicine* 16, 678 (Jun. 23, 2010); R. M. Borzi et al., Matrix metalloproteinase 13 loss associated with impaired extracellular matrix remodeling disrupts chondrocyte differentiation by concerted effects on multiple regulatory factors. *Arthritis & amp; Rheumatism* 62, 2370 (May 13, 2010); J. D. Kay et al., Intra-articular gene delivery and expression of interleukin-1Ra mediated by self-complementary adeno-associated virus. *The journal of gene medicine* 11, 605 (July, 2009)). Mice with loss of function mutation in Hif2a are also protected from osteoarthritis development, highlighting the importance of the hypoxia pathway in cartilage homeostasis. Unfortunately, despite significant investment, the development of inhibitors of such pathways has not proven effective in the clinical setting.

Interestingly, loss-of-function mutations in proteoglycan 4 (PRG4) in humans cause Camptodactyly-Arthropathy-Coxa Vara-Pericarditis Syndrome (J. Marcelino et al., CACP, encoding a secreted proteoglycan, is mutated in camptodactyly-arthropathy-coxa vara-pericarditis syndrome. *Nature genetics* 23, 319 (November, 1999)), which is characterized by early onset osteoarthritis. In addition, genetic knockout of PRG4 in mice also results in early osteoarthritis development (D. K. Rhee et al., The secreted glycoprotein lubricin protects cartilage surfaces and inhibits synovial cell overgrowth, *J Clin Invest* 115, 622 (March, 2005); J. M. Coles et al., Loss of cartilage structure, stiffness, and frictional properties in mice lacking PRG4. *Arthritis & amp; Rheumatism* 62, 1666 (Jul. 1, 2010)).

PRG4 is also known as lubricin or superficial zone protein or megakaryocyte stimulating factor precursor. It is a component of the cartilage extracellular matrix and synovial fluid (D. K. Rhee et al., The secreted glycoprotein lubricin protects cartilage surfaces and inhibits synovial cell overgrowth, *J Clin Invest* 115, 622 (March, 2005)). PRG4 is present in synovial fluid and on the surface (superficial layer) of articular cartilage and therefore plays an important role in joint lubrication and synovial homeostasis. Unlike previous osteoarthritis targets, it is a secreted protein produced by superficial zone chondrocytes of the articular cartilage and by synovial lining cells in mammals (D, K. Rhee et al., The secreted glycoprotein lubricin protects cartilage surfaces and inhibits synovial cell overgrowth. *J Clin Invest* 115, 622 (March, 2005)). The PRG4 gene encodes for glycoprotein of approximately 345 kDa. PRG4 provides synovial fluid with the ability to dissipate strain energy under load and its recombinant protein has been reported to exert chondroprotective effects during the progression of OA in rats (G. D. Jay, J. R. Torres, M. L. Warman, M. C. Lederer, K. S. Breuer, The role of lubricin in the mechanical behavior of synovial fluid. *Proc Natl Acad Sci USA* 104, 6194 (Apr. 10, 2007); C. R. Flannery et al., Prevention of cartilage degeneration in a rat model of osteoarthritis by intraarticular treatment with recombinant lubricin. *Arthritis & amp; Rheumatism* 60, 840 (April, 2009)). However, the long-term biological effects of PRG4 over-expression and the molecular mechanism of its potential therapeutic benefits are still poorly understood.

U.S. Pat. No. 6,743,774 A describes a gene therapy approach by administering to a mammal a nucleic acid encoding a therapeutic lubricating polypeptide, such as a lubricating fragment of megakaryocyte stimulating factor precursor by standard vectors and/or gene delivery systems. The gene delivery systems described include liposomes, receptor-mediated delivery systems, naked DNA, viral vectors such as herpes viruses, retro viruses, adenoviruses and adeno-associated viruses. U.S. Pat. No. 7,393,029 A describes polynucleotides for use in gene therapy encoding for recombinant lubricin.

Although some approaches suggest gene therapy for treating or preventing joint disorders such as osteoarthritis, no curative treatments are currently available. Medical treatment is mostly aimed at alleviating the symptoms using analgesic drugs rather than establishing worn away cartilage. An analgesic treatment usually involves steroids and non-steroidal anti-inflammatory drugs (NSAIDS), which have shown efficacy in the treatment of osteoarthritis for some decades. However, while these drugs can suppress joint inflammation, many of them are known to have deteriorating effects on the cartilage, which further worsens the underlying process of osteoarthritis development. Hyaluronic acid, which restores viscoelasticity and lubrication of the joints, has also been widely used. Furthermore, polysulphated glycosaminoglycans injected into the joint or intramuscularly as well as orally administered glucosamine and chondroitin sulphate have been used in the treatment for osteoarthritis, however, the efficacy has not been proven in large randomized trials. Thus, currently used therapies have only limited efficacy in the treatment of joint disorders such as osteoarthritis and their success often depends on the severity of the case. Moreover, these drugs must be administered frequently; sometimes in combination with each other. However, frequent drug injections into the joint are laborious, bear the risk for infections, cause stress for the patient and are costly. It follows that there is a clear and yet unmet medical need for more efficacious and sustained treatments that are at the same time also cost effective in the long run.

The role of PRG4 in joint disorders has been discussed. In addition, during osteoarthritis, interleukin-1 (Il-1) functions as a central mediator of inflammation (Daheshia, M., and YAO, J. Q. (2008). The Interleukin 1β Pathway in the Pathogenesis of Osteoarthritis, J Rheumatol 35, 2306). Moreover, Il-1 strongly inhibits cartilage matrix synthesis and can trigger matrix breakdown (Evans, C. H., Gouze, J. N. Gouze, E., Robbins, P. D, and Ghivizzani, S. C. (2004)). Osteoarthritis gene therapy, Gene Ther 11, 379-389). To neutralize the effect of Il-1 on synovial inflammation, treatment with interleukin-1 receptor antagonist (Il-1Ra) constitutes a promising concept in the therapy of osteoarthritis (Evans, C. H., Gauze, J. N., Gauze, E., Robbins, P. D., and Ghivizzani. S. C. (2004). Osteoarthritis gene therapy. Gene Ther 11, 379-389; Caron J P et al. Chondroprotective effect of intraarticular injections of interleukin-1 receptor antagonist in experimental osteoarthritis. Suppression of collagenase-1 expression. Arthritis Rheum 1996; 39: 1535-1544)). On nucleic acid level, Il-1Ra is considerably conserved among mammalian species. For example, the cDNA sequences of human Il-1Ra (Accession no: NM_173842) shares 82% homology with the murine variant (Accession no: NM_031167), 84% with the equine variant (Accession no: NM_001082525), 84% with the canine variant (Accession no: NM_001003096), 84% with the lapine variant (Accession no: NM_001082770) and 82% with the bovine variant (Accession no: NM_174357).

Although gene therapy approaches using various gene therapy vectors are known, there is a need for a gene therapy delivery and expression system, which allows for the specific delivery of a therapeutic amount of an active agent to its target. In addition, the active agent shall exhibit its therapeutic effects for a prolonged amount of time. Adeno-associated viruses (AAV) are among the most widely used gene therapy vectors and have shown efficient transduction and long-term transgene expression in many tissues. AAVs have also been used in gene therapy approaches for joints. However, AAV transduction efficiency in joints has never been directly compared to transduction efficiency of other viral gene therapy vectors such as adenoviruses including helper-dependent adenoviral vectors.

Helper-dependent adenoviruses (HDAd), also known as gutless or high-capacity adenoviruses, are the latest generation of adenoviral vectors (Mitani, K., Graham, F. L. Caskey, C. T. & Kochanek, S. Rescue, propagation, and partial purification of a helper virus-dependent adenovirus vector. Proc Natl Acad Sci USA 92, 3854-3858 (1995); Parks, R. J. et al. A Helper-dependent adenovirus vector system: removal of helper virus by Cre-mediated excision of the viral packaging signal. Proc Natl Acad Sci USA 93, 13565-13570 (1996); Parks, R. J. Improvements in adenoviral vector technology: overcoming barriers for gene therapy. Clin. Genet. 58, 1-11 (2000)). These vectors are devoid of all viral sequences and are able to mediate long-term gene expression in various tissues (e.g. 7 years in the liver) in contrast to the more immunogenic first generation adenoviruses (Brunetti-Pierri, N., Ng, T., Iannitti, D., Cioffi, W., Stapleton, G., Law, M., Breinholt, J., Palmer; D., Grove, N., Rice, K., et al. (2013). Transgene Expression up to 7 Years in Nonhuman Primates Following Hepatic Transduction with Helper-Dependent Adenoviral Vectors. Hum Gene Ther 24, 761-765).

BRIEF SUMMARY OF THE INVENTION

In one aspect, provided herein is a gene therapy delivery and expression system, comprising at least one helper-dependent adenoviral vector containing a nucleic acid sequence encoding proteoglycan 4 (PRG4), or a biologically active fragment thereof, which has chondoprotective activity, left and right adenoviral inverted terminal repeats (L ITR and R ITR), adenoviral packaging signal sequences and non-viral, non-coding stuffer nucleic acid sequences, wherein PRG4 expression in the at least one helper-dependent adenoviral vector is controlled by a ubiquitous, constitutive promoter, wherein (i) the helper-dependent adenoviral vector additionally comprises a nucleic acid sequence encoding interleukin-1 receptor antagonist (Il-1Ra), or (ii) the delivery and expression system comprises a second helper-dependent adenoviral vector comprising a nucleic acid sequence encoding interleukin-1 receptor antagonist (Il-1Ra).

In some embodiments, the ubiquitous constitutive promoter is selected from the group consisting of elongation factor 1 alpha (EF1 alpha) promoter, cytomegalovirus (CMV) promoter, beta-actin promoter, simian virus 40 (SV4O) early promoter, ubiquitin c promoter, glyceraldehyde 3-phosphate dehydrogenase (GAPDH) promoter, phosphoglycerate kinase (PGK) promoter.

In some embodiments, the helper-dependent adenoviral vector containing a nucleic acid sequence encoding proteoglycan 4 (PRG4) comprises a nucleic acid sequence set forth in SEQ ID NO 1, or SEQ ID NO 2, or a biologically active fragment thereof, or a nucleic acid sequence which has at least 50%, 60%, 70%, 80% or 90% sequence homology with a nucleic acid sequence set forth in SEQ ID NO 1, or SEQ ID NO 2, or a biologically active fragment thereof, wherein the helper-dependent adenoviral vector containing a nucleic acid sequence encoding PRG4, which comprises a biologically active fragment of SEQ ID NO 1, or SEQ ID NO 2, or a nucleic acid sequence which has at least 50%, 60%, 70%, 80% or 90% sequence homology with a nucleic acid sequence set forth in SEQ ID NO 1. or SEQ ID NO 2, or a biologically active fragment thereof, mediates chondoprotective activity.

In some embodiments, the nucleic acid sequence encoding proteoglycan 4 (PRG4) comprises a nucleic acid sequence set forth in SEQ ID NO 3, or SEQ ID NO 4, or a biologically active fragment thereof, or a homolog thereof from any other species, or a nucleic acid sequence which has at least 50%, 60%, 70%, 80% or 90% sequence homology with a nucleic acid sequence set forth in SEQ ID NO 3, or SEQ ID NO 4, or a biologically active fragment thereof, wherein the PRG4 encoded by the biologically active fragment of SEQ ID NO 3, or SEQ ID NO 4, or a nucleic acid sequence which has at least 50%, 60%, 70%, 80% or 90% sequence homology with a nucleic acid sequence set forth in SEQ ID NO 3, or SEQ ID NO 4, or a biologically active fragment thereof, has chondoprotective activity.

In some embodiments, the amino acid sequence of proteoglycan 4 (PRG4) comprises an amino acid sequence set forth in SEQ ID NO 5, or SEQ ID NO 6, or a biologically active fragment thereof, or a homolog thereof from any other species, or an amino acid sequence which has at least 50%, 60%, 70%, 80% or 90% sequence homology with an amino acid sequence set forth in SEQ ID NO 5, or SEQ ID NO 6, or a biologically active fragment thereof, wherein the amino acid sequence of PRG4, which comprises a biologically active fragment of the amino acid SEQ ID NO 5, or SEQ ID NO 6, or has at least 50%, 60%, 70%, 80% or 90% sequence homology with an amino acid sequence set forth in SEQ ID NO 5, or SEQ ID NO 6, or a biologically active fragment thereof, has chondoprotective activity.

In some embodiments, expression of interleukin-1 receptor antagonist (Il-1Ra) is controlled by an inflammation-inducible promoter selected from the group consisting of NF-κB promoter, interleukin 6 (Il-6) promoter, interleukin-1 (Il-1) promoter, tumor necrosis factor (TNF) promoter, cyclooxygenase 2 (COX-2) promoter, complement factor 3 (C3) promoter, serum amyloid A3 (SAA3) promoter, macrophage inflammatory protein-1α (MIP-1α) promoter, or hybrid constructs of the above.

In some embodiments, the helper-dependent adenoviral vector comprising the nucleic acid sequence encoding interleukin-1 receptor antagonist (Il-1Ra), comprises a nucleic acid sequence which has at least 50%, 60%, 70%, 80% or 90% sequence homology with a nucleic acid sequence set forth in SEQ ID NO 7, or SEQ ID NO 8, or SEQ ID NO 9, or a biologically active fragment thereof, wherein the helper-dependent adenoviral vector comprising the nucleic acid sequence encoding Il-1Ra, which comprises a nucleic acid sequence which has at least 50%, 60%, 70%, 80% or 90% sequence homology with a nucleic acid sequence set forth in SEQ ID NO 7, or SEQ ID NO 8, or SEQ ID NO 9, or a biologically active fragment thereof, has Il1-Ra activity of inhibiting inflammatory and cartilage destructive mediators.

In some embodiments, the nucleic acid sequence encoding interleukin-1 receptor antagonist (Il-1Ra) comprises a nucleic acid sequence set forth in SEQ ID NO 10, or SEQ ID NO 11, or SEQ ID NO 12, or a biologically active fragment thereof, or wherein the nucleic acid sequence encoding for interleukin-1 receptor antagonist (Il-1Ra) comprises a nucleic acid sequence which has at least 50%, 60%, 70%, 80% or 90% sequence homology with a nucleic acid sequence set forth in SEQ ID NO 10, or SEQ ID NO 11, or SEQ ID NO 12, or a biologically active fragment thereof, wherein the Il-1Ra encoded by the biologically active fragment of SEQ ID NO 10, or SEQ ID NO 11, or SEQ ID NO 12, or the nucleic acid sequence which has at least 50%, 60%, 70%, 80% or 90% sequence homology with a nucleic acid sequence set forth in SEQ ID NO 10, or SEQ ID NO 11, or SEQ ID NO 12, or the biologically active fragment thereof, mediates Il1-Ra activity of inhibiting inflammatory and cartilage destructive mediators.

In some embodiments, the amino acid sequence of interleukin-1 receptor antagonist (Il-1Ra) comprises an amino acid sequence set forth in SEQ ID NO 13, SEQ ID NO 14, SEQ ID NO 15, or a biologically active fragment thereof, which has Il1-Ra activity of inhibiting inflammatory and cartilage destructive mediators.

In another aspect, provided herein is a pharmaceutical composition, comprising a therapeutically effective amount of at least one helper-dependent adenoviral vector containing a nucleic acid sequence encoding proteoglycan 4 (PRG4), or a biologically active fragment thereof, which has chondoprotective activity, left and right adenoviral inverted terminal repeats (L ITR and R ITR), adenoviral packaging signal sequences and non-viral, non-coding stuffer nucleic acid sequences, wherein PRG4 expression in the at least one helper-dependent adenoviral vector is controlled by a ubiquitous, constitutive promoter, wherein (i) the helper-dependent adenoviral vector additionally comprises a nucleic acid sequence encoding interleukin-1 receptor antagonist (Il-1Ra), or (ii) the delivery and expression system comprises a second helper-dependent adenoviral vector comprising a nucleic acid sequence encoding interleukin-1 receptor antagonist (Il-1Ra).

In some embodiments, the ubiquitous constitutive promoter is selected from the group consisting of elongation factor 1 alpha (EF 1 alpha) promoter, cytomegalovirus (CMV) promoter, beta-actin promoter, simian virus 40 (SV40) early promoter, ubiquitin c promoter, glyceraldehyde 3-phosphate dehydrogenase (GAPDH) promoter, phosphoglycerate kinase (PGK) promoter.

In some embodiments, wherein the helper-dependent adenoviral vector containing a nucleic acid sequence encoding proteoglycan 4 (PRG4) comprises a nucleic acid sequence set forth in SEQ ID NO 1, or SEQ ID NO 2, or a biologically active fragment thereof, or a nucleic acid sequence which has at least 50%, 60%, 70%, 80% or 90% sequence homology with a nucleic acid sequence set forth in SEQ ID NO 1, or SEQ ID NO 2, or a biologically active fragment thereof, wherein the helper-dependent adenoviral vector containing a nucleic acid sequence encoding PRG4, which comprises a biologically active fragment of SEQ ID NO 1, or SEQ ID NO 2, or a nucleic acid sequence which has at least 50%, 60%, 70%, 80% or 90% sequence homology with a nucleic acid sequence set forth in SEQ ID NO 1. or SEQ ID NO 2, or a biologically active fragment thereof, mediates chondoprotective activity.

In some embodiments, the nucleic acid sequence encoding proteoglycan 4 (PRG4) comprises a nucleic acid sequence set forth in SEQ ID NO 3, or SEQ ID NO 4, or a biologically active fragment thereof, or a homolog thereof from any other species, or a nucleic acid sequence which has at least 50%, 60%, 70%, 80% or 90% sequence homology with a nucleic acid sequence set forth in SEQ ID NO 3, SEQ ID NO 4, or a biologically active fragment thereof, wherein the PRG4 encoded by the biologically active fragment of SEQ ID NO 3, or SEQ ID NO 4, or a nucleic acid sequence which has at least 50%, 60%, 70%, 80% or 90% sequence homology with a nucleic acid sequence set forth in SEQ ID NO 3, or SEQ ID NO 4, or a biologically active fragment thereof, has chondoprotective activity.

In some embodiments, the amino acid sequence of proteoglycan 4 (PRG4) comprises an amino acid sequence set forth in SEQ ID NO 5, or SEQ ID NO 6, or a biologically active fragment thereof, or a homolog thereof from any other species, or an amino acid sequence which has at least 50%, 60%, 70%, 80% or 90% sequence homology with an amino acid sequence set forth in SEQ ID NO 5, or SEQ ID NO 6, or a biologically active fragment thereof, wherein the amino acid sequence of PRG4, which comprises a biologically active fragment of the amino acid SEQ ID NO 5, or SEQ ID NO 6, or has at least 50%, 60%, 70%, 80% or 90% sequence homology with an amino acid sequence set forth in SEQ ID NO 5, or SEQ ID NO 6, or a biologically active fragment thereof, has chondoprotective activity.

In some embodiments, expression of interleukin-1 receptor antagonist (Il-1Ra) is controlled by an inflammation-inducible promoter selected from the group consisting of NF-κB promoter, interleukin 6 (Il-6) promoter, interleukin-1 (Il-1) promoter, tumor necrosis factor (INF) promoter, cyclooxygenase 2 (COX-2) promoter, complement factor 3 (C3) promoter, serum amyloid A3 (SAA3) promoter, macrophage inflammatory protein-1α (MIP-1α) promoter, or hybrid constructs of the above.

In some embodiments, the helper-dependent adenoviral vector comprising the nucleic acid sequence encoding interleukin-1 receptor antagonist (Il-1Ra), comprises a nucleic acid sequence which has at least 50%, 60%, 70%, 80 or 90% sequence homology with a nucleic acid sequence set forth in SEQ ID NO 7, or SEQ ID NO 8, or SEQ ID NO 9, or a biologically active fragment thereof, wherein the helper-dependent adenoviral vector comprising the nucleic acid sequence encoding Il-1Ra, which comprises a nucleic acid sequence which has at least 50%, 60%, 70%, 80% or 90% sequence homology with a nucleic acid sequence set forth in SEQ ID NO 7, or SEQ ID NO 8, or SEQ ID NO 9, or a biologically active fragment thereof, has Il1-Ra activity of inhibiting inflammatory and cartilage destructive mediators.

In some embodiments, the nucleic acid sequence encoding interleukin-1 receptor antagonist (Il-1Ra) comprises a nucleic acid sequence set forth in SEQ ID NO 10, or SEQ ID NO 11, or SEQ ID NO 12, or a biologically active fragment thereof, or wherein the nucleic acid sequence encoding for interleukin-1 receptor antagonist (Il-1Ra) comprises a nucleic acid sequence which has at least 50%, 60%, 70%, 80% or 90% sequence homology with a nucleic acid sequence set forth in SEQ ID NO 10, or SEQ ID NO 11, or SEQ ID NO 12, or a biologically active fragment thereof, wherein the Il-1Ra encoded by the biologically active fragment of SEQ ID NO 10, or SEQ ID NO 11, or SEQ ID NO 12, or the nucleic acid sequence which has at least 50%, 60%, 70%, 80% or 90% sequence homology with a nucleic acid sequence set forth in SEQ ID NO 10, or SEQ ID NO 11, or SEQ ID NO 12, or the biologically active fragment thereof, mediates Il1-Ra activity of inhibiting inflammatory and cartilage destructive mediators.

In some embodiments, the amino acid sequence of interleukin-1 receptor antagonist (Il-1Ra) comprises an amino acid sequence set forth in SEQ ID NO 13, SEQ ID NO 14, SEQ ID NO 15, or a biologically active fragment thereof, which has Il1-Ra activity of inhibiting inflammatory and cartilage destructive mediators.

In another aspect, provided herein is the gene therapy delivery and expression system according to any of the preceding embodiments for use in the prevention and/or treatment of camptodactyly-arthropathy-coxa vara-pericarditis (CACP) syndrome, or a musculoskeletal disorder, or a joint disorder or disease. In some embodiments, the disease or disorder is selected from the group consisting of arthropathies, all types of arthritis, including arthritis-related disorders, osteoarthritis, rheumatoid arthritis, gout and pseudo-gout, septic arthritis, psoriatic arthritis, ankylosing spondylitis, juvenile idiopathic arthritis, Still's disease, Reiter's syndrome, or tendinopathies including tendonitis, tendinosis, tenosynovitis; synovial disorders including synovitis; Bursa disorders including bursitis; equine musculoskeletal disorders including bone spavin, navicular syndrome, osselet.

Red arrow indicates loss of cartilage, Scale bar, 500 μm. D, Quantification of articular cartilage volume and surface area of bone covered by cartilage in mouse joints by phase contrast μCT (*P<0.01, **P<0.05, N.S.=not significant, n=5-6, ANOVA). E, Average time that mice stayed on rotating rod 2 months after cruciate ligament transection in rotarod analysis (*P<0.05, n=15, ANOVA). F, Response time of mice after placement onto a 55° C. platform in hotplate analysis (*P<0.05, n=10, ANOVA), Error bars indicate s.e.m.

Figure 3:
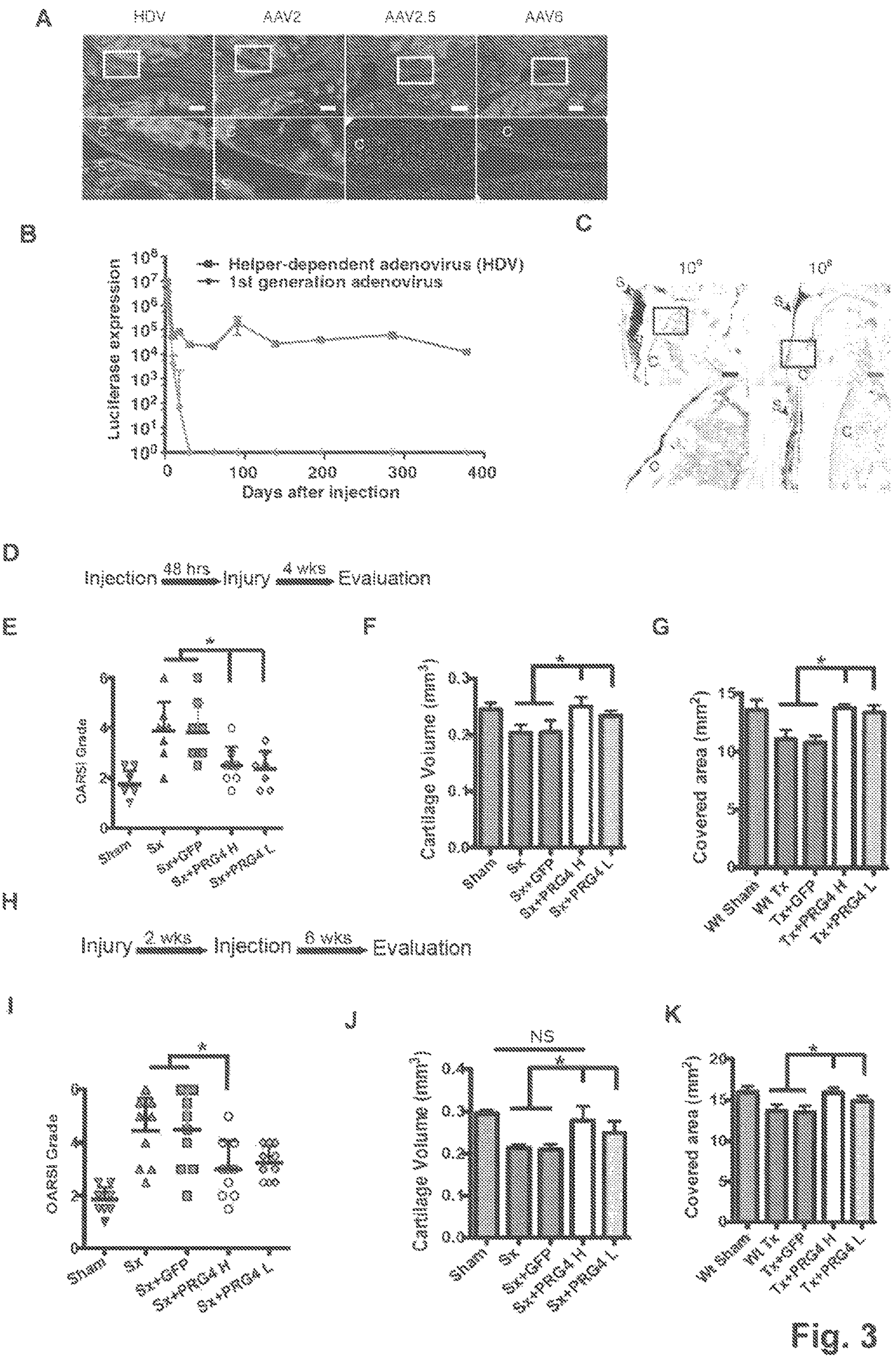

FIG. 3: PRG4 delivered by helper-dependent adenoviral vectors (HDAd) protects mice from development of osteoarthritis. A, Representative image comparing intra-articular injection of HDAd and different serotypes of AAV. Vectors ($10^9$ viral particles) each expressing GFP were injected intraarticularly into the knee joint. The lower panels are enlarged images of the boxed areas in the upper panels. Green: GFP, blue: DAPI. C: cartilage, S: synovium. Scale bar, 100 μm. B, Comparison of luciferase expression after intra-articular injection of first-generation adenoviral vector (FGV) and helper-dependent adenoviral vector (HDAd) (n=6) into the knee joint. C, Representative image of expression patterns of intra-articular injections of different doses of HDAD encoding □-galactosidase. The bottom images are enlarged areas of the black box in the upper images of saggital sections through the knee joint. C: Cartilage; S: Synovium. Scale bar, 100 μm. D-G, Scheme of experiment comparing the preventive effect HDAd-PRG4 injection and evaluation by OARSI grade and cartilage volume (D). Before transection, wild type mice were injected with HDAd-PRG4 intra-articularly at $10^9$ vp/joint (Sx+PRG4 H) or $10^8$ vp/joint (Sx+PRG4 L). Sham, transection without treatment (Sx) and injection of virus without transgene before transection (Sx+Vector) served as controls. Degree of osteoarthritis is presented by OARSI grade (E), cartilage volume (F) and cartilage surface area (G) (*P<0.05, n=8-10 in OARSI grading, n=5-6 in cartilage volume analysis, ANOVA). H-K, Scheme of experiment comparing the protective effect HDAd-PRG4 injection and evaluation by OARSI grade and cartilage volume (H). Two weeks after transection, wild type mice were injected with HDAd-PRG4 intra-articularly at $10^9$ vp/joint (Sx+PRG4 L) or $10^8$ vp/joint (Sx+PRG4 L), Sham, no treatment (Sx) and HDAd-GFP injection (Sx+GFP) served as controls. Degree of OA is presented by OARSI grade (I), cartilage volume (J) and cartilage surface area (K) (*P<0.05, n=8-10 in OARSI grading, n=5-6 in cartilage volume analysis, ANOVA). Error bars indicate s.e.m.

Figure 4:
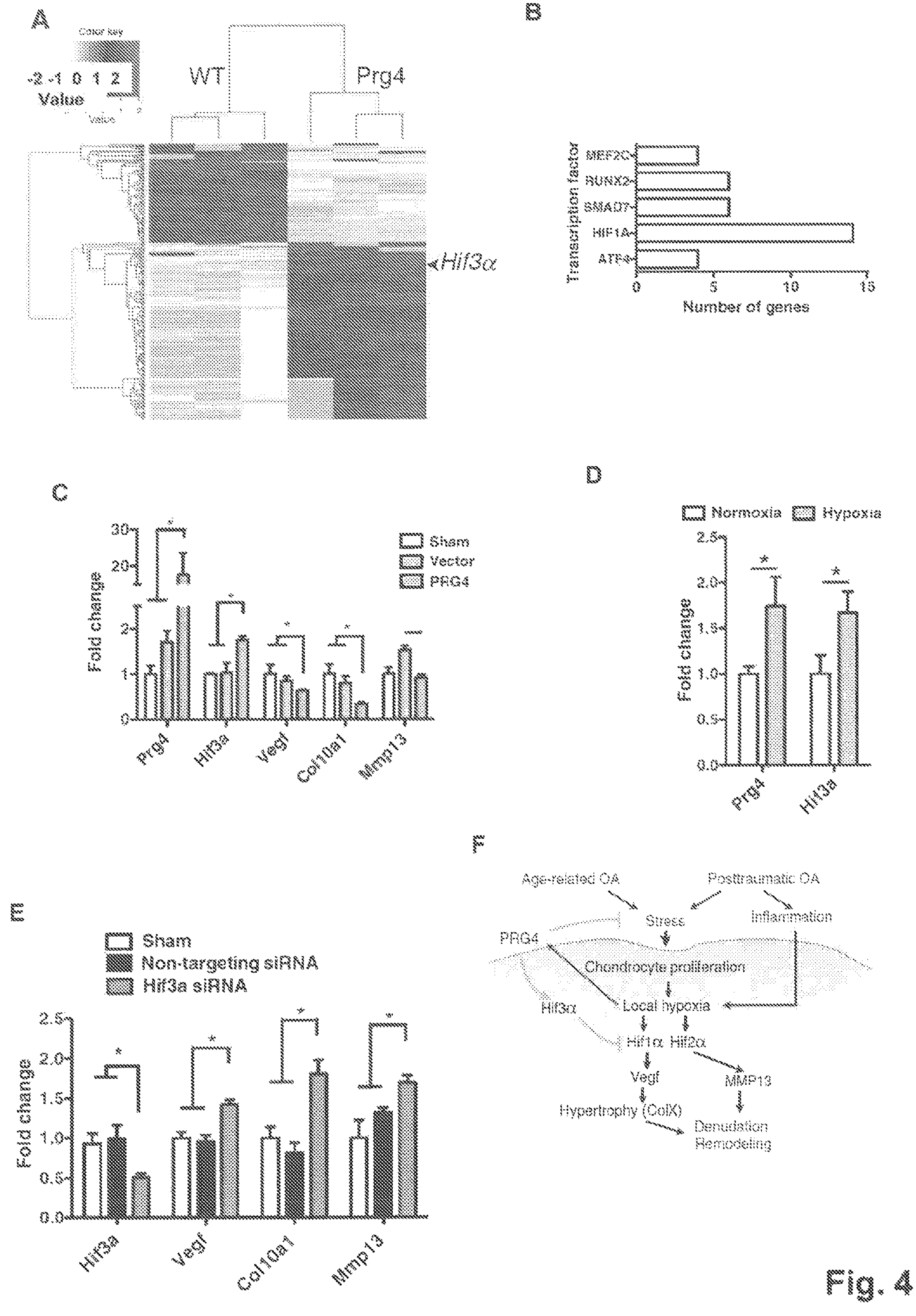

FIG. 4: PRG4 delays osteoarthritis by inhibiting cartilage catabolism and terminal hypertrophy. A, Microarray heat map analysis comparing superficial zone cartilage of wild type and Prg4 transgenic mice, Genes with expression changes larger than 1.5 fold and p-value less than 0.05 are plotted. B, Transcription factor activity changes predicted by Ingenuity Pathway Analysis. All transcription factors shown here were predicted to be suppressed by Ingenuity Pathway Analysis. X-axis indicates the number of genes/gene groups controlled by each transcription pathway in the gene list submitted. C, Changes in gene expression (Prg4, Hif3a, Vegf, Col10a1 and Mmp13) in C3H10T1/2 cells under hypoxia (1% oxygen for 8 hours). Cells are sham treated, infected with empty HDAd (vector) or with HDAd-PRG4 (PRG4) (*P<0.05, n=3, ANOVA). D, Changes of PRG4 and Hif3alpha expression under normoxia and hypoxia in TC71 Ewing sarcoma cells (*P<0.05, n=3, t-test). E, Changes of gene expression after Hif3alpha knockdown by siRNA (*P<0.05, n=3, ANOVA). F, Proposed model of PRG4 function in prevention of osteoarthritis development. Error bars indicate s.e.m.

Figure 5:
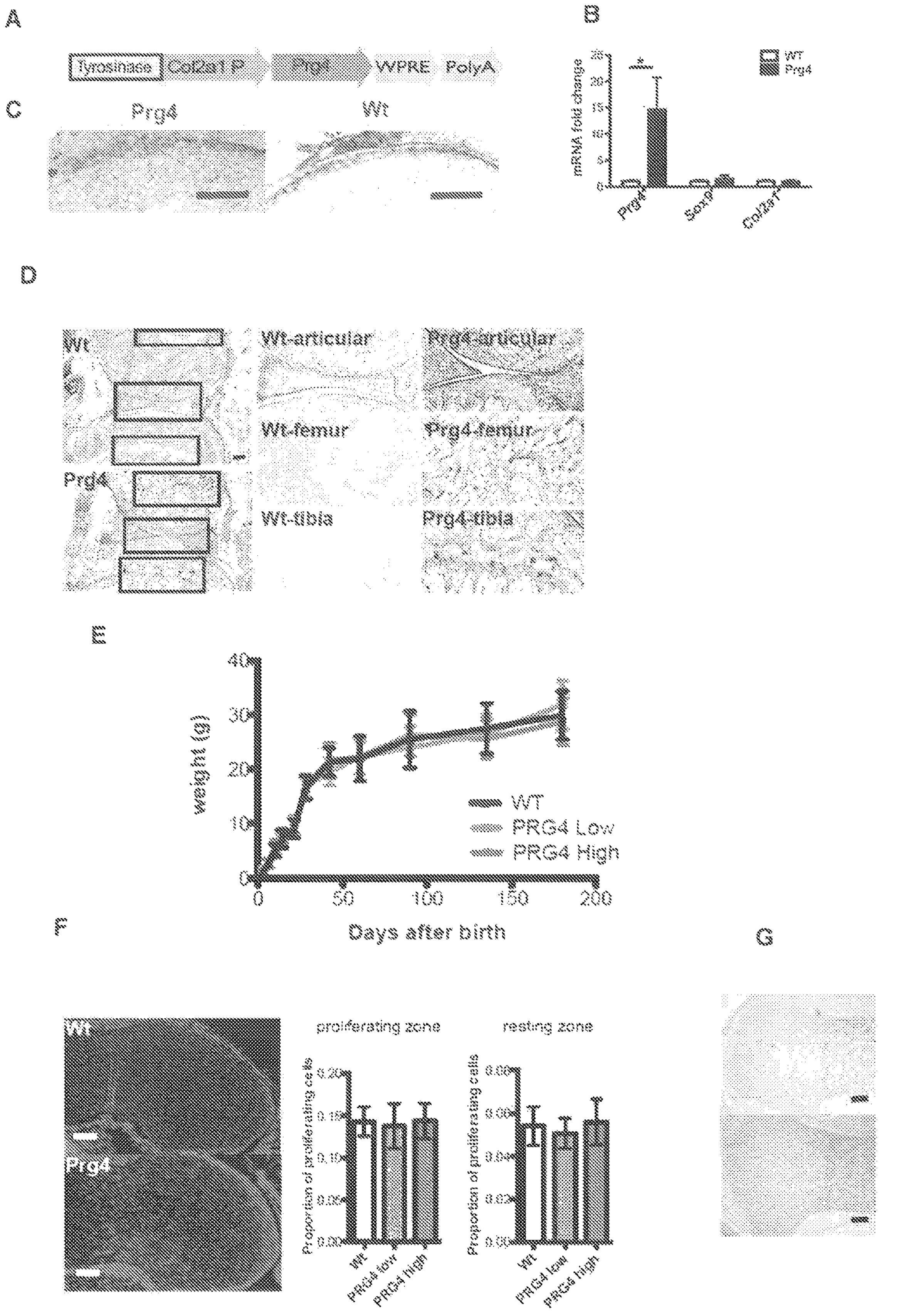

FIG. 5: PRG4 over-expression under the Col2al promoter does not adversely affect the development of mice. A, Schematic figure of the Prg4 transgenic mice construct. B, Rib cartilage expression levels of PRG4, Sox9 and Col2al in newborns (P1) PRG4 transgenic and wild type mice (*P<0.05, n=7-8, student t-test). C, Comparison of anti-PRG4 antibody stained femoral head section in wild type and Prg4 transgenic newborn mice. Scale bars, 100 μm. D, Comparison of anti-PRG4 antibody stained knee joints in Prg4 transgenic and wild type 3 month-old mice. The boxed areas to the left (articular area, distal femoral growth plate and proximal tibial growth plate) are enlarged at the right. Scale bars, 100 μm. E, Weight of Prg4 high expresser, low expresser and wild type mice (P<0.05, n=10-11). F, Representative image of BrdU (red) and DAPI (blue) staining in wild type and Prg4 transgenic P3 hind limbs. Staining signals were quantified by image J (P<0.05, n=7). Scale bars, 100 μm. G, Representative image of TUNEL (brown) and methyl green staining in wild type and Prg4 transgenic P3 hind limbs. No positive signals were visible in cartilage but they were present in overlying dermis and skin. Scale bar, 100 μm. Error bars indicate s.e.m.

Figure 6:
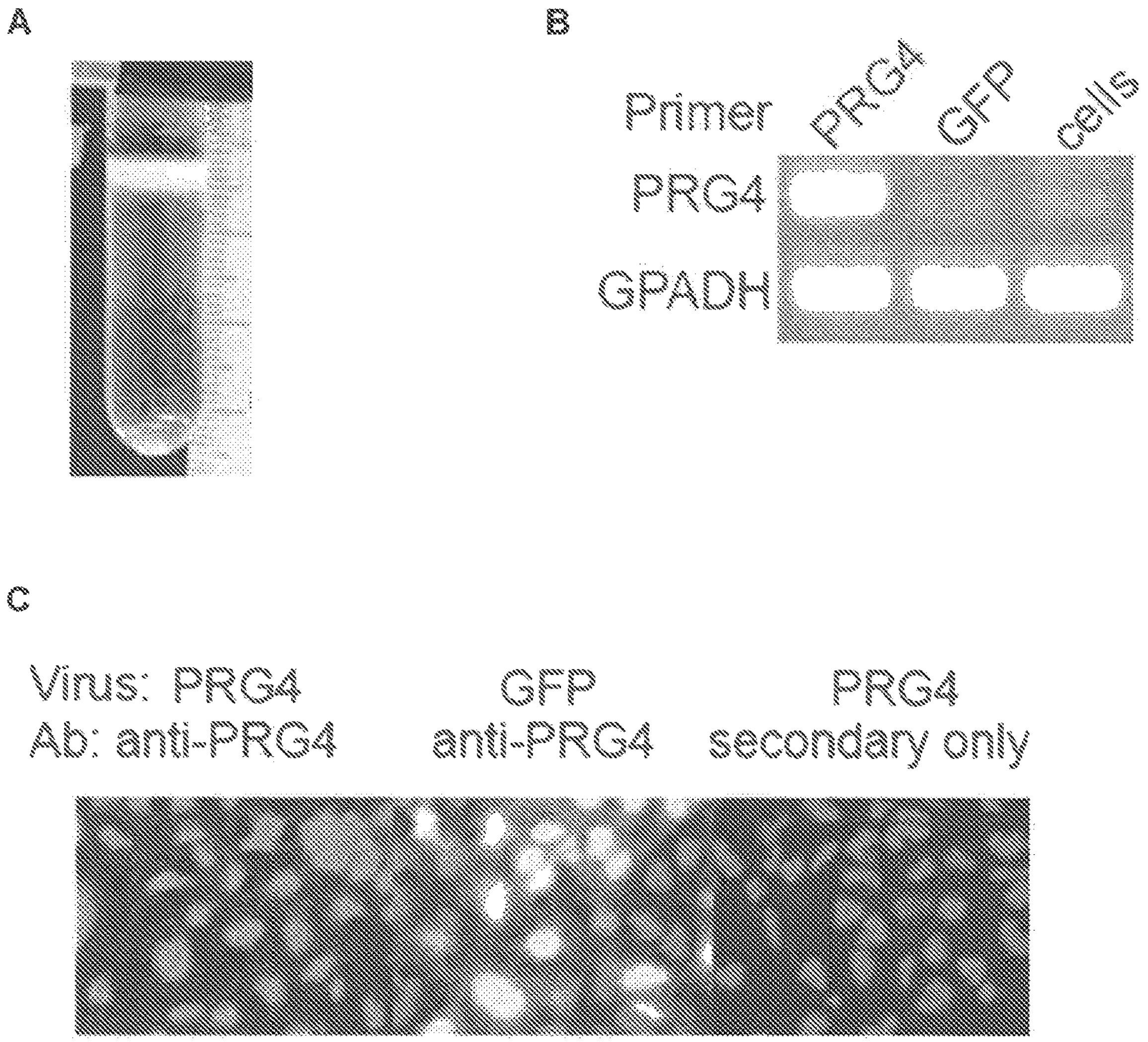

FIG. 6: Generation and characterization of HDAd-PRG4. A, HDAd-PRG4 band is visible in the last step of cesium chloride ultracentrifugation. The purified virus is the white band in the tube. B, PCR determination of PRG4 expression of HEK293 cells infected with HDAd-PRG4 (PRG4), HDAd-GFP (GFP), and sham treatment (cells). Gapdh is used as loading control. C, Immunofluorescence of HEK293 cells infected with HDAd-PRG4 (PRG4, red) and HDAd-GFP (GFP, green). DAPI (blue) was used as counter-stain.

Figure 7:
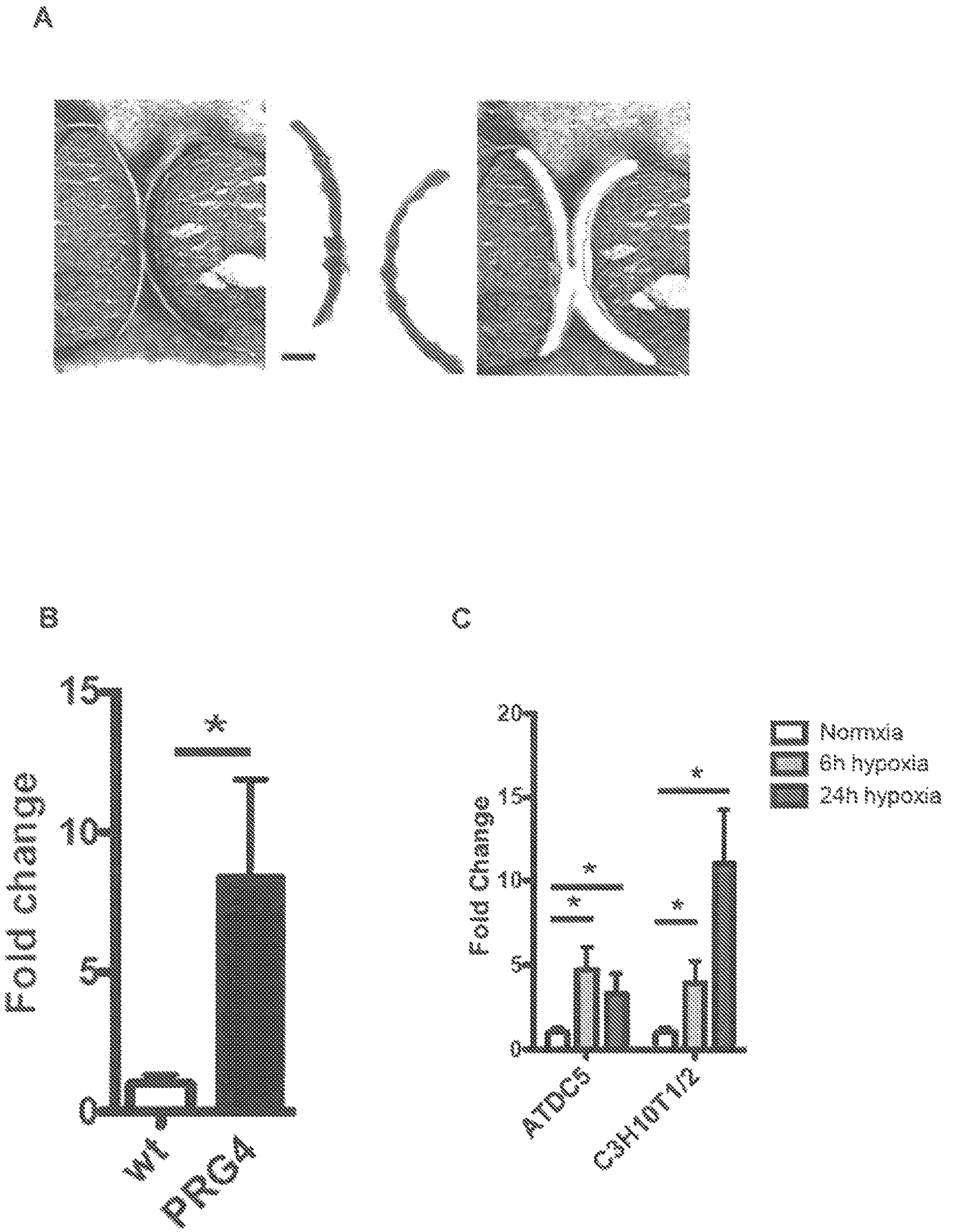

FIG. 7: Gene expression profiling of wild type vs. Prg4 transgenic superficial layer chondrocytes. A, Laser capture micro-dissection of superficial layer chondrocytes. Left to right: tissue before capturing, captured tissue on HS cap, and remaining tissue on the slide. Scale bar, 100 μm. B, Evaluation of Hif3a expression in superficial layer chondrocytes of wild type vs. Prg4 mice (*Py0.05, n=3, t-test). C, Evaluation of PRG4 expression in ATDC5 and C3H10T1/2 cells under normoxic and hypoxic conditions (*P<0.05, n=3, t-test), Error bars indicate s.e.m.

Figure 8:
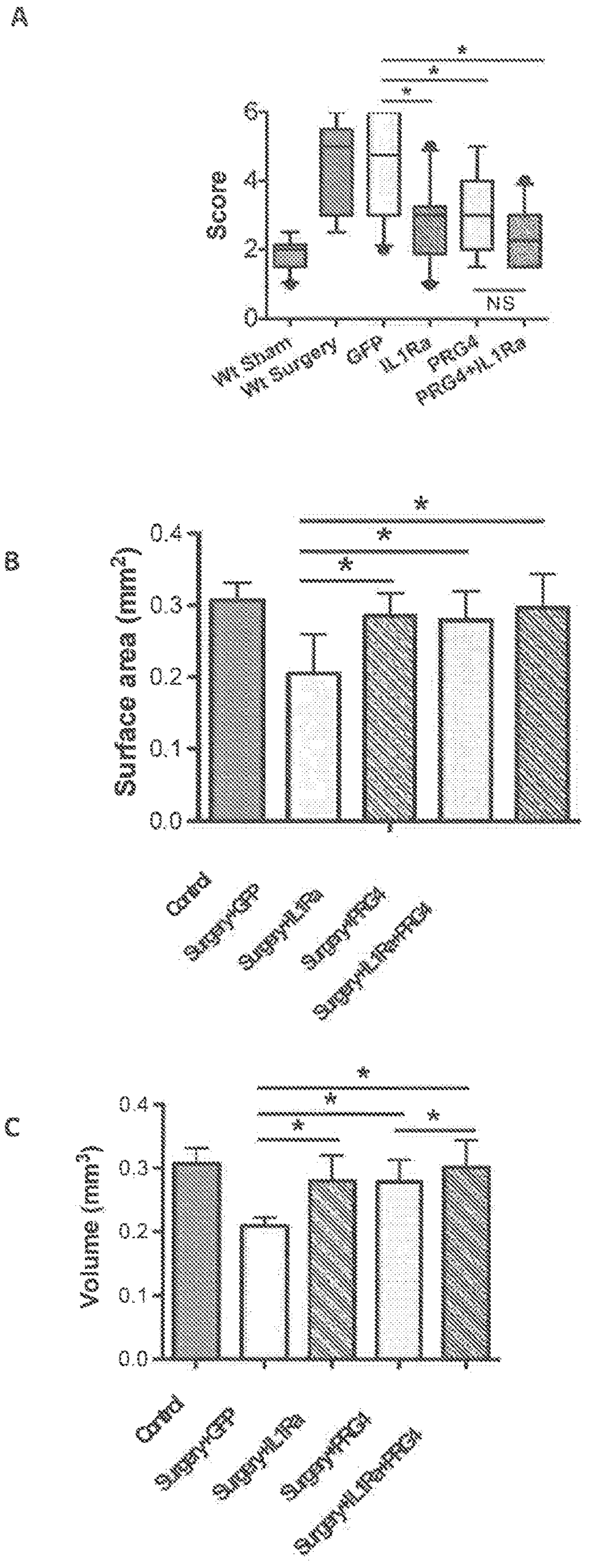

FIG. 8: A, Mice were treated with HDAd-PRG4 (PRG4), HDAd-Il-1Ra (Il1Ra) and combination therapy (PRG4+Il1Ra) according to the scheme shown in FIG. 3 H. All three groups showed significantly lower histological score compared to no treatment and placebo treatment, suggesting therapeutic effects to HDAd-PRG4 and HDM-Il-1Ra. The combination therapy showed a trend of being more effective, (ANOVA, N=8-10, *p<0.05); B, C, Mice were treated with HDAd-PRG4 (PRG4), HDAd-Il1-Ra (Il1Ra) and combination therapy according to the scheme shown in FIG. 3 H. Cartilage surface area (B) and cartilage volume (C) were quantified. All three groups showed significantly higher cartilage volume and surface area compared to no treatment and placebo treatment, suggesting therapeutic effects of HDAd-PRG4 and HDAd-Il1Ra. The knees under combination therapy had more preserved cartilage volume and surface area (ANOVA, N=5, *p<0.05).

DETAILED DESCRIPTION

It is therefore an object of the present invention to provide an improved delivery and expression system that allows for long-term expression of biologically active proteoglycan 4

(PRG4) for use in the prevention and/or treatment of PRG4-dependent disorders such as camptodactyly-arthropathy-coxa vara-pericarditis (CACP) and disorders in which PRG4 overexpression is beneficial such as musculoskeletal disorders in particular joint disorders.

The solution for the problem is provided by a gene therapy delivery and expression system, comprising the technical features as claimed in claim 1. Preferred embodiments of the invention are subject-matter of the dependent claims.

The gene therapy delivery and expression system according to the present invention comprises at least one helper-dependent adenoviral vector containing a nucleic acid sequence encoding for proteoglycan 4 (PRG4), or a biologically active fragment thereof, left and right adenoviral inverted terminal repeats (L ITR and R ITR), adenoviral packaging signal sequences and non-viral, non-coding stuffer nucleic acid sequences.

Any known left or right adenoviral inverted terminal repeats (L ITR and R ITR), adenoviral packaging signal sequences and non-viral, non-coding stuffer nucleic acid sequences can be used for the production of the helper-dependent adenoviral vector (Parks, R. J., Chen, L., Anton, M., Sankar, U., Rudnicki, M. A., and Graham, F. L. (1996). A helper-dependent adenovirus vector system: removal of helper virus by Cre-mediated excision of the viral packaging signal. Proc Natl Acad Sci USA 93, 13565-13570; Palmer, D. and Ng, P. (2003). Improved system for helper-dependent adenoviral vector production. Mol Ther 8, 846-852).

The results and data shown herein are based on helper-dependent adenoviral constructs (HDAd) using in a first embodiment nucleic acid sequences or amino-acid sequences encoding for proteoglycan 4 (PRG4). Any homolog or variant showing a certain degree of sequence homology with either a nucleic acid sequence or an amino-acid sequence of proteoglycan 4 (PRG4) (or their variant such as lubricin, superficial zone protein or megakaryocyte stimulating factor precursor) is further comprised by the present invention. A homolog includes but is not limited to peptides, polypeptides, proteins or nucleic acid sequences from any species that shows homology with any proteoglycan (PRG4) described herein, For long-term expression of PRG4 in the affected tissue, for example in joints or osteoarthritic tissues, the at least one helper-dependent adenoviral vector of the invention is preferably controlled by a ubiquitous, constitutive promoter. Suitable promoters include, but are not limited to elongation factor 1 alpha (EF1 alpha) promoter, cytomegalovirus (CMV) promoter, beta-actin promoter, simian virus 40 (SV40) early promoter, ubiquitin c promoter, glyceraldehyde 3-phosphate dehydrogenase (GAPDH) promoter, phosphoglycerate kinase (PGK) promoter and other HDAd-suitable ubiquitous, constitutive promoters.

In a preferred embodiment, the helper-dependent adenoviral vector comprising proteoglycan 4 (PRG4) comprises a nucleic acid sequence set forth in SEQ ID NO 1 (human HDAd) or SEQ ID NO 2 (murine HDAd). Preferably, the nucleic acid sequence comprises a cDNA sequence of the PRG4 gene or a fragment thereof. Furthermore, any biologically active fragment such as nucleic acid sequences having sequence identity or a certain degree of homology with the human or murine PRG4 sequence disclosed herein is comprised by the present invention. The HDAd of the invention may vary in its non-coding elements as well as in the length of its coding insert. Therefore, also smaller or greater vector sizes of the helper-dependent adenoviral vector of the invention can be utilized for the purpose of the present invention in order to achieve the desired biological effects.

In a preferred embodiment, the helper-dependent adenoviral vector comprises a nucleic acid sequence which has at least 50%, 60%, 70%, 80% or 90% sequence homology with a vector sequence comprising a nucleic acid sequence set forth in SEQ ID NO 1 or SEQ ID NO 2, or a biologically effective fragment thereof.

A sequence homology of at least 50% with a nucleic acid sequence set forth in SEQ ID NO 1 or SEQ ID NO 2 can be sufficient in order to generate long-term expression of PRG4 at the target sites as along as the expressed PRG4 protein is biologically active.

In one embodiment the helper-dependent adenoviral vector comprises a nucleic sequence encoding for proteoglycan 4 (PRG4). The expression of human or mammalian PRG4 is preferred. The inserted nucleic acid sequence into the HDAd can be anyone, which shows sequence identity or sequence homology with a nucleic acid sequence set forth in SEQ ID NO 3 or SEQ ID NO 4. For the purpose of expression, it can be sufficient that only a part of the nucleic acid sequence set forth in SEC ID NO 3 or SEQ ID NO 4, or an extended version is sufficient for the generation of the vector and its biological activity. The biological activity can be measured by investigating chondoprotection.

Furthermore, also mutants, variants and homologs containing nucleic acid replacements within the amino acid or nucleic acid sequence of proteoglycan 4 (PRG4) are comprised by the present invention. In particular, the invention comprises a homolog of PRG4 from any other animal species having sequence homology with a sequence set forth in SEQ ID NO 3 or SEQ ID NO 4. For example, a homolog containing a nucleic acid sequence encoding for proteoglycan 4 (PRG4) preferably comprises a nucleic acid sequence, which has at least 50%, 60%, 70%, 80% or 90% sequence homology with a nucleic acid sequence set forth in SEQ ID NO 3, or SEQ ID NO 4, or a biologically effective fragment thereof.

The proteoglycan 4 (PRG4) used in the construction of the vector of the present invention can be also described by its amino acid sequence. Preferably, the proteoglycan 4 (PRG4) comprises an amino acid sequence set forth in SEQ ID NO 5 or SEQ ID NO 6, or a biologically active fragment thereof, or a homolog thereof from any other species. In a preferred embodiment, the amino acid sequence encoding for proteoglycan 4 (PRG4) comprises an amino acid sequence which has at least 50%, 60%, 70%, 80% or 90% sequence homology with an amino acid sequence set forth in SEQ ID NO 5, or SEQ ID NO 6, or a biologically active fragment thereof, or a homolog thereof from any other species.

The inventors show herein that a helper-dependent adenoviral vector containing the cDNA sequence of murine or human proteoglycan 4 (PRG4) under the control of a ubiquitous, constitutive promoter results in an overexpression of PRG4 in joints, which results in protection of mice from osteoarthritis. Since overexpression of PRG4 can be beneficial in many other diseases, the helper-dependent vector of the invention can be used for the manufacture of a medicament for the treatment and/or prevention of a variety musculoskeletal diseases and PRG4-dependent diseases. In particular, musculoskeletal disorders, which benefit from PRG4 over-expression would be characterised as those disorders where high concentrations of PRG4 confer a therapeutic or preventive effect. PRG4-dependent diseases or disorders would be characterised in that natural PRG4 expression is limited or inhibited, or in that intracellular or extracellular PRG4 RNA or protein levels are significantly reduced.

The inventors compared joint transduction efficiency of helper-dependent adenoviral vectors with different AAV serotype that had been reported by others to be useful in joint gene therapy approaches. Surprisingly, the inventors found that helper-dependent adenoviral vectors showed superior transduction compared with all tested AAV serotypes resulting in transduction of synoviocytes and chondrocytes. The inventors further showed that helper-dependent adenoviral vectors allow for transgene expression that persists for an extended period, whereby the need for repeated administrations of the medicament to an object suffering from a disease in which overexpression of PRG4 may be beneficial will be greatly reduced. In a model of osteoarthritis in mice, the inventors demonstrated that treatment of osteoarthritic joints with the HDAd-PRG4 results in lower osteoarthritis histology scores, indicating that PRG4 exhibits its biological effect by protecting the subject from post-traumatic osteoarthritis. Protection against osteoarthritis with HDAd-PRG4 was demonstrated using two different schemes. In the first scheme mice were injected with HDAd-PRG4 before osteoarthritis was induced. The results of this experiment show that HDAd-PRG4 can be used in the prevention of osteoarthritis. In the second scheme, osteoarthritis was induced before HDAd-PRG4 was injected. The results of this experiment demonstrate that HDAd-PRG4 can be used in the treatment of (pre-existing) osteoarthritis. In support of the biological effects of PRG4 in joints, experiments using Prg4-transgenic mice revealed a protection of the subjects against the development of osteoarthritis without other bone phenotypes.

Thus, overexpression of PRG4 under the control of a suitable ubiquitous, constitutive promoter in a HDAd allows for prevention and/or treatment of a variety of musculoskeletal diseases such as arthropathies, all types of arthritis, including arthritis-related disorders, osteoarthritis, rheumatoid arthritis, gout and pseudo-gout, septic arthritis, psoriatic arthritis, ankylosing spondylitis, juvenile idiopathic arthritis. Still's disease, Reiter's syndrome, or tendinopathies including tendonitis, tendinosis, tenosynovitis; synovial disorders including synovitis; Bursa disorders including bursitis; equine musculoskeletal disorders including bone spavin, navicular syndrome, osselet.

Surprisingly, the inventors further found that a combined expression of PRG4 as induced by HDAd-PRG4 and inhibitors of inflammatory and cartilage destructive mediators results in beneficial therapeutic and protective effects. In particular, a combination of expressing of PRG4 and expressing interleukin-1 receptor antagonist (Il-1Ra) resulted in an increased efficiency in the treatment and/or prevention of musculoskeletal disorders.

In a preferred embodiment, the helper-dependent adenoviral vector therefore comprises a nucleic acid sequence encoding for inhibitors of inflammatory and cartilage destructive mediators such as cytokines including Il-1, TNFa, Il-6, Il-7 Il-8, Il-11, Il-15, Il-17, Il-18, Il-21, leukemia inhibitory factor (LIF), oncostatin M; matrix metalloproteases including MMP-1,3,9,13; aggrecanases including ADAMTS-1,4,5; toll-like receptors (TLR) such as TLR2, TLR4; and nuclear factor 'kappa-light-chain-enhancer' of activated B-cells (NF-κB).

In a preferred embodiment, the inhibitor of inflammatory and cartilage destructive mediator is interleukin-1 receptor antagonist (Il-1Ra). A combination of overexpression of PRG4 and Il-1Ra is beneficial for the treatment and/or prevention of the diseases mentioned therein. In a first embodiment, the cDNA sequence of interleukin-1 receptor antagonist can be contained in the same helper-dependent adenoviral vector, which contains the cDNA sequence encoding for proteoglycan 4 (PRG4). In a further embodiment, the cDNA sequence of interleukin-1 receptor antagonist can be contained in a second helper-dependent adenoviral vector, which only contains the cDNA sequence encoding for Il-1Ra.

The delivery and expression system of the invention can therefore comprise a second or further helper-dependent adenoviral vector comprising a nucleic acid sequence encoding for inhibitors of inflammatory and cartilage destructive mediators such as interleukin-1 receptor antagonist (Il-1Ra).

In a preferred embodiment, the cDNA of the inhibitor of inflammatory and cartilage destructive mediator (e.g. Il1-Ra cDNA) inserted into HDAd is controlled by an inflammation-inducible promoter. Preferred promoters include, but are not limited to promoters selected from the group consisting of NF-κB promoter, interleukin 6 (Il-6) promoter, interleukin-1 (Il-1) promoter, tumor necrosis factor (TNF) promoter, cyclooxygenase 2 (COX-2) promoter, complement factor 3 (C3) promoter, serum amyloid A3 (SAA3) promoter, macrophage inflammatory protein-1α (MIP-1α) promoter, or hybrid constructs of the above. The use of NF-κB promoter in HDAd for the purpose of an inflammation-dependent expression of Il-1Ra at the target sites is preferred.

In a preferred embodiment, the helper-dependent adenoviral vector containing the interleukin-1 receptor antagonist (Il-1Ra) comprises a nucleic acid sequence which has at least 50%, 60%, 70%, 80% or 90% sequence homology with a nucleic acid sequence set forth in SEQ ID NO 7 (human Il-1Ra), or SEQ ID NO 8 (murine Il-1Ra), SEQ ID NO 9 (equine Il-1Ra), or a biologically effective fragment thereof.

In a further embodiment, the nucleic acid sequence encoding for interleukin-1 receptor antagonist (Il-1Ra) comprises a nucleic acid sequence set forth in SEQ ID NO 10 (human Il-1Ra), or SEQ ID NO 11 (murine Il-1Ra), or SEQ ID NO 12 (equine Il-1Ra), or a biologically active fragment thereof, or a homolog thereof from any other species.

In a preferred embodiment, the amino acid sequence encoding for interleukin-1 receptor antagonist (Il-1Ra) comprises an amino acid sequence set forth in SEQ ID NO 13 (human Il-1Ra), or SEQ ID NO 14 (murine Il-1Ra), or SEQ ID NO 15 (equine Il-1Ra), or a biologically active fragment thereof, or a homolog thereof from any other species.

The present invention also relates to a pharmaceutical composition, comprising a therapeutically effective amount of at least one helper-dependent adenoviral vector containing a nucleic acid sequence encoding for proteoglycan 4 (PRG4), or a biologically active fragment thereof. Preferred embodiments of the pharmaceutical composition comprise helper-dependent adenoviral vectors or a combination of different helper-dependent adenoviral vectors comprising features as described above in more detail.

The gene therapy delivery and expression system according to the present invention is suitable for the preparation of a medicament for the use in the prevention and/or treatment of a variety of PRG4-dependent diseases. In a first embodiment the gene therapy delivery and expression system is used in the treatment and/or prevention of camptodactyly-arthropathy-coxa vara-pericarditis (CACP). The helper-dependent adenoviral vectors of the invention can further be used in the prevention and/or treatment of a musculoskeletal disorder, in particular the prevention and/or treatment of a joint disorder or disease. Examples of such diseases are arthropathies, all types of arthritis, including arthritis-related disorders, osteoarthritis, rheumatoid arthritis, gout and pseudo-gout, septic arthritis, psoriatic arthritis, ankylosing spondylitis, juvenile idiopathic arthritis, Still's disease, Reiter's syndrome, or tendinopathies including tendonitis, tendinosis, tenosynovitis; synovial disorders including synovitis; Bursa disorders including bursitis; equine musculoskeletal disorders including bone spavin, navicular syndrome, osselet.

The following examples show the beneficial therapeutic uses of the gene therapy delivery and expression system according to the present invention. In particular, it will be shown that intra-articular expression of proteoglycan 4 (PRG4) in mice protects against development of osteoarthritis (OA). The data are supported by long-term PRG4 expression under the type II collagen promoter (Col2a1) in transgenic mice. Accordingly long-term expression of PRG4 does not adversely affect skeletal development but protects from developing signs of age-related osteoarthritis.

The protective effect is also shown in a model of post-traumatic osteoarthritis created by cruciate ligament transection (CLT). Moreover, intra-articular injection of helper-dependent adenoviral virus (HDAd) expressing PRG4 protected against the development of post-traumatic osteoarthritis when administered either before or after injury. Gene expression profiling of mouse articular cartilage and in vitro cell studies show that PRG4 expression inhibits the transcriptional programs that promote cartilage catabolism and hypertrophy through the up-regulation of hypoxia inducible factor 3 alpha. Analyses of available human osteoarthritis datasets are consistent with the predictions of this model. Hence, the data provide insight into the mechanisms for osteoarthritis development and offer a potential chondroprotective approach to its treatment.

Moreover, injection of helper-dependent adenoviral vectors expressing PRG4 (HDAd-PRG4) and Il-1Ra (HDAd-Il1-Ra) in combination into joints of wild type mice after transection of cruciate ligaments exhibited protective effects against osteoarthritis. Co-injection of HDAd-PRG4 and HDAd-Il1-Ra at the same dose results in a greater extent of cartilage preservation compared to single vector injections.

As such PRG4 in single application or in combination with Il-1Ra is a novel target in chondoprotection using the helper-dependent adenoviral vectors of the invention.

Examples

Results

PRG4 Prevents Development of Age Related Osteoarthritis Changes

To investigate the long-term effect of Prg4 over-expression, the inventors generated transgenic mice expressing Prg4 under the cartilage specific type II collagen promoter (Col2a1) (FIG. 5A). PRG4 transgenic mice expressed Prg4 ectopically in growth plate cartilage and over-express Prg4 in articular cartilage throughout development and adulthood (FIG. 5B-D). Macroscopically, the inventors detected no differences in growth or skeletal development in Prg4 transgenic mice when assessed by weight (FIG. 5E). Microscopically, markers of chondrocyte proliferation or apoptosis remained the same in Prg4 mice vs. wild type mice as assessed by BrdU staining (p=n.s. in both proliferating and resting zone of P1 chondrocytes) (FIG. 5F) and TUNEL staining (no positive signals in P1 chondrocytes) (FIG. 5G), respectively. These data suggested that ectopic over-expression of Prg4 in cartilage did not significantly affect chondrocyte or skeletal homeostasis.

Figure 1:
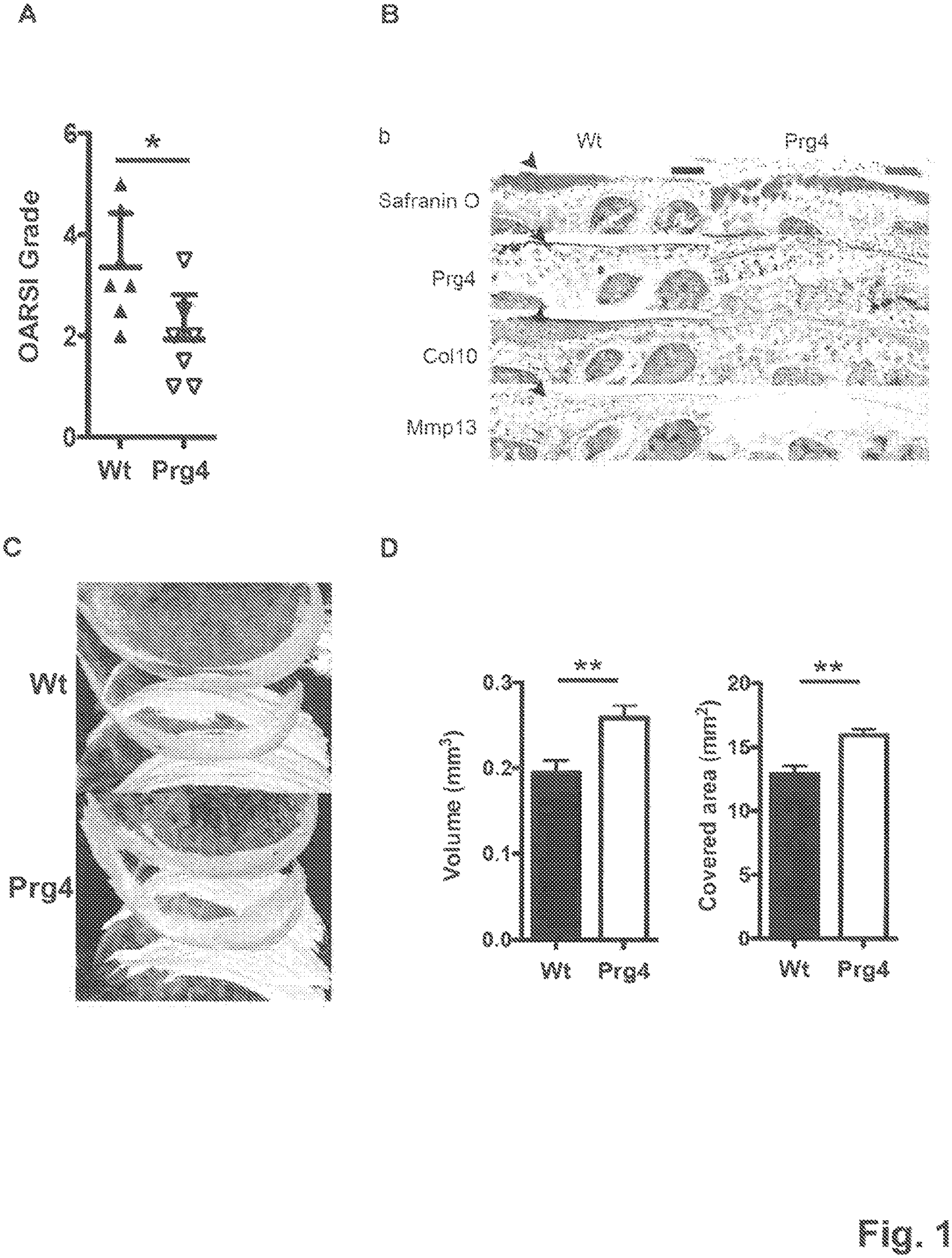
FIG. 1. Prg4 transgenic mice are protected from development of age-related osteoarthritis. A, Comparison of 10 month-old wild type mice and Prg4 transgenic mice knee joints by OARSI grade (*P<0.05, n=7. Wilcox rank test). B, Safranin O staining and immunohistochemistry (antibody used to the left) of 10 month-old wild type (Wt) and Prg4 transgenic mice. Black arrows indicate osteoarthritis changes in proximal tibial articular cartilage in sagittal section, Scale bar, 100 pm μm. C, Representative image of the reconstruction of articular cartilage in 10-month-old wild type and Prg4 transgenic mouse with femoral cartilage shown in blue and tibial cartilage shown in yellow. Red arrow indicates loss of cartilage. Scale bar, 500 μm. D, Quantification of articular cartilage volume and surface area of bone covered by cartilage in mouse knee joints by phase contrast μCT. (*P<0.01, n=5, t-test). Error bars indicate s.e.m.

The inventors sought to determine whether Prg4 over-expression in particular chondrocytes protected mice from age-related osteoarthritic changes. Relatively few studies have been performed to assess the development of age-related osteoarthritis in animal models (M. Silbermann, E. Livne, Age-related degenerative changes in the mouse mandibular joint. *Journal of Anatomy* 129, 507 (October, 1979). Moreover, no gain of function model has been shown to be protective against age-related osteoarthritis. In an aging cohort, as assessed by the Osteoarthritis Research Society International (OARSI) histological grading scale (S. S. Glasson, M. G. Chambers, W. B. van den Berg, C. B. Little, The OARSI histopathology initiative—recommendations for histological assessments of osteoarthritis in the mouse. *Osteoarthritis and cartilage/OARSI, Osteoarthritis Research Society* 18, S17 (Oct. 1, 2010), the inventors observed that wild type FVB/N mice developed changes consistent with moderate osteoarthritis by 10 months of age, with a mean OARSI grade of 3.5. However, PRG4 transgenic mice at the same age exhibited a mean OARSI grade of 2 ($p<0.05$), suggesting less severe signs of osteoarthritis (FIG. 1A). The inventors next assessed the molecular differences in particular chondrocytes between the PRG4 and wild type mice. As Collagen type X (Col10a1) and matrix metalloproteinase 13 (Mmp13) are markers of cartilage hypertrophy and degradation, respectively, increased expression of Mmp13 and Col10a1 above the tide marks are hallmarks of osteoarthritis (T. Saito et al., Transcriptional regulation of endochondral ossification by HIF-2α during skeletal growth and osteoarthritis development. *Nature Medicine* 16, 678 (Jun. 23, 2010)). Encouragingly, the inventors detected increased expression of Col10a1 and Mmp13 in wild type mice with aging, while Prg4 transgenic mice did not show a qualitative increase in either marker in the noncalcified region of articular cartilage (FIG. 1b). These results suggest that Prg4 overexpression had a protective effect against osteoarthritis at the molecular and histological levels.

A disadvantage of conventional histological endpoints is the lack of three-dimensional quantification as well as ascertainment bias based on choice of sections. Hence, the inventors applied an approach to quantify cartilage properties (e.g., volume, surface area, bone area covered by cartilage) based on three-dimensional reconstructions of phase contrast µCT imaging data (M. Ruan et al., Quantitative imaging of murine osteoarthritic cartilage by phase contrast micro-computed tomography. *Arthritis Rheum*, (2012)). Using this imaging technique, the inventors found that wild type mice showed a decrease in articular cartilage volume as well as in the bone area covered by cartilage (FIG. 1C,D). In contrast, Prg4 transgenic mice showed preservation of articular cartilage volumes and surface area ($p<0.01$) (FIG. 1C,D). Thus, as compared to wild type mice after transection, Prg4 transgenic mice had none of the histological, molecular and imaging findings characteristic of osteoarthritis. These data suggested that PRG4 over-expression may have protective effects in the context of age-related osteoarthritic-like changes.

PRG4 Prevents Development of Post-Traumatic Osteoarthritis

To test whether PRG4 over-expression protects mice from the development of more aggressive, post-traumatic osteoarthritis, the inventors applied the knee cruciate ligament transection model recently developed in the inventors' lab, to both wild type and Prg4 transgenic mice (M. Ruan et al., Quantitative imaging of murine osteoarthritic cartilage by phase contrast micro-computed tomography. *Arthritis*

Figure 2:
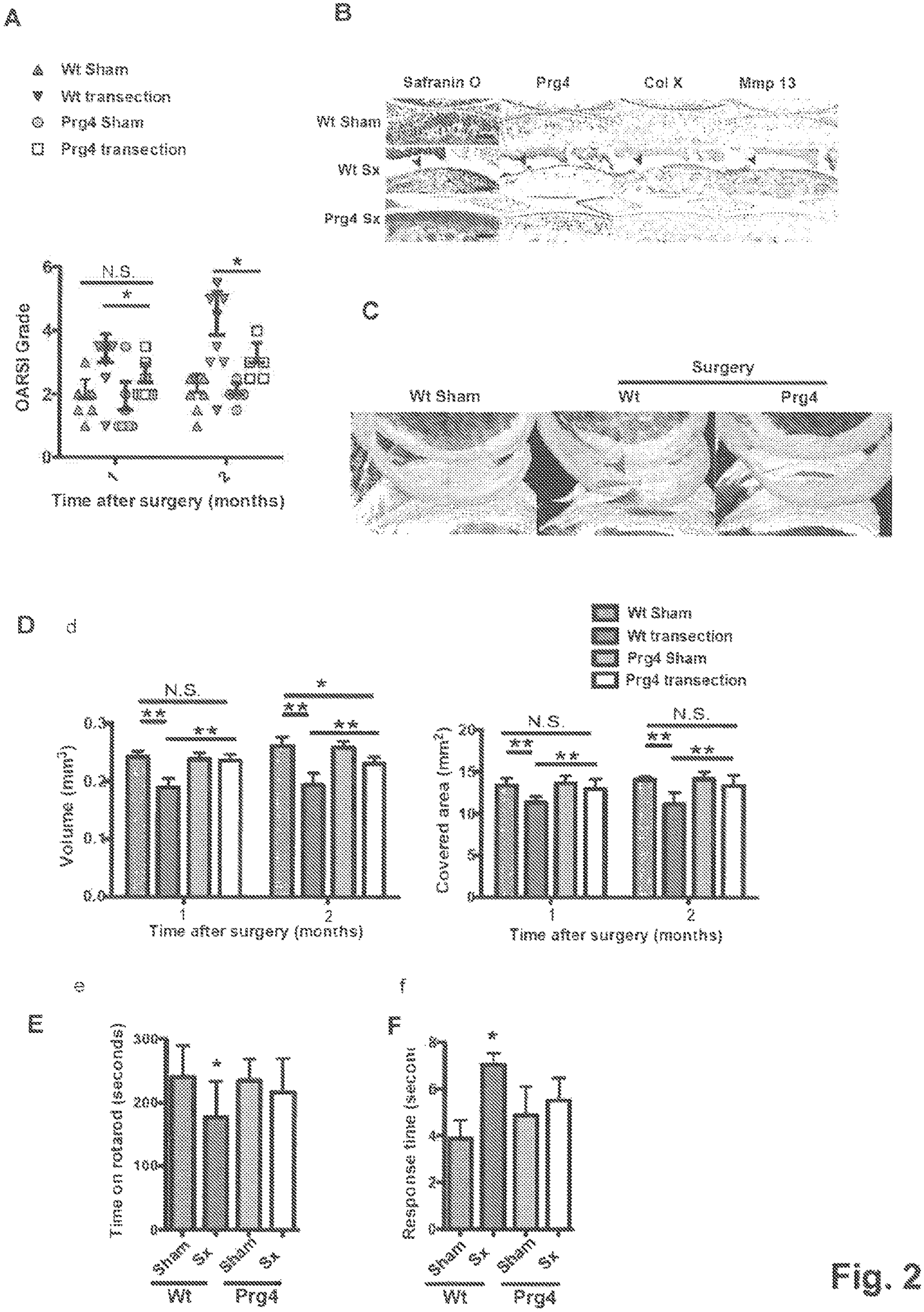
FIG. 2. Prg4 transgenic mice are protected from the development of post-traumatic osteoarthritis, A, Comparison of Prg4 transgenic mice and wild type mice knee joints by OARSI grade (*P<0.05, n=8, ANOVA). B, Safranin O staining and immunohistochemistry (antibody used listed above each column) of wild type sham (Wt Sham), wild type with transection (Wt Sx) and Prg4 transgenic mice with transection (Prg4 Sx). Black arrows indicate areas with osteoarthritis changes in saggital sections through the knee. Scale bar, 100 μm. C, Representative images of reconstruction of knee joints with phase contrast μCT with femoral cartilage shown in blue and tibial cartilage shown in yellow.

Rheum, (2012). The inventors chose this approach because anterior cruciate ligament tears are a common cause of post-traumatic arthritis in humans. As assessed by the OARSI histological grading scale, wild type mice developed moderate and severe osteoarthritis one and two months after transection, respectively (FIG. 2A) (M. Ruan et al., Quantitative imaging of murine osteoarthritic cartilage by phase contrast micro-computed tomography. *Arthritis Rheum*, (2012). Prg4 transgenic mice showed a lower grade OARSI score compared to wild type mice one and two months after transection (FIG. 2A), Interestingly, one month after transection, the OARSI grade of cartilage from Prg4 transgenic mice was not significantly different from wild type mice after sham surgery (FIG. 2A), further supporting that PRG4 expression had a protective effect against osteoarthritis. In addition, the inventors detected increased expression of Col10a1 and Mmp13 in the noncalcified articular cartilage of wild type transected mice, but not in transected Prg4 transgenic mice or wild type mice after sham surgery (FIG. 2B).

The inventors next assessed the cartilage volume and bone area covered by cartilage after surgical transection using phase-contrast microCT (M. Ruan et al., Quantitative imaging of murine osteoarthritic cartilage by phase contrast micro-computed tomography. *Arthritis Rheum*, (2012)). After transection, wild type mice showed decrease in both cartilage volume and bone area covered by cartilage ($p<0.01$). In contrast, Prg4 transgenic mice showed articular cartilage volumes and areas similar to wild type mice after sham surgery (FIG. 2C,D). Thus, as compared to wild type mice after transection, Prg4 transgenic mice had none of the histological, molecular or imaging findings characteristic of osteoarthritis.

Pain and motor dysfunction are also hallmarks of osteoarthritis and are typical causes of chronic disability (M. B. Goldling, S. R. Goldring, Osteoarthritis. *Journal of Cellular Physiology* 213, 626 (2007)), They also serve as important clinical end points for interventional trials. Therefore, the inventors applied rodent behavioral testing, i.e., rotarod and hotplate analyses, to evaluate for potential motor and/or sensory dysfunction in wild type vs. Prg4 transgenic mice after osteoarthritis induction. Surgically transected wild type mice showed a decreased time on the rotarod ($p<0.05$) and increased time on the hotplate ($p<0.05$), while Prg4 transgenic mice with and without transection were indistinguishable from wild type mice after sham surgery (p=n.s.) (FIG. 2E,F). This suggested that Prg4 transgenic mice after transection had less motor or sensory impairments as compared to wild type mice, supporting that PRG4 prevented functional impairment in post-traumatic osteoarthritis.

Gene Transfer with HDAd-PRG4 Effectively Treats Osteoarthritis

To translate localized expression of PRG4 into a therapeutic approach, the inventors tested whether gene transfer into the joint could mediate long-term expression and chondroprotection in osteoarthritis. Since delivery of recombinant protein is often therapeutically limited by their short half-life, the inventors chose to use a viral gene transfer approach. The most studied viral vectors for gene transfer related to osteoarthritis treatment are adeno-associated virus (AAV) and adenovirus. Both have been shown to transduce chondrocytes in vitro in primary chondrocyte and cartilage organ cultures and in vivo in rabbit and rat knee joints (J. D. Kay et al., Intra-articular gene delivery and expression of interleukin-1Ra mediated by self-complementary adeno-associated virus. *The journal of gene medicine* 11, 605 (July, 2009); Y. Arai et al., Gene delivery to human chondrocytes by an adeno associated virus vector. *journal of Rheumatol* 27, 979 (April, 2000); J. Gouze, Adenovirus-mediated gene transfer of glutamine: fructose-6-phosphate amidotransferase antagonizes the effects of interleukin-1β on rat chondrocytes. *Osteoarthritis and Cartilage* 12, 217 (April, 2004)). However, no direct comparison has been made between the two viruses. After injection of GFP expressing helper-dependent adenovirus and AAVs of the serotypes 2; 2.5 and 6 into mouse knee joints ($10^9$ viral particles per joint in 5 ul), helper-dependent adenovirus was noted to exhibit higher transduction efficiency at 2 weeks post-injection (FIG. 3A).

While first generation adenovirus vectors (FGV) can mediate highly efficient tissue transduction, the immune response to viral proteins limits transgene expression. Previous studies performed by the inventors and others showed that helper-dependent adenoviral vectors (HDAd) devoid of viral coding genes could overcome this problem (D. J. Palmer, D. J. P. D. P. Ng, Helper-dependent adenoviral vectors for gene therapy. *Human gene therapy* 16, 1 (2005)). For example, a single injection of HDAd can mediate long-term transgene expression in small and large animal models for over 7 years in liver (N. Brunetti-Pierri, P. Ng, Helper-dependent adenoviral vectors for liver-directed gene therapy. *Hum Mol Genet* 20, R7 (Jun. 13, 2011)). Thus, the inventors tested whether HDAd could mediate long-term expression of luciferase in mouse joint compared to FGVs. Indeed, the inventors found that after a single infra-articular injection, HDAds mediated expression of luciferase in mouse knee joints for over one year, while FGV-mediated luciferase expression was lost by one month (FIG. 3B). To evaluate the dose response and cellular distribution of transduction, the inventors assessed mouse knee joints injected with $10^9$ vs. $10^8$ viral particles HDAd expressing beta-galactosidase. These doses were at least 10 and 100 times lower than the maximum tolerated systemic dose in humans (K. Relph, K. Harrington, H. Pandha, Recent developments and current status of gene therapy using viral vectors in the United Kingdom. *BMJ* (*Clinical research ed.*) 329, 839 (Oct. 9, 2004)).

At the higher dose, HDAd transduced superficial layer chondrocytes and synoviocytes, while only synoviocytes were transduced at the lower dose (FIG. 3C). Thus, the inventors showed that HDAd was able to efficiently transduce synoviocytes and chondrocytes with maintaining transgene expression for at least one year.

To compare the effects of PRG4 expression from superficial layer chondrocytes vs. synoviocytes, the inventors treated mice at both doses with HDAd expressing PRG4 (FIGS. 6A-C) 48 hours prior to surgical cruciate ligament transection. The inventors found that both low dose (mediating expression only in synoviocytes) and high dose (mediating expression in both synoviocytes and superficial zone chondrocytes) treatment with HDAd-PRG4 vector protected joints from osteoarthritis development (FIG. 3D-G). Since the clinical application of PRG4 for osteoarthritis would likely be administrated after an injury, the inventors next tested the efficacy of HDAd-PRG4 injection two weeks after osteoarthritis induction. In this context, injection of the lower dose of HDAd-PRG4 was sufficient to preserve cartilage volumes and prevent cartilage degradation as assessed by μCT, while higher dose injection showed protective effects both by histological OARSI grading and μCT assessment. Importantly, these data suggested that ectopic expression from synoviocytes was sufficient to achieve a certain degree of chondroprotection by acting in a non-cell-autonomous fashion (FIG. 3H-K).

PRG4 Inhibits Transcriptional Programs of Chondrocyte Hypertrophy and Hypoxic Inducible Factors in Cartilage The potential mechanisms of the protective effects of PRG4 have only been partially deciphered. While previous studies have shown that PRG4 relieves mechanical stress in joints by changing synovial fluid dynamics and providing boundary lubrication (G. D. Jay, J. R, Torres, M. L. Warman, M. C. Laderer, K. S. Breuer, The role of lubricin in the mechanical behavior of synovial fluid. *Proc Natl Acad Sci USA* 104, 6194 (Apr. 10, 2007)), the inventors investigated whether PRG4 could directly affect cartilage metabolism and homeostasis. To assess the molecular effects of PRG4 on chondrocytes, the inventors performed transcriptional profiling on superficial layer chondrocytes obtained by laser capture in newborn wild type vs. Prg4 transgenic mice (FIG. 4A and FIG. 7A). Genes that were either up-regulated or repressed by greater than 1.5 fold (Dataset 1) were analyzed by Ingenuity Pathway Analysis to identify transcriptional programs that would be affected by Prg4 expression (Dataset 2). Interestingly, transcription factors that mediate chondrocyte hypertrophy and terminal differentiation (e.g. Mef2c, Runx2 and Atf4) showed decreased activity with PRG4 over-expression (K. S. Lee et al., Runx2 Is a Common Target of Transforming Growth Factor beta 1 and Bone Morphogenetic Protein 2, and Cooperation between Runx2 and Smad5 Induces Osteoblast-Specific Gene Expression in the Pluripotent Mesenchymal Precursor Cell Line C2C12. *Molecular and cellular biology* 20, 8783 (Dec. 1, 2000); X. Yang et al., ATF4 is a substrate of RSK2 and an essential regulator of osteoblast biology; implication for Coffin-Lowry Syndrome. *Cell* 117, 387 (May 30, 2004); M. A. Arnold et al., MEF2C Transcription Factor Controls Chondrocyte Hypertrophy and Bone Development. *Developmental Cell* 12, 377 (April, 2007)). In addition, the inventors also noted down-regulation of Smad7, an inhibitor of the TGF-beta signaling pathway (A. Nakao et al., Identification of Smad7, a TGFbeta-inducible antagonist of TGF-beta signalling. *Nature* 389, 631 (Oct. 9, 1997)). TGFbeta signaling negatively regulates terminal differentiation of chondrocytes, and hence. PRG4 again would suppress hypertrophy by its actions on Smad7 (X. Yang et al., TGF-beta/Smad3 signals repress chondrocyte hypertrophic differentiation and are required for maintaining articular cartilage. *The Journal of cell biology* 153, 35 (May 2, 2001)). Finally, Hypoxia inducible factor 1 alpha unit (Hif1alpha), an essential transcription factor induced in response to hypoxia, was also predicted to have lower activity (FIG. 4B), while Hif3alpha a post-translational negative regulator of Hif1alpha and Hif2alpha was up-regulated (Y. Makino et al., Inhibitory PAS domain protein is a negative regulator of hypoxia-inducible gene expression. *Nature* 414, 550 (Nov. 29, 2001)). (FIG. 4A and FIG. 7B).

The inventors hypothesized that PRG4 could up-regulate Hif3alpha under hypoxic conditions to inhibit cartilage turnover. This effect would be mediated by down-regulating the Hif1alpha and Hif2alpha transcriptional activities. To test our hypothesis, the inventors measured Hif3alpha expression and downstream Hif target genes relevant to osteoarthritis progression under hypoxic conditions in C3H10T1/2 (mesenchymal stromal) cells. After injection of HDAd-PRG4, Hif3alpha was transcriptionally up-regulated while Vegf, Col101a1 and Mmp13, all markers of hypertrophy, were all down-regulated compared to empty vector (FIG. 4C) (T. Saito et al., Transcriptional regulation of endochondral ossification by HIF-2α during skeletal growth and osteoarthritis development. *Nature Medicine* 16, 678 (Jun. 23, 2010)). Next, the inventors assessed whether knock down of Hif3alpha suppressed the effects caused by over-expression of PRG4. Since the expression of Hif3alpha is low in C3H10T1/2 cells, the inventors tested its expression in alternative chondrogenic lines. Interestingly, compared to under normoxic conditions, all cell lines tested showed increased PRG4 expression under hypoxic conditions (FIG. 4D and FIG. 7C). Consistent with this, Genomatix analysis identified a hypoxia response element in the promoter region of PRG4. The inventors found that Hif3alpha was highly expressed in TC71 Ewing sarcoma cells and further increased with up-regulation of PRG4 under hypoxic conditions (FIG. 4D). As predicted by our previous transcriptomic analysis, knockdown of Hif3alpha in TC71 cells led to down regulation of Hif1alpha and Hif2alpha target genes in the face of PRG4 up regulation (FIG. 4E). Our findings suggested that the secreted protein PRG4 could modify the balance of anabolic and catabolic programs in the context of osteoarthritis pathogenesis.

To investigate whether the signalling pathway discovered in mouse is conserved in humans, the inventors performed in silico analysis on gene expression profiling performed in human osteoarthritis patient samples available from the GEO database (S, Koelling et al., Migratory Chondrogenic Progenitor Cells from Repair Tissue during the Later Stages of Human Osteoarthritis, Stem Cell 4, 324 (May 3, 2009); T, Dehne, C. Karlsson, J. Ringe, M. Sittinger, A. Lindahl, Chondrogenic differentiation potential of osteoarthritic chondrocytes and their possible use in matrix-associated autologous chondrocyte transplantation. Arthritis research & therapy 11, R133 (2009)). The inventors discovered PRG4 and the proposed downstream effector, HIF3alpha, are upregulated in chondrocyte progenitor cells in OA patients by 2.6 fold (p<0.05) and 1.5 fold (p<0.01) respectively. In an independent array set comparing 3 dimensional cultured chondrocytes from osteoarthritis and healthy donors, the inventors observed a similar trend: PRG4 was upregulated by 1.4 fold (p<0.05) and HIF3alpha upregulated by 1.3 fold (p<0.05). In the context of osteoarthritis development, PRG4 and H1F3alpha may both be upregulated as a repair response. In contrast to the sustained over expression of PRG4 in our therapeutic models, this normal response in humans may be insufficient to prevent disease progression.

These data together showed that under the hypoxic conditions of cartilage, PRG4 over-expression may prevent osteoarthritis progression not only by exerting biomechanical effects on the synovial fluid and cartilage interface, but also by regulating the transcriptional networks that specify chondrocyte hypertrophy and catabolism. Cartilage turnover mediated by Hif1alpha and Hif2alpha was inhibited by up-regulation of Hif3alpha. As cartilage degradation and hypertrophy are two hallmarks of osteoarthritis progression, it is not surprising that PRG4 has chondroprotective effects both in age-related and post-injury osteoarthritis (FIG. 4F).

Osteoarthritis Gene Therapy can be Enhanced by Combined Gene Transfer of PRG4 and Il-1Ra The inventors sought to evaluate whether the beneficial effect of over-expressing PRG4 in osteoarthritis joints can be further improved by combining it with gene therapy mediated expression of Il-1Ra. Il-1Ra blocks the effects of Il-1beta, which is one of the key drivers of inflammation and cartilage catabolism in osteoarthritis. Based on the different pathways that PRG4 and Il-1Ra exert their effects on, a combination of both might result in optimized inhibition of both cartilage breakdown and inflammation.

Mice had osteoarthritis induced and were injected with gene therapy vectors two weeks later. HDAd-PRG4. HDAd- Il-1Ra and the combination of both resulted in significantly lower osteoarthritis histology scores compared to the control vector HDAd-GFP and the no treatment group (FIG. 8A). Cartilage surface area was significantly higher in the HDAd-PRG4, HDAd-Il-1Ra and combination group compared with HDAd-GFP (FIG. 8B). Furthermore, cartilage volume was significantly higher in the HDAd-PRG4, HDAd-Il-1Ra and combination group compared with HDAd-GFP (FIG. 8C). The combination of HDAd-PRG and HDAd-Il-1Ra resulted in significantly higher cartilage volume compared with single vector treatment. The combination therapy resulted also in lower average osteoarthritis score and higher average cartilage surface area; however, the difference in these parameters did not reach statistical significance although a trend to significance was present.

Discussion

The invention shows by using both transgenic mice expressing Proteoglycan 4 (PRG4), and intra-articular, helper-dependent adenoviral virus (HDAd) gene transfer that PRG4 is protective against the development of both post-traumatic and age-related osteoarthritis, without significant adverse effects on cartilage development. Gene therapy treatment with HDAd-PRG4 was effective when injected before and after onset of osteoarthritis suggesting that the treatment is both preventive and therapeutic. The beneficial effect can be further improved by combining PRG4 with anti-inflammatory Il-1Ra gene therapy. The protective effects are demonstrated at molecular, histological and functional levels. The inventors further show that PRG4 over-expression inhibits transcriptional programs that promote cartilage catabolism and hypertrophy in part through the up-regulation of Hif3alpha. The concordant changes of PRG4 and HIF3alpha expression is also observed in gene expression profiling in human osteoarthritic patient samples.

Most genetics models reported to date show protection from osteoarthritis using histological endpoints at one month after surgical destabilization of the medical meniscus (DMM) to induce a mild, single condylar post-traumatic osteoarthritis, In addition, studies on osteoarthritis have been largely focused on loss of function mutations of genes in bone development such as Adamts5, Mmp13, Hif2alpha and Syndecan4 (F. Echtermeyer et al., Syndecan-4 regulates ADAMTS-5 activation and cartilage breakdown in osteoarthritis. *Nature Medicine,* 1 (Mar. 30, 2102); T. Saito et al., Transcriptional regulation of endochondral ossification by HIF-2α during skeletal growth and osteoarthritis development. *Nature Medicine* 16, 678 (Jun. 23, 2010); S, S. Glasson et al., Deletion of active ADAMTS5 prevents cartilage degradation in a murine model of osteoarthritis. *Nature* 434, 644 (Apr. 31, 2005); C. B. Little et al., Matrix metalloproteinase 13-deficient mice are resistant to osteoarthritic cartilage erosion but not chondrocyte hypertrophy or osteophyte development. *Arthritis & Rheumatism* 60, 3723 (December, 2009)). In contrast to these studies, the inventors report the gain of function genetic model with a secreted protein PRG4 that protects against osteoarthritis development at least 2 months after transection of cruciate ligaments, This model mimics a common injury in humans and leads to osteoarthritis in both condylar structures of the knee. The establishment of a gain of function model using an endogenously produced secreted protein may make for easier clinical translation as compared to previous approaches targeting inhibition of specific matrix enzymes and/or intracellular transcription factors. Moreover, the demonstration of a beneficial effect on age-related cartilage changes supports the further study of this approach beyond injury model.

The established mechanisms that protect animals from osteoarthritis development mostly depend on inhibition of cartilage catabolic enzymes. ADAMTS5 was the first target to be discovered via in vivo genetic experiments (S. S. Glasson et al., Deletion of active ADAMTS5 prevents cartilage degradation in a murine model of osteoarthritis. *Nature* 434, 644 (Apr. 31, 2005)). Loss of Syndecan 4, similarly, works through ADAMTS5 inhibition (F. Echtermeyer et al., Syndecan-4 regulates ADAMTS-5 activation and cartilage breakdown in osteoarthritis. *Nature Medicine,* 1 (Mar. 30, 2102)). Recently, the discovery of the protective effects of Hif2alpha loss of function in OA extends this approach as Hif2alpha transcriptionally regulates the expression of catabolic enzymes including several MMPs and ADAMTSs (T. Saito et al., Transcriptional regulation of endochondral ossification by HIF-2α during skeletal growth and osteoarthritis development. *Nature Medicine* 16, 678 (Jun. 23, 2010)). However, targeting anabolic pathways, including cell growth, differentiation and matrix synthesis, is equally important in osteoarthritis since chondrocyte proliferation, metaplasia and abnormal matrix synthesis have been long observed in osteoarthritis progression (K. P. Pritzker et al., Osteoarthritis cartilage histopathology: grading and staging. Osteoarthritis Cartilage 14, 13 (January, 2006)). An interaction between cartilage anabolic and catabolic pathways is required to maintain homeostasis and their imbalance leads to osteoarthritis progression. A therapy that can affect both programs would potentially be most effective.

Low-grade inflammation is commonly observed in osteoarthritic joints (Felson D T. 2006. Clinical practice. Osteoarthritis of the knee. N Engl J Med 354:841-848). Besides maintaining and amplifying inflammation, the key inflammatory mediators in osteoarthritis such as Il-1beta also trigger the expression of cartilage degrading enzymes such as collagenases and aggrecanases (Daheshia, M., and YAO, J. Q. (2008). The Interleukin 1p Pathway in the Pathogenesis of Osteoarthritis. J Rheumatol 35, 2306). Therefore, it seems important to inhibit both cartilage catabolism and joint inflammation in order to achieve efficient osteoarthritis treatment. Along these lines, the inventors show here that a gene therapy treatment combining helper-dependent adenoviral vectors expressing PRG4 and the anti-inflammatory Il-1Ra seems to further improve osteoarthritis treatment over gene therapy with PRG4.alone.

Materials and Methods

Generation of transgenic mice. FVB/N mice were purchased from Jackson Laboratories (Bar Harbor, Me.). This strain is the common background strain for transgenic mouse lines. All studies were performed with approval from the Baylor College of Medicine Institutional Animal Care and Use Committee (IACUC). All mice were housed under pathogen-free conditions in less than five per cage. Mice had free access to feed and water. Transgenic mice were generated by pronuclear microinjection. Founders were outcrossed for at least 3 generations to eliminate multiple insertions. Different lines were tested at the beginning to rule out position effect. Genotyping primers were designed to detect the VVPRE element in the transgene cassette: F: TCTCTTTATGAGGAGTTGTGGCCC (SEQ ID NO: 40), R: CGACAACACCACGGAATTGTCAGT (SEQ ID NO: 41). To avoid the effects of potential post-menopausal bone loss, all the mice used in OA evaluation were males.

Cruciate ligament transection (CLT) surgery. CLT surgery and sham were performed as previously described in 8-week old male FVB/N mice and PRG4 transgenic mice (M. Ruan et al., Quantitative imaging of murine osteoarthritic cartilage by phase contrast micro-computed tomography. *Arthritis Rheum*, (2012). Investigators were blinded to the genotype of the mice when surgery was performed.

Histology and immunohistochemistry. Mice were euthanized and samples were fixed with 4% paraformaldehyde (Sigma-Aldrich) overnight in 4° C. on a shaker. Samples from mice older than 4 days were decalcified in 14% EDTA for 5 days in 4° C. on a shaker. Samples from mice younger than 3 days were not decalcified. Paraffin embedding was performed as previously described. Samples were sectioned at 6 μm. Samples were stained with safranin O and fast green using standard protocols. Samples were scored by two independent pathologists masked to the procedure and genotypes. Immunohistochemistry were performed using primary antibody: anti-PRG4 (Abcam, ab 28484), anti-MMP13 (Millipore, MAB 13424), anti-ColX (generous gift from Dr. Greg Lunstrum, Shriners Hospital for Children, Portland, Oreg.), and secondary antibody: one-dropper-bottle HRP polymer conjugates (Invitrogen). BrdU staining was performed using anti-BrdU Alexa Fluor 594 (A21304, Invitrogen). Histomark trueblue (KPL) was used as developing reagent. TUNEL staining was performed using ApopTag Plus Peroxidase In situ Apoptosis Detection (Millipore Kit S7101) following manufacturer's protocol. All staining in the same experiment were done at the same time. Observer who quantified of BrdU and TUNEL staining was blinded to the genotype of the mice.

Beta-galactosidase staining. Staining was performed on samples embedded in optimal cutting temperature compound after fixation and decalcification. Samples were sectioned at 6 μm and stained with X-gal (X428IC Gold biotechnology) overnight and nuclear fast red (N3020 Sigma) as counter stain.

Rotarod analysis. Mice were placed onto an accelerating rotarod (UGO Basile, Varese, Italy). The duration to first failure to stay atop the rod was marked as first ride-around time. To rule out differences in learning skills between the two groups of mice, each group was assessed over three trials per day for 2 consecutive days (trials 1 to 6) before surgery. Mice were then randomly assigned into different groups. Another 6 trials were performed using the same conditions at the different time points after the surgery. Mice were given a 30 minutes inter-trial rest interval. Each trial had a maximum time of 5 minutes. Observer was blinded to the genotype and the procedure of the mice.

Hotplate analysis. Mice were placed on the hotplate at 55° C. (Columbus Instruments, Columbus, Ohio). The latency period for hind limb response (e.g. shaking, jumping, or licking) was recorded as response time before at different time points after surgery. Observer was blinded to the genotype and the procedure of the mice.

Phase contrast μCT scanning. Samples were prepared as previously described and scanned by Xradia μXCT at source voltage=40 kV, source power=8 W, detector distance from sample=75 mm, source distance from sample=100 mm, image number taken=500, and exposure time for each image=30 (M. Ruan et al., Quantitative imaging of murine osteoarthritic cartilage by phase contrast micro-computed tomography. *Arthritis Rheum*, (2012)). The resolution of the scanning is 4 μm. After scanning, a random number was assigned to each sample to ensure blinded assessment during image processing.

Reconstruction and analysis of μCT data. Reconstruction of the data was performed using Xradia software and was transformed into dicom files. Reconstruction involves correction for beam hardening (constant=0.3), and correcting for center shift effects caused by difference between the center of sample rotation and the center of the detector. Samples were analyzed using TriBON software (RATOC, Tokyo, Japan). Observers were blinded to the procedure and sample number (M. Ruan et al., Quantitative imaging of murine osteoarthritic cartilage by phase contrast micro-computed tomography. *Arthritis Rheum*, (2012)).

Intra-articular Injection. Mice were anesthetized using 3% isoflurane. Joint area was shaved. HDAds were diluted in sterile PBS in 5 μl and injected by 25 μl CASTIGHT syringes (1702 Hamilton Company) and 33 gauge needles (7803-05 Hamilton Company).

Luciferase assay. Mice were injected with 2 mg D-luciferin (L9504 SIGMA) diluted in 100 μl PBS per mouse (25 grams) intraperitoneally. Mice were anesthetized using 3% isoflurane. Images were taken by Xenogen IVIS optical in vivo imaging system. Quantification was performed by living Imaging 4.2 using default settings. Image was collected for 10 minutes after the injection and normalized to control mice without luciferase injection.

Laser capture microdissection and RNA purification. Hind limbs of P1 littermates were collected and snap-frozen in liquid nitrogen. Then, samples were embedded in optimal cutting temperature compound. Frozen sections of 10 μm were generated on polyethylene napthalate (PEN)-membrane slides. Superficial layer chondrocytes were captured using HS Capsure LCM caps by Applied Biosciences Acturus Systems. RNA was then purified by Picopure RNA isolation kit.

Mouse Microarray and analysis. Microarrays were performed using Mouse WG-6 v2.0 Expression BeadChip (Illumina). Data was processed using the lumi package within the R statistical package. Variance-stabilizing transformation (VST) was performed, followed by quantile normalization of the resulting expression values. Differential expression was calculated using the limma package within R. Heat map was generated using normalized fold change. The resulting lists were then annotated and reviewed for candidates.

Human gene expression analysis. GEO archives GSE10575 titled "Migratory chondrogenic progenitor cells from repair tissue during the later stages of human osteoarthritis" (PMID: 19341622) and GSE16464, titled "Chondrogenic differentiation potential of osteoarthritis chondrocytes and their use in autologous chondrocyte transplantation" (PMID: 19723327) were both downloaded and analyzed using the web-based GEO2R, using the default settings, available through the GEO site. In archive GSE10575, three arrays of chondrogenic progenitor cells from osteoarthritis males were compared to two control arrays of the same cell type. Female samples were excluded because control samples are males (shown by the level of Xist expression). In archive GSE 16464, 3D-cultured chondrocytes from normal donors and 3D-cultured chondrocytes from OA donors were compared. Both archives used the Affymetrix Human Genome U133 Plus 2.0 Array platform.

Cell culture, transfection and infection. C3H10T1/2 cells were maintained in DMEM with 10% FBS; TC71 cells were maintained in RPMI 1640 with 10% FBS; ATDC5 cells were maintained in DMEM/F-12 1:1 mixture supplemented with 10% FBS. Cells were plated the day before transfection/infection so that it reached 70% confluency the next day. Lipofectamine 2000 was used as transfection reagent following protocols provided by manufacturer. Dharmacon on-target siRNA was used in the knockdown assay. HDAds were generated as previously described (M. Suzuki et al., Large-scale production of high-quality helper-dependent adenoviral vectors using adherent cells in all factories. *Human gene therapy* 21,120 (February, 2010)). HDAd-PRG4 carries the murine PRG4 gene controlled by the constitutive EF1 promoter. HDAd-Il-1Ra carries the murine Il-1Ra gene controlled by an inflammation-inducible NF-κB promoter. To infect cells. HDAds were diluted at 5000 vp/cell and added in serum free media with minimal volume covering cells after aspiration. Two hours later, media containing virus was aspirated and culturing media was added back. For hypoxia experiments, cells were transferred to hypoxia chamber with 1% oxygen.

RNA purification and quantitative PCR. Cells were lysed with Trizol reagents (Invitrogen) and RNA was purified following manufacturer's protocol. To eliminate DNA contamination, samples were treated with RNase-free recombinant DNaseI (Roche). Reverse-transcript PCR was conducted by superscript III first strand (18080-051Invitrogen) following manufacturer's protocol. Taqman Universal PCR mastermix (Applied biosciences) and PerfeCTa SYBR Green SuperMix (Quanta BioSciences) were used in quantitative PCR. Primers used in quantitative PCR are listed as follows: mouse

```
F:
                                  (SEQ ID NO: 16)
ACTTCAGCTAAAGAGACACGGAGT,

R:
                                  (SEQ ID NO: 17)
GTTCAGGTGGTTCCTTGGTTGTAGTAA;

Sox9:
F:
                                  (SEQ ID NO: 18)
AAGCCACACGTCAAGCGACC,

R:
                                  (SEQ ID NO: 19)
GTGCTGCTGATGCCGTAACT;

Col2a1:
F:
                                  (SEQ ID NO: 20)
GCTCATCCAGGGCTCCAATGATGTAG,

R:
                                  (SEQ ID NO: 21)
CGGGAGGTCTTCTGTGATCGGTA;

Gapdh:
F:
                                  (SEQ ID NO: 22)
GCAAGAGAGGCCCTATCCCAA;

R:
                                  (SEQ ID NO: 23)
CTCCCTAGGCCCCTCCTGTTATT;

Vegf:
F:
                                  (SEQ ID NO: 24)
TGGACTTGTGTTGGGAGGAGGATG,

R:
                                  (SEQ ID NO: 25)
GCCTCTTCTTCCACCACCGTGTC;

Mmp13:
F:
                                  (SEQ ID NO: 26)
GCAATCTTTCTTTGGCTTAGAGGT,
```

-continued

```
R:
                                  (SEQ ID NO: 27)
GGTGTTTTGGGATGCTTAGGGT;

Col10a1:
F:
                                  (SEQ ID NO: 28)
AAAGCTTACCCAGCAGTAGG,

R:
                                  (SEQ ID NO: 29)
ACGTACTCAGAGGAGTAGAG;

GAPDH:
F:
                                  (SEQ ID NO: 30)
ATACCAGGAAATGAGCTTGACAAA,

R:
                                  (SEQ ID NO: 31)
TGAAGGTCGGAGTCAACGGA;

VEGF:
F:
                                  (SEQ ID NO: 32)
GATCGGTGACAGTCACTAGCTTATCT,

R:
                                  (SEQ ID NO: 33)
TACACACAAATACAAGTTGCCA;

MMP13:
F:
                                  (SEQ ID NO: 34)
TGCCCTTCTTCACACAGACACTAACGAAA,

R:
                                  (SEQ ID NO: 35)
GGCCACATCTACTATTCTTACCACTGCTC;

COL10A1:
F:
                                  (SEQ ID NO: 36)
GCCCACTACCCAAGACCAAGAC;

R:
                                  (SEQ ID NO: 37)
GACCCCTCTCACCTGGACGAC;

HIF3A:
F:
                                  (SEQ ID NO: 38)
GGCTGTTCCGCCTACGAGTA;

R:
                                  (SEQ ID NO: 39)
AGCAAGGTGGATGCTCTTG;
PRG4: Hs00981633_m1 (applied biosciences);
mouse Hif3a: Mm00469375_m1 (applied bicsciences).
```

Statistics. Statistical significance comparing two groups with parametric data was assessed by Student's t test, Statistical analysis comparing multiple groups with parametric data was performed by one-way ANOVA followed by Tukey's post-hoc. Statistical analysis comparing different genotype with different procedure was performed by two-way ANOVA followed by Tukey's post-hoc, Normality was tested by Shapiro-Wilk Normality test. Histological grades were compared by Wilcox rank test. All analyses were performed by SPSS software or Sigma Plot. A P value of <0.05 was considered statistically significant.

Dataset 1: List of genes showing more than 1.5 fold change in the microarray analysis.

| | WTP1_1 | WTP1_2 | WTP1_3 | PG4P1_1 | PG4P1_2 | PG4P1_3 |
|---|---|---|---|---|---|---|
| 4930546H06Rik_ILMN_2717117 | 1.256363 | 1.360731 | 1.425929 | −1.48447 | −1.59768 | −1.52108 |
| Sesn1_ILMN_2654074 | −1.25604 | −1.26072 | −1.28391 | 1.234927 | 1.170478 | 1.226371 |
| Ypel5_ILMN_1251071 | 1.224517 | 1.294585 | 1.311664 | −1.44517 | −1.32632 | −1.38253 |
| Bglap-rs1_ILMN_1233122 | 1.301868 | 2.023561 | 1.628096 | −3.0338 | −3.05449 | −2.56761 |
| AK038070_ILMN_2466021 | 1.257255 | 1.181603 | 1.204158 | −1.30391 | −1.20282 | −1.31808 |
| AK011460_ILMN_2452717 | −1.52912 | −1.85077 | −1.48354 | 1.474372 | 1.352955 | 1.304319 |
| Bglap1_ILMN_2610166 | 1.404137 | 2.037433 | 1.6235 | −4.09687 | −3.29889 | −2.57926 |
| Med18_ILMN_1214050 | −1.48231 | −1.26813 | −1.3871 | 1.212726 | 1.267995 | 1.335163 |
| Bglap1_ILMN_3101908 | 1.459117 | 2.042785 | 1.496434 | −3.82431 | −3.03438 | −2.43533 |
| Ppp1r3c_ILMN_2667091 | −1.65083 | −1.56199 | −1.48727 | 1.4376 | 1.167941 | 1.476123 |
| Bglap-rs1_ILMN_1220829 | 1.261849 | 2.094587 | 1.691356 | −3.64532 | −3.48459 | −2.55816 |
| Zfp46_ILMN_1215740 | −1.35114 | −1.26299 | −1.37143 | 1.277394 | 1.136789 | 1.32476 |
| Hist1h1c_ILMN_2855315 | 1.196666 | 1.423895 | 1.348674 | −1.49333 | −1.34167 | −1.62396 |
| Zfand2a_ILMN_1230489 | 1.273059 | 1.140929 | 1.34758 | −1.36636 | −1.26743 | −1.39361 |
| Ddx21_ILMN_2546724 | 1.305544 | 1.217222 | 1.179125 | −1.34811 | −1.20085 | −1.382 |
| Hist1h1c_ILMN_2774537 | 1.170861 | 1.384453 | 1.428754 | −1.41392 | −1.42079 | −1.65332 |
| Ddx54_ILMN_2689678 | 1.130087 | 1.286618 | 1.299302 | −1.39565 | −1.2461 | −1.30723 |
| Rps15a_ILMN_2717621 | 1.315098 | 1.139016 | 1.449143 | −1.36561 | −1.52841 | −1.40807 |
| Bglap-rs1_ILMN_2944508 | 1.303982 | 2.185122 | 1.520279 | −3.70241 | −3.45533 | −2.31957 |
| Slc7a5_ILMN_2711948 | 1.201827 | 1.326767 | 1.430059 | −1.67471 | −1.48398 | −1.29808 |
| Csnk1d_ILMN_2739965 | 1.11045 | 1.255629 | 1.292397 | −1.37356 | −1.22945 | −1.24982 |
| Dyrk1b_ILMN_3053158 | −1.46521 | −1.31006 | −1.19201 | 1.182241 | 1.294858 | 1.238163 |
| Hist2h3b_ILMN_2934120 | 1.254913 | 1.119073 | 1.304197 | −1.38431 | −1.299 | −1.20538 |
| Nmd3_ILMN_1228859 | 1.262366 | 1.122484 | 1.224622 | −1.20301 | −1.36721 | −1.20793 |
| 1190005F20Rik_ILMN_2697918 | −1.21616 | −1.40512 | −1.44745 | 1.36511 | 1.269442 | 1.140632 |
| Lrrc59_ILMN_1252817 | 1.334493 | 1.222121 | 1.168151 | −1.47501 | −1.29518 | −1.21186 |
| Dusp8_ILMN_1228031 | 1.288724 | 1.069707 | 1.275318 | −1.27037 | −1.24915 | −1.28446 |
| AK053260_ILMN_1228804 | −1.53513 | −1.52115 | −1.78747 | 1.594074 | 1.424237 | 1.113431 |
| Eif1a_ILMN_2698107 | 1.399002 | 1.348068 | 1.07882 | −1.44405 | −1.34553 | −1.35426 |
| AK021349_ILMN_1258961 | 1.382804 | 1.270095 | 1.173873 | −1.34656 | −1.59361 | −1.2452 |
| Csnk1d_ILMN_1231035 | 1.104983 | 1.305878 | 1.354114 | −1.47277 | −1.23751 | −1.33697 |
| Cirbp_ILMN_2761594 | 1.08657 | 1.233789 | 1.298241 | −1.23605 | −1.35285 | −1.20021 |
| Plekhf2_ILMN_2798694 | 1.124677 | 1.171659 | 1.32521 | −1.2892 | −1.34384 | −1.16463 |
| Nfatc1_ILMN_1216522 | 1.286293 | 1.080945 | 1.308693 | −1.21468 | −1.39646 | −1.27436 |
| Clk1_ILMN_2428301 | −1.36643 | −1.38464 | −1.9415 | 1.450046 | 1.301662 | 1.279182 |
| Trove2_ILMN_1252725 | 1.195356 | 1.139589 | 1.272322 | −1.22692 | −1.41043 | −1.15117 |
| EG639396_ILMN_2877059 | −1.19236 | −1.20876 | −1.39289 | 1.317211 | 1.11903 | 1.179859 |
| Heatr1_ILMN_1214036 | 1.317403 | 1.264432 | 1.223294 | −1.64477 | −1.32574 | −1.20107 |
| BC027809_ILMN_1252263 | 1.357622 | 1.055984 | 1.444709 | −1.34453 | −1.47672 | −1.38744 |
| Ccdc130_ILMN_2756733 | −1.17101 | −1.26787 | −1.41093 | 1.342647 | 1.169009 | 1.136904 |
| Tmcc1_ILMN_1249710 | −1.26174 | −1.39677 | −1.70812 | 1.477478 | 1.22952 | 1.199067 |
| Arrdc4_ILMN_2648967 | 1.045261 | 1.574252 | 1.593893 | −1.83439 | −1.7299 | −1.50742 |
| AK044963_ILMN_1247942 | 1.321698 | 1.257721 | 1.270333 | −1.18779 | −1.38985 | −1.69824 |
| Arf2_ILMN_1214810 | 1.546019 | 1.353128 | 1.087012 | −1.4972 | −1.66445 | −1.34205 |
| 2610101N10Rik_ILMN_1252490 | −1.14039 | −1.40709 | −1.51568 | 1.290925 | 1.162057 | 1.299667 |
| Lrrc47_ILMN_2628551 | 1.117726 | 1.123233 | 1.383986 | −1.31904 | −1.23011 | −1.2438 |
| Srm_ILMN_2809611 | 1.485302 | 1.196046 | 1.150938 | −1.54798 | −1.39998 | −1.23852 |
| Gprc5a_ILMN_2854943 | 1.320606 | 1.042922 | 1.353049 | −1.29647 | −1.25915 | −1.39294 |
| Ddx11_ILMN_2700550 | −1.20131 | −1.24547 | −1.33501 | 1.353463 | 1.204601 | 1.057541 |
| Deb1_ILMN_2652971 | 1.548657 | 1.086404 | 1.190474 | −1.36664 | −1.38753 | −1.38497 |
| Mif_ILMN_2867835 | 1.125532 | 1.187658 | 1.327057 | −1.3999 | −1.32759 | −1.12086 |
| Hoxd3_ILMN_1219807 | −1.19061 | −1.30954 | −1.55302 | 1.334377 | 1.316337 | 1.101846 |
| Cdc7_ILMN_1238374 | −1.31242 | −1.26666 | −1.86596 | 1.253473 | 1.281007 | 1.378172 |
| Zfp187_ILMN_3067831 | −1.18727 | −1.40885 | −1.54414 | 1.457655 | 1.221198 | 1.121467 |
| 3300001P08Rik_ILMN_2727004 | −1.16879 | −1.39116 | −1.32235 | 1.224787 | 1.064016 | 1.380551 |
| Hoxc6_ILMN_1217328 | −1.33051 | −1.47422 | −1.40075 | 1.339994 | 1.496705 | 1.019485 |
| Rbm5_ILMN_2942492 | −1.29365 | −1.62199 | −1.68464 | 1.66198 | 1.236204 | 1.11868 |
| AK012053_ILMN_2469320 | −1.10834 | −1.3099 | −1.40348 | 1.32378 | 1.110387 | 1.187654 |
| Tmem128_ILMN_1248235 | 1.125965 | 1.138522 | 1.441919 | −1.45467 | −1.29997 | −1.19488 |
| Rbm5_ILMN_2942499 | −1.45228 | −1.59992 | −1.84238 | 1.607189 | 1.534819 | 1.001613 |
| E130016E03Rik_ILMN_3161959 | −1.2783 | −1.50572 | −1.71101 | 1.568022 | 1.337492 | 1.063614 |
| Tnfrsf12a_ILMN_2424299 | 1.680884 | 1.277593 | 1.075987 | −1.78329 | −1.46531 | −1.38442 |
| Prdm2_ILMN_1250454 | 1.173017 | 1.20632 | 1.256779 | −1.14469 | −1.19644 | −1.52795 |
| Srm_ILMN_1225880 | 1.332372 | 1.120064 | 1.166016 | −1.4506 | −1.22663 | −1.14034 |
| Cpt2_ILMN_2775123 | −1.20532 | −1.33083 | −1.38724 | 1.104396 | 1.131549 | 1.462135 |
| Twf1_ILMN_1244219 | 1.25757 | 1.126966 | 1.235596 | −1.49415 | −1.20089 | −1.13911 |
| AK076052_ILMN_2429108 | 1.076837 | 1.140505 | 1.40668 | −1.19618 | −1.25719 | −1.34308 |
| Farsa_ILMN_1257639 | 1.213878 | 1.216622 | 1.352934 | −1.12429 | −1.38604 | −1.65116 |
| Zfp84_ILMN_2506757 | −1.16964 | −1.18995 | −1.49011 | 1.301893 | 1.104954 | 1.226727 |
| Rnase4_ILMN_1235657 | −1.46403 | −1.24206 | −1.12261 | 1.323919 | 1.163284 | 1.133851 |
| Pim3_ILMN_2717667 | 1.123427 | 1.144501 | 1.541166 | −1.42121 | −1.21509 | −1.50536 |
| Rab5b_ILMN_1237467 | −1.54934 | −1.50901 | −1.79875 | 1.824154 | 1.27382 | 1.037959 |
| Tk1_ILMN_2605890 | −1.14797 | −1.19726 | −1.52316 | 1.200172 | 1.303368 | 1.13359 |
| Nrp1_ILMN_1247094 | −1.34674 | −1.14618 | −1.60363 | 1.244615 | 1.403199 | 1.113605 |
| 6030458C11Rik_ILMN_1234196 | −1.5397 | −1.45778 | −2.22228 | 1.702852 | 1.461039 | 1.050668 |
| Pold1_ILMN_2655577 | −1.24471 | −1.24541 | −1.4781 | 1.425738 | 1.253099 | 1.038272 |
| Prss35_ILMN_2609897 | 1.480951 | −1.03832 | 1.608742 | −1.44299 | −1.64698 | −1.54549 |

-continued

Dataset 1: List of genes showing more than 1.5 fold change in the microarray analysis.

| | WTP1_1 | WTP1_2 | WTP1_3 | PG4P1_1 | PG4P1_2 | PG4P1_3 |
|---|---|---|---|---|---|---|
| Tppp3_ILMN_2655929 | −1.08048 | −1.39071 | −1.3892 | 1.218015 | 1.318692 | 1.098879 |
| Clec2d_ILMN_2603647 | −1.73457 | −1.2971 | −2.52661 | 1.280941 | 1.696474 | 1.279334 |
| Hif3a_ILMN_2649671 | −1.78312 | −1.6431 | −1.32223 | 1.73224 | 1.313779 | 1.028263 |
| Pnrc2_ILMN_2861331 | −1.12969 | −1.18773 | −1.58246 | 1.161941 | 1.19852 | 1.280471 |
| Myd116_ILMN_2722938 | 1.38863 | 1.149001 | 1.09759 | −1.13863 | −1.23126 | −1.4829 |
| Eln_ILMN_2697304 | 1.09603 | 1.310437 | 1.235098 | −1.20273 | −1.1346 | −1.54888 |
| Fbxo31_ILMN_2452855 | −1.16259 | −1.1719 | −1.62377 | 1.23252 | 1.296053 | 1.142115 |
| Zmym2_ILMN_2781493 | −1.1322 | −1.205 | −1.65697 | 1.259404 | 1.17403 | 1.249941 |
| Rad54l_ILMN_2741985 | −1.14435 | −1.14233 | −1.57512 | 1.210268 | 1.2324 | 1.17319 |
| Nedd9_ILMN_2654186 | 1.300471 | 1.369214 | 1.006802 | −1.27054 | −1.16693 | −1.47168 |
| Gadd45g_ILMN_2744890 | 1.159873 | 1.093824 | 1.401321 | −1.50495 | −1.10425 | −1.29047 |
| Syncrip_ILMN_1258420 | 1.212463 | 1.238146 | 1.1686 | −1.42916 | −1.42482 | −1.02121 |
| Ier3_ILMN_1216764 | 1.881239 | 1.019378 | 1.168521 | −1.48139 | −1.66306 | −1.52784 |
| Galt_ILMN_2677567 | −1.21625 | −1.36275 | −1.40341 | 1.540977 | 1.172451 | 1.018011 |
| Map3k1_ILMN_2614380 | −1.22523 | −1.25855 | −1.72004 | 1.286516 | 1.479816 | 1.041544 |
| Rrp12_ILMN_2728118 | 1.330091 | 1.265982 | 1.182798 | −1.73253 | −1.45231 | −1.0467 |
| Dbp_ILMN_2616226 | −1.3989 | −1.2558 | −2.17137 | 1.654516 | 1.166472 | 1.207322 |
| Sfrs7_ILMN_2552490 | −1.09319 | −1.37266 | −1.50612 | 1.421972 | 1.225556 | 1.045249 |
| Tmem100_ILMN_1224014 | −1.53254 | −1.20266 | −1.67189 | 1.499528 | 1.458731 | −1.04208 |
| Rpap1_ILMN_1238065 | −1.22594 | −1.19869 | −1.41188 | 1.480394 | 1.120412 | 1.040978 |
| AK017419_ILMN_2416218 | 1.258403 | −1.04994 | 1.597254 | −1.40368 | −1.39738 | −1.30912 |
| Trpc2_ILMN_1220948 | −1.1478 | −1.20737 | −1.48702 | 1.435121 | 1.116418 | 1.076493 |
| Il11ra1_ILMN_1229957 | −1.17181 | −1.34116 | −1.36512 | 1.51528 | 1.033071 | 1.120113 |
| AK007736_ILMN_1258587 | −1.30198 | −1.1931 | −1.5084 | 1.02934 | 1.151676 | 1.549816 |
| Atpbd4_ILMN_1230688 | 1.212165 | 1.044319 | 1.518026 | −1.1629 | −1.29912 | −1.67838 |
| Tuba1c_ILMN_2476139 | 1.185176 | 1.22582 | 1.255489 | −1.65104 | −1.03071 | −1.31991 |
| Abhd14b_ILMN_3007862 | −1.17428 | −1.31793 | −1.82363 | 1.555108 | 1.207257 | 1.078925 |
| Ifi27l2a_ILMN_2762944 | 1.023728 | 1.619691 | 1.164394 | −1.58706 | −1.19828 | −1.37445 |
| Mll5_ILMN_1217776 | −1.08848 | −1.35305 | −1.70073 | 1.363244 | 1.345082 | 1.045908 |
| AK029312_ILMN_1246692 | −1.1321 | −1.22047 | −1.47253 | 1.301738 | −1.00965 | 1.326047 |
| Cars2_ILMN_1218543 | −1.15407 | −1.26682 | −1.75735 | 1.471686 | 1.249823 | 1.053571 |
| Raver2_ILMN_1213278 | −1.20699 | −1.23934 | −1.94009 | 1.342784 | 1.066234 | 1.440154 |
| Mid1_ILMN_3159435 | 1.127098 | 1.038972 | 1.460931 | −1.13274 | −1.25072 | −1.44792 |
| AK078053_ILMN_1222351 | −1.10161 | −1.27506 | −1.55656 | 1.45516 | 1.108898 | 1.101466 |
| AK028672_ILMN_1246030 | 1.223792 | 1.161685 | 1.206628 | −1.02194 | −1.2642 | −1.56654 |
| AK043421_ILMN_2575994 | −1.26016 | −1.2699 | −2.19263 | 1.481949 | 1.406903 | 1.07406 |
| AK085118_ILMN_2505392 | −1.11638 | −1.20699 | −1.48486 | 1.360363 | 1.232508 | 1.009408 |
| Lpp_ILMN_2463260 | 1.144334 | 1.172656 | 1.289494 | 1.004724 | −1.44657 | −1.43369 |
| NR_001461_ILMN_2445958 | −1.33534 | −1.58378 | −1.69795 | 1.861753 | 1.221821 | −1.05574 |
| Zfp52_ILMN_2838139 | −1.25077 | −1.21913 | −1.67899 | 1.544861 | 1.244823 | −1.00507 |
| AK004187_ILMN_2513451 | −1.30128 | −1.18771 | −1.30172 | 1.256082 | 1.421114 | −1.05914 |
| Gp1bb_ILMN_2653205 | 1.310991 | −1.01749 | 1.499583 | −1.20277 | −1.26174 | −1.71629 |
| BC037034_ILMN_1257019 | −1.07956 | −1.19392 | −1.58424 | 1.197539 | 1.32752 | 1.079839 |
| AK086317_ILMN_2580737 | 1.974206 | 1.266016 | 1.059287 | −1.17028 | −2.25587 | −2.48319 |
| NR002848_ILMN_2966602 | −1.34056 | −1.63363 | −1.01451 | 1.281704 | 1.267341 | 1.107163 |
| Asns_ILMN_2643513 | 1.12627 | 1.082326 | 1.473384 | −1.63603 | −1.22191 | −1.12562 |
| AK005089_ILMN_2451115 | 1.054101 | 1.319016 | 1.421071 | −1.13881 | −1.24881 | −1.89777 |
| 6430706D22Rik_ILMN_3011719 | −1.33993 | −1.32228 | −1.58013 | 1.622833 | 1.345146 | −1.11534 |
| 5330401P04Rik_ILMN_2520011 | −1.1508 | −1.17966 | −1.63107 | 1.427003 | 1.221601 | 1.021642 |
| Flcn_ILMN_1213483 | −1.17513 | −1.1274 | −1.55513 | 1.410583 | 1.179933 | 1.028483 |
| Per2_ILMN_2987862 | −1.21694 | −1.06498 | −1.65428 | 1.267989 | 1.067504 | 1.299293 |
| Ppm1m_ILMN_1224437 | −1.16175 | −1.17068 | −1.91121 | 1.437044 | 1.159707 | 1.165048 |
| AK084113_ILMN_2451389 | −1.16976 | −1.13767 | −1.70942 | 1.283512 | 1.371085 | 1.026543 |
| AK007605_ILMN_1239776 | 1.119895 | 1.118125 | 1.47604 | −1.14506 | −1.18395 | −1.76057 |
| Depdc6_ILMN_3163001 | −1.13115 | −1.20253 | −1.78263 | 1.08135 | 1.165515 | 1.47653 |
| Mterf_ILMN_2624809 | −1.0454 | −1.20426 | −1.5987 | 1.344071 | 1.147785 | 1.095675 |
| AK014695_ILMN_2748880 | −1.23553 | −1.24466 | −2.42903 | 1.564719 | 1.31189 | 1.098905 |
| Vat1l_ILMN_1226356 | −1.17602 | −1.20391 | −1.46333 | 1.144397 | −1.02032 | 1.511196 |
| Ankzf1_ILMN_2703321 | −1.20097 | −1.19701 | −1.82856 | 1.447617 | 1.36439 | −1.02771 |
| Tha1_ILMN_2594768 | −1.09096 | −1.25311 | −1.78214 | 1.402023 | 1.303303 | 1.018911 |
| Plekhf1_ILMN_2993334 | −1.08624 | −1.16026 | −1.78844 | 1.297336 | 1.242747 | 1.118284 |
| Gprasp1_ILMN_3142384 | −1.15055 | −1.14972 | −1.66918 | 1.014435 | 1.224737 | 1.422807 |
| Pdgfra_ILMN_1235932 | −1.28478 | −1.3484 | −1.50982 | 1.62719 | 1.311287 | −1.13736 |
| Mcm10_ILMN_2970532 | −1.0688 | −1.14651 | −1.70048 | 1.161108 | 1.296402 | 1.146574 |
| Fbp2_ILMN_2634905 | −1.67939 | −1.76924 | −2.20592 | −1.36206 | 1.508826 | 2.142995 |
| 1110007M04Rik_ILMN_2734060 | 1.125411 | 1.216839 | 1.439906 | −1.77901 | −1.60341 | 1.032062 |
| Suv420h2_ILMN_1260420 | −1.06155 | −1.32955 | −2.05337 | 1.396444 | 1.349127 | 1.073276 |
| Adat2_ILMN_2705097 | 1.042499 | 1.080097 | 1.530343 | −1.07116 | −1.36781 | −1.46542 |
| 1200016B10Rik_ILMN_1236716 | −1.08228 | −1.17359 | −1.66229 | 1.410154 | 1.112488 | 1.099721 |
| AK021262_ILMN_2546861 | −2.55735 | −2.96551 | −2.04609 | 2.589175 | 1.589228 | −1.65394 |
| NR_002848_ILMN_2438819 | −1.04157 | −1.19208 | −1.62472 | 1.102605 | 1.130335 | 1.352612 |
| Iqcb1_ILMN_2635348 | −1.25858 | −1.51247 | −1.07587 | 1.479027 | 1.112991 | 1.022781 |
| Sirpa_ILMN_2722996 | −1.55085 | 1.020695 | −1.42422 | 1.095271 | 1.397855 | 1.139231 |
| Kif1b_ILMN_2587761 | −1.10748 | −1.26856 | −1.71852 | −1.03298 | 1.275994 | 1.482789 |
| Gtpbp2_ILMN_2600113 | −1.03362 | −1.24214 | −1.75238 | 1.314034 | 1.280253 | 1.062528 |

-continued

Dataset 1: List of genes showing more than 1.5 fold change in the microarray analysis.

| | WTP1_1 | WTP1_2 | WTP1_3 | PG4P1_1 | PG4P1_2 | PG4P1_3 |
|---|---|---|---|---|---|---|
| Akap8l_ILMN_1242769 | −1.70634 | −1.79935 | −1.46855 | 1.863393 | 1.552434 | −1.31333 |
| AK029270_ILMN_1246021 | −1.36249 | −1.13168 | −2.29819 | 1.675332 | 1.15085 | 1.121103 |
| Timm8a1_ILMN_2896552 | 1.183976 | 1.065901 | 1.33591 | −1.5964 | −1.26281 | −1.0041 |
| Cpt2_ILMN_2775122 | −1.31568 | −1.57523 | −1.10064 | −1.0034 | 1.133167 | 1.566763 |
| Mif_ILMN_1260512 | 1.004975 | 1.323347 | 1.316609 | −1.60996 | −1.34456 | −1.0099 |
| Cenpl_ILMN_2676726 | −1.07561 | −1.16457 | −1.74209 | 1.300334 | 1.282306 | 1.05495 |
| Ccdc86_ILMN_2730003 | 1.079631 | 1.174875 | 1.493109 | −1.81679 | −1.39094 | −1.01727 |
| Cited2_ILMN_2477221 | −1.25941 | −1.07229 | −1.54732 | −1.01603 | 1.188502 | 1.45439 |
| Tle6_ILMN_2900617 | −1.25696 | −1.29766 | −2.43442 | 1.763195 | 1.23855 | 1.021292 |
| Mrm1_ILMN_2649654 | −1.12291 | −1.18885 | −1.88148 | 1.496945 | 1.102948 | 1.136915 |
| Tsc22d3_ILMN_3150811 | −1.46991 | −1.23229 | −1.52848 | 1.715752 | 1.257691 | −1.13571 |
| Wnk1_ILMN_1234955 | −1.1436 | −1.18321 | −1.62288 | 1.476736 | 1.220566 | −1.03422 |
| Gstt3_ILMN_2665715 | −1.15761 | −1.16266 | −1.67614 | 1.531124 | 1.053215 | 1.095113 |
| Ppm1k_ILMN_2923615 | −1.08558 | −1.15334 | −1.64931 | 1.404428 | 1.134997 | 1.066046 |
| Clk4_ILMN_2851710 | −1.15318 | −1.33127 | −1.79737 | 1.595963 | 1.307868 | −1.08522 |
| Il11ra2_ILMN_2619594 | −1.04918 | −1.28561 | −1.57792 | 1.475052 | 1.023734 | 1.136498 |
| Cars2_ILMN_2670601 | −1.09189 | −1.14083 | −1.62876 | 1.389033 | 1.161988 | 1.042614 |
| Pbx1_ILMN_2559669 | −1.2673 | −1.25299 | −2.278 | 1.703366 | 1.314599 | −1.04615 |
| Acot11_ILMN_1227579 | −1.16373 | −1.10948 | −1.73831 | 1.422989 | 1.008933 | 1.232184 |
| Neat1_ILMN_2493030 | −1.1433 | −1.74898 | −4.34058 | 1.651763 | 1.528512 | 1.142921 |
| AK020467_ILMN_2506727 | −1.09908 | −1.81523 | −1.30434 | 1.576618 | 1.226821 | −1.03184 |
| Calb2_ILMN_2827729 | −1.13166 | −1.24465 | −1.58857 | 1.188467 | 1.548766 | −1.05688 |
| Rassf4_ILMN_2956092 | −1.19773 | −1.02283 | −1.71608 | 1.100194 | 1.347195 | 1.157291 |
| Tia1_ILMN_1215055 | −1.07031 | −1.11087 | −1.74002 | 1.144017 | 1.141023 | 1.305753 |
| Csnk2a1_ILMN_1218670 | −1.22304 | −1.30599 | −2.00138 | 1.579869 | 1.464052 | −1.14536 |
| INV_ILMN_1257729 | −1.19494 | −1.45406 | −1.54665 | 1.780692 | 1.124428 | −1.08257 |
| Fam109a_ILMN_2668178 | −1.1457 | −1.10631 | −2.07282 | 1.126329 | 1.371624 | 1.242875 |
| Clspn_ILMN_2858359 | −1.09104 | −1.12459 | −2.01152 | 1.193798 | 1.211273 | 1.292024 |
| AK051059_ILMN_2419748 | −1.0608 | −1.16991 | −1.93243 | 1.379757 | 1.164043 | 1.141268 |
| Unc5c_ILMN_2461668 | −1.01081 | 1.174419 | 1.441474 | −1.35249 | −1.00552 | −1.51306 |
| AK078921_ILMN_2462678 | −1.11083 | −1.23212 | −1.74051 | 1.561371 | 1.188618 | −1.03775 |
| Sgk_ILMN_1213954 | 1.274151 | 1.55087 | −1.15069 | −1.29135 | −1.183 | −1.4572 |
| Disp1_ILMN_2772288 | −1.08894 | −1.41679 | −1.49469 | 1.632533 | 1.126658 | −1.05526 |
| Gadd45g_ILMN_2903945 | 1.451953 | 1.318414 | 1.04743 | −2.13919 | 1.014627 | −1.42835 |
| LOC100040259_ILMN_1244853 | −1.18313 | 1.187774 | 1.974228 | −1.83552 | −1.42003 | −1.34451 |
| _ILMN_1245646 | −1.02956 | 1.218253 | 1.413033 | −1.59167 | −1.26363 | −1.02272 |
| Tmem129_ILMN_2429215 | −1.09374 | −1.11964 | −2.07634 | 1.200101 | 1.167903 | 1.342939 |
| Tusc4_ILMN_2454195 | −1.08831 | −1.10728 | −1.85511 | 1.369108 | 1.179966 | 1.089908 |
| Map3k12_ILMN_2725370 | −1.12888 | −1.35818 | −2.18302 | 1.726495 | 1.263127 | −1.07506 |
| Ndrg2_ILMN_2771991 | −1.07046 | −1.1445 | −2.06977 | 1.291192 | 1.095454 | 1.322285 |
| Rrp15_ILMN_2629856 | 1.004134 | −1.02887 | 1.835562 | −1.43385 | −1.48925 | −1.22032 |
| Mum1_ILMN_1215647 | −1.06142 | −1.13778 | −1.74536 | 1.418322 | 1.083703 | 1.103988 |
| AK052106_ILMN_1255302 | −1.05526 | −1.20509 | −1.60772 | 1.39953 | 1.257665 | −1.06004 |
| Tlcd1_ILMN_2781458 | −1.02375 | −1.3448 | −2.10692 | 1.475982 | 1.34724 | −1.0186 |
| Trps1_ILMN_1226073 | −1.06444 | −1.5275 | −1.78979 | 1.757446 | 1.159398 | −1.07492 |
| Ly6a_ILMN_1255416 | −3.17206 | −1.0932 | −1.29711 | 1.461767 | 1.331041 | 1.206246 |
| Accs_ILMN_2776485 | −1.22008 | −1.009 | −1.65779 | 1.41732 | 1.13865 | 1.030122 |
| Appl2_ILMN_1219978 | −1.24559 | −1.27531 | −2.11094 | 1.865122 | 1.161517 | −1.09567 |
| Cox4i2_ILMN_2612178 | 1.089127 | 1.158668 | 1.326957 | 1.008061 | −1.18331 | −1.74794 |
| Clk1_ILMN_1254814 | −1.07911 | −1.22534 | −2.01559 | 1.568467 | 1.193925 | −1.00131 |
| Clspn_ILMN_2623056 | −1.05233 | −1.08879 | −1.82761 | 1.147235 | 1.150539 | 1.28634 |
| Ncrna00166_ILMN_1222196 | −1.03988 | −1.16428 | −1.98635 | 1.39944 | 1.094827 | 1.181747 |
| C4b_ILMN_3049559 | −1.10606 | −1.15706 | −2.05407 | 1.351722 | 1.414119 | −1.0215 |
| Nfatc4_ILMN_2647331 | −1.37338 | −1.25155 | −1.20467 | 1.5856 | 1.183728 | −1.14491 |
| AK036974_ILMN_1222598 | −1.0959 | −1.17652 | −1.59093 | 1.5362 | 1.079376 | −1.00664 |
| Slc5a3_ILMN_1233078 | −1.17885 | −1.23164 | −1.89385 | 1.499145 | 1.458686 | −1.17105 |
| Abcd4_ILMN_1245547 | −1.16716 | −1.03031 | −1.70307 | 1.428297 | 1.110164 | 1.047001 |
| Spnb2_ILMN_1214394 | −1.0152 | −1.12231 | −1.88513 | 1.152147 | 1.231002 | 1.210335 |
| Prelp_ILMN_2739760 | −1.11189 | −1.53571 | −1.7425 | 1.801632 | 1.224774 | −1.17762 |
| 5830411K21Rik_ILMN_1217032 | −1.39544 | −1.00477 | −1.90468 | 1.069172 | 1.653072 | 1.04086 |
| Bmp4_ILMN_1215252 | −1.23614 | −1.17177 | −1.52917 | 1.595397 | 1.230579 | −1.16592 |
| Hoxd8_ILMN_2693052 | −1.07822 | −1.07856 | −1.81581 | 1.155206 | 1.051639 | 1.387814 |
| 1810013L24Rik_ILMN_2616630 | −1.18506 | 1.006997 | −2.02702 | 1.342216 | 1.132491 | 1.18112 |
| 5430432N15Rik_ILMN_2622089 | −1.48775 | −1.75547 | 1.115626 | 1.119898 | 1.119461 | 1.403214 |
| Stxbp3a_ILMN_1245393 | −1.41728 | −1.33413 | −1.13258 | 1.577382 | 1.23735 | −1.18035 |
| Ehd1_ILMN_2628757 | −1.17445 | 1.186862 | 1.650685 | −1.45395 | −1.2074 | −1.25788 |
| Raf1_ILMN_1237730 | −1.07621 | −1.19935 | −1.61396 | 1.5239 | 1.171328 | −1.08435 |
| Tbc1d2b_ILMN_2819859 | −1.07046 | −1.08129 | −2.17266 | 1.290826 | 1.221243 | 1.168665 |
| Ppox_ILMN_2826816 | −1.06553 | −1.21576 | −1.96091 | 1.443881 | 1.371369 | −1.09439 |
| Eraf_ILMN_2619200 | −1.14473 | 1.597198 | 1.416693 | −2.1079 | 1.035463 | −1.65928 |
| Hbb-b1_ILMN_1244316 | 1.271854 | 1.441461 | 1.216162 | −2.80858 | 1.193409 | −1.91916 |
| Chst5_ILMN_2665754 | 1.01614 | −1.33756 | −1.72423 | 1.103901 | −1.00597 | 1.558293 |

Dataset 2: List of transcription factors predicted by Ingenuity Pathway Analysis to be activated or inhibited. Positive z score suggests activation and negative z score.

| Transcription Regulator | Regulation z-score | p-value of overlap | Target molecules in dataset | Molecular Type |
|---|---|---|---|---|
| PPARA | 2.196 | 1.89E−01 | ASNS, CHKA, Clec2d (includes others), CPT2, FABP3, HIST1H1C, IGFBP5, KIF2C, LGALS4, RETSAT, SRM, TOP2A | ligand-dependent nuclear receptor |
| STAT5B | 2.038 | 1.42E−01 | MYL2, TNNC1, TNNT1, TPM3, TROVE2 | transcription regulator |
| PPARD | 2.036 | 1.29E−01 | ACTG2, CPT2, FABP3, FN1, LGALS4, TNFRSF12A | ligand-dependent nuclear receptor |
| ESR1 | 2.021 | 3.42E−01 | BMP4, Clec2d (includes others), DDX21, HOXC6, IER3, IGFBP5, SGK1, TGFB3 | ligand-dependent nuclear receptor |
| FOXO3 | −2.188 | 2.97E−01 | IER3, PPP1R15A, SGK1, SLC1A4 | transcription regulator |
| MEF2C | −2.359 | 2.06E−02 | Bglap (includes others), IBSP, MYL2, TNNC1 | transcription regulator |
| FOS | −2.58 | 3.37E−01 | CASZ1, CDON, FN1, HBA1/HBA2, HBB, IBSP, IGFBP5, KIF1B, LGALS4, NFATC1, S100A8, S100A9, SIRPA | transcription regulator |
| GATA4 | −2.64 | 1.61E−02 | ACTC1, ACTG2, MYL4, MYLPF, TNNC1 | transcription regulator |
| MYOCD | −2.976 | 1.88E−04 | ACTG2, GJA5, LPP, MYL2, MYL4, MYLPF | transcription regulator |
| SRF | −3.454 | 1.05E−03 | ACTC1, ACTG2, GADD45G, HIF3A, LBH, MYL2, MYL3, MYL4, Myl9, MYLPF, RAF1, TNNC1, TNNT1, ZMYM2 | transcription regulator |
| GLI1 | 1.845 | 1.78E−01 | LMNA, NDRG2, PDGFRA, S100A9, TMEM100, WIF1 | transcription regulator |
| E2F1 | 1.844 | 3.83E−01 | BMP4, DDX11/DOX12P, MCM10 (includes EG: 307126), NRP1 (includes EG: 18186), POLD1, PRDM2, RAD54L, TK1, TOP2A | transcription regulator |
| SATB1 | 0.865 | 3.41E−02 | ABTB1, HBB, HSPA8, SGK1, TSC22D3, YPEL5 | transcription regulator |
| CEBPD | 0.795 | 3.70E−02 | ASNS, IGFBP5, MBP, MIA, PDGFRA | transcription regulator |
| TFAP2C | 0.427 | 3.11E−03 | HIST1H1C, MBP, NRP1 (includes EG: 18186), TK1, ZMYND11 | transcription regulator |
| SMARCB1 | 0.271 | 3.27E−02 | C4B (includes others), CDC7 (includes EG: 12545), KIF23, MCM10 (includes EG: 307126), PLXNB2, PPP1R3C, RAB5B, RAD54B | transcription regulator |
| RUNX2 | −0.09 | 7.90E−03 | ACTG2, Bglap (includes others), C4B (includes others), COL24A1, FN1, IBSP | transcription regulator |
| SMAD7 | −0.265 | 4.16E−02 | ACTG2, CITED2, FN1, MYLPF, TGFB3, TPM3 | transcription regulator |
| PGR (includes EG: 18667) | −0.275 | 5.84E−03 | CPT2, DDX21, IER3, IGFBP5, NEDD9, SRSF7, TGFB3, TK1, TSC22D3 | ligand-dependent nuclear receptor |
| TP53 (includes EG: 22059) | −0.709 | 1.68E−03 | ASNS, BMP1, CCDC80, CDC7 (includes EG: 12545), CSNK1D, DBP, FABP3, FN1, GADD45G, GSTM1, HDC, HJURP, HK2, HSPA8, IER3, IGF3P5, IKBIP, IQCB1, KIF23, LPP, Ly6a (includes others), MYL4, Myl9, NDRG2, NRP1 (includes EG: 18186), PDGFRA, PEG3, PLXNB2, POLD1, PPP1R15A, PQLC3, RAD54B, RAF1, RNASE4, SESN1, SGK1, TOP2A, TSC22D3 | transcription regulator |
| CEBPB (includes EG: 1051) | −1.133 | 2.42E−02 | ACTG2, ARPP19, ASNS, CIRBP, Gnas (mouse), HBB, HDC, IER3, MBP, MIA, NRP1 (includes EG: 18186), PDGFRA, PPP1R15A, SGK1 | transcription regulator |
| MITF | −1.373 | 3.65E−02 | CHKA, CMA1, EDNRB, GPNMB, MBP, MYL4, Tpsab1 | transcription regulator |
| KDM5B | −1.459 | 1.71E−02 | EHD1, IARS2, KIF2C, NEDD9, PPOX, PSIP1, TOP2A | transcription regulator |
| GATA1 | −1.697 | 1.36E−02 | AHSP, ALAS2, GP1BB, HBA1/HBA2, HBB, MBP | transcription regulator |
| HIF1A | −1.714 | 3.60E−03 | ACTG2, ASNS, CHKA, CITED2, FN1, HIF3A, HIST1H1C, HK2, IGFBP5, MIF, PFKL, SC29A1, TGFB3, TMEM128 | transcription regulator |
| SMARCA4 | −1.791 | 9.94E−03 | ACTG2, ASNS, Bglap (includes others), BMP4, CLK1, FN1, HBB, IGFBP5, LMNA, MYH3, MYL4, MYLPF, NRP1 (includes EG: 18186) | transcription regulator |
| MYOD1 | −1.839 | 6.25E−03 | ACTC1, ACTG2, GADD45G, IGFBP5, MYH3, MYL4, MYLPF, SPT8N1, TNNC1, TNNT1 | transcription regulator |
| ATF4 | −1.848 | 7.63E−03 | ASNS, Bglap (includes others), IBSP, IGFBP5, PPP1R15A, SLC7A5, TNFRSF12A | transcription regulator |

SEQUENCE LISTING OVERVIEW

SEQ ID NO 1 HDAd-huPRG4

SEQ ID NO 2 HDAd-muPRG4

SEQ ID NO 3 huPRG4

SEQ ID NO 4 muPRG4

SEQ ID NO 5 huPRG4 protein

SEQ ID NO 6 muPRG4 protein

SEQ ID NO 7 HDAd-hulL1 Ra
SEQ ID NO 8 HDAd-mulI1 Ra
SEQ ID NO 9 HDAd-eqlI1 Ra
SEQ ID NO 10 huIl1Ra
SEQ ID NO 11 muIl1 Ra
SEQ ID NO 12 eqIl1Ra
SEQ ID NO 13 huIl1 Ra protein
SEQ ID NO 14 muIl1 Ra protein
SEQ ID NO 15 eqIl1Ra protein
hu=human; mu=murine; eq=equine

The invention claimed is:

1. A pharmaceutical composition, comprising a therapeutically effective amount of at least one helper-dependent adenoviral vector containing a nucleic acid sequence encoding proteoglycan 4 (PRG4), or a biologically active fragment thereof, which has chondoprotective activity, a left and a right adenoviral inverted terminal repeats (L ITR and R ITR), adenoviral packaging signal sequences and non-viral, non-coding stuffer nucleic acid sequences, wherein i. the at least one helper-dependent adenoviral vector additionally comprises a nucleic acid sequence encoding interleukin-1 receptor antagonist (II-1Ra), or ii the composition comprises a second helper-dependent adenoviral vector comprising a nucleic acid sequence encoding Il-1Ra;

wherein PRG4 expression is controlled by an elongation factor 1 alpha (EF 1 alpha) promoter and expression of Il-1Ra is controlled by an NF-κB promoter, and wherein the at least one helper-dependent adenoviral vector containing a nucleic acid sequence encoding PRG4, comprises a nucleic acid sequence which has at least 90% sequence homology with the nucleic acid sequence set forth in SEQ ID NO: 1, or SEQ ID NO: 2.

2. The pharmaceutical composition according to claim 1, wherein the nucleic acid sequence encoding PRG4 comprises a nucleic acid sequence set forth in SEQ ID NO 3, or SEQ ID NO 4, or a biologically active fragment thereof, or a homolog thereof from any other species, or a nucleic acid sequence which has at least 90% sequence homology with a nucleic acid sequence set forth in SEQ ID NO 3, or SEQ ID NO 4, or a biologically active fragment thereof, wherein the PRG4 encoded by the biologically active fragment of SEQ ID NO 3, or SEQ ID NO 4, or a nucleic acid sequence which has at least 90% sequence homology with a nucleic acid sequence set forth in SEQ ID NO 3, or SEQ ID NO 4, or a biologically active fragment thereof, has chondoprotective activity.

3. The pharmaceutical composition according to claim 1, wherein the amino acid sequence of PRG4 comprises an amino acid sequence set forth in SEQ ID NO 5, or SEQ ID NO 6, or a biologically active fragment thereof, or a homolog thereof from any other species, or an amino acid sequence which has at least 90% sequence homology with an amino acid sequence set forth in SEQ ID NO 5, or SEQ ID NO 6, or a biologically active fragment thereof, wherein the amino acid sequence of PRG4, which comprises a biologically active fragment of the amino acid SEQ ID NO 5, or SEQ ID NO 6, or has at least 90% sequence homology with an amino acid sequence set forth in SEQ ID NO 5, or SEQ ID NO 6, or a biologically active fragment thereof, has chondoprotective activity.

4. The pharmaceutical composition according to claim 1, wherein the at least one helper-dependent adenoviral vector comprising the nucleic acid sequence encoding Il-1Ra, comprises a nucleic acid sequence which has at least 90% sequence homology with a nucleic acid sequence set forth in SEQ ID NO 7, or SEQ ID NO 8, or SEQ ID NO 9, or a biologically active fragment thereof, wherein the at least one helper-dependent adenoviral vector comprising the nucleic acid sequence encoding II-1Ra, which comprises a nucleic acid sequence which has at least 90% sequence homology with a nucleic acid sequence set forth in SEQ ID NO 7, or SEQ ID NO 8, or SEQ ID NO 9, or a biologically active fragment thereof, has II-1Ra activity of inhibiting inflammatory and cartilage destructive mediators.

5. The pharmaceutical composition according to claim 1, wherein the nucleic acid sequence encoding Il-1Ra comprises a nucleic acid sequence set forth in SEQ ID NO 10, or SEQ ID NO 11, or SEQ ID NO 12, or a biologically active fragment thereof, or wherein the nucleic acid sequence encoding for Il-1Ra comprises a nucleic acid sequence which has at least 90% sequence homology with a nucleic acid sequence set forth in SEQ ID NO 10, or SEQ ID NO 11, or SEQ ID NO 12, or a biologically active fragment thereof, wherein the Il-1Ra encoded by the biologically active fragment of SEQ ID NO 10, or SEQ ID NO 11, or SEQ ID NO 12, or the nucleic acid sequence which has at least 90% sequence homology with a nucleic acid sequence set forth in SEQ ID NO 10, or SEQ ID NO 11, or SEQ ID NO 12, or the biologically active fragment thereof, mediates II1-Ra activity of inhibiting inflammatory and cartilage destructive mediators.

6. The pharmaceutical composition according to claim 1, wherein the amino acid sequence of Il-1Ra comprises the amino acid sequence of human IL-1Ra (SEQ ID NO 13), murine IL-1Ra (SEQ ID NO: 14), equine IL-1Ra (SEQ ID NO: 15), or a biologically active fragment thereof, or a homolog thereof from any other species, which has Il-1Ra activity of inhibiting inflammatory and cartilage destructive mediators.

* * * * *

SEQUENCE LISTING

<160> NUMBER OF SEQ ID NOS: 41

<210> SEQ ID NO 1
<211> LENGTH: 33136
<212> TYPE: DNA
<213> ORGANISM: Artificial Sequence
<220> FEATURE:
<223> OTHER INFORMATION: HDV with human PRG4

<400> SEQUENCE: 1
aaacatcatc aataatatac cttattttgg attgaagcca atatgataat gagggggtgg 60
agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
ttccgggtca aagttggcgt tttgatatca agcttatcga taccgtaaac aagtctttaa 480
ttcaagcaag actttaacaa gttaaaagga gcttatgggt aggaagtagt gttatgatgt 540
atgggcataa agggttttaa tgggatagtg aaaatgtcta taataatact taaatggctg 600
cccaatcacc tacaggattg atgtaaacat ggaaaaggtc aaaaacttgg gtcactaaaa 660
tagatgatta atggagagga tgaggttgat agttaaatgt agataagtgg tcttattctc 720
aataaaaatg tgaacataag gcgagtttct acaaagatgg acaggactca ttcatgaaac 780
agcaaaaact ggacatttgt tctaatcttt gaagagtatg aaaaattcct attttaaagg 840
taaaacagta actcacagga aataccaacc caacataaaa tcagaaacaa tagtctaaag 900
taataaaaat caaacgtttg cacgatcaaa ttatgaatga aattcactac taaaattcac 960
actgattttg tttcatccac agtgtcaatg ttgtgatgca tttcaattgt gtgacacagg 1020
cagactgtgg atcaaaagtg gtttctggtg cgacttactc tcttgagtat acctgcagtc 1080
ccctttctta agtgtgttaa aaaaaaaggg ggatttcttc aattcgccaa tactctagct 1140
ctccatgtgc tttctaggaa acaagtgtta acccacctta tttgtcaaac ctagctccaa 1200
aggacttttg actccccaca aaccgatgta gctcaagaga gggtatctgt caccagtatg 1260
tatagtgaaa aaagtatccc aagtcccaac agcaattcct aaaaggagtt tatttaaaaa 1320
accacacaca cctgtaaaat aagtatatat cctccaaggt gactagtttt aaaaaaacag 1380
tattggcttt gatgtaaagt actagtgaat atgttagaaa aatctcactg taaccaagtg 1440
aaatgaaagc aagtatggtt tgcagagatt caaagaaaat ataagaaaac ctactgttgc 1500
cactaaaaag aatcatatat taaatatact cacacaatag ctcttcagtc tgataaaatc 1560
tacagtcata ggaatggatc tatcactatt tctattcagt gctttgatgt aatccagcag 1620
gtcagcaaag aatttatagc ccccccttgag cacacagagg gctacaatgt gatggcctcc 1680
catctccttc atcacatctc gagcaagacg ttcagtccta cagaaataaa atcaggaatt 1740
taatagaaag tttcatacat taaactttat aacaaacacc tcttagtcat taaacttcca 1800

-continued

```
caccaacctg ggcaatatag tgagacccca tgcctgcaaa aaaaaaaaaa ttagccaggc   1860
atggtagcat gtacctgtag tcccagctac ttgagaggtg aggtgggaaa atcactttag   1920
tgcaggatgt tgaggctgga gtgaactgtg attgtgccac tgcactccag cctggacaat   1980
agagcaagac cttgtctcaa aaaaatgcat taaaaatttt ttttaaatct tccacgtatc   2040
acatcctttg ccctcatgtt tcataaggta aaaaatttga taccttcaaa aaaaccaagc   2100
ataccactat cataattttt tttaaatgca aataaaaaca agataccatt ttcacctatc   2160
agactggcag gttctgatta aatgaaattt tctggataat atacaatatt aagagagact   2220
gtagaaactg ggccagtggc tcatgcctgt aatcccagca ctttgggagg ctgggtaaca   2280
tggcgaaccc tgtttctaca aaataaaaat attagctggg agtggtggcg cacacctata   2340
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaatttc aagctagatg tgcataataa taaaaatctg accttgcctt   3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
agatcttact tacctgtcca taattagtcc atgaggaata aacacccttt ccaaatcctc   3480
agcataatga ttaggtatgc aaaataaatc aaggtcataa cctggttcat catcactaat   3540
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
```

-continued

```
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tatttttca ttttcaatgt catttttatt agttaattta taatacccat   6240
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
```

-continued

```
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
ctatacagca ggcagaagtc aatattgatt tgtttttaaa gaaacatgta ctactttcat   6840
aagcagaaaa aatttctatt cttgggggaa aagattatgc cagatcctct aggattaaat   6900
gctgatgcat ctgctaaacc ttcacatatc agaacatatt tactatagaa agaatgaaaa   6960
tgggacattt gtgtgtcacc tatgtgaaca ttccaaaaat attttacaac aactaagtat   7020
tttataaatt ttatgaactg aaatttagtt caagttctag gaaaatacaa accttgctag   7080
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
aagttgtttt gttttattgc atcctagatt ttattttttt gatttatggt ttactttaag   7620
cataaaaaat ttgtcaatac aactcttccc aaaaggcata aacaaaaatt cataaaactt   7680
gcatcacttg agatacttca ggtatgaatt cacaactttg ttacaactta ctatatatat   7740
gcacacatat atatatattt gggtatattg ggggggttct aatttaagaa atgcataatt   7800
ggctatagac agacagttgt cagaacttgg caatgggtac gtgcaggttc attataccaa   7860
gtctacttgt agttgttcaa aatgtatcat aatacaaggc cgggcgaggt cgtcacgcct   7920
gtaatcccag cattttggga ggctaaggca ggaggattgc ttgaggtcag gagtttgtga   7980
ccagcctggg caacagagca agaccctgtc tccaaaaaga aaaaaaataa tttttttacaa   8040
aataaaaaca aaatgtatca tcagacgaaa ttaaataaga ggcaattcat ttaaatgaca   8100
acttttccca gcttgacatt taacaaaaag tctaagtcct cttaattcat atttaatgat   8160
caaatatcaa atactaattt tttttttttt tttttttttg agacggagtc tcgctctgtc   8220
gcccaggctg gagtgcagtg gcgcgatcct ggctcactgc aagctccgcc tcccgggttc   8280
acgccattct cctgcctcag cctcccgagt agctgggatt acagacatgc gccaccacgc   8340
ccggctaatt ttgtattttt agtagagatg gggtttctcc atgttggtca ggctggtctt   8400
gaatttccca cctcaggtga tctgcctgcc tcagcctcac aaagcagtag ctgggactac   8460
aggcacccac caccacactt ggttaattct tttgtatttt ttttgtaaag acgggatttc   8520
accatgttag ccaggatggt ctcgatctcc tgatctcatg atccgcccgc ctcagcctcc   8580
caaagtgctg ggattacagg cgtgagccac cccgcccggc catcaaatac taattcttaa   8640
atggtaagga cccactattc agaacctgta tccttatcac taatatgcaa atatttattg   8700
aatacttact atgtcatgca tactagagag agttagataa atttgataca gctaccctca   8760
cagaacttac agtgtaatag atggcatgac atgtacatga gtaactgtga acagtgttaa   8820
attgctattt aaaaaaaaag acggctgggc gctgtggctc atgcctgtaa tcccagcact   8880
ttgggaggcc aaggcaagtt gatcgctcga ggtcaagagt tcgagaccag cctggccaac   8940
```

-continued

```
gtggtaaaac cccgtctcta ctaaaaatac aaaaaaaaaa ttagccaggc atggtggcac   9000
aggcctgtaa tcccagctac tagggaggct gagacatgga gaactgcttg aatccaggag   9060
gcagaggtta cagtgagccg agatcatacc actacactcc agcctgagtg acagagcgag   9120
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc ttttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
```

-continued

```
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaaa aaagacatgt tggccagatg  11760
cggtggctca cacctgtaat cccagcactt tgggaggctg aggtgggcgg atcacccctg  11820
gcctgcccaa catggtgaaa ccccgtctct actaaaaaca caaaaattag ctgggcgtgg  11880
tggcgggcgc ctgtaattcc agctactcgg gaggctgagg caggagaatt gctagaaccc  11940
aggaggcaga gattgcagtg agctgagatt gcaccattgc actacagtct gggcaacaaa  12000
agtgaaactc catcttaaaa aaaaaaagac aatgttcgtg ggtccaaaca agacttaatg  12060
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta ccttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aatttttcct tttattagtg  12900
tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
agtagattat cttagtagta gtgaattatt gtaaatgtta gtaatttggc agccactggg  13080
cagaaaaata agaattgagg ctcaatattg atattaatgg tggtgattga cacataaatt  13140
ttatcaagtc tacacaatat aaaattacag aaaggtagaa gagtatacca gtacaacttc  13200
aacatatctt cactacaagg gagtaaaatg acatggccta gttactatct aatgaactgc  13260
agaaaactaa aagaaaactc caaggcaact cttctctgct gatctggttg gtccttttcc  13320
taccttttgc aatacccaga tacaaacaat ggatagaaaa caaagtagac ttgtagtatg  13380
caggtcacag tgctaaattc acagaaagaa acccctgaac tgaactgctc tatttcctgg  13440
tggtcacaaa gagtaattct ggtttacacc tacagattga tgtcaatcta caccctgttg  13500
ataacagtgt ggccaaggac aaaaaaaagg tgctccgttt taccaattct gtaaaaaatt  13560
attggcaggg taagctcggc tagggcagga ttacatttct aggactacca tccccgaaat  13620
ttagaagata ttatatccac ataaagcata tctttcacat taatttgcaa aaatctaaaa  13680
```

```
gctttttctt agctcaagtg tgtccaagtt taccctggca gtttaaaacg atagttacaa  13740
gcagcatggg ttgtatcaga cacatttgag ggccaatttc atgtaagtga tattgggcaa  13800
gttacttcaa ctatctgtgc ctccaaggtc atactagtgt ttatttacct aaagggtacc  13860
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
cttgagctca ggagttcaag accagcctgg acaacatggc aaaacaccat ctctacaaaa  14460
aatacaaata ttaggccggg cgcagtggct cacgcctgta atcccagcac tttgggaggc  14520
caaggcgggt ggatcacctg agatcaggag ttcgagagta gcctggccaa catggtgaaa  14580
cctcgtctct attaaaaata caaaaaatta gccaggcatg gtggcaggcg cctgtaatcc  14640
cagctactca gggggatgag gtaggagaat cgcttgaacc cgggaggcag aggttgcact  14700
gagccgagat catgccactg tactccagcc cgggcaacaa gagcgaaact ccatctcaaa  14760
aaataaataa ataaataaat aaaataaagt acaaatatta gccagggatg gtggtgcgca  14820
cctgtagtcc cagctacttg ggaggctgaa gtgggagaat cccctgagcc tggggagaat  14880
cacccgagcc cgggaagtcg aggctgcagt gagcagtgat tgtgccactg cactccatcc  14940
taggtgacag agtgagaccc tgtctcaaaa aaaagaaatt ggcagaatta agtaagttga  15000
tgtttagaga tgaaaaatca acatttttc ctcagcaact gaataaaaac aacagccact  15060
accatttttt tgagtaccta tttgtagcct attttttaac tggtattact cgagagagag  15120
agagctaggt tcgagacaga gctccttctc ttaataactg tatgacctag ggtatgtctg  15180
ttagcctctc tgaggcttca aaggttcctc atctgtaaaa tggtaataat cataccattg  15240
ctacagggct gttttgaaga ctaattagga ctatgtaagt aaacatgatg atggctatta  15300
ttactgttcc ccgccagggg ccatgcaagg gttgctgatt cacatagact gtcttataat  15360
cctctcaata actccaagag gtagccagca cctcagatat acataaaatg acttaagccc  15420
agagaggtga agtaagttgc ccacagccac acaactagta aatagcccaa acaagctgga  15480
ttcccagtta gactccgtta atagcactgc tctttacctt aagtcattac aatgcctaat  15540
atgaaataga atcgcttctt tcttagggtt caagtggtta attatttaat gtattcattc  15600
aacaaaccat catcgaggac ctcttacaag ccaagtactg tgctaagtgc tagagttacg  15660
gcggtgattc ctgcccttaa aaagttttag tgggagaaac aacaggtaac caggtcattg  15720
ccaaaacaac aaaaataatc ataataaagc aggctaaagc atatttaact ggccggggtt  15780
ttgactattt tagcaagcat gatcagaacg gttgaggagg gaggccagca gcttggccgg  15840
ttcaacaaac aagaaaaaac cagtgagggt ggagctaaga taccagaggc tgattacggt  15900
taagaatgtt cttgaaggta aggaccagat tctcattttc tatatcctgg ggcatcggtc  15960
agcatggaat ctggattcta gcacatgtga atttcggctt gaaatgacct aatgcctttt  16020
```

-continued

```
ccctagttcc ttcgtgtgtc aaatacgcat ggttaccgct accagagctg tagtggggct  16080
tcaatgaggc catgagcatc tccataaaga tgaactacag tgtgtgcaaa actaaaggca  16140
aaacctggtc cccacacgcc ctcccaggtg gtcgctttcc gtgccgaggc ccctccagag  16200
gtgccccgag aacctcacca tcgcacccca aacttccagg gaagggcctc tcccgagaaa  16260
gcccccacgc ccccaccccg cgccatcatt cccgaatctg ccctcggccc ctccccgcag  16320
cacgctcgca ggcggcacat gtcaaccaaa acgccatttc caccttctct tcccacacgc  16380
agtcctcttt tcccagggct cccccgagga gggacccacc ccaaaccccg ccattccgtc  16440
ctccctgccg ccctcgcgtg acgtaaagcc gaacccggga aactggccgc ccccgcctgc  16500
ggggttccct gggcccggcc gctctagaac tagtggatcc caattgaagg cctggtctaa  16560
atgactccaa aatcaccact taattcaaga gactgatttc cctgagtcag gccccttaaa  16620
gcagctattt caatgggaca gggaaacaac cctaggatct ggattagaat cacttggggg  16680
ctgccacacc cccagggctc tgatcctgcc cttctcccac acgcacattc acatactgct  16740
gcagtgacct tccatttcta atgggttcct gggccatctg tcaggtatag ggaatggaaa  16800
aggggttggg gaggctctgc ttcagaaagt ttgtgtcagg ggctcccaga gcctccacag  16860
atagatagca ggggtcccca ccctaccatg gcagctataa atgtgatcaa catttattgg  16920
cctaggatac agcagttagc aaaatgcctg atgtagttcc cactccgtgg aggttgcagg  16980
ctagccaaga agtcatgagt tcagcaaccc ttacgcacca gtgggatgag attggaccag  17040
gccgagggta gtcttgggaa cactcagcat ttgtctgagg gccagaagag gctgcttgcc  17100
ctcagacagg aggtcagcat ctttattgta gcccatgaca cctctacacc attgctcttc  17160
tggtcttatg gaagacatct ttgggcctga taacagcgga gtctgtgtcc cacttgtcca  17220
ggctggagtg ccacatcagg cacactccag ttgcagggac agcacagaca agtttcagga  17280
aggctggtgg cctccaggag gttaacctta taaggccaga ttgtaaccta gttgaaaaac  17340
atacacatgc catgataata aaagaaccta ggcaccatta caagagaaaa aatcattttt  17400
gtagatacga gcatggattc ttgggtgggt cagacacact gggcttgtgc tctgactgca  17460
ctgtctcccc tacctgacct tgggtaaacc ataagactgc tgcatgactc agtgtccacc  17520
ccaaaaaagt accggtagat attggccaca gtagatatca gctagagtgg actctcatga  17580
caatgagggg agatgtattc cccatcttag gcacctggga ctctaccttc catcttctgc  17640
tccgtgtctc tccatcccca ggctcttcag aactcaggga gtccagaatg tcagctccca  17700
gatttcagcc ttcagaaagg aaacccatta ccgttcagtt gaacaaatgt tgtctgagcc  17760
ccagatctgg gctcagaggc catctaggct atgagacaag aggggaacaa agcaccgtct  17820
gcactcactc accacactca cttgctgtcc caggtcacat ccatcgggta gagaatctaa  17880
gaggctgagc tagctcccgc caccagccca gcccacccca cctggcccct tccttccttc  17940
tacaaaatat gcaccacctg tcaaagggtg ggcagtgcca ggcctgcata cagagcactg  18000
agtgtaaaag cagacatgga ccctgacctc caggagcttc caattttctt gaagagacaa  18060
atcagctggc atttcagtcc agtgtgatct gctcttggtg agcacagacc tagggagttg  18120
gggcagcttc ccagaagaac tgcagtccag gctgagggca gagaaatgag gggaatggcg  18180
aggaattggg gagcaggggg gagctcagta gagagccaag ggcgggaggt gagaagtccg  18240
tgttgggcca ggagctaccc tccggtggcc acagccgaag tcgaggatgc ctttggaact  18300
catccccact tctctctttc tgtatgtagc cgtccaagaa caagtcacct ccaagtgtag  18360
ccggatcaag gcaagccccc catctagcaa gcacttgatg ccacccagaa ctgggcttct  18420
```

```
tcagaacaat ctgagtccag gaatgatccc actcaccagg caccagagct gcgagggcat  18480
gggagtgatc tcaccaactc tggggaagcg gcaaggaatt ttcacctcca gcccccagtg  18540
tcccatcctc tcacactcag gccagactcc cctgggcaga cttgactctg tctgccagca  18600
tatgcagagc cccaaggcca ccccaccaga agtgcccctg cctgggttct gtcccagctc  18660
cctgggcacc cagtccttga gtccccacca gctcagacgg cctagtgtgc caagaatgcc  18720
cactgcgttc aacaatgctg catgggtcac agcggcagca gctgtgacca cagcagtttc  18780
ggggaaaaca cccctcagcc aagtggataa tagcgttcag cagcactcac cttctggcca  18840
ggcctgcctt cagaggccat ctgattggga ggcacaagtg cccgctgcga tgggaacaca  18900
agtgcccctg gccaacaacc ccagcttcag cctgctgggc agccagagcc tcaggcagag  18960
cccggtacag ggcccggtgc ctgtagcaaa caccaccaag ttcctccagc agggtatggc  19020
cagctttagt cccctgagcc ccatacaggg catcgagcca ccaagctatg tggctgctgc  19080
tgccaccgct gctgctgctt ctgccgttgc tgccagccag ttcccaggtc cgttcgacag  19140
aacggatatt ccccctgagc tgccacctgc cgactttttg cgccagcccc aacccccact  19200
aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcaccca  19380
ggatgctggg gcactttaaa tctgagcagg atgcccatag aaacccccat ggtgacatca  19440
ctctaggaag tggtgtcgat ccatacccgc agttgtctcc cgttacaatt tgagtggtgt  19500
tgtcagccca tgcttatccc tctctctacc tgtgacaaaa tggaaagctg gtgatttttc  19560
aagctacgtg tacatatttg aaaattttgt aaatggtttt cctaaacatt aatgacagaa  19620
gtatttatac ttcattttgt gactttgtaa ataaagcgac ggcttttgtt tcagtagagt  19680
tgtgtttact atgcattgtt ttgtgtttat tatacaatgt tacaaatatg cagaccgtgt  19740
tgtttgctcc agtgatacct tgttaagcta ggtggctgag tcgcttatgg ttttaatgca  19800
atgagcaatg tggatatgac caagagttgt tgtgcaagtt gacaaatgcc aaatagaaaa  19860
ccacttggcc atttatttct atgttcacta aaaatcctat tgccttgtgt gattcttaat  19920
ctcttttgcg aacctttcag tctccgctag ctctttccta atgagcttta cagcagaagc  19980
tgttttatcg ttaagtgccc cacagagaca ctttaccagg aggctgggag agttctccag  20040
atttgggaga ggcgcagaga cagtgtgtga gccgagccct gtctcagcaa tccacctgga  20100
ggagctagag tatcctcctc cctttaccat tcagaccgag agaaaaagcc cagcttgtgt  20160
gcaccctcgt ggggttaagg cgagctgttc ctggtttaaa gcctttcagt atttgttttg  20220
atgtaaggct ctgtggtttg ggggggaaca tctgtaaaca ttattagttg atttggggtt  20280
tgtctttgat ggtttctatc tgcaattatc gtcatgtata tttaagtgtc tgttatagaa  20340
aacccacacc cactgtcctg taaacttttc tcagtgtcca gactttctgt aatcacattt  20400
taattgccac ctcgtatttc acctctacat ttgaaatctg gcgtctgttt caagccagtg  20460
tgttttttct tcgttctgta ataaacagcc aggagaaaag tgcctctatg tttttatttt  20520
tcaagggagt attcagtacc tacaaaccca agtcaggaag cctgctagtg gctttggttc  20580
tttcagaggc tgctcgatgc cttgtgtgtc agaaagaaag attcagcagt tttgcatcat  20640
ggcaaagaag cctgttattt tggggctcag cccctcattt tatagaggat gaaacagagg  20700
gggatgggag gtcacaaaga caactgcccc gggagcaggt gtgggggaga cttgccctga  20760
```

```
gggtctagac gctctgcacc accgtcctgt ctcccttgct gaagaccaca catgcccttc  20820
tttgaccaga ccctgccacc tgataggcca ggacctggta ggcgggtacc caggtttcat  20880
ggatggaacc acatctcccc aaaagtgggg aggtagctac tgggatgcac gcctcccgcc  20940
atgtgctata ggagagcagc tgaagcaaca gttgggatca gatgtagtca caattgaatg  21000
catcatcaca tttatccctc taagtggctg ggagagttga tatcctcatc cctaaggtac  21060
aaaatgttcc aatttgatca gtggctttca ggagctgaga aaggcatgtg ctctgaggca  21120
gagctgttat gtcccgcaga gcctaaaaat gctctaagaa catgctccct gccaaaattc  21180
tcaatggctg tgacaaggga caacgatcga ccaatggggg tggaagcaga cctccgcagt  21240
ccaggggcca gagctaggac agaggggtcg gagaaagagt cattttccca acactccagc  21300
tcttggccag tcctcacaca gtcccctcct gcttcctgct gagagagata tcctcatagg  21360
tctgggtaaa gtccttcagt cagctttcat tccctgtcac caactttgtc tctgttctcc  21420
ctgcccgtct caggcagcac tcctcaggaa acctctccaa gagccagcct cactgcagcg  21480
cccactattg tccctctgcc tcaagtgtcc catccatgcc aggccccagg caggctgcag  21540
ctttccctca gggccacacc aaagcacttg ggctcagctg tgctgtcccc ctccatcact  21600
gagctcaggg gcagcagggg tggggtgcca ggaggcccat tcacccttct ctggctctgt  21660
gttggaccca cctgcccagc cactgctgct tagaacctac ccgctgggaa aatgaagccc  21720
tcccggaggg gccacctcaa cctgagagcc tcacggatca cagttgtccc cactcagctc  21780
tgccagccct cagagaccca tagataaaag ctgagcttgg ctcgcagagc tggttccatc  21840
ttccattccc agagggttca acttcctacc ccaaccacac agggaacctc aaggctgagc  21900
cagtgtgggc tgcagtgcag accagcttcc tggacacgtc ctgccacctg accccaggct  21960
ggcctcactg cccctggcac tcctgaccct atcctcattc ctcctggcag tgcgtgttct  22020
gccattccgc tttcccttag ctgtcctctc actgtactgt cagcttctcc ttttccaggt  22080
gccccccagg ggctttccac atgaccctgt caccccacag cccatccagc accaattcca  22140
gctctctgcc acccttcaaa ggagtgacag tgccctgctt cacctcccac tcacccctca  22200
acccagagca atctggctcc agtcttgcct ccttcccccct aagtactcta gtcacagttc  22260
caaattcctc ctggtcataa agccaaatga agcttcctgg tcctcagcgg acttgccact  22320
tcagcagtac tggactctct cctcccagaa acctgtttcc ccttggctcc tggagcccac  22380
actctgctgg aatccttctg cctctctggc ctgtagcctg gccctctctc ccaacctgag  22440
gtccattctc tcctgctcct ccacaagatg ttgctccttc cattacttcc tccctctcaa  22500
ccaaagctcc ttcattagct ctttatcttc tggtttcttc ccctgggcag acgaatggat  22560
tcaagagcct gtggcccagc agcccagcac tccaggatct cagcacttca gcatcccagt  22620
accctagcat ctcaataccc cagcacccca gcaccatagt attccagcac cccattgtcc  22680
aagcatctca gcactccagc atcccagcac cccaacactc cagcagccca gaatctcagc  22740
accctagcac tgcagcatct caggacccca gcacttcagc atcccagcac actagtactc  22800
cagcatctcg gcaccccagc acctaggcat cccaacaccc agcaccccag cacttaagca  22860
tcccaccact acagtatctc aacactccag caccccagca ccatagtgtt ccagcacccc  22920
agcatcccaa caccccagca cttaagcatc ccaacacctc ggcatcccaa caccccagca  22980
ctgcagcatc tcagcacctt agcatcccag tgccctagca tctcaatgct ccagcacacc  23040
agtactacag tattccagca ccccagcact ccagcatctc agcactgcag cactgcagca  23100
ctccagcatc ccaaaatccc agcatcccaa caccccagca gaccagcaga ccagcatctc  23160
```

-continued agcaccgcag catccaagga ctatcccagc atcccagcaa cccagcacct cagcatccca 23220
acaccccagc atttcagcat ggcaacaccc cagtacccca gcacttcagc accccagtat 23280
cccagcatct cagcgaccca gtatcacaaa acctcagcat cctagcaccc cagcacccca 23340
gcaccttagc accttagcat cccagcatct cagcgcctca gcatcttgat attctggctg 23400
aggtcagcgt ggtgtatcta gtcagggtcc taactttcac ttcgcaggga aatgctgctg 23460
gactgggtct catgttgggc tgaagctctc tagacccctt gaagacagca taaaagagct 23520
tggagacgct gggtgtcccc catggaagag ttcactctca tcctgctttg acaacagcct 23580
tctctggggt ccctcacggg cccctctttc ttactgcaag tttgtctctg agaagactgt 23640
gatgcagaag tcactcagct gcctgtggct cctgaagagc tgaaggtgga ggcctgtagg 23700
cctccctatg agaggcgcag aaaaaaccat gattgctagt ggggaggtgc tccctctaca 23760
acccactcca taatctgccc ccgcccagct ctgaggccag ccccagggga aaatgccaga 23820
tccccaggga ggtgtgtgag acctcagggg ctccctcctc ccttacagca ggctcaggcc 23880
cctgggggcc tcagggccaa ggtctgtggg taagctacta tctctcactt gtcctctagc 23940
cacaaaagcc agggagatct ggcaatggac atgaggttct gaagaagcac atatgactgg 24000
cttcctaatg cgtggttgtt cagtgattca ataaacacgc atgggccagg catggggaaa 24060
tagacaaaca tgatccccaa cctctcccag agtgaactgg gagggaggag tgttcatccc 24120
tcaggattac accagagaaa caaaccagca ggagatatat atggttttgg ggggtcaaga 24180
aagaggaaaa acctggcaag gcaagtccaa aatcatagga caggctgtca ggaagggcag 24240
cctggaacct ctcaagcagg agctgatgct gcagtccaca ggcagaattt cttcttcctc 24300
ggggaaatct cagctttgtt cttaaggcct ttcaactgat tggctgaggt ctgccccttc 24360
ccccacattc tccaggataa tcttccttac ttaaagtcaa ctattaatca cagctacaaa 24420
atcccttcac agctacacat agatcagtgt ttgattgacg aacagcccct acagcctagc 24480
caagttgaca cataaaacta accatcacag ggggacaaat gatgtaaaca catcaacaaa 24540
taaaacagta acaagttaag gtctatggaa aaaacacaga aggggcagag agaaagaaag 24600
caagaaggag agtcccagtt tgctagggct tgtgggaagt ggggagcagt tctctttagc 24660
taggatattt gggaaaggca tatctgaagg agtgatattt gagcttagat taaaagatgg 24720
gaaggagcaa gccatgcaaa gagctaggat gttccaagca gagacggaac agcaagtgca 24780
aatgtcagga ggaatagaag gaggctggtg ggtggggtcc agtgagcaag aggagggcag 24840
gcaggagagg ggatggggag gtgggcaggc ccagaccacc cagggccctg gagactatcc 24900
tgatccaaca agggaagcct tgagtcactt cagtgtccat gtggagaatg gacctcagac 24960
tgaatgaggg aggcagtaag gagggcctct acctccaggg cttcgccctg tggactgcgc 25020
atagacatct ccaactcaga aagtctgaac caaactttcc atagttcccc caagtctggg 25080
catcctccta ctcagtgaaa ggcagccatc acacctccct gccctgctcc cggatgcccc 25140
aaatcctctt ggtctccaag tccagaacct gagacttgtc cttgatgttt gtctttccct 25200
cacccttctt gtattctggg aagatgggtt tttttccccc agatgaatct gtaaaacttc 25260
tgtgatcaca ataaaaattc tggcagtatt attttctgga acatgacaaa gtgattcaaa 25320
attatttatc tggaagacta caaaacaaga atagccagga aatttctaaa aagaaagaag 25380
aaggaggagg agaaagaagg aggaggaaaa ggaggagaag aagaaaagaa aaagaaccaa 25440
gaaagggttc tagctctacc aaatattaaa acatatcatg aagctattta aaacaatatg 25500
gttgtggata ctgaaaaaga tgtgaataaa gtggaaggaa aataaataga aatgcacatg 25560
gggattgaga ctgtgaaaaa ggcagcatct cacatcagtg agggatgttc aacacctggt 25620
gttgggaaaa ctggctagtc atttaaacca aacaactggg tcctctacct cactcctgac 25680
attaagatac atttagatga ttcaaagagt aagacagaaa aaataacacg tgaaaacact 25740
atcagaaaac aacgtgggcc aggtgtggtg ggtcacgcct gtaatcccag cactttggga 25800
ggccgaggca gacagatcac ctgaggtggg gagttcaaga ccagcctgac caacatggtg 25860
aaatcctgtc tctactaaaa atacaaaatt agctgagcgt ggtggcgcat gcctgtaatc 25920
ccagctactc aggaggccga ggcaggagaa tcacttgaac ctgggaggca gaggttgtgg 25980
tgagccgaga tcacgccatt gcactccagc ctgggcaaca agagtgaaaa tccatctaaa 26040
aaaaaaaaaa aaagccaagg tggatatttt tatagtatca gggtagatca agcttctcca 26100
atcatgacat gaaacccaga aaccataaaa gaaaagaatg ataaaattgc ccacgtaaag 26160
taaaaagctt gcacacagaa aaacaccata caggttacaa gatgagcagc aaaatcagag 26220
aaaaaacatt gcaattcagg acacacagag gctattgttc ctaatattta aaaataaaag 26280
tagtggattg tctacaaaaa gatgaagaca agaatttcag aaaaccaaat actgcatgtt 26340
ttcacttaca agtggaagct aaacactgag tacacgtgta cacaaagaat ggaaccatag 26400
gccaggcacc gtggctcacg cctgtaatcc cagtactttg cgaggccgaa gcgggcggat 26460
cacctgaggt gaggagttcg agaccatcct ggccaacatg gtgaaaccca gtctctacta 26520
aaaatacaaa aattagccgg gcgtggtggt gggtgcctgt aatcccagct actcgggagg 26580
ctgcggcagt agaatcgctt gaaccctgga ggtggacctt gcagtgagcc gagatcgcac 26640
cactgcactc cagcctgggc aacagagtga gactccatct caaaaaaaaa aaaaaggaat 26700
agaacaatag acactggggc ctacttgagg gaggagggtg aggatcaaaa acctgcctat 26760
caggtactat gcttattacc tgggtggtga aataatctgt acaccaaacc ccagtgacat 26820
gcaatttacc gatgtaacaa acctgcccat gtacccgctg aacctaaaat aaaagttgga 26880
aaaaaatata gaaattttct ttgtaatagc caaaaactgc aaacagccca ggtgtctatt 26940
agtagaatgc ataaacaaac tcgggcatgt tcatacaatg taaaactact catcaataaa 27000
aagtgatact tctcagcaat gaaaagaaac tagctactga taccagctac aacatggatg 27060
gatttcaagt gctttatgat gagagcaaga agccagacac aaaagtgtct atatatatat 27120
acagtatata tacgtatata tacacatata tacagtatat atatacatat acatgtatat 27180
atatactgta tatatactgt atatatatac acagtatata tatacatata tacagtgtat 27240
atatactgtg tatatataca tgtatatata ctgtgtatat atacatgtat atatactgtg 27300
tatatataca tgtatatata ctgtgtatat atacatgtat atatatgtat actgtatata 27360
tactgtatat atatatacac atatatacag tatatatata cagtatatac tgtatatata 27420
cagtatatac gtgtatatat acatatatac agtatatatg taaatataca tatatacagt 27480
atatatgtaa atatacatat atacatgtat atatatacac tatatatata catatatagt 27540
gtatatatac atatatacat gtatatattt actatatgat tccatttata taaagtgcca 27600
aaacagtcaa aaataatcta tgtggaaaaa atcaacaaag ggatccccccg ggctgcagga 27660
attcgatggc gcgccgtcga cccaacgcgt tgggagctct ccggatccaa gcttcgaggg 27720
gctcgcatct ctccttcacg cgcccgccgc cctacctgag gccgccatcc acgccggttg 27780
agtcgcgttc tgccgcctcc cgcctgtggt gcctcctgaa ctgcgtccgc cgtctaggta 27840
agtttaaagc tcaggtcgag accgggcctt tgtccggcgc tcccttggag cctacctaga 27900
ctcagccggc tctccacgct ttgcctgacc ctgcttgctc aactctacgt ctttgtttcg 27960
ttttctgttc tgcgccgtta cagatccaag ctgtgaccgg cgcctacgta agtgatatct 28020
actagattta tcaaaaagag tgttgacttg tgagcgctca caattgatac ttagattcat 28080
cgagagggac acgtcgacta ctaaccttct tctctttcct acagctgaga tcaccggcga 28140
aggagggcca ccatgcatgg catggaaaac acttcccatt tacctgttgt tgctgctgtc 28200
tgttttcgtg attcagcaag tttcatctca agatttatca agctgtgcag ggagatgtgg 28260
ggaagggtat tctagagatg ccacctgcaa ctgtgattat aactgtcaac actacatgga 28320
gtgctgccct gatttcaaga gagtctgcac tgcggagctt tcctgtaaag gccgctgctt 28380
tgagtccttc gagagaggga gggagtgtga ctgcgacgcc caatgtaaga agtatgacaa 28440
gtgctgtccc gattatgaga gtttctgtgc agaagtgcat aatcccacat caccaccatc 28500
ttcaaagaaa gcacctccac cttcaggagc atctcaaacc atcaaatcaa caaccaaacg 28560
ttcacccaaa ccaccaaaca agaagaagac taagaaagtt atagaatcag aggaaataac 28620
agaagaacat tctgtttctg aaaatcaaga gtcctcctcc tcctcctcct cttcctcttc 28680
ttcttcaaca attcggaaaa tcaagtcttc caaaaattca gctgctaata gagaattaca 28740
gaagaaactc aaagtaaaag ataacaagaa gaacagaact aaaaagaaac ctaccccca 28800
accaccagtt gtagatgaag ctggaagtgg attggacaat ggtgacttca aggtcacaac 28860
tcctgacacg tctaccaccc aacacaataa agtcagcaca tctcccaaga tcacaacagc 28920
aaaaccaata aatcccagac ccagtcttcc acctaattct gatacatcta aagagacgtc 28980
tttgacagtg aataaagaga caacagttga aactaaagaa actactacaa caaataaaca 29040
gacttcaact gatggaaaag agaagactac ttccgctaaa gagacacaaa gtatagagaa 29100
aacatctgct aaagatttag cacccacatc taaagtgctg gctaaaccta cacccaaagc 29160
tgaaactaca accaaaggcc ctgctctcac cactcccaag gagcccacgc ccaccactcc 29220
caaggagcct gcatctacca cacccaaaga gcccacacct accaccatca agtctgcacc 29280
caccaccccc aaggagcctg cacccaccac caccaagtct gcacccacca ctcccaagga 29340
gcctgcaccc accaccacca aggagcctgc acccaccact cccaaggagc ctgcacccac 29400
caccaccaag gagcctgcac ccaccaccac caagtctgca cccaccactc ccaaggagcc 29460
tgcacccacc acccccaaga agcctgcccc aactaccccc aaggagcctg cacccaccac 29520
tcccaaggag cctacaccca ccactcccaa ggagcctgca cccaccacca aggagcctgc 29580
acccaccact cccaaagagc ctgcacccac tgcccccaag aagcctgccc caactacccc 29640
caaggagcct gcacccacca ctcccaagga gcctgcaccc accaccacca aggagccttc 29700
acccaccact cccaaggagc ctgcacccac caccaccaag tctgcaccca ccactaccaa 29760
ggagcctgca cccaccacta ccaagtctgc acccaccact cccaaggagc cttcacccac 29820
caccaccaag gagcctgcac ccaccactcc caaggagcct gcacccacca cccccaagaa 29880
gcctgcccca actaccccca aggagcctgc acccaccact cccaaggaac ctgcacccac 29940
caccaccaag aagcctgcac ccaccactcc caaagagcct gccccaacta cccccaagga 30000
gactgcaccc accaccccca agaagctcac gcccaccacc cccgagaagc tcgcacccac 30060
cacccctgag aagcccgcac ccaccacccc tgaggagctc gcacccacca cccctgagga 30120
gcccacaccc accacccctg aggagcctgc tcccaccact cccaaggcag cggctcccaa 30180
cacccctaag gagcctgctc caactacccc taaggagcct gctccaacta cccctaagga 30240

```
gcctgctcca actaccccta aggagactgc tccaactacc cctaaaggga ctgctccaac  30300
taccctcaag gaacctgcac ccactactcc caagaagcct gcccccaagg agcttgcacc  30360
caccaccacc aaggagccca catccaccac ctgtgacaag cccgctccaa ctacccctaa  30420
ggggactgct ccaactaccc ctaaggagcc tgctccaact accccctaagg agcctgctcc  30480
aactacccct aaggggactg ctccaactac cctcaaggaa cctgcaccca ctactcccaa  30540
gaagcctgcc cccaaggagc ttgcacccac caccaccaag ggcccacat ccaccacctc  30600
tgacaagcct gctccaacta cacctaagga gactgctcca actaccccca aggagcctgc  30660
acccactacc cccaagaagc ctgctccaac tactcctgag acacctcctc caaccacttc  30720
agaggtctct actccaacta ccaccaagga gcctaccact atccacaaaa gccctgatga  30780
atcaactcct gagctttctg cagaacccac accaaaagct cttgaaaaca gtcccaagga  30840
acctggtgta cctacaacta agactcctgc agcgactaaa cctgaaatga ctacaacagc  30900
taaagacaag acaacagaaa gagacttacg tactacacct gaaactacaa ctgctgcacc  30960
taagatgaca aaagagacag caactacaac agaaaaaact accgaatcca aaataacagc  31020
tacaaccaca caagtaacat ctaccacaac tcaagatacc acaccattca aaattactac  31080
tcttaaaaca actactcttg cacccaaagt aactacaaca aaaaagacaa ttactaccac  31140
tgagattatg aacaaacctg aagaaacagc taaaccaaaa gacagagcta ctaattctaa  31200
agcgacaact cctaaacctc aaaagccaac caaagcaccc aaaaaaccca cttctaccaa  31260
aaagccaaaa acaatgccta gagtgagaaa accaaagacg acaccaactc cccgcaagat  31320
gacatcaaca atgccagaat tgaaccctac ctcaagaata gcagaagcca tgctccaaac  31380
caccaccaga cctaaccaaa ctccaaactc caaactagtt gaagtaaatc caaagagtga  31440
agatgcaggt ggtgctgaag gagaaacacc tcatatgctt ctcaggcccc atgtgttcat  31500
gcctgaagtt actcccgaca tggattactt accgagagta cccaatcaag gcattatcat  31560
caatcccatg ctttccgatg agaccaatat atgcaatggt aagccagtag atggactgac  31620
tactttgcgc aatgggacat tagttgcatt ccgaggtcat tatttctgga tgctaagtcc  31680
attcagtcca ccatctccag ctcgcagaat tactgaagtt tggggtattc cttcccccat  31740
tgatactgtt tttactaggt gcaactgtga aggaaaaact ttcttcttta aggattctca  31800
gtactggcgt tttaccaatg atataaaaga tgcagggtac cccaaaccaa ttttcaaagg  31860
atttggagga ctaactggac aaatagtggc agcgctttca acagctaaat ataagaactg  31920
gcctgaatct gtgtattttt tcaagagagg tggcagcatt cagcagtata tttataaaca  31980
ggaacctgta cagaagtgcc ctggaagaag gcctgctcta aattatccag tgtatggaga  32040
aacgacacag gttaggagac gtcgctttga acgtgctata ggaccttctc aaacacacac  32100
catcagaatt caatattcac ctgccagact ggcttatcaa gacaaaggtg tccttcataa  32160
tgaagttaaa gtgagtatac tgtggagagg acttccaaat gtggttacct cagctatatc  32220
actgcccaac atcagaaaac ctgacggcta tgattactat gccttttcta aagatcaata  32280
ctataacatt gatgtgccta gtagaacagc aagagcaatt actactcgtt ctgggcagac  32340
cttatccaaa gtctggtaca actgtcctta gaaaaaaaaa aaaaaaaagg ccacatgtgc  32400
tcgagctgca ggtcgcggcc ctagctcgac atgataagat acattgatga gtttggacaa  32460
accacaacta gaatgcagtg aaaaaaatgc tttatttgtg aaatttgtga tgctattgct  32520
ttatttgtga aatttgtgat gctattgctt tatttgtaac cattataagc tgcaataaac  32580
aagttaacaa caacaattgc attcatttta tgtttcaggt tcagggggag gtgtgggagg  32640
```

-continued

```
tttttaaag caagtaaaac ctctacaaat gtggtagatc atttggggta ccgaattcct  32700

cgagtctaga ggagcatgcg acgtcggcgc gcctaccagt aaaaaagaaa acctattaaa  32760

aaaacaccac tcgacacggc accagctcaa tcagtcacag tgtaaaaaag ggccaagtgc  32820

agagcgagta tatataggac taaaaaatga cgtaacggtt aaagtccaca aaaaacaccc  32880

agaaaaccgc acgcgaacct acgcccagaa acgaaagcca aaaaacccac aacttcctca  32940

aatcgtcact tccgttttcc cacgttacgt cacttcccat tttaagaaaa ctacaattcc  33000

caacacatac aagttactcc gccctaaaac ctacgtcacc cgccccgttc ccacgccccg  33060

cgccacgtca caaactccac cccctcatta tcatattggc ttcaatccaa aataaggtat  33120

attattgatg atgttt                                                  33136
```

<210> SEQ ID NO 2
<211> LENGTH: 31815
<212> TYPE: DNA
<213> ORGANISM: Artificial Sequence
<220> FEATURE:
<223> OTHER INFORMATION: HDAd with murine PRG4

<400> SEQUENCE: 2

```
aaacatcatc aataatatac cttattttgg attgaagcca atatgataat gagggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240

tagtaaattt gggcgtaacc gagtaagatt tggccatttt cgcgggaaaa ctgaataaga    300

ggaagtgaaa tctgaataat tttgtgttac tcatagcgcg taatatttgt ctagggccgc    360

ggggactttg accgtttacg tggagactcg cccaggtgtt tttctcaggt gttttccgcg    420

ttccgggtca aagttggcgt tttgatatca agcttatcga taccgtaaac aagtctttaa    480

ttcaagcaag actttaacaa gttaaaagga gcttatgggt aggaagtagt gttatgatgt    540

atgggcataa agggttttaa tgggatagtg aaaatgtcta taataatact taaatggctg    600

cccaatcacc tacaggattg atgtaaacat ggaaaaggtc aaaaacttgg gtcactaaaa    660

tagatgatta atggagagga tgaggttgat agttaaatgt agataagtgg tcttattctc    720

aataaaaatg tgaacataag gcgagtttct acaaagatgg acaggactca ttcatgaaac    780

agcaaaaact ggacatttgt tctaatcttt gaagagtatg aaaaattcct attttaaagg    840

taaaacagta actcacagga aataccaacc caacataaaa tcagaaacaa tagtctaaag    900

taataaaaat caaacgtttg cacgatcaaa ttatgaatga aattcactac taaaattcac    960

actgattttg tttcatccac agtgtcaatg ttgtgatgca tttcaattgt gtgacacagg   1020

cagactgtgg atcaaaagtg gtttctggtg cgacttactc tcttgagtat acctgcagtc   1080

ccctttctta agtgtgttaa aaaaaaaggg ggatttcttc aattcgccaa tactctagct   1140

ctccatgtgc tttctaggaa acaagtgtta acccacctta tttgtcaaac ctagctccaa   1200

aggacttttg actccccaca aaccgatgta gctcaagaga gggtatctgt caccagtatg   1260

tatagtgaaa aaagtatccc aagtcccaac agcaattcct aaaaggagtt tatttaaaaa   1320

accacacaca cctgtaaaat aagtatatat cctccaaggt gactagtttt aaaaaaacag   1380

tattggcttt gatgtaaagt actagtgaat atgttagaaa aatctcactg taaccaagtg   1440

aaatgaaagc aagtatggtt tgcagagatt caaagaaaat ataagaaaac ctactgttgc   1500
```

-continued cactaaaaag aatcatatat taaatatact cacacaatag ctcttcagtc tgataaaatc 1560
tacagtcata ggaatggatc tatcactatt tctattcagt gctttgatgt aatccagcag 1620
gtcagcaaag aatttatagc ccccttgag cacacagagg gctacaatgt gatggcctcc 1680
catctccttc atcacatctc gagcaagacg ttcagtccta cagaaataaa atcaggaatt 1740
taatagaaag tttcatacat taaactttat aacaaacacc tcttagtcat taaacttcca 1800
caccaacctg ggcaatatag tgagacccca tgcctgcaaa aaaaaaaaaa ttagccaggc 1860
atggtagcat gtacctgtag tcccagctac ttgagaggtg aggtgggaaa atcactttag 1920
tgcaggatgt tgaggctgga gtgaactgtg attgtgccac tgcactccag cctggacaat 1980
agagcaagac cttgtctcaa aaaaatgcat taaaaatttt ttttaaatct tccacgtatc 2040
acatcctttg ccctcatgtt tcataaggta aaaaatttga taccttcaaa aaaaccaagc 2100
ataccactat cataattttt tttaaatgca aataaaaaca agataccatt ttcacctatc 2160
agactggcag gttctgatta aatgaaattt tctggataat atacaatatt aagagagact 2220
gtagaaactg ggccagtggc tcatgcctgt aatcccagca ctttgggagg ctgggtaaca 2280
tggcgaaccc tgtttctaca aaataaaaat attagctggg agtggtggcg cacacctata 2340
gtcccagcta ctcaggaggc tgaggtggaa ggatcgcttg aacccaggag gttgagactg 2400
cagtgaactg tgatcattct gctgcactgc accccagcct gggcaacaga gaccttgtct 2460
caaaaaaaaa aaaaaaagag acaaattgtg aagagaaagg tactctcata taacatcagg 2520
agtataaaat gattcaactt cttagaggaa aatttggcaa taccaaaata ttcaataaac 2580
tctttcccct tgacccagaa attccacttg aataaagctg aacaagtacc aaacatgtaa 2640
aagaatgttt cttctagtac agtcggtaag aacaaaatag tgtctatcaa tagtggactg 2700
gttaaatcag ttatggtatc tccataagac agaatgctat gcaacccttta aaatatatta 2760
gatagctcta gacacactaa tattaaaagt gtccaataac atttaaaact atactcatac 2820
gttaaaatat aaatgtatat atgtactttt gcatatagta tacatgcata ggccagtgct 2880
tgagaagaaa tgtgtacaga aggctgaaag gagagaactt tagtcttctt gtttatggcc 2940
tccatagtta gaatatttta taacacaaat attttgatat tataatttta aaataaaaac 3000
acagaatagc cagacataca atgcaagcat tcaataccag gtaaggtttt tcactgtaat 3060
tgacttaaca gaaaatttc aagctagatg tgcataataa taaaaatctg accttgcctt 3120
catgtgattc agccccagtc cattaccctg tttaggactg agaaatgcaa gactctggct 3180
agagttcctt cttccatctc ccttcaatgt ttactttgtt ctggtcccta cagagtccca 3240
ctataccaca actgatacta agtaattagt aaggccctcc tcttttattt ttaataaaga 3300
agattttaga aagcatcagt tatttaataa gttggcctag tttatgttca aatagcaagt 3360
actcagaaca gctgctgatg tttgaaatta acacaagaaa aagtaaaaaa cctcatttta 3420
agatcttact tacctgtcca taattagtcc atgaggaata aacacccttt ccaaatcctc 3480
agcataatga ttaggtatgc aaaataaatc aaggtcataa cctggttcat catcactaat 3540
ctgaaaaaga aatatagctg tttcaatgag agcattacag gatacaaaca tttgattgga 3600
ttaagatgtt aaaaaataac cttagtctat cagagaaatt taggtgtaag atgatattag 3660
taactgttaa ctttgtaggt atgataatga attatgtaag aaaacaacag gccgggcggg 3720
ttggttcaca cgtgtaatcc cagcactttg ggaggctgag gcaggcagac tgcctgagct 3780
caggagttcg agaccagcct gggcaacacg gtgaaatccc gtctctacta aaaatacaaa 3840
aaaattagcc gggtgtggtg acacatgcct gtagtcccag ctacttggga ggctgaggca 3900

-continued

```
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tattttttca ttttcaatgt catttttatt agttaattta taatacccat   6240
```

-continued

```
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
ctatacagca ggcagaagtc aatattgatt tgtttttaaa gaaacatgta ctactttcat   6840
aagcagaaaa aatttctatt cttgggggaa aagattatgc cagatcctct aggattaaat   6900
gctgatgcat ctgctaaacc ttcacatatc agaacatatt tactatagaa agaatgaaaa   6960
tgggacattt gtgtgtcacc tatgtgaaca ttccaaaaat attttacaac aactaagtat   7020
tttataaatt ttatgaactg aaatttagtt caagttctag gaaaatacaa accttgctag   7080
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
aagttgtttt gttttattgc atcctagatt ttattttttt gatttatggt ttactttaag   7620
cataaaaaat ttgtcaatac aactcttccc aaaaggcata aacaaaaatt cataaaactt   7680
gcatcacttg agatacttca ggtatgaatt cacaactttg ttacaactta ctatatatat   7740
gcacacatat atatatattt gggtatattg ggggggttct aatttaagaa atgcataatt   7800
ggctatagac agacagttgt cagaacttgg caatgggtac gtgcaggttc attataccaa   7860
gtctacttgt agttgttcaa aatgtatcat aatacaaggc cgggcgaggt cgtcacgcct   7920
gtaatcccag catttgggga ggctaaggca ggaggattgc ttgaggtcag gagtttgtga   7980
ccagcctggg caacagagca agaccctgtc tccaaaaaga aaaaaaataa tttttttacaa  8040
aataaaaaca aaatgtatca tcagacgaaa ttaaataaga ggcaattcat ttaaatgaca   8100
acttttccca gcttgacatt taacaaaaag tctaagtcct cttaattcat atttaatgat   8160
caaatatcaa atactaattt tttttttttt tttttttttg agacggagtc tcgctctgtc   8220
gcccaggctg gagtgcagtg gcgcgatcct ggctcactgc aagctccgcc tcccgggttc   8280
acgccattct cctgcctcag cctcccgagt agctgggatt acagacatgc gccaccacgc   8340
ccggctaatt ttgtattttt agtagagatg gggtttctcc atgttggtca ggctggtctt   8400
gaatttccca cctcaggtga tctgcctgcc tcagcctcac aaagcagtag ctgggactac   8460
aggcacccac caccacactt ggttaattct tttgtatttt ttttgtaaag acgggatttc   8520
accatgttag ccaggatggt ctcgatctcc tgatctcatg atccgcccgc ctcagcctcc   8580
caaagtgctg ggattacagg cgtgagccac cccgcccggc catcaaatac taattcttaa   8640
```

-continued

```
atggtaagga cccactattc agaacctgta tccttatcac taatatgcaa atatttattg   8700
aatacttact atgtcatgca tactagagag agttagataa atttgataca gctaccctca   8760
cagaacttac agtgtaatag atggcatgac atgtacatga gtaactgtga acagtgttaa   8820
attgctattt aaaaaaaaag acggctgggc gctgtggctc atgcctgtaa tcccagcact   8880
ttgggaggcc aaggcaagtt gatcgctcga ggtcaagagt tcgagaccag cctggccaac   8940
gtggtaaaac cccgtctcta ctaaaaatac aaaaaaaaaa ttagccaggc atggtggcac   9000
aggcctgtaa tcccagctac tagggaggct gagacatgga gaactgcttg aatccaggag   9060
gcagaggtta cagtgagccg agatcatacc actacactcc agcctgagtg acagagcgag   9120
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc ttttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
```

-continued

```
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaaa aaagacatgt tggccagatg  11760
cggtggctca cacctgtaat cccagcactt tgggaggctg aggtgggcgg atcacccctg  11820
gcctgcccaa catggtgaaa ccccgtctct actaaaaaca caaaaattag ctgggcgtgg  11880
tggcgggcgc ctgtaattcc agctactcgg gaggctgagg caggagaatt gctagaaccc  11940
aggaggcaga gattgcagtg agctgagatt gcaccattgc actacagtct gggcaacaaa  12000
agtgaaactc catcttaaaa aaaaaaagac aatgttcgtg ggtccaaaca agacttaatg  12060
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta ccttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aatttttcct tttattagtg  12900
tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
agtagattat cttagtagta gtgaattatt gtaaatgtta gtaatttggc agccactggg  13080
cagaaaaata agaattgagg ctcaatattg atattaatgg tggtgattga cacataaatt  13140
ttatcaagtc tacacaatat aaaattacag aaaggtagaa gagtatacca gtacaacttc  13200
aacatatctt cactacaagg gagtaaaatg acatggccta gttactatct aatgaactgc  13260
agaaaactaa aagaaaactc caaggcaact cttctctgct gatctggttg gtccttttcc  13320
taccttttgc aatacccaga tacaaacaat ggatagaaaa caaagtagac ttgtagtatg  13380
```

-continued

```
caggtcacag tgctaaattc acagaaagaa acccctgaac tgaactgctc tatttcctgg  13440
tggtcacaaa gagtaattct ggtttacacc tacagattga tgtcaatcta caccctgttg  13500
ataacagtgt ggccaaggac aaaaaaaagg tgctccgttt taccaattct gtaaaaaatt  13560
attggcaggg taagctcggc tagggcagga ttacatttct aggactacca tccccgaaat  13620
ttagaagata ttatatccac ataaagcata tctttcacat taatttgcaa aaatctaaaa  13680
gctttttctt agctcaagtg tgtccaagtt taccctggca gtttaaaacg atagttacaa  13740
gcagcatggg ttgtatcaga cacatttgag ggccaatttc atgtaagtga tattgggcaa  13800
gttacttcaa ctatctgtgc ctccaaggtc atactagtgt ttatttacct aaagggtacc  13860
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
cttgagctca ggagttcaag accagcctgg acaacatggc aaaacaccat ctctacaaaa  14460
aatacaaata ttaggccggg cgcagtggct cacgcctgta atcccagcac tttgggaggc  14520
caaggcgggt ggatcacctg agatcaggag ttcgagagta gcctggccaa catggtgaaa  14580
cctcgtctct attaaaaata caaaaaatta gccaggcatg gtggcaggcg cctgtaatcc  14640
cagctactca gggggatgag gtaggagaat cgcttgaacc cgggaggcag aggttgcact  14700
gagccgagat catgccactg tactccagcc cgggcaacaa gagcgaaact ccatctcaaa  14760
aaataaataa ataaataaat aaaataaagt acaaatatta gccagggatg gtggtgcgca  14820
cctgtagtcc cagctacttg ggaggctgaa gtgggagaat cccctgagcc tggggagaat  14880
cacccgagcc cgggaagtcg aggctgcagt gagcagtgat tgtgccactg cactccatcc  14940
taggtgacag agtgagaccc tgtctcaaaa aaaagaaatt ggcagaatta agtaagttga  15000
tgtttagaga tgaaaaatca acattttttc ctcagcaact gaataaaaac aacagccact  15060
accatttttt tgagtaccta tttgtagcct attttttaac tggtattact cgagagagag  15120
agagctaggt tcgagacaga gctccttctc ttaataactg tatgacctag ggtatgtctg  15180
ttagcctctc tgaggcttca aaggttcctc atctgtaaaa tggtaataat cataccattg  15240
ctacagggct gttttgaaga ctaattagga ctatgtaagt aaacatgatg atggctatta  15300
ttactgttcc ccgccagggg ccatgcaagg gttgctgatt cacatagact gtcttataat  15360
cctctcaata actccaagag gtagccagca cctcagatat acataaaatg acttaagccc  15420
agagaggtga agtaagttgc ccacagccac acaactagta aatagcccaa acaagctgga  15480
ttcccagtta gactccgtta atagcactgc tctttacctt aagtcattac aatgcctaat  15540
atgaaataga atcgcttctt tcttagggtt caagtggtta attatttaat gtattcattc  15600
aacaaaccat catcgaggac ctcttacaag ccaagtactg tgctaagtgc tagagttacg  15660
gcggtgattc ctgcccttaa aaagttttag tgggagaaac aacaggtaac caggtcattg  15720
```

-continued

```
ccaaaacaac aaaaataatc ataataaagc aggctaaagc atatttaact ggccggggtt  15780
ttgactattt tagcaagcat gatcagaacg gttgaggagg gaggccagca gcttggccgg  15840
ttcaacaaac aagaaaaaac cagtgagggt ggagctaaga taccagaggc tgattacggt  15900
taagaatgtt cttgaaggta aggaccagat tctcattttc tatatcctgg ggcatcggtc  15960
agcatggaat ctggattcta gcacatgtga atttcggctt gaaatgacct aatgcctttt  16020
ccctagttcc ttcgtgtgtc aaatacgcat ggttaccgct accagagctg tagtggggct  16080
tcaatgaggc catgagcatc tccataaaga tgaactacag tgtgtgcaaa actaaaggca  16140
aaacctggtc cccacacgcc ctcccaggtg gtcgctttcc gtgccgaggc ccctccagag  16200
gtgccccgag aacctcacca tcgcacccca aacttccagg gaagggcctc tcccgagaaa  16260
gcccccacgc ccccaccccg cgccatcatt cccgaatctg ccctcggccc ctccccgcag  16320
cacgctcgca ggcggcacat gtcaaccaaa acgccatttc caccttctct tcccacacgc  16380
agtcctcttt tcccagggct cccccgagga gggacccacc ccaaaccccg ccattccgtc  16440
ctccctgccg ccctcgcgtg acgtaaagcc gaacccggga aactggccgc ccccgcctgc  16500
ggggttccct gggcccggcc gctctagaac tagtggatcc caattgaagg cctggtctaa  16560
atgactccaa aatcaccact taattcaaga gactgatttc cctgagtcag gcccccttaaa  16620
gcagctattt caatgggaca gggaaacaac cctaggatct ggattagaat cacttggggg  16680
ctgccacacc cccagggctc tgatcctgcc cttctcccac acgcacattc acatactgct  16740
gcagtgacct tccatttcta atgggttcct gggccatctg tcaggtatag ggaatggaaa  16800
aggggttggg gaggctctgc ttcagaaagt ttgtgtcagg ggctcccaga gcctccacag  16860
atagatagca ggggtcccca ccctaccatg gcagctataa atgtgatcaa catttattgg  16920
cctaggatac agcagttagc aaaatgcctg atgtagttcc cactccgtgg aggttgcagg  16980
ctagccaaga agtcatgagt tcagcaaccc ttacgcacca gtgggatgag attggaccag  17040
gccgagggta gtcttgggaa cactcagcat ttgtctgagg gccagaagag gctgcttgcc  17100
ctcagacagg aggtcagcat ctttattgta gcccatgaca cctctacacc attgctcttc  17160
tggtcttatg gaagacatct ttgggcctga taacagcgga gtctgtgtcc cacttgtcca  17220
ggctggagtg ccacatcagg cacactccag ttgcagggac agcacagaca agtttcagga  17280
aggctggtgg cctccaggag gttaacctta taaggccaga ttgtaaccta gttgaaaaac  17340
atacacatgc catgataata aaagaaccta ggcaccatta caagagaaaa aatcattttt  17400
gtagatacga gcatggattc ttgggtgggt cagacacact gggcttgtgc tctgactgca  17460
ctgtctcccc tacctgacct tgggtaaacc ataagactgc tgcatgactc agtgtccacc  17520
ccaaaaaagt accggtagat attggccaca gtagatatca gctagagtgg actctcatga  17580
caatgagggg agatgtattc cccatcttag gcacctggga ctctaccttc catcttctgc  17640
tccgtgtctc tccatcccca ggctcttcag aactcaggga gtccagaatg tcagctccca  17700
gatttcagcc ttcagaaagg aaacccatta ccgttcagtt gaacaaatgt tgtctgagcc  17760
ccagatctgg gctcagaggc catctaggct atgagacaag aggggaacaa agcaccgtct  17820
gcactcactc accacactca cttgctgtcc caggtcacat ccatcgggta gagaatctaa  17880
gaggctgagc tagctcccgc caccagccca gcccacccca cctggcccct tccttccttc  17940
tacaaaatat gcaccacctg tcaaagggtg ggcagtgcca ggcctgcata cagagcactg  18000
agtgtaaaag cagacatgga ccctgacctc caggagcttc caattttctt gaagagacaa  18060
atcagctggc atttcagtcc agtgtgatct gctcttggtg agcacagacc tagggagttg  18120
```

gggcagcttc ccagaagaac tgcagtccag gctgagggca gagaaatgag gggaatggcg 18180
aggaattggg gagcaggggg gagctcagta gagagccaag ggcgggaggt gagaagtccg 18240
tgttgggcca ggagctaccc tccggtggcc acagccgaag tcgaggatgc ctttggaact 18300
catccccact tctctctttc tgtatgtagc cgtccaagaa caagtcacct ccaagtgtag 18360
ccggatcaag gcaagccccc catctagcaa gcacttgatg ccacccagaa ctgggcttct 18420
tcagaacaat ctgagtccag gaatgatccc actcaccagg caccagagct gcgagggcat 18480
gggagtgatc tcaccaactc tggggaagcg gcaaggaatt ttcacctcca gcccccagtg 18540
tcccatcctc tcacactcag gccagactcc cctgggcaga cttgactctg tctgccagca 18600
tatgcagagc cccaaggcca ccccaccaga agtgcccctg cctgggttct gtcccagctc 18660
cctgggcacc cagtccttga gtccccacca gctcagacgg cctagtgtgc caagaatgcc 18720
cactgcgttc aacaatgctg catgggtcac agcggcagca gctgtgacca cagcagtttc 18780
ggggaaaaca cccctcagcc aagtggataa tagcgttcag cagcactcac cttctggcca 18840
ggcctgcctt cagaggccat ctgattggga ggcacaagtg cccgctgcga tgggaacaca 18900
agtgcccctg gccaacaacc ccagcttcag cctgctgggc agccagagcc tcaggcagag 18960
cccggtacag ggcccggtgc ctgtagcaaa caccaccaag ttcctccagc agggtatggc 19020
cagctttagt cccctgagcc ccatacaggg catcgagcca ccaagctatg tggctgctgc 19080
tgccaccgct gctgctgctt ctgccgttgc tgccagccag ttcccaggtc cgttcgacag 19140
aacggatatt ccccctgagc tgccacctgc cgactttttg cgccagcccc aacccccact 19200
aaatgatctg atttcgtcac ctgactgcaa tgaggtagat ttcattgaag ctctcttgaa 19260
aggctcctgt gtgagcccag atgaagactg ggtgtgcaac ttgaggctga tcgacgacat 19320
tttggaacag catgctgctg ctcaaaatgc cacagcccag aattctgggc aagtcaccca 19380
ggatgctggg gcactttaaa tctgagcagg atgcccatag aaacccccat ggtgacatca 19440
ctctaggaag tggtgtcgat ccatacccgc agttgtctcc cgttacaatt tgagtggtgt 19500
tgtcagccca tgcttatccc tctctctacc tgtgacaaaa tggaaagctg gtgatttttc 19560
aagctacgtg tacatatttg aaaattttgt aaatggtttt cctaaacatt aatgacagaa 19620
gtatttatac ttcattttgt gactttgtaa ataaagcgac ggcttttgtt tcagtagagt 19680
tgtgtttact atgcattgtt ttgtgtttat tatacaatgt tacaaatatg cagaccgtgt 19740
tgtttgctcc agtgatacct tgttaagcta ggtggctgag tcgcttatgg ttttaatgca 19800
atgagcaatg tggatatgac caagagttgt tgtgcaagtt gacaaatgcc aaatagaaaa 19860
ccacttggcc atttatttct atgttcacta aaaatcctat tgccttgtgt gattcttaat 19920
ctcttttgcg aacctttcag tctccgctag ctctttccta atgagcttta cagcagaagc 19980
tgttttatcg ttaagtgccc cacagagaca ctttaccagg aggctgggag agttctccag 20040
atttgggaga ggcgcagaga cagtgtgtga gccgagccct gtctcagcaa tccacctgga 20100
ggagctagag tatcctcctc cctttaccat tcagaccgag agaaaaagcc cagcttgtgt 20160
gcaccctcgt ggggttaagg cgagctgttc ctggtttaaa gcctttcagt atttgttttg 20220
atgtaaggct ctgtggtttg ggggggaaca tctgtaaaca ttattagttg atttggggtt 20280
tgtctttgat ggtttctatc tgcaattatc gtcatgtata tttaagtgtc tgttatagaa 20340
aacccacacc cactgtcctg taaacttttc tcagtgtcca gactttctgt aatcacattt 20400
taattgccac ctcgtatttc acctctacat ttgaaatctg gcgtctgttt caagccagtg 20460

-continued tgttttttct tcgttctgta ataaacagcc aggagaaaag tgcctctatg tttttatttt 20520
tcaagggagt attcagtacc tacaaaccca agtcaggaag cctgctagtg gctttggttc 20580
tttcagaggc tgctcgatgc cttgtgtgtc agaaagaaag attcagcagt tttgcatcat 20640
ggcaaagaag cctgttattt tggggctcag cccctcattt tatagaggat gaaacagagg 20700
gggatgggag gtcacaaaga caactgcccc gggagcaggt gtgggggaga cttgccctga 20760
gggtctagac gctctgcacc accgtcctgt ctcccttgct gaagaccaca catgcccttc 20820
tttgaccaga ccctgccacc tgataggcca ggacctggta ggcgggtacc caggtttcat 20880
ggatggaacc acatctcccc aaaagtgggg aggtagctac tgggatgcac gcctcccgcc 20940
atgtgctata ggagagcagc tgaagcaaca gttgggatca gatgtagtca caattgaatg 21000
catcatcaca tttatccctc taagtggctg ggagagttga tatcctcatc cctaaggtac 21060
aaaatgttcc aatttgatca gtggctttca ggagctgaga aaggcatgtg ctctgaggca 21120
gagctgttat gtcccgcaga gcctaaaaat gctctaagaa catgctccct gccaaaattc 21180
tcaatggctg tgacaaggga caacgatcga ccaatggggg tggaagcaga cctccgcagt 21240
ccaggggcca gagctaggac agaggggtcg gagaaagagt cattttccca acactccagc 21300
tcttggccag tcctcacaca gtcccctcct gcttcctgct gagagagata tcctcatagg 21360
tctgggtaaa gtccttcagt cagctttcat tccctgtcac caactttgtc tctgttctcc 21420
ctgcccgtct caggcagcac tcctcaggaa acctctccaa gagccagcct cactgcagcg 21480
cccactattg tccctctgcc tcaagtgtcc catccatgcc aggccccagg caggctgcag 21540
ctttccctca gggccacacc aaagcacttg ggctcagctg tgctgtcccc ctccatcact 21600
gagctcaggg gcagcagggg tggggtgcca ggaggcccat tcacccttct ctggctctgt 21660
gttggaccca cctgcccagc cactgctgct tagaacctac ccgctgggaa aatgaagccc 21720
tcccggaggg gccacctcaa cctgagagcc tcacggatca cagttgtccc cactcagctc 21780
tgccagccct cagagaccca tagataaaag ctgagcttgg ctcgcagagc tggttccatc 21840
ttccattccc agagggttca acttcctacc ccaaccacac agggaacctc aaggctgagc 21900
cagtgtgggc tgcagtgcag accagcttcc tggacacgtc ctgccacctg accccaggct 21960
ggcctcactg cccctggcac tcctgaccct atcctcattc ctcctggcag tgcgtgttct 22020
gccattccgc tttcccttag ctgtcctctc actgtactgt cagcttctcc ttttccaggt 22080
gccccccagg ggctttccac atgaccctgt caccccacag cccatccagc accaattcca 22140
gctctctgcc accettcaaa ggagtgacag tgccctgctt cacctcccac tcacccctca 22200
acccagagca atctggctcc agtcttgcct ccttcccccct aagtactcta gtcacagttc 22260
caaattcctc ctggtcataa agccaaatga agcttcctgg tcctcagcgg acttgccact 22320
tcagcagtac tggactctct cctcccagaa acctgtttcc ccttggctcc tggagcccac 22380
actctgctgg aatccttctg cctctctggc ctgtagcctg gccctctctc ccaacctgag 22440
gtccattctc tcctgctcct ccacaagatg ttgctccttc cattacttcc tccctctcaa 22500
ccaaagctcc ttcattagct ctttatcttc tggtttcttc ccctgggcag acgaatggat 22560
tcaagagcct gtggcccagc agcccagcac tccaggatct cagcacttca gcatcccagt 22620
accctagcat ctcaataccc cagcacccca gcaccatagt attccagcac cccattgtcc 22680
aagcatctca gcactccagc atcccagcac cccaacactc cagcagccca gaatctcagc 22740
accctagcac tgcagcatct caggacccca gcacttcagc atcccagcac actagtactc 22800
cagcatctcg gcaccccagc acctaggcat cccaacaccc agcaccccag cacttaagca 22860
tcccaccact acagtatctc aacactccag caccccagca ccatagtgtt ccagcacccc 22920
agcatcccaa caccccagca cttaagcatc ccaacacctc ggcatcccaa caccccagca 22980
ctgcagcatc tcagcacctt agcatcccag tgccctagca tctcaatgct ccagcacacc 23040
agtactacag tattccagca ccccagcact ccagcatctc agcactgcag cactgcagca 23100
ctccagcatc ccaaaatccc agcatcccaa caccccagca gaccagcaga ccagcatctc 23160
agcaccgcag catccaagga ctatcccagc atcccagcaa cccagcacct cagcatccca 23220
acaccccagc atttcagcat ggcaacaccc cagtacccca gcacttcagc accccagtat 23280
cccagcatct cagcgaccca gtatcacaaa acctcagcat cctagcaccc cagcacccca 23340
gcaccttagc accttagcat cccagcatct cagcgcctca gcatcttgat attctggctg 23400
aggtcagcgt ggtgtatcta gtcagggtcc taactttcac ttcgcaggga aatgctgctg 23460
gactgggtct catgttgggc tgaagctctc tagacccctt gaagacagca taaaagagct 23520
tggagacgct gggtgtcccc catggaagag ttcactctca tcctgctttg acaacagcct 23580
tctctggggt ccctcacggg cccctctttc ttactgcaag tttgtctctg agaagactgt 23640
gatgcagaag tcactcagct gcctgtggct cctgaagagc tgaaggtgga ggcctgtagg 23700
cctccctatg agaggcgcag aaaaaaccat gattgctagt ggggaggtgc tccctctaca 23760
acccactcca taatctgccc ccgcccagct ctgaggccag ccccagggga aaatgccaga 23820
tccccaggga ggtgtgtgag acctcagggg ctccctcctc ccttacagca ggctcaggcc 23880
cctgggggcc tcagggccaa ggtctgtggg taagctacta tctctcactt gtcctctagc 23940
cacaaaagcc agggagatct ggcaatggac atgaggttct gaagaagcac atatgactgg 24000
cttcctaatg cgtggttgtt cagtgattca ataaacacgc atgggccagg catggggaaa 24060
tagacaaaca tgatccccaa cctctcccag agtgaactgg gagggaggag tgttcatccc 24120
tcaggattac accagagaaa caaaccagca ggagatatat atggttttgg ggggtcaaga 24180
aagaggaaaa acctggcaag gcaagtccaa aatcatagga caggctgtca ggaagggcag 24240
cctggaacct ctcaagcagg agctgatgct gcagtccaca ggcagaattt cttcttcctc 24300
ggggaaatct cagctttgtt cttaaggcct ttcaactgat tggctgaggt ctgccccttc 24360
ccccacattc tccaggataa tcttccttac ttaaagtcaa ctattaatca cagctacaaa 24420
atcccttcac agctacacat agatcagtgt ttgattgacg aacagcccct acagcctagc 24480
caagttgaca cataaaacta accatcacag ggggacaaat gatgtaaaca catcaacaaa 24540
taaaacagta acaagttaag gtctatggaa aaaacacaga aggggcagag agaaagaaag 24600
caagaaggag agtcccagtt tgctagggct tgtgggaagt ggggagcagt tctctttagc 24660
taggatattt gggaaaggca tatctgaagg agtgatattt gagcttagat taaaagatgg 24720
gaaggagcaa gccatgcaaa gagctaggat gttccaagca gagacggaac agcaagtgca 24780
aatgtcagga ggaatagaag gaggctggtg ggtggggtcc agtgagcaag aggagggcag 24840
gcaggagagg ggatggggag gtgggcaggc ccagaccacc cagggccctg gagactatcc 24900
tgatccaaca agggaagcct tgagtcactt cagtgtccat gtggagaatg gacctcagac 24960
tgaatgaggg aggcagtaag gagggcctct acctccaggg cttcgccctg tggactgcgc 25020
atagacatct ccaactcaga aagtctgaac caaactttcc atagttcccc caagtctggg 25080
catcctccta ctcagtgaaa ggcagccatc acacctccct gccctgctcc cggatgcccc 25140
aaatcctctt ggtctccaag tccagaacct gagacttgtc cttgatgttt gtctttccct 25200

```
caccctttct gtattctggg aagatgggtt tttttccccc agatgaatct gtaaaacttc  25260
tgtgatcaca ataaaaattc tggcagtatt attttctgga acatgacaaa gtgattcaaa  25320
attatttatc tggaagacta caaaacaaga atagccagga aatttctaaa aagaaagaag  25380
aaggaggagg agaaagaagg aggaggaaaa ggaggagaag aagaaaagaa aaagaaccaa  25440
gaaagggttc tagctctacc aaatattaaa acatatcatg aagctattta aaacaatatg  25500
gttgtggata ctgaaaaaga tgtgaataaa gtggaaggaa aataaataga aatgcacatg  25560
gggattgaga ctgtgaaaaa ggcagcatct cacatcagtg agggatgttc aacacctggt  25620
gttgggaaaa ctggctagtc atttaaacca aacaactggg tcctctacct cactcctgac  25680
attaagatac atttagatga ttcaaagagt aagacagaaa aaataacacg tgaaaacact  25740
atcagaaaac aacgtgggcc aggtgtggtg ggtcacgcct gtaatcccag cactttggga  25800
ggccgaggca gacagatcac ctgaggtggg gagttcaaga ccagcctgac caacatggtg  25860
aaatcctgtc tctactaaaa atacaaaatt agctgagcgt ggtggcgcat gcctgtaatc  25920
ccagctactc aggaggccga ggcaggagaa tcacttgaac ctgggaggca gaggttgtgg  25980
tgagccgaga tcacgccatt gcactccagc ctgggcaaca agagtgaaaa tccatctaaa  26040
aaaaaaaaaa aaagccaagg tggatatttt tatagtatca gggtagatca agcttctcca  26100
atcatgacat gaaacccaga aaccataaaa gaaaagaatg ataaaattgc ccacgtaaag  26160
taaaaagctt gcacacagaa aaacaccata caggttacaa gatgagcagc aaaatcagag  26220
aaaaaacatt gcaattcagg acacacagag gctattgttc ctaatattta aaaataaaag  26280
tagtggattg tctacaaaaa gatgaagaca agaatttcag aaaaccaaat actgcatgtt  26340
ttcacttaca agtggaagct aaacactgag tacacgtgta cacaaagaat ggaaccatag  26400
gccaggcacc gtggctcacg cctgtaatcc cagtactttg cgaggccgaa gcgggcggat  26460
cacctgaggt gaggagttcg agaccatcct ggccaacatg gtgaaaccca gtctctacta  26520
aaaatacaaa aattagccgg gcgtggtggt gggtgcctgt aatcccagct actcgggagg  26580
ctgcggcagt agaatcgctt gaaccctgga ggtggacctt gcagtgagcc gagatcgcac  26640
cactgcactc cagcctgggc aacagagtga gactccatct caaaaaaaaa aaaaaggaat  26700
agaacaatag acactggggc ctacttgagg gaggagggtg aggatcaaaa acctgcctat  26760
caggtactat gcttattacc tgggtggtga aataatctgt acaccaaacc ccagtgacat  26820
gcaatttacc gatgtaacaa acctgcccat gtacccgctg aacctaaaat aaaagttgga  26880
aaaaaatata gaaattttct ttgtaatagc caaaaactgc aaacagccca ggtgtctatt  26940
agtagaatgc ataaacaaac tcgggcatgt tcatacaatg taaaactact catcaataaa  27000
aagtgatact tctcagcaat gaaaagaaac tagctactga taccagctac aacatggatg  27060
gatttcaagt gctttatgat gagagcaaga agccagacac aaaagtgtct atatatatat  27120
acagtatata tacgtatata tacacatata tacagtatat atatacatat acatgtatat  27180
atatactgta tatatactgt atatatatac acagtatata tatacatata tacagtgtat  27240
atatactgtg tatatataca tgtatatata ctgtgtatat atacatgtat atatactgtg  27300
tatatataca tgtatatata ctgtgtatat atacatgtat atatatgtat actgtatata  27360
tactgtatat atatatacac atatatacag tatatatata cagtatatac tgtatatata  27420
cagtatatac gtgtatatat acatatatac agtatatatg taaatataca tatatacagt  27480
atatatgtaa atatacatat atacatgtat atatatacac tatatatata catatatagt  27540
gtatatatac atatatacat gtatatattt actatatgat tccatttata taaagtgcca  27600
```

-continued

```
aaacagtcaa aaataatcta tgtggaaaaa atcaacaaag ggatcccccg ggctgcagga  27660
attcgatggc gcgccgtcga cccaacgcgt tgggagctct ccggatccaa gcttcgaggg  27720
gctcgcatct ctccttcacg cgcccgccgc cctacctgag gccgccatcc acgccggttg  27780
agtcgcgttc tgccgcctcc cgcctgtggt gcctcctgaa ctgcgtccgc cgtctaggta  27840
agtttaaagc tcaggtcgag accgggcctt tgtccggcgc tcccttggag cctacctaga  27900
ctcagccggc tctccacgct ttgcctgacc ctgcttgctc aactctacgt ctttgtttcg  27960
ttttctgttc tgcgccgtta cagatccaag ctgtgaccgg cgcctacgta agtgatatct  28020
actagattta tcaaaaagag tgttgacttg tgagcgctca caattgatac ttagattcat  28080
cgagagggac acgtcgacta ctaaccttct tctctttcct acagctgaga tcaccggcga  28140
aggagggcca ccatgcatgg ggtggaaaat acttcccgtc tgcttgtcgc tgctgcttcc  28200
tgttgtcttg attcaacagg tttcatctca agagctctcc tgcaaaggac gctgcttcga  28260
gtccttcgct cgagggaggg agtgtgactg tgactcccag tgtaaacagt atggcaagtg  28320
ctgtgcagat tatgacagct tctgtgaaga agtaaaagat aacaagaaaa acacccctaa  28380
aaagaaaccc aatccagaac cgccggctgt ggatgaagct ggaagcgggc tggataatgg  28440
tgagttcaag ctcaccccac ctcctcctga ccctcctact actccacaca gcaaagtcgc  28500
cacatctccc aagactacag cagcaaaacc agtaactcct aaacccagtc ttgcacctaa  28560
ttctgagaca tccaaagagg catctttagc atccaataaa gagacaacag ttgaaacgaa  28620
agagactact gcaacaaata aacaatcttc tgccagtaaa aaaaagacga cttcagttaa  28680
agagacacgg agtgcagaga aaacatctga taaagatgtt gagcccacat ctacaactcc  28740
caagaactca gctcccacta ctaccaagaa gcctgttact acaaccaagg aatccaagtt  28800
cctaccactc ccacaggagc ctgaacccac aactgccaag gaaccacctc caaccaccaa  28860
gaagcctgaa cccaccaccc gcaaggagcc tgaacccaca actcccaagg agcctgaacc  28920
caccaccccc aaggagcctg aacccaccac tcccaaggag cctgaaccca caactcccaa  28980
ggaaccacct ccaaccacca agaagcctga acccaccacc cccaaggagc ctggacccac  29040
aactcccaag gagcctgaac ccaccaccac caaggagcct gaacccacca ccaccaagga  29100
gcctgaatcc accactcgca aggagcctga acccaccact cccaaggagc ctgaacccac  29160
aactcccaag gagcctgaac ctacaaccct caaggagcct gaacccacaa ctcccaagga  29220
gcctgaaccc accactccca aggagcctga acccacaact cccaaggagc ctgaacccac  29280
aactcccaag gagcctgaac ccaccacgcc caaggagcct gaacccacaa ctcccaagga  29340
gcctgaaccc accacgccca aggagcctga acccacaacc cccaaggagc ctgaacccac  29400
aactcccaag aaacctgaac ccacaactcc caaggagcct gtacctacaa cccccaagga  29460
gcctgaaccc accaccccca aggagcctga acccaccacg cccaaggagc ctgaacccac  29520
aactcgcaag gagcctgaac ctacaactcc caaggagcct gaacctacaa cccccaagga  29580
gcctgaaccc acaactccca agaagcctga acccaccacc acatcaccca aaaccactac  29640
tctgaaagca acaactcttg cacccaaagt aactgctcca gcagaagaga ttcagaacaa  29700
acctgaagaa acaactcctg catcagaaga ttctgatgat tctaaaacaa ctctaaaacc  29760
acagaagcca accaaagcac ccaagcctac caaaaagcca accaaagcac ccaagaagcc  29820
cacctctacc aaaaagccaa agacaccaaa aacaagaaaa ccaaaaacta caccagctcc  29880
tctaaagacg acttcagcaa cacctgaact gaataccacc cctctagaag tcatgctgcc  29940
```

```
aaccaccacc atccctaaac aaactccaaa ccctgaaaca gctgaagtaa atccagatca  30000
tgaagatgca gatggaggtg aaggagaaaa acctctgatt cccgggcccc ctgtgctatt  30060
ccccacagct attccaggca ctgatctttt ggccgggaga ctcaatcgag gcattaacat  30120
caatcccatg ccttcagatg agaccaattt atgcaatggt aagccagtgg atggactgac  30180
tacgctgcgc aatgggacat tagttgcatt tcgaggtcat tatttctgga tgctgaatcc  30240
attcagacca ccatctccac cacgcagaat taccgaagtt tggggtattc cctctcctat  30300
tgacacagtt tttactagat gtaactgtga aggaaaaact ttcttcttta aggattctca  30360
gtactggcgc ttcaccaatg atgtggtaga tcctgggtat cctaaacaaa ttgtcaaagg  30420
ctttggagga ctaacaggga agatagtggc tgctctttca atagccaagt acaaggacag  30480
gcctgaatct gtgtacttct tcaagagagg tggcaacatt cagcagtaca cttataaaca  30540
ggagccaatg aagaagtgca cagggaggcg gcctgccatc aactactcgg tgtacgggga  30600
ggcagcacag gtcaggaggc gccgctttga gcgtgctgtt ggacctttcc agacacacac  30660
cttcaggatc cattactcgg tgcccatgag agtttcttat caagacaaag gtttcctcca  30720
caatgaagtc aaagtgagta caatgtggag agggtttcca aatgttgtta cttcagcgat  30780
aacactgcct aacattagga aacctgatgg ctatgattac tacgcctttt ccaaagatca  30840
atactataac attgatgtgc ctacaagaac agcaagagca attaccacac gttcagggca  30900
gaccctctcc aaaatctggt acaactgtcc ttgaactgat tgacaaagaa gagtcatcaa  30960
aatgaaatga agaaaacagt gatacttttt gacattgaaa tacattttat taataaagaa  31020
tgttgaaatg agcataccta tttaaataca aaaaaaaaaa aaaaaaaggc cacatgtgct  31080
cgagctgcag gtcgcggccc tagctcgaca tgataagata cattgatgag tttggacaaa  31140
ccacaactag aatgcagtga aaaaaatgct ttatttgtga aatttgtgat gctattgctt  31200
tatttgtgaa atttgtgatg ctattgcttt atttgtaacc attataagct gcaataaaca  31260
agttaacaac aacaattgca ttcattttat gtttcaggtt caggggagg tgtgggaggt  31320
tttttaaagc aagtaaaacc tctacaaatg tggtagatca tttggggtac cgaattcctc  31380
gagtctagag gagcatgcga cgtcggcgcg cctaccagta aaaaagaaaa cctattaaaa  31440
aaacaccact cgacacggca ccagctcaat cagtcacagt gtaaaaaagg gccaagtgca  31500
gagcgagtat atataggact aaaaaatgac gtaacggtta aagtccacaa aaaacaccca  31560
gaaaaccgca cgcgaaccta cgcccagaaa cgaaagccaa aaaacccaca acttcctcaa  31620
atcgtcactt ccgttttccc acgttacgtc acttcccatt ttaagaaaac tacaattccc  31680
aacacataca agttactccg ccctaaaacc tacgtcaccc gccccgttcc cacgccccgc  31740
gccacgtcac aaactccacc ccctcattat catattggct tcaatccaaa ataaggtata  31800
ttattgatga tgttt                                                   31815
```

<210> SEQ ID NO 3
<211> LENGTH: 4215
<212> TYPE: DNA
<213> ORGANISM: Homo sapiens

<400> SEQUENCE: 3

```
atggcatgga aaacacttcc catttacctg ttgttgctgc tgtctgtttt cgtgattcag     60
caagtttcat ctcaagattt atcaagctgt gcagggagat gtggggaagg gtattctaga    120
gatgccacct gcaactgtga ttataactgt caacactaca tggagtgctg ccctgatttc    180
aagagagtct gcactgcgga gctttcctgt aaaggccgct gctttgagtc cttcgagaga    240
```

-continued

```
gggagggagt gtgactgcga cgcccaatgt aagaagtatg acaagtgctg tcccgattat    300
gagagtttct gtgcagaagt gcataatccc acatcaccac catcttcaaa gaaagcacct    360
ccaccttcag gagcatctca aaccatcaaa tcaacaacca aacgttcacc caaaccacca    420
aacaagaaga agactaagaa agttatagaa tcagaggaaa taacagaaga acattctgtt    480
tctgaaaatc aagagtcctc ctcctcctcc tcctcttcct cttcttcttc aacaattcgg    540
aaaatcaagt cttccaaaaa ttcagctgct aatagagaat tacagaagaa actcaaagta    600
aaagataaca agaagaacag aactaaaaag aaacctaccc ccaaaccacc agttgtagat    660
gaagctggaa gtggattgga caatggtgac ttcaaggtca caactcctga cacgtctacc    720
acccaacaca ataaagtcag cacatctccc aagatcacaa cagcaaaacc aataaatccc    780
agacccagtc ttccacctaa ttctgataca tctaaagaga cgtctttgac agtgaataaa    840
gagacaacag ttgaaactaa agaaactact acaacaaata aacagacttc aactgatgga    900
aaagagaaga ctacttccgc taaagagaca caaagtatag agaaaacatc tgctaaagat    960
ttagcaccca catctaaagt gctggctaaa cctacaccca aagctgaaac tacaaccaaa   1020
ggccctgctc tcaccactcc caaggagccc acgcccacca ctcccaagga gcctgcatct   1080
accacaccca aagagcccac acctaccacc atcaagtctg cacccaccac ccccaaggag   1140
cctgcaccca ccaccaccaa gtctgcaccc accactccca aggagcctgc acccaccacc   1200
accaaggagc ctgcacccac cactcccaag gagcctgcac ccaccaccac caaggagcct   1260
gcacccacca ccaccaagtc tgcacccacc actcccaagg agcctgcacc caccaccccc   1320
aagaagcctg ccccaactac ccccaaggag cctgcaccca ccactcccaa ggagcctaca   1380
cccaccactc ccaaggagcc tgcacccacc accaaggagc ctgcacccac cactcccaaa   1440
gagcctgcac ccactgcccc caagaagcct gccccaacta cccccaagga gcctgcaccc   1500
accactccca aggagcctgc acccaccacc accaaggagc cttcacccac cactcccaag   1560
gagcctgcac ccaccaccac caagtctgca cccaccacta ccaaggagcc tgcacccacc   1620
actaccaagt ctgcacccac cactcccaag gagccttcac ccaccaccac caaggagcct   1680
gcacccacca ctcccaagga gcctgcaccc accaccccca agaagcctgc cccaactacc   1740
cccaaggagc ctgcacccac cactcccaag gaacctgcac ccaccaccac caagaagcct   1800
gcacccacca ctcccaaaga gcctgcccca actaccccca aggagactgc acccaccacc   1860
cccaagaagc tcacgcccac cacccccgag aagctcgcac ccaccacccc tgagaagccc   1920
gcacccacca cccctgagga gctcgcaccc accacccctg aggagcccac acccaccacc   1980
cctgaggagc ctgctcccac cactcccaag gcagcggctc ccaacacccc taaggagcct   2040
gctccaacta cccctaagga gcctgctcca actaccccta aggagcctgc tccaactacc   2100
cctaaggaga ctgctccaac taccccctaaa gggactgctc caactaccct caaggaacct   2160
gcacccacta ctcccaagaa gcctgccccc aaggagcttg cacccaccac caccaaggag   2220
cccacatcca ccacctgtga caagcccgct ccaactaccc ctaaggggac tgctccaact   2280
acccctaagg agcctgctcc aactacccct aaggagcctg ctccaactac ccctaagggg   2340
actgctccaa ctaccctcaa ggaacctgca cccactactc ccaagaagcc tgcccccaag   2400
gagcttgcac ccaccaccac caaggggccc acatccacca cctctgacaa gcctgctcca   2460
actacaccta aggagactgc tccaactacc cccaaggagc ctgcacccac tacccccaag   2520
aagcctgctc caactactcc tgagacacct cctccaacca cttcagaggt ctctactcca   2580
```

-continued

```
actaccacca aggagcctac cactatccac aaaagccctg atgaatcaac tcctgagctt   2640

tctgcagaac ccacaccaaa agctcttgaa aacagtccca aggaacctgg tgtacctaca   2700

actaagactc ctgcagcgac taaacctgaa atgactacaa cagctaaaga caagacaaca   2760

gaaagagact tacgtactac acctgaaact acaactgctg cacctaagat gacaaaagag   2820

acagcaacta caacagaaaa aactaccgaa tccaaaataa cagctacaac cacacaagta   2880

acatctacca caactcaaga taccacacca ttcaaaatta ctactcttaa aacaactact   2940

cttgcaccca aagtaactac aacaaaaaag acaattacta ccactgagat tatgaacaaa   3000

cctgaagaaa cagctaaacc aaaagacaga gctactaatt ctaaagcgac aactcctaaa   3060

cctcaaaagc caaccaaagc acccaaaaaa cccacttcta ccaaaaagcc aaaaacaatg   3120

cctagagtga gaaaaccaaa gacgacacca actccccgca agatgacatc aacaatgcca   3180

gaattgaacc ctacctcaag aatagcagaa gccatgctcc aaaccaccac cagacctaac   3240

caaactccaa actccaaact agttgaagta aatccaaaga gtgaagatgc aggtggtgct   3300

gaaggagaaa cacctcatat gcttctcagg ccccatgtgt tcatgcctga agttactccc   3360

gacatggatt acttaccgag agtacccaat caaggcatta tcatcaatcc catgctttcc   3420

gatgagacca atatatgcaa tggtaagcca gtagatggac tgactacttt gcgcaatggg   3480

acattagttg cattccgagg tcattatttc tggatgctaa gtccattcag tccaccatct   3540

ccagctcgca gaattactga agtttggggt attccttccc ccattgatac tgtttttact   3600

aggtgcaact gtgaaggaaa aactttcttc tttaaggatt ctcagtactg gcgttttacc   3660

aatgatataa aagatgcagg gtaccccaaa ccaattttca aaggatttgg aggactaact   3720

ggacaaatag tggcagcgct ttcaacagct aaatataaga actggcctga atctgtgtat   3780

tttttcaaga gaggtggcag cattcagcag tatatttata aacaggaacc tgtacagaag   3840

tgccctggaa gaaggcctgc tctaaattat ccagtgtatg gagaaacgac acaggttagg   3900

agacgtcgct ttgaacgtgc tataggacct tctcaaacac acaccatcag aattcaatat   3960

tcacctgcca gactggctta tcaagacaaa ggtgtccttc ataatgaagt taaagtgagt   4020

atactgtgga gaggacttcc aaatgtggtt acctcagcta tatcactgcc caacatcaga   4080

aaacctgacg gctatgatta ctatgccttt tctaaagatc aatactataa cattgatgtg   4140

cctagtagaa cagcaagagc aattactact cgttctgggc agaccttatc caaagtctgg   4200

tacaactgtc cttag                                                    4215
```

<210> SEQ ID NO 4
<211> LENGTH: 2894
<212> TYPE: DNA
<213> ORGANISM: Mus musculus

<400> SEQUENCE: 4

```
atggggtgga aaatacttcc cgtctgcttg tcgctgctgc ttcctgttgt cttgattcaa     60

caggtttcat ctcaagagct ctcctgcaaa ggacgctgct tcgagtcctt cgctcgaggg    120

agggagtgtg actgtgactc ccagtgtaaa cagtatggca agtgctgtgc agattatgac    180

agcttctgtg aagaagtaaa agataacaag aaaaacaccc ctaaaaagaa acccaatcca    240

gaaccgccgg ctgtggatga agctggaagc gggctggata atggtgagtt caagctcacc    300

ccacctcctc ctgaccctcc tactactcca cacagcaaag tcgccacatc tcccaagact    360

acagcagcaa aaccagtaac tcctaaaccc agtcttgcac ctaattctga gacatccaaa    420

gaggcatctt tagcatccaa taaagagaca acagttgaaa cgaaagagac tactgcaaca    480
```

```
aataaacaat cttctgccag taaaaaaaag acgacttcag ttaaagagac acggagtgca    540
gagaaaacat ctgataaaga tgttgagccc acatctacaa ctcccaagaa ctcagctccc    600
actactacca agaagcctgt tactacaacc aaggaatcca agttcctacc actcccacag    660
gagcctgaac ccacaactgc caaggaacca cctccaacca ccaagaagcc tgaacccacc    720
acccgcaagg agcctgaacc cacaactccc aaggagcctg aacccaccac ccccaaggag    780
cctgaaccca ccactcccaa ggagcctgaa cccacaactc ccaaggaacc acctccaacc    840
accaagaagc ctgaacccac cacccccaag gagcctggac ccacaactcc caaggagcct    900
gaacccacca ccaccaagga gcctgaaccc accaccacca aggagcctga atccaccact    960
cgcaaggagc ctgaacccac cactcccaag gagcctgaac ccacaactcc caaggagcct   1020
gaacctacaa ccctcaagga gcctgaaccc acaactccca aggagcctga acccaccact   1080
cccaaggagc ctgaacccac aactcccaag gagcctgaac ccacaactcc caaggagcct   1140
gaacccacca cgcccaagga gcctgaaccc acaactccca aggagcctga acccaccacg   1200
cccaaggagc ctgaacccac aacccccaag gagcctgaac ccacaactcc caagaaacct   1260
gaacccacaa ctcccaagga gcctgtacct acaaccccca aggagcctga acccaccacc   1320
cccaaggagc ctgaacccac cacgcccaag gagcctgaac ccacaactcg caaggagcct   1380
gaacctacaa ctcccaagga gcctgaacct acaaccccca aggagcctga acccacaact   1440
cccaagaagc ctgaacccac caccacatca cccaaaacca ctactctgaa agcaacaact   1500
cttgcaccca aagtaactgc tccagcagaa gagattcaga acaaacctga agaaacaact   1560
cctgcatcag aagattctga tgattctaaa acaactctaa aaccacagaa gccaaccaaa   1620
gcacccaagc ctaccaaaaa gccaaccaaa gcacccaaga agcccacctc taccaaaaag   1680
ccaaagacac caaaaacaag aaaaccaaaa actacaccag ctcctctaaa gacgacttca   1740
gcaacacctg aactgaatac cacccctcta gaagtcatgc tgccaaccac caccatccct   1800
aaacaaactc caaaccctga aacagctgaa gtaaatccag atcatgaaga tgcagatgga   1860
ggtgaaggag aaaaacctct gattcccggg ccccctgtgc tattccccac agctattcca   1920
ggcactgatc ttttggccgg gagactcaat cgaggcatta acatcaatcc catgccttca   1980
gatgagacca atttatgcaa tggtaagcca gtggatggac tgactacgct gcgcaatggg   2040
acattagttg catttcgagg tcattatttc tggatgctga atccattcag accaccatct   2100
ccaccacgca gaattaccga agtttggggt attccctctc ctattgacac agtttttact   2160
agatgtaact gtgaaggaaa aactttcttc tttaaggatt ctcagtactg gcgcttcacc   2220
aatgatgtgg tagatcctgg gtatcctaaa caaattgtca aaggctttgg aggactaaca   2280
gggaagatag tggctgctct ttcaatagcc aagtacaagg acaggcctga atctgtgtac   2340
ttcttcaaga gaggtggcaa cattcagcag tacacttata aacaggagcc aatgaagaag   2400
tgcacaggga ggcggcctgc catcaactac tcggtgtacg gggaggcagc acaggtcagg   2460
aggcgccgct ttgagcgtgc tgttggacct ttccagacac acaccttcag gatccattac   2520
tcggtgccca tgagagtttc ttatcaagac aaaggtttcc tccacaatga agtcaaagtg   2580
agtacaatgt ggagagggtt tccaaatgtt gttacttcag cgataacact gcctaacatt   2640
aggaaacctg atggctatga ttactacgcc ttttccaaag atcaatacta taacattgat   2700
gtgcctacaa gaacagcaag agcaattacc acacgttcag ggcagaccct ctccaaaatc   2760
tggtacaact gtccttgaac tgattgacaa agaagagtca tcaaaatgaa atgaagaaaa   2820
```

```
cagtgatact ttttgacatt gaaatacatt ttattaataa agaatgttga aatgagcata   2880

cctatttaaa taca                                                      2894


<210> SEQ ID NO 5
<211> LENGTH: 1404
<212> TYPE: PRT
<213> ORGANISM: Homo sapiens

<400> SEQUENCE: 5

Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Pro Ser Gly Ala Ser Gln Thr
        115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
```

```
        355                 360                 365

Thr Thr Ile Lys Ser Ala Pro Thr Thr Pro Lys Glu Pro Ala Pro Thr
    370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
            420                 425                 430

Lys Glu Pro Ala Pro Thr Thr Pro Lys Lys Pro Ala Pro Thr Thr Pro
        435                 440                 445

Lys Glu Pro Ala Pro Thr Thr Pro Lys Glu Pro Thr Pro Thr Thr Pro
    450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
            500                 505                 510

Glu Pro Ser Pro Thr Thr Pro Lys Glu Pro Ala Pro Thr Thr Thr Lys
        515                 520                 525

Ser Ala Pro Thr Thr Thr Lys Glu Pro Ala Pro Thr Thr Thr Lys Ser
    530                 535                 540

Ala Pro Thr Thr Pro Lys Glu Pro Ser Pro Thr Thr Thr Lys Glu Pro
545                 550                 555                 560

Ala Pro Thr Thr Pro Lys Glu Pro Ala Pro Thr Thr Pro Lys Lys Pro
                565                 570                 575

Ala Pro Thr Thr Pro Lys Glu Pro Ala Pro Thr Thr Pro Lys Glu Pro
            580                 585                 590

Ala Pro Thr Thr Thr Lys Lys Pro Ala Pro Thr Thr Pro Lys Glu Pro
        595                 600                 605

Ala Pro Thr Thr Pro Lys Glu Thr Ala Pro Thr Thr Pro Lys Lys Leu
    610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
            660                 665                 670

Ala Pro Asn Thr Pro Lys Glu Pro Ala Pro Thr Thr Pro Lys Glu Pro
        675                 680                 685

Ala Pro Thr Thr Pro Lys Glu Pro Ala Pro Thr Thr Pro Lys Glu Thr
    690                 695                 700

Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Cys Asp Lys Pro Ala Pro Thr
            740                 745                 750

Thr Pro Lys Gly Thr Ala Pro Thr Thr Pro Lys Glu Pro Ala Pro Thr
        755                 760                 765

Thr Pro Lys Glu Pro Ala Pro Thr Thr Pro Lys Gly Thr Ala Pro Thr
    770                 775                 780
```

-continued

```
Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
            820                 825                 830

Glu Pro Ala Pro Thr Thr Pro Lys Lys Pro Ala Pro Thr Thr Pro Glu
        835                 840                 845

Thr Pro Pro Pro Thr Thr Ser Glu Val Ser Thr Pro Thr Thr Thr Lys
    850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
            900                 905                 910

Thr Thr Ala Lys Asp Lys Thr Thr Glu Arg Asp Leu Arg Thr Thr Pro
        915                 920                 925

Glu Thr Thr Thr Ala Ala Pro Lys Met Thr Lys Glu Thr Ala Thr Thr
    930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Thr Lys Lys Thr Ile
            980                 985                 990

Thr Thr Thr Glu Ile Met Asn Lys  Pro Glu Glu Thr Ala  Lys Pro Lys
        995                 1000                1005

Asp Arg  Ala Thr Asn Ser Lys  Ala Thr Thr Pro Lys  Pro Gln Lys
    1010                1015                1020

Pro Thr  Lys Ala Pro Lys Lys  Pro Thr Ser Thr Lys  Lys Pro Lys
    1025                1030                1035

Thr Met  Pro Arg Val Arg Lys  Pro Lys Thr Thr Pro  Thr Pro Arg
    1040                1045                1050

Lys Met  Thr Ser Thr Met Pro  Glu Leu Asn Pro Thr  Ser Arg Ile
    1055                1060                1065

Ala Glu  Ala Met Leu Gln Thr  Thr Thr Arg Pro Asn  Gln Thr Pro
    1070                1075                1080

Asn Ser  Lys Leu Val Glu Val  Asn Pro Lys Ser Glu  Asp Ala Gly
    1085                1090                1095

Gly Ala  Glu Gly Glu Thr Pro  His Met Leu Leu Arg  Pro His Val
    1100                1105                1110

Phe Met  Pro Glu Val Thr Pro  Asp Met Asp Tyr Leu  Pro Arg Val
    1115                1120                1125

Pro Asn  Gln Gly Ile Ile Ile  Asn Pro Met Leu Ser  Asp Glu Thr
    1130                1135                1140

Asn Ile  Cys Asn Gly Lys Pro  Val Asp Gly Leu Thr  Thr Leu Arg
    1145                1150                1155

Asn Gly  Thr Leu Val Ala Phe  Arg Gly His Tyr Phe  Trp Met Leu
    1160                1165                1170

Ser Pro  Phe Ser Pro Pro Ser  Pro Ala Arg Arg Ile  Thr Glu Val
    1175                1180                1185
```

-continued

Trp Gly Ile Pro Ser Pro Ile Asp Thr Val Phe Thr Arg Cys Asn
1190 1195 1200

Cys Glu Gly Lys Thr Phe Phe Phe Lys Asp Ser Gln Tyr Trp Arg
1205 1210 1215

Phe Thr Asn Asp Ile Lys Asp Ala Gly Tyr Pro Lys Pro Ile Phe
1220 1225 1230

Lys Gly Phe Gly Gly Leu Thr Gly Gln Ile Val Ala Ala Leu Ser
1235 1240 1245

Thr Ala Lys Tyr Lys Asn Trp Pro Glu Ser Val Tyr Phe Phe Lys
1250 1255 1260

Arg Gly Gly Ser Ile Gln Gln Tyr Ile Tyr Lys Gln Glu Pro Val
1265 1270 1275

Gln Lys Cys Pro Gly Arg Arg Pro Ala Leu Asn Tyr Pro Val Tyr
1280 1285 1290

Gly Glu Thr Thr Gln Val Arg Arg Arg Arg Phe Glu Arg Ala Ile
1295 1300 1305

Gly Pro Ser Gln Thr His Thr Ile Arg Ile Gln Tyr Ser Pro Ala
1310 1315 1320

Arg Leu Ala Tyr Gln Asp Lys Gly Val Leu His Asn Glu Val Lys
1325 1330 1335

Val Ser Ile Leu Trp Arg Gly Leu Pro Asn Val Val Thr Ser Ala
1340 1345 1350

Ile Ser Leu Pro Asn Ile Arg Lys Pro Asp Gly Tyr Asp Tyr Tyr
1355 1360 1365

Ala Phe Ser Lys Asp Gln Tyr Tyr Asn Ile Asp Val Pro Ser Arg
1370 1375 1380

Thr Ala Arg Ala Ile Thr Thr Arg Ser Gly Gln Thr Leu Ser Lys
1385 1390 1395

Val Trp Tyr Asn Cys Pro
1400

<210> SEQ ID NO 6
<211> LENGTH: 925
<212> TYPE: PRT
<213> ORGANISM: Mus musculus

<400> SEQUENCE: 6

Met Gly Trp Lys Ile Leu Pro Val Cys Leu Ser Leu Leu Leu Pro Val
1 5 10 15

Val Leu Ile Gln Gln Val Ser Ser Gln Glu Leu Ser Cys Lys Gly Arg
20 25 30

Cys Phe Glu Ser Phe Ala Arg Gly Arg Glu Cys Asp Cys Asp Ser Gln
35 40 45

Cys Lys Gln Tyr Gly Lys Cys Cys Ala Asp Tyr Asp Ser Phe Cys Glu
50 55 60

Glu Val Lys Asp Asn Lys Lys Asn Thr Pro Lys Lys Lys Pro Asn Pro
65 70 75 80

Glu Pro Pro Ala Val Asp Glu Ala Gly Ser Gly Leu Asp Asn Gly Glu
85 90 95

Phe Lys Leu Thr Pro Pro Pro Pro Asp Pro Pro Thr Thr Pro His Ser
100 105 110

Lys Val Ala Thr Ser Pro Lys Thr Thr Ala Ala Lys Pro Val Thr Pro
115 120 125

Lys Pro Ser Leu Ala Pro Asn Ser Glu Thr Ser Lys Glu Ala Ser Leu
130 135 140

-continued

```
Ala Ser Asn Lys Glu Thr Thr Val Glu Thr Lys Glu Thr Thr Ala Thr
145                 150                 155                 160

Asn Lys Gln Ser Ser Ala Ser Lys Lys Lys Thr Thr Ser Val Lys Glu
                165                 170                 175

Thr Arg Ser Ala Glu Lys Thr Ser Asp Lys Asp Val Glu Pro Thr Ser
            180                 185                 190

Thr Thr Pro Lys Asn Ser Ala Pro Thr Thr Thr Lys Lys Pro Val Thr
        195                 200                 205

Thr Thr Lys Glu Ser Lys Phe Leu Pro Leu Pro Gln Glu Pro Glu Pro
    210                 215                 220

Thr Thr Ala Lys Glu Pro Pro Pro Thr Thr Lys Lys Pro Glu Pro Thr
225                 230                 235                 240

Thr Arg Lys Glu Pro Glu Pro Thr Thr Pro Lys Glu Pro Glu Pro Thr
                245                 250                 255

Thr Pro Lys Glu Pro Glu Pro Thr Thr Pro Lys Glu Pro Glu Pro Thr
            260                 265                 270

Thr Pro Lys Glu Pro Pro Pro Thr Thr Lys Lys Pro Glu Pro Thr Thr
        275                 280                 285

Pro Lys Glu Pro Gly Pro Thr Thr Pro Lys Glu Pro Glu Pro Thr Thr
    290                 295                 300

Thr Lys Glu Pro Glu Pro Thr Thr Thr Lys Glu Pro Glu Ser Thr Thr
305                 310                 315                 320

Arg Lys Glu Pro Glu Pro Thr Thr Pro Lys Glu Pro Glu Pro Thr Thr
                325                 330                 335

Pro Lys Glu Pro Glu Pro Thr Thr Leu Lys Glu Pro Glu Pro Thr Thr
            340                 345                 350

Pro Lys Glu Pro Glu Pro Thr Thr Pro Lys Glu Pro Glu Pro Thr Thr
        355                 360                 365

Pro Lys Glu Pro Glu Pro Thr Thr Pro Lys Glu Pro Glu Pro Thr Thr
    370                 375                 380

Pro Lys Glu Pro Glu Pro Thr Thr Pro Lys Glu Pro Glu Pro Thr Thr
385                 390                 395                 400

Pro Lys Glu Pro Glu Pro Thr Thr Pro Lys Glu Pro Glu Pro Thr Thr
                405                 410                 415

Pro Lys Lys Pro Glu Pro Thr Thr Pro Lys Glu Pro Val Pro Thr Thr
            420                 425                 430

Pro Lys Glu Pro Glu Pro Thr Thr Pro Lys Glu Pro Glu Pro Thr Thr
        435                 440                 445

Pro Lys Glu Pro Glu Pro Thr Thr Arg Lys Glu Pro Glu Pro Thr Thr
    450                 455                 460

Pro Lys Glu Pro Glu Pro Thr Thr Pro Lys Glu Pro Glu Pro Thr Thr
465                 470                 475                 480

Pro Lys Lys Pro Glu Pro Thr Thr Thr Ser Pro Lys Thr Thr Thr Leu
                485                 490                 495

Lys Ala Thr Thr Leu Ala Pro Lys Val Thr Ala Pro Ala Glu Glu Ile
            500                 505                 510

Gln Asn Lys Pro Glu Glu Thr Thr Pro Ala Ser Glu Asp Ser Asp Asp
        515                 520                 525

Ser Lys Thr Thr Leu Lys Pro Gln Lys Pro Thr Lys Ala Pro Lys Pro
    530                 535                 540

Thr Lys Lys Pro Thr Lys Ala Pro Lys Lys Pro Thr Ser Thr Lys Lys
545                 550                 555                 560
```

```
Pro Lys Thr Pro Lys Thr Arg Lys Pro Lys Thr Thr Pro Ala Pro Leu
                565                 570                 575

Lys Thr Thr Ser Ala Thr Pro Glu Leu Asn Thr Thr Pro Leu Glu Val
            580                 585                 590

Met Leu Pro Thr Thr Thr Ile Pro Lys Gln Thr Pro Asn Pro Glu Thr
        595                 600                 605

Ala Glu Val Asn Pro Asp His Glu Asp Ala Asp Gly Gly Glu Gly Glu
    610                 615                 620

Lys Pro Leu Ile Pro Gly Pro Pro Val Leu Phe Pro Thr Ala Ile Pro
625                 630                 635                 640

Gly Thr Asp Leu Leu Ala Gly Arg Leu Asn Arg Gly Ile Asn Ile Asn
                645                 650                 655

Pro Met Pro Ser Asp Glu Thr Asn Leu Cys Asn Gly Lys Pro Val Asp
            660                 665                 670

Gly Leu Thr Thr Leu Arg Asn Gly Thr Leu Val Ala Phe Arg Gly His
        675                 680                 685

Tyr Phe Trp Met Leu Asn Pro Phe Arg Pro Pro Ser Pro Pro Arg Arg
    690                 695                 700

Ile Thr Glu Val Trp Gly Ile Pro Ser Pro Ile Asp Thr Val Phe Thr
705                 710                 715                 720

Arg Cys Asn Cys Glu Gly Lys Thr Phe Phe Phe Lys Asp Ser Gln Tyr
                725                 730                 735

Trp Arg Phe Thr Asn Asp Val Val Asp Pro Gly Tyr Pro Lys Gln Ile
            740                 745                 750

Val Lys Gly Phe Gly Gly Leu Thr Gly Lys Ile Val Ala Ala Leu Ser
        755                 760                 765

Ile Ala Lys Tyr Lys Asp Arg Pro Glu Ser Val Tyr Phe Phe Lys Arg
    770                 775                 780

Gly Gly Asn Ile Gln Gln Tyr Thr Tyr Lys Gln Glu Pro Met Lys Lys
785                 790                 795                 800

Cys Thr Gly Arg Arg Pro Ala Ile Asn Tyr Ser Val Tyr Gly Glu Ala
                805                 810                 815

Ala Gln Val Arg Arg Arg Arg Phe Glu Arg Ala Val Gly Pro Phe Gln
            820                 825                 830

Thr His Thr Phe Arg Ile His Tyr Ser Val Pro Met Arg Val Ser Tyr
        835                 840                 845

Gln Asp Lys Gly Phe Leu His Asn Glu Val Lys Val Ser Thr Met Trp
    850                 855                 860

Arg Gly Phe Pro Asn Val Val Thr Ser Ala Ile Thr Leu Pro Asn Ile
865                 870                 875                 880

Arg Lys Pro Asp Gly Tyr Asp Tyr Tyr Ala Phe Ser Lys Asp Gln Tyr
                885                 890                 895

Tyr Asn Ile Asp Val Pro Thr Arg Thr Ala Arg Ala Ile Thr Thr Arg
            900                 905                 910

Ser Gly Gln Thr Leu Ser Lys Ile Trp Tyr Asn Cys Pro
        915                 920                 925
```

<210> SEQ ID NO 7
<211> LENGTH: 29265
<212> TYPE: DNA
<213> ORGANISM: Artificial Sequence
<220> FEATURE:
<223> OTHER INFORMATION: helper-dependent adenoviral vector containing human Il-1Ra

<400> SEQUENCE: 7
aaacatcatc aataatatac cttattttgg attgaagcca atatgataat gagggggtgg 60
agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
ttccgggtca aagttggcgt tttgatatca agcttatcga taccgtaaac aagtctttaa 480
ttcaagcaag actttaacaa gttaaaagga gcttatgggt aggaagtagt gttatgatgt 540
atgggcataa agggttttaa tgggatagtg aaaatgtcta taataatact taaatggctg 600
cccaatcacc tacaggattg atgtaaacat ggaaaaggtc aaaaacttgg gtcactaaaa 660
tagatgatta atggagagga tgaggttgat agttaaatgt agataagtgg tcttattctc 720
aataaaaatg tgaacataag gcgagtttct acaaagatgg acaggactca ttcatgaaac 780
agcaaaaact ggacatttgt tctaatcttt gaagagtatg aaaaattcct attttaaagg 840
taaaacagta actcacagga aataccaacc caacataaaa tcagaaacaa tagtctaaag 900
taataaaaat caaacgtttg cacgatcaaa ttatgaatga aattcactac taaaattcac 960
actgattttg tttcatccac agtgtcaatg ttgtgatgca tttcaattgt gtgacacagg 1020
cagactgtgg atcaaaagtg gtttctggtg cgacttactc tcttgagtat acctgcagtc 1080
ccctttctta agtgtgttaa aaaaaaaggg ggatttcttc aattcgccaa tactctagct 1140
ctccatgtgc tttctaggaa acaagtgtta acccacctta tttgtcaaac ctagctccaa 1200
aggacttttg actccccaca aaccgatgta gctcaagaga gggtatctgt caccagtatg 1260
tatagtgaaa aaagtatccc aagtcccaac agcaattcct aaaaggagtt tatttaaaaa 1320
accacacaca cctgtaaaat aagtatatat cctccaaggt gactagtttt aaaaaaacag 1380
tattggcttt gatgtaaagt actagtgaat atgttagaaa aatctcactg taaccaagtg 1440
aaatgaaagc aagtatggtt tgcagagatt caaagaaaat ataagaaaac ctactgttgc 1500
cactaaaaag aatcatatat taaatatact cacacaatag ctcttcagtc tgataaaatc 1560
tacagtcata ggaatggatc tatcactatt tctattcagt gctttgatgt aatccagcag 1620
gtcagcaaag aatttatagc cccccttgag cacacagagg gctacaatgt gatggcctcc 1680
catctccttc atcacatctc gagcaagacg ttcagtccta cagaaataaa atcaggaatt 1740
taatagaaag tttcatacat taaactttat aacaaacacc tcttagtcat taaacttcca 1800
caccaacctg ggcaatatag tgagacccca tgcctgcaaa aaaaaaaaaa ttagccaggc 1860
atggtagcat gtacctgtag tcccagctac ttgagaggtg aggtgggaaa atcactttag 1920
tgcaggatgt tgaggctgga gtgaactgtg attgtgccac tgcactccag cctggacaat 1980
agagcaagac cttgtctcaa aaaaatgcat taaaaatttt ttttaaatct tccacgtatc 2040
acatcctttg ccctcatgtt tcataaggta aaaaatttga taccttcaaa aaaaccaagc 2100
ataccactat cataattttt tttaaatgca aataaaaaca agataccatt ttcacctatc 2160
agactggcag gttctgatta aatgaaattt tctggataat atacaatatt aagagagact 2220
gtagaaactg ggccagtggc tcatgcctgt aatcccagca ctttgggagg ctgggtaaca 2280
tggcgaaccc tgtttctaca aaataaaaat attagctggg agtggtggcg cacacctata 2340

-continued

```
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaatttc aagctagatg tgcataataa taaaaatctg accttgcctt    3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
agatcttact tacctgtcca taattagtcc atgaggaata aacacccttt ccaaatcctc   3480
agcataatga ttaggtatgc aaaataaatc aaggtcataa cctggttcat catcactaat   3540
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
```

-continued gttgcttgag gccaggagtt caagaccgac atggggaatg tagcaagacc ccgtccctac 4800
aaaaaacttt gtaaaaattt gccaggtatg gtggtgcata cctgtagtcc cagctactcg 4860
ggaggcggag gcagaaggaa tcacttgagc ccaggagttt gaggctgcag tgagctacga 4920
tcataccaca gcactccagc gtggacaaca gagtaagacc ctatctcaaa aacaaaacaa 4980
aacaaaacaa acaaaaaaaa ccacaagaaa aactgctggc tgatgcagcg gctcatgcct 5040
gtaatcccag tattttggga ggcccaggtg ggcgtatcac ctgaggtcag gagttagaga 5100
ccagcctggc caacatggtg aaaccccatc tctactaaaa atacaaaatt agccaggcat 5160
gtggcacgcg cctgtagtcc cagttactgg gaggctgaag caggaggatc acctgagccc 5220
gggaggtgga ggttgcagtg agccgagatc acaccactgc actccagcct gggtgacaca 5280
gcaataccct acctcaaaat aaaaaagaaa aagaaaagaa aagttgctgt ccccgctacc 5340
ccaatcccaa atccaaacag cctctctcat ctcacagtaa gggggaaaaa tcacccaaaa 5400
aagctaagtg atcttttgaa aacccaaact cttagaagtc taagattatt atagtcaact 5460
catgaagtgt catcataaaa gatactctaa tattatttaa gtagaaccac atattggttg 5520
tcttggtatg tctagcccct ggcatacaaa atatttaata acactgatat ggtacctgtg 5580
atgtgaaaat gtactatgag tacagcttta taaatactat atatgtacct atatacagaa 5640
aaaaatacaa caaaatcata aaagcactta tctttgaaag aggagttaca gcaattttat 5700
ttagttcttt attgctttgc tatatattct aaattttttt caatgaatat atatcacttt 5760
taaaaaaatt caatggtctt tcttataaat tatctttggc agcatgcgtt tttatatata 5820
catataaaat gtatgggaaa tttttaaagg atacattaaa ttaaagcaaa atatacaaac 5880
aaaaaatcag aatacaaaaa gataaaaaga ttgggaaggg agggagggag taaggaggaa 5940
gggtgggtgg gtatagagaa atataccaaa taatggtaag aagtggggtc ttgacacttt 6000
ctacactttt tttaaataaa aaaaattttt ttctctctct ttttttttt tagagacgaa 6060
gtctcgctat gttgcccagg ctggtcttga actcctggga tcaagagatc ctcctgcctc 6120
agcctcccaa ggtgcttgga ttacaggtgt gagccaccac gcctggtcac tttctacact 6180
ttaatatata tatttttca ttttcaatgt catttttatt agttaattta taatacccat 6240
tcaccattat attcaaagtc tatttgaaga aataaaccag aaagaatgaa atactctagc 6300
tcacatgcta ttcaatacta aattaccttt caaatcacat tcaagaagct gatgatttaa 6360
gctttggcgg tttccaataa atattggtca aaccataatt aaatctcaat atatcagtta 6420
gtacctattg agcatctcct tttacaacct aagcattgta ttaggtgctt aaatacaagc 6480
agcttgactt ttaatacatt taaaaataca tatttaagac ttaaaatctt atttatggaa 6540
ttcagttata ttttgaggtt tccagtgctg agaaatttga ggtttgtgct gtctttcagt 6600
ccccaaagct cagttctgag ttctcagact ttggtggaac ttcatgtatt gtcaggttgg 6660
cccgtaatac ctgtgggaca acttcagccc ctgtgcacat ggccaggagg ctggttgcaa 6720
acattttcag gtaggtggac caggacatgc ccctggtcat ggccaggtgg aggcatagtg 6780
ctatacagca ggcagaagtc aatattgatt tgtttttaaa gaaacatgta ctactttcat 6840
aagcagaaaa aatttctatt cttgggggaa aagattatgc cagatcctct aggattaaat 6900
gctgatgcat ctgctaaacc ttcacatatc agaacatatt tactatagaa agaatgaaaa 6960
tgggacattt gtgtgtcacc tatgtgaaca ttccaaaaat attttacaac aactaagtat 7020
tttataaatt ttatgaactg aaatttagtt caagttctag gaaaatacaa accttgctag 7080

-continued

```
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
aagttgtttt gttttattgc atcctagatt ttattttttt gatttatggt ttactttaag   7620
cataaaaaat ttgtcaatac aactcttccc aaaaggcata aacaaaaatt cataaaactt   7680
gcatcacttg agatacttca ggtatgaatt cacaactttg ttacaactta ctatatatat   7740
gcacacatat atatatattt gggtatattg ggggggttct aatttaagaa atgcataatt   7800
ggctatagac agacagttgt cagaacttgg caatgggtac gtgcaggttc attataccaa   7860
gtctacttgt agttgttcaa aatgtatcat aatacaaggc cgggcgaggt cgtcacgcct   7920
gtaatcccag cattttggga ggctaaggca ggaggattgc ttgaggtcag gagtttgtga   7980
ccagcctggg caacagagca agaccctgtc tccaaaaaga aaaaaaataa tttttttacaa  8040
aataaaaaca aaatgtatca tcagacgaaa ttaaataaga ggcaattcat ttaaatgaca   8100
acttttccca gcttgacatt taacaaaaag tctaagtcct cttaattcat atttaatgat   8160
caaatatcaa atactaattt tttttttttt tttttttttg agacggagtc tcgctctgtc   8220
gcccaggctg gagtgcagtg gcgcgatcct ggctcactgc aagctccgcc tcccgggttc   8280
acgccattct cctgcctcag cctcccgagt agctgggatt acagacatgc gccaccacgc   8340
ccggctaatt ttgtattttt agtagagatg gggtttctcc atgttggtca ggctggtctt   8400
gaatttccca cctcaggtga tctgcctgcc tcagcctcac aaagcagtag ctgggactac   8460
aggcacccac caccacactt ggttaattct tttgtatttt ttttgtaaag acgggatttc   8520
accatgttag ccaggatggt ctcgatctcc tgatctcatg atccgcccgc ctcagcctcc   8580
caaagtgctg ggattacagg cgtgagccac cccgcccggc catcaaatac taattcttaa   8640
atggtaagga cccactattc agaacctgta tccttatcac taatatgcaa atatttattg   8700
aatacttact atgtcatgca tactagagag agttagataa atttgataca gctaccctca   8760
cagaacttac agtgtaatag atggcatgac atgtacatga gtaactgtga acagtgttaa   8820
attgctattt aaaaaaaaag acggctgggc gctgtggctc atgcctgtaa tcccagcact   8880
ttgggaggcc aaggcaagtt gatcgctcga ggtcaagagt tcgagaccag cctggccaac   8940
gtggtaaaac cccgtctcta ctaaaaatac aaaaaaaaaa ttagccaggc atggtggcac   9000
aggcctgtaa tcccagctac tagggaggct gagacatgga gaactgcttg aatccaggag   9060
gcagaggtta cagtgagccg agatcatacc actacactcc agcctgagtg acagagcgag   9120
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
```

```
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc tttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaaa aaagacatgt tggccagatg  11760
cggtggctca cacctgtaat cccagcactt tgggaggctg aggtgggcgg atcacccctg  11820
```

-continued

```
gcctgcccaa catggtgaaa ccccgtctct actaaaaaca caaaaattag ctgggcgtgg 11880
tggcgggcgc ctgtaattcc agctactcgg gaggctgagg caggagaatt gctagaaccc 11940
aggaggcaga gattgcagtg agctgagatt gcaccattgc actacagtct gggcaacaaa 12000
agtgaaactc catcttaaaa aaaaaaagac aatgttcgtg ggtccaaaca agacttaatg 12060
gaagtgagtc taaaaatgag ctatgtgggc caggcgtagt ggctcccacc tgtaatccca 12120
gcactttggg aggccgaagc aggcagatca tgaggtcagg agatggagac catcctggcc 12180
aacacggtga aatcctgtct ctacaaaaat tagctgggcg tggtggtgcc tgcctgtaat 12240
cccagctact cagaaggctc aggcaggaga atcgcttgaa ccagggagtc ggtggctaga 12300
gtgagccgag atttgcatca ctgcactcct gcctggtgac agagcaagac tccatctcaa 12360
aaaaaacaaa caaaaataaa agataaaaat gagctatgtg aattaaaaga ggtataacaa 12420
tagataaacc atattttatt taattcctag taatgagtaa tatttccaaa cttctggaat 12480
gggcagaaat tgctagttgg catattttta ccttttatat tcagatacat taaaattctc 12540
aaaaaaaaac acctcaaagc agatgatccg ccatctcctt ggataatttg tgttaactca 12600
ggataacaga aaaccaaaat tatgagttac tgatgcaata ttcctaaatg taaaaataat 12660
taaagctaat agtagattca tcttccaatt tcatatcagt cttacaaata aactacatat 12720
ataacttgct tgccttccct tctgagggat aaagctgtta gaagaattaa aatcagcatt 12780
cttgactatt caaccaaggg agggataaat tattactcat tctagggaca tgggctcata 12840
actactacat gtgtaaggac atgaatttac ccaatattac aatttttcct tttattagtg 12900
tgtacagtgg aagaatagac atgttcactc tggacaaaaa aaaaattata cttatcagtt 12960
atcagaagca caatgctgaa gacagtagtt ccataacaat ttgaagtatg tgatcgaact 13020
agtagattat cttagtagta gtgaattatt gtaaatgtta gtaatttggc agccactggg 13080
cagaaaaata agaattgagg ctcaatattg atattaatgg tggtgattga cacataaatt 13140
ttatcaagtc tacacaatat aaaattacag aaaggtagaa gagtatacca gtacaacttc 13200
aacatatctt cactacaagg gagtaaaatg acatggccta gttactatct aatgaactgc 13260
agaaaactaa aagaaaactc caaggcaact cttctctgct gatctggttg gtccttttcc 13320
taccttttgc aatacccaga tacaaacaat ggatagaaaa caaagtagac ttgtagtatg 13380
caggtcacag tgctaaattc acagaaagaa acccctgaac tgaactgctc tatttcctgg 13440
tggtcacaaa gagtaattct ggtttacacc tacagattga tgtcaatcta caccctgttg 13500
ataacagtgt ggccaaggac aaaaaaaagg tgctccgttt taccaattct gtaaaaaatt 13560
attggcaggg taagctcggc tagggcagga ttacatttct aggactacca tccccgaaat 13620
ttagaagata ttatatccac ataaagcata tctttcacat taatttgcaa aaatctaaaa 13680
gctttttctt agctcaagtg tgtccaagtt taccctggca gtttaaaacg atagttacaa 13740
gcagcatggg ttgtatcaga cacatttgag ggccaatttc atgtaagtga tattgggcaa 13800
gttacttcaa ctatctgtgc ctccaaggtc atactagtgt ttatttacct aaagggtacc 13860
tgttatgtaa ctttagggtg tttacattag ataatgcctg caaaatattt acttcaacgc 13920
ctaaaacata gttaagtatt caataaatac ctactattgt cactactaac ttaaaagttt 13980
agagattaag agcagaatct ggggtgagac aaacttaggt tcaaatccta gtattgttgg 14040
gtaatcttgg gcaagttact taacctctct gatttgtgta atttaaaaaa ttagttaata 14100
tacataacag ggcttagaag agtatctagc acatagcacc atttaagcat ttgttattgc 14160
taacatgcaa acaatttaag ggaaagaaat tttttaaaaa ggaagaggga tttgcaaact 14220
```

aaaaacaatg agtatcttat gttcaaagaa aactaacaaa cagccagctc tagcaataat 14280
taaattcact atatactggg gcaggcatca caccccaaag ctaaaagcgt ctacctaggc 14340
caggcacggt ggctcatgcc tgtaatccca gcactttggg aagcagaggc gggcagatcg 14400
cttgagctca ggagttcaag accagcctgg acaacatggc aaaacaccat ctctacaaaa 14460
aatacaaata ttaggccggg cgcagtggct cacgcctgta atcccagcac tttgggaggc 14520
caaggcgggt ggatcacctg agatcaggag ttcgagagta gcctggccaa catggtgaaa 14580
cctcgtctct attaaaaata caaaaaatta gccaggcatg gtggcaggcg cctgtaatcc 14640
cagctactca gggggatgag gtaggagaat cgcttgaacc cgggaggcag aggttgcact 14700
gagccgagat catgccactg tactccagcc cgggcaacaa gagcgaaact ccatctcaaa 14760
aaataaataa ataaataaat aaaataaagt acaaatatta gccagggatg gtggtgcgca 14820
cctgtagtcc cagctacttg ggaggctgaa gtgggagaat cccctgagcc tggggagaat 14880
cacccgagcc cgggaagtcg aggctgcagt gagcagtgat tgtgccactg cactccatcc 14940
taggtgacag agtgagaccc tgtctcaaaa aaaagaaatt ggcagaatta agtaagttga 15000
tgtttagaga tgaaaaatca acatttttc ctcagcaact gaataaaaac aacagccact 15060
accatttttt tgagtaccta tttgtagcct attttttaac tggtattact cgagagagag 15120
agagctaggt tcgagacaga gctccttctc ttaataactg tatgacctag ggtatgtctg 15180
ttagcctctc tgaggcttca aaggttcctc atctgtaaaa tggtaataat cataccattg 15240
ctacagggct gttttgaaga ctaattagga ctatgtaagt aaacatgatg atggctatta 15300
ttactgttcc ccgccagggg ccatgcaagg gttgctgatt cacatagact gtcttataat 15360
cctctcaata actccaagag gtagccagca cctcagatat acataaaatg acttaagccc 15420
agagaggtga agtaagttgc ccacagccac acaactagta aatagcccaa acaagctgga 15480
ttcccagtta gactccgtta atagcactgc tctttacctt aagtcattac aatgcctaat 15540
atgaaataga atcgcttctt tcttagggtt caagtggtta attatttaat gtattcattc 15600
aacaaaccat catcgaggac ctcttacaag ccaagtactg tgctaagtgc tagagttacg 15660
gcggtgattc ctgcccttaa aaagttttag tgggagaaac aacaggtaac caggtcattg 15720
ccaaaacaac aaaaataatc ataataaagc aggctaaagc atatttaact ggccggggtt 15780
ttgactattt tagcaagcat gatcagaacg gttgaggagg gaggccagca gcttggccgg 15840
ttcaacaaac aagaaaaaac cagtgagggt ggagctaaga taccagaggc tgattacggt 15900
taagaatgtt cttgaaggta aggaccagat tctcattttc tatatcctgg ggcatcggtc 15960
agcatggaat ctggattcta gcacatgtga atttcggctt gaaatgacct aatgcctttt 16020
ccctagttcc ttcgtgtgtc aaatacgcat ggttaccgct accagagctg tagtggggct 16080
tcaatgaggc catgagcatc tccataaaga tgaactacag tgtgtgcaaa actaaaggca 16140
aaacctggtc cccacacgcc ctcccaggtg gtcgctttcc gtgccgaggc ccctccagag 16200
gtgccccgag aacctcacca tcgcacccca aacttccagg gaagggcctc tcccgagaaa 16260
gcccccacgc ccccaccccg cgccatcatt cccgaatctg ccctcggccc ctccccgcag 16320
cacgctcgca ggcggcacat gtcaaccaaa acgccatttc caccttctct tcccacacgc 16380
agtcctcttt tcccagggct cccccgagga gggacccacc ccaaaccccg ccattccgtc 16440
ctccctgccg ccctcgcgtg acgtaaagcc gaacccggga aactggccgc ccccgcctgc 16500
ggggttccct gggcccggcc gctctagaac tagtggatcc caattgaagg cctggtctaa 16560

-continued

```
atgactccaa aatcaccact taattcaaga gactgatttc cctgagtcag gccccttaaa  16620
gcagctattt caatgggaca gggaaacaac cctaggatct ggattagaat cacttggggg  16680
ctgccacacc cccagggctc tgatcctgcc cttctcccac acgcacattc acatactgct  16740
gcagtgacct tccatttcta atgggttcct gggccatctg tcaggtatag ggaatggaaa  16800
aggggttggg gaggctctgc ttcagaaagt ttgtgtcagg ggctcccaga gcctccacag  16860
atagatagca ggggtcccca ccctaccatg gcagctataa atgtgatcaa catttattgg  16920
cctaggatac agcagttagc aaaatgcctg atgtagttcc cactccgtgg aggttgcagg  16980
ctagccaaga agtcatgagt tcagcaaccc ttacgcacca gtgggatgag attggaccag  17040
gccgagggta gtcttgggaa cactcagcat ttgtctgagg gccagaagag gctgcttgcc  17100
ctcagacagg aggtcagcat ctttattgta gcccatgaca cctctacacc attgctcttc  17160
tggtcttatg gaagacatct ttgggcctga taacagcgga gtctgtgtcc cacttgtcca  17220
ggctggagtg ccacatcagg cacactccag ttgcagggac agcacagaca agtttcagga  17280
aggctggtgg cctccaggag gttaacctta taaggccaga ttgtaaccta gttgaaaaac  17340
atacacatgc catgataata aaagaaccta ggcaccatta caagagaaaa aatcattttt  17400
gtagatacga gcatggattc ttgggtgggt cagacacact gggcttgtgc tctgactgca  17460
ctgtctcccc tacctgacct tgggtaaacc ataagactgc tgcatgactc agtgtccacc  17520
ccaaaaaagt accggtagat attggccaca gtagatatca gctagagtgg actctcatga  17580
caatgagggg agatgtattc cccatcttag gcacctggga ctctaccttc catcttctgc  17640
tccgtgtctc tccatcccca ggctcttcag aactcaggga gtccagaatg tcagctccca  17700
gatttcagcc ttcagaaagg aaacccatta ccgttcagtt gaacaaatgt tgtctgagcc  17760
ccagatctgg gctcagaggc catctaggct atgagacaag aggggaacaa agcaccgtct  17820
gcactcactc accacactca cttgctgtcc caggtcacat ccatcgggta gagaatctaa  17880
gaggctgagc tagctcccgc caccagccca gcccacccca cctggcccct tccttccttc  17940
tacaaaatat gcaccacctg tcaaagggtg ggcagtgcca ggcctgcata cagagcactg  18000
agtgtaaaag cagacatgga ccctgacctc caggagcttc caattttctt gaagagacaa  18060
atcagctggc atttcagtcc agtgtgatct gctcttggtg agcacagacc tagggagttg  18120
gggcagcttc ccagaagaac tgcagtccag gctgagggca gagaaatgag gggaatggcg  18180
aggaattggg gagcaggggg gagctcagta gagagccaag ggcgggaggt gagaagtccg  18240
tgttgggcca ggagctaccc tccggtggcc acagccgaag tcgaggatgc ctttggaact  18300
catccccact tctctctttc tgtatgtagc cgtccaagaa caagtcacct ccaagtgtag  18360
ccggatcaag gcaagccccc catctagcaa gcacttgatg ccacccagaa ctgggcttct  18420
tcagaacaat ctgagtccag gaatgatccc actcaccagg caccagagct gcgagggcat  18480
gggagtgatc tcaccaactc tggggaagcg gcaaggaatt ttcacctcca gcccccagtg  18540
tcccatcctc tcacactcag gccagactcc cctgggcaga cttgactctg tctgccagca  18600
tatgcagagc cccaaggcca ccccaccaga agtgcccctg cctgggttct gtcccagctc  18660
cctgggcacc cagtccttga gtccccacca gctcagacgg cctagtgtgc caagaatgcc  18720
cactgcgttc aacaatgctg catgggtcac agcggcagca gctgtgacca cagcagtttc  18780
ggggaaaaca cccctcagcc aagtggataa tagcgttcag cagcactcac cttctggcca  18840
ggcctgcctt cagaggccat ctgattggga ggcacaagtg cccgctgcga tgggaacaca  18900
agtgcccctg gccaacaacc ccagcttcag cctgctgggc agccagagcc tcaggcagag  18960
```

-continued

```
cccggtacag ggcccggtgc ctgtagcaaa caccaccaag ttcctccagc agggtatggc  19020
cagctttagt cccctgagcc ccatacaggg catcgagcca ccaagctatg tggctgctgc  19080
tgccaccgct gctgctgctt ctgccgttgc tgccagccag ttcccaggtc cgttcgacag  19140
aacggatatt ccccctgagc tgccacctgc cgactttttg cgccagcccc aaccccccact  19200
aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcaccca  19380
ggatgctggg gcactttaaa tctgagcagg atgcccatag aaacccccat ggtgacatca  19440
ctctaggaag tggtgtcgat ccatacccgc agttgtctcc cgttacaatt tgagtggtgt  19500
tgtcagccca tgcttatccc tctctctacc tgtgacaaaa tggaaagctg gtgatttttc  19560
aagctacgtg tacatatttg aaaattttgt aaatggtttt cctaaacatt aatgacagaa  19620
gtatttatac ttcattttgt gactttgtaa ataaagcgac ggcttttgtt tcagtagagt  19680
tgtgtttact atgcattgtt ttgtgtttat tatacaatgt tacaaatatg cagaccgtgt  19740
tgtttgctcc agtgatacct tgttaagcta ggtggctgag tcgcttatgg ttttaatgca  19800
atgagcaatg tggatatgac caagagttgt tgtgcaagtt gacaaatgcc aaatagaaaa  19860
ccacttggcc atttatttct atgttcacta aaaatcctat tgccttgtgt gattcttaat  19920
ctcttttgcg aacctttcag tctccgctag ctctttccta atgagcttta cagcagaagc  19980
tgttttatcg ttaagtgccc cacagagaca ctttaccagg aggctgggag agttctccag  20040
atttgggaga ggcgcagaga cagtgtgtga gccgagccct gtctcagcaa tccacctgga  20100
ggagctagag tatcctcctc cctttaccat tcagaccgag agaaaaagcc cagcttgtgt  20160
gcaccctcgt ggggttaagg cgagctgttc ctggtttaaa gcctttcagt atttgttttg  20220
atgtaaggct ctgtggtttg ggggggaaca tctgtaaaca ttattagttg atttggggtt  20280
tgtctttgat ggtttctatc tgcaattatc gtcatgtata tttaagtgtc tgttatagaa  20340
aacccacacc cactgtcctg taaacttttc tcagtgtcca gactttctgt aatcacattt  20400
taattgccac ctcgtatttc acctctacat ttgaaatctg gcgtctgttt caagccagtg  20460
tgttttttct tcgttctgta ataaacagcc aggagaaaag tgcctctatg tttttatttt  20520
tcaagggagt attcagtacc tacaaaccca agtcaggaag cctgctagtg gctttggttc  20580
tttcagaggc tgctcgatgc cttgtgtgtc agaaagaaag attcagcagt tttgcatcat  20640
ggcaaagaag cctgttattt tggggctcag cccctcattt tatagaggat gaaacagagg  20700
gggatgggag gtcacaaaga caactgcccc gggagcaggt gtgggggaga cttgccctga  20760
gggtctagac gctctgcacc accgtcctgt ctcccttgct gaagaccaca catgcccttc  20820
tttgaccaga ccctgccacc tgataggcca ggacctggta ggcgggtacc caggtttcat  20880
ggatggaacc acatctcccc aaaagtgggg aggtagctac tgggatgcac gcctcccgcc  20940
atgtgctata ggagagcagc tgaagcaaca gttgggatca gatgtagtca caattgaatg  21000
catcatcaca tttatccctc taagtggctg ggagagttga tatcctcatc cctaaggtac  21060
aaaatgttcc aatttgatca gtggctttca ggagctgaga aaggcatgtg ctctgaggca  21120
gagctgttat gtcccgcaga gcctaaaaat gctctaagaa catgctccct gccaaaattc  21180
tcaatggctg tgacaaggga caacgatcga ccaatggggg tggaagcaga cctccgcagt  21240
ccaggggcca gagctaggac agaggggtcg gagaaagagt cattttccca acactccagc  21300
```

-continued

```
tcttggccag tcctcacaca gtcccctcct gcttcctgct gagagagata tcctcatagg  21360
tctgggtaaa gtccttcagt cagctttcat tccctgtcac caactttgtc tctgttctcc  21420
ctgcccgtct caggcagcac tcctcaggaa acctctccaa gagccagcct cactgcagcg  21480
cccactattg tccctctgcc tcaagtgtcc catccatgcc aggccccagg caggctgcag  21540
ctttccctca gggccacacc aaagcacttg ggctcagctg tgctgtcccc ctccatcact  21600
gagctcaggg gcagcagggg tggggtgcca ggaggcccat tcacccttct ctggctctgt  21660
gttggaccca cctgcccagc cactgctgct tagaacctac ccgctgggaa aatgaagccc  21720
tcccggaggg gccacctcaa cctgagagcc tcacggatca cagttgtccc cactcagctc  21780
tgccagccct cagagaccca tagataaaag ctgagcttgg ctcgcagagc tggttccatc  21840
ttccattccc agagggttca acttcctacc ccaaccacac agggaacctc aaggctgagc  21900
cagtgtgggc tgcagtgcag accagcttcc tggacacgtc ctgccacctg accccaggct  21960
ggcctcactg cccctggcac tcctgaccct atcctcattc ctcctggcag tgcgtgttct  22020
gccattccgc tttcccttag ctgtcctctc actgtactgt cagcttctcc ttttccaggt  22080
gccccccagg ggctttccac atgaccctgt caccccacag cccatccagc accaattcca  22140
gctctctgcc acccttcaaa ggagtgacag tgccctgctt cacctcccac tcacccctca  22200
acccagagca atctggctcc agtcttgcct ccttcccccct aagtactcta gtcacagttc  22260
caaattcctc ctggtcataa agccaaatga agcttcctgg tcctcagcgg acttgccact  22320
tcagcagtac tggactctct cctcccagaa acctgtttcc ccttggctcc tggagcccac  22380
actctgctgg aatccttctg cctctctggc ctgtagcctg gccctctctc ccaacctgag  22440
gtccattctc tcctgctcct ccacaagatg ttgctccttc cattacttcc tccctctcaa  22500
ccaaagctcc ttcattagct ctttatcttc tggtttcttc ccctgggcag acgaatggat  22560
tcaagagcct gtggcccagc agcccagcac tccaggatct cagcacttca gcatcccagt  22620
accctagcat ctcaataccc cagcacccca gcaccatagt attccagcac cccattgtcc  22680
aagcatctca gcactccagc atcccagcac cccaacactc cagcagccca gaatctcagc  22740
accctagcac tgcagcatct caggacccca gcacttcagc atcccagcac actagtactc  22800
cagcatctcg gcaccccagc acctaggcat cccaacaccc agcaccccag cacttaagca  22860
tcccaccact acagtatctc aacactccag caccccagca ccatagtgtt ccagcacccc  22920
agcatcccaa caccccagca cttaagcatc ccaacacctc ggcatcccaa caccccagca  22980
ctgcagcatc tcagcacctt agcatcccag tgccctagca tctcaatgct ccagcacacc  23040
agtactacag tattccagca ccccagcact ccagcatctc agcactgcag cactgcagca  23100
ctccagcatc ccaaaatccc agcatcccaa caccccagca gaccagcaga ccagcatctc  23160
agcaccgcag catccaagga ctatcccagc atcccagcaa cccagcacct cagcatccca  23220
acaccccagc atttcagcat ggcaacaccc cagtacccca gcacttcagc accccagtat  23280
cccagcatct cagcgaccca gtatcacaaa acctcagcat cctagcaccc cagcacccca  23340
gcaccttagc accttagcat cccagcatct cagcgcctca gcatcttgat attctggctg  23400
aggtcagcgt ggtgtatcta gtcagggtcc taactttcac ttcgcaggga aatgctgctg  23460
gactgggtct catgttgggc tgaagctctc tagacccctt gaagacagca taaaagagct  23520
tggagacgct gggtgtcccc catggaagag ttcactctca tcctgctttg acaacagcct  23580
tctctggggt ccctcacggg cccctctttc ttactgcaag tttgtctctg agaagactgt  23640
gatgcagaag tcactcagct gcctgtggct cctgaagagc tgaaggtgga ggcctgtagg  23700
```

cctccctatg agaggcgcag aaaaaaccat gattgctagt ggggaggtgc tccctctaca 23760
acccactcca taatctgccc ccgcccagct ctgaggccag ccccagggga aaatgccaga 23820
tccccaggga ggtgtgtgag acctcagggg ctccctcctc ccttacagca ggctcaggcc 23880
cctgggggcc tcagggccaa ggtctgtggg taagctacta tctctcactt gtcctctagc 23940
cacaaaagcc agggagatct ggcaatggac atgaggttct gaagaagcac atatgactgg 24000
cttcctaatg cgtggttgtt cagtgattca ataaacacgc atgggccagg catggggaaa 24060
tagacaaaca tgatccccaa cctctcccag agtgaactgg gagggaggag tgttcatccc 24120
tcaggattac accagagaaa caaaccagca ggagatatat atggttttgg ggggtcaaga 24180
aagaggaaaa acctggcaag gcaagtccaa aatcatagga caggctgtca ggaagggcag 24240
cctggaacct ctcaagcagg agctgatgct gcagtccaca ggcagaattt cttcttcctc 24300
ggggaaatct cagctttgtt cttaaggcct ttcaactgat tggctgaggt ctgccccttc 24360
ccccacattc tccaggataa tcttccttac ttaaagtcaa ctattaatca cagctacaaa 24420
atcccttcac agctacacat agatcagtgt ttgattgacg aacagcccct acagcctagc 24480
caagttgaca cataaaacta accatcacag gggacaaat gatgtaaaca catcaacaaa 24540
taaaacagta acaagttaag gtctatggaa aaaacacaga aggggcagag agaaagaaag 24600
caagaaggag agtcccagtt tgctagggct tgtgggaagt ggggagcagt tctctttagc 24660
taggatattt gggaaaggca tatctgaagg agtgatattt gagcttagat taaaagatgg 24720
gaaggagcaa gccatgcaaa gagctaggat gttccaagca gagacggaac agcaagtgca 24780
aatgtcagga ggaatagaag gaggctggtg ggtggggtcc agtgagcaag aggagggcag 24840
gcaggagagg ggatggggag gtgggcaggc ccagaccacc cagggccctg gagactatcc 24900
tgatccaaca agggaagcct tgagtcactt cagtgtccat gtggagaatg gacctcagac 24960
tgaatgaggg aggcagtaag gagggcctct acctccaggg cttcgccctg tggactgcgc 25020
atagacatct ccaactcaga aagtctgaac caaactttcc atagttcccc caagtctggg 25080
catcctccta ctcagtgaaa ggcagccatc acacctccct gccctgctcc cggatgcccc 25140
aaatcctctt ggtctccaag tccagaacct gagacttgtc cttgatgttt gtctttccct 25200
cacccctttct gtattctggg aagatgggtt tttttccccc agatgaatct gtaaaacttc 25260
tgtgatcaca ataaaaattc tggcagtatt attttctgga acatgacaaa gtgattcaaa 25320
attatttatc tggaagacta caaaacaaga atagccagga aatttctaaa aagaaagaag 25380
aaggaggagg agaaagaagg aggaggaaaa ggaggagaag aagaaaagaa aaagaaccaa 25440
gaaagggttc tagctctacc aaatattaaa acatatcatg aagctattta aaacaatatg 25500
gttgtggata ctgaaaaaga tgtgaataaa gtggaaggaa aataaataga aatgcacatg 25560
gggattgaga ctgtgaaaaa ggcagcatct cacatcagtg agggatgttc aacacctggt 25620
gttgggaaaa ctggctagtc atttaaacca aacaactggg tcctctacct cactcctgac 25680
attaagatac atttagatga ttcaaagagt aagacagaaa aaataacacg tgaaaacact 25740
atcagaaaac aacgtgggcc aggtgtggtg ggtcacgcct gtaatcccag cactttggga 25800
ggccgaggca gacagatcac ctgaggtggg gagttcaaga ccagcctgac caacatggtg 25860
aaatcctgtc tctactaaaa atacaaaatt agctgagcgt ggtggcgcat gcctgtaatc 25920
ccagctactc aggaggccga ggcaggagaa tcacttgaac ctgggaggca gaggttgtgg 25980
tgagccgaga tcacgccatt gcactccagc ctgggcaaca agagtgaaaa tccatctaaa 26040

-continued

```
aaaaaaaaaa aaagccaagg tggatatttt tatagtatca gggtagatca agcttctcca  26100
atcatgacat gaaacccaga aaccataaaa gaaaagaatg ataaaattgc ccacgtaaag  26160
taaaaagctt gcacacagaa aaacaccata caggttacaa gatgagcagc aaaatcagag  26220
aaaaaacatt gcaattcagg acacacagag gctattgttc ctaatattta aaaataaaag  26280
tagtggattg tctacaaaaa gatgaagaca agaatttcag aaaaccaaat actgcatgtt  26340
ttcacttaca agtggaagct aaacactgag tacacgtgta cacaaagaat ggaaccatag  26400
gccaggcacc gtggctcacg cctgtaatcc cagtactttg cgaggccgaa gcgggcggat  26460
cacctgaggt gaggagttcg agaccatcct ggccaacatg gtgaaaccca gtctctacta  26520
aaaatacaaa aattagccgg gcgtggtggt gggtgcctgt aatcccagct actcgggagg  26580
ctgcggcagt agaatcgctt gaaccctgga ggtggacctt gcagtgagcc gagatcgcac  26640
cactgcactc cagcctgggc aacagagtga gactccatct caaaaaaaaa aaaaaggaat  26700
agaacaatag acactggggc ctacttgagg gaggagggtg aggatcaaaa acctgcctat  26760
caggtactat gcttattacc tgggtggtga aataatctgt acaccaaacc ccagtgacat  26820
gcaatttacc gatgtaacaa acctgcccat gtacccgctg aacctaaaat aaaagttgga  26880
aaaaaatata gaaattttct ttgtaatagc caaaaactgc aaacagccca ggtgtctatt  26940
agtagaatgc ataaacaaac tcgggcatgt tcatacaatg taaaactact catcaataaa  27000
aagtgatact tctcagcaat gaaaagaaac tagctactga taccagctac aacatggatg  27060
gatttcaagt gctttatgat gagagcaaga agccagacac aaaagtgtct atatatatat  27120
acagtatata tacgtatata tacacatata tacagtatat atatacatat acatgtatat  27180
atatactgta tatatactgt atatatatac acagtatata tatacatata tacagtgtat  27240
atatactgtg tatatataca tgtatatata ctgtgtatat atacatgtat atatactgtg  27300
tatatataca tgtatatata ctgtgtatat atacatgtat atatatgtat actgtatata  27360
tactgtatat atatatacac atatatacag tatatatata cagtatatac tgtatatata  27420
cagtatatac gtgtatatat acatatatac agtatatatg taaatataca tatatacagt  27480
atatatgtaa atatacatat atacatgtat atatatacac tatatatata catatatagt  27540
gtatatatac atatatacat gtatatattt actatatgat tccatttata taaagtgcca  27600
aaacagtcaa aaataatcta tgtggaaaaa atcaacaaag ggatcccccg ggctgcagga  27660
attcgatggc gcgccgtcga cccaacgcgt tgggagctct ccggatccaa gcttgttggg  27720
tcgaagctcg acatgataag atacattgat gagtttggac aaaccacaac tagaatgcag  27780
tgaaaaaaat gctttatttg tgaaatttgt gatgctattg ctttatttgt gaaatttgtg  27840
atgctattgc tttatttgta accattataa gctgcaataa acaagttaac aacaacaatt  27900
gcattcattt tatgtttcag gttcaggggg aggtgtggga ggttttttaa agcaagtaaa  27960
acctctacaa atgtggtaga tccatttaaa tgttaaggat cccgcggccg cctactcgtc  28020
ctcctggaag tagaatttgg tgaccatgac gccttcgtca ggcatattgg tgaggctgac  28080
gggctggtca gcttccatcg ctgtgcagag gaaccaaccg gggcaggcgg cagactcaaa  28140
actggtggtg gggccactgt ctgagcggat gaaggcgaag cgcttgtcct gctttctgtt  28200
ctcgctcagg tcagtgatgt taactgcctc cagctggagt ctggtctcat caccagactt  28260
gacacaggac aggcacatct tccctccatg gattcccaag aacagagcat gaggctcaat  28320
gggtaccaca tctatctttt cttctaaatt gacatttggt ccttgcaagt atccagcaac  28380
tagttggttg ttcctcagat agaaggtctt ctggttaaca tcccagattc tgaaggcttg  28440
```

-continued catcttgctg gattttctcc cagagggtcg gcagatcgtc tctgaatgga acaggaagag 28500
gaggagagtg attaggtgac tgcggaggcc tctgcagatt tccataccgg tggatccatg 28560
gctctgtctc aggtcagtat aggagctttg atgtgaagtc agccaagaac agctgaacac 28620
tacttcctct gaggcccttt tataggaggg attgcttcct gtgaataata ggaggatatt 28680
gtccacatcc agtaaagagg aaatccccaa ctgcatccaa aaagttttct gggaatatcc 28740
actgctgcag gagtggaaag tccccagtgg aaagtcccca gtggaaagtc cccagtggaa 28800
agtccccagt ggaaagtccc cagaatttcg acgtctagag gagcatgcga cgtcggcgcg 28860
cctaccagta aaaaagaaaa cctattaaaa aaacaccact cgacacggca ccagctcaat 28920
cagtcacagt gtaaaaaagg gccaagtgca gagcgagtat atataggact aaaaaatgac 28980
gtaacggtta aagtccacaa aaaacaccca gaaaaccgca cgcgaaccta cgcccagaaa 29040
cgaaagccaa aaaacccaca acttcctcaa atcgtcactt ccgttttccc acgttacgtc 29100
acttcccatt ttaagaaaac tacaattccc aacacataca agttactccg ccctaaaacc 29160
tacgtcaccc gccccgttcc cacgccccgc gccacgtcac aaactccacc ccctcattat 29220
catattggct tcaatccaaa ataaggtata ttattgatga tgttt 29265

<210> SEQ ID NO 8
<211> LENGTH: 29612
<212> TYPE: DNA
<213> ORGANISM: Artificial Sequence
<220> FEATURE:
<223> OTHER INFORMATION: helper-dependent adenoviral vector containing murine Il-1Ra

<400> SEQUENCE: 8
aaacatcatc aataatatac cttattttgg attgaagcca atatgataat gagggggtgg 60
agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
ttccgggtca aagttggcgt tttgatatca agcttatcga taccgtaaac aagtctttaa 480
ttcaagcaag actttaacaa gttaaaagga gcttatgggt aggaagtagt gttatgatgt 540
atgggcataa agggttttaa tgggatagtg aaaatgtcta taataatact taaatggctg 600
cccaatcacc tacaggattg atgtaaacat ggaaaaggtc aaaaacttgg gtcactaaaa 660
tagatgatta atggagagga tgaggttgat agttaaatgt agataagtgg tcttattctc 720
aataaaaatg tgaacataag gcgagtttct acaaagatgg acaggactca ttcatgaaac 780
agcaaaaact ggacatttgt tctaatcttt gaagagtatg aaaaattcct attttaaagg 840
taaaacagta actcacagga aataccaacc caacataaaa tcagaaacaa tagtctaaag 900
taataaaaat caaacgtttg cacgatcaaa ttatgaatga aattcactac taaaattcac 960
actgattttg tttcatccac agtgtcaatg ttgtgatgca tttcaattgt gtgacacagg 1020
cagactgtgg atcaaaagtg gtttctggtg cgacttactc tcttgagtat acctgcagtc 1080
ccctttctta agtgtgttaa aaaaaaaggg ggatttcttc aattcgccaa tactctagct 1140
ctccatgtgc tttctaggaa acaagtgtta acccacctta tttgtcaaac ctagctccaa 1200

-continued

```
aggacttttg actccccaca aaccgatgta gctcaagaga gggtatctgt caccagtatg   1260
tatagtgaaa aaagtatccc aagtcccaac agcaattcct aaaaggagtt tatttaaaaa   1320
accacacaca cctgtaaaat aagtatatat cctccaaggt gactagtttt aaaaaaacag   1380
tattggcttt gatgtaaagt actagtgaat atgttagaaa aatctcactg taaccaagtg   1440
aaatgaaagc aagtatggtt tgcagagatt caaagaaaat ataagaaaac ctactgttgc   1500
cactaaaaag aatcatatat taaatatact cacacaatag ctcttcagtc tgataaaatc   1560
tacagtcata ggaatggatc tatcactatt tctattcagt gctttgatgt aatccagcag   1620
gtcagcaaag aatttatagc ccccttgag cacacagagg gctacaatgt gatggcctcc   1680
catctccttc atcacatctc gagcaagacg ttcagtccta cagaaataaa atcaggaatt   1740
taatagaaag tttcatacat taaactttat aacaaacacc tcttagtcat taaacttcca   1800
caccaacctg ggcaatatag tgagacccca tgcctgcaaa aaaaaaaaaa ttagccaggc   1860
atggtagcat gtacctgtag tcccagctac ttgagaggtg aggtgggaaa atcactttag   1920
tgcaggatgt tgaggctgga gtgaactgtg attgtgccac tgcactccag cctggacaat   1980
agagcaagac cttgtctcaa aaaaatgcat taaaaatttt ttttaaatct tccacgtatc   2040
acatcctttg ccctcatgtt tcataaggta aaaaatttga taccttcaaa aaaaccaagc   2100
ataccactat cataattttt tttaaatgca aataaaaaca agataccatt ttcacctatc   2160
agactggcag gttctgatta aatgaaattt tctggataat atacaatatt aagagagact   2220
gtagaaactg ggccagtggc tcatgcctgt aatcccagca ctttgggagg ctgggtaaca   2280
tggcgaaccc tgtttctaca aaataaaaat attagctggg agtggtggcg cacacctata   2340
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaattttc aagctagatg tgcataataa taaaaatctg accttgcctt   3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
agatcttact tacctgtcca taattagtcc atgaggaata aacacccttt ccaaatcctc   3480
agcataatga ttaggtatgc aaaataaatc aaggtcataa cctggttcat catcactaat   3540
```

-continued

```
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
```

-continued

```
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tattttttca ttttcaatgt catttttatt agttaattta taatacccat   6240
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
ctatacagca ggcagaagtc aatattgatt tgtttttaaa gaaacatgta ctactttcat   6840
aagcagaaaa aatttctatt cttgggggaa aagattatgc cagatcctct aggattaaat   6900
gctgatgcat ctgctaaacc ttcacatatc agaacatatt tactatagaa agaatgaaaa   6960
tgggacattt gtgtgtcacc tatgtgaaca ttccaaaaat attttacaac aactaagtat   7020
tttataaatt ttatgaactg aaatttagtt caagttctag gaaaatacaa accttgctag   7080
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
aagttgtttt gttttattgc atcctagatt ttattttttt gatttatggt ttactttaag   7620
cataaaaaat ttgtcaatac aactcttccc aaaaggcata aacaaaaatt cataaaactt   7680
gcatcacttg agatacttca ggtatgaatt cacaactttg ttacaactta ctatatatat   7740
gcacacatat atatatattt gggtatattg ggggggttct aatttaagaa atgcataatt   7800
ggctatagac agacagttgt cagaacttgg caatgggtac gtgcaggttc attataccaa   7860
gtctacttgt agttgttcaa aatgtatcat aatacaaggc cgggcgaggt cgtcacgcct   7920
gtaatcccag cattttggga ggctaaggca ggaggattgc ttgaggtcag gagtttgtga   7980
ccagcctggg caacagagca agaccctgtc tccaaaaaga aaaaaaataa tttttttacaa   8040
aataaaaaca aaatgtatca tcagacgaaa ttaaataaga ggcaattcat ttaaatgaca   8100
acttttccca gcttgacatt taacaaaaag tctaagtcct cttaattcat atttaatgat   8160
caaatatcaa atactaattt tttttttttt tttttttttg agacggagtc tcgctctgtc   8220
gcccaggctg gagtgcagtg gcgcgatcct ggctcactgc aagctccgcc tcccgggttc   8280
```

-continued

```
acgccattct cctgcctcag cctcccgagt agctgggatt acagacatgc gccaccacgc   8340
ccggctaatt ttgtattttt agtagagatg gggtttctcc atgttggtca ggctggtctt   8400
gaatttccca cctcaggtga tctgcctgcc tcagcctcac aaagcagtag ctgggactac   8460
aggcacccac caccacactt ggttaattct tttgtatttt ttttgtaaag acgggatttc   8520
accatgttag ccaggatggt ctcgatctcc tgatctcatg atccgcccgc ctcagcctcc   8580
caaagtgctg ggattacagg cgtgagccac cccgcccggc catcaaatac taattcttaa   8640
atggtaagga cccactattc agaacctgta tccttatcac taatatgcaa atatttattg   8700
aatacttact atgtcatgca tactagagag agttagataa atttgataca gctaccctca   8760
cagaacttac agtgtaatag atggcatgac atgtacatga gtaactgtga acagtgttaa   8820
attgctattt aaaaaaaaag acggctgggc gctgtggctc atgcctgtaa tcccagcact   8880
ttgggaggcc aaggcaagtt gatcgctcga ggtcaagagt tcgagaccag cctggccaac   8940
gtggtaaaac cccgtctcta ctaaaaatac aaaaaaaaaa ttagccaggc atggtggcac   9000
aggcctgtaa tcccagctac tagggaggct gagacatgga gaactgcttg aatccaggag   9060
gcagaggtta cagtgagccg agatcatacc actacactcc agcctgagtg acagagcgag   9120
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc tttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
```

-continued

```
gctaatttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaaa aaagacatgt tggccagatg  11760
cggtggctca cacctgtaat cccagcactt tgggaggctg aggtgggcgg atcacccctg  11820
gcctgcccaa catggtgaaa ccccgtctct actaaaaaca caaaaattag ctgggcgtgg  11880
tggcgggcgc ctgtaattcc agctactcgg gaggctgagg caggagaatt gctagaaccc  11940
aggaggcaga gattgcagtg agctgagatt gcaccattgc actacagtct gggcaacaaa  12000
agtgaaactc catcttaaaa aaaaaaagac aatgttcgtg ggtccaaaca agacttaatg  12060
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta cctttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aatttttcct tttattagtg  12900
tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
```

agtagattat cttagtagta gtgaattatt gtaaatgtta gtaatttggc agccactggg 13080
cagaaaaata agaattgagg ctcaatattg atattaatgg tggtgattga cacataaatt 13140
ttatcaagtc tacacaatat aaaattacag aaaggtagaa gagtatacca gtacaacttc 13200
aacatatctt cactacaagg gagtaaaatg acatggccta gttactatct aatgaactgc 13260
agaaaactaa aagaaaactc caaggcaact cttctctgct gatctggttg gtccttttcc 13320
taccttttgc aatacccaga tacaaacaat ggatagaaaa caaagtagac ttgtagtatg 13380
caggtcacag tgctaaattc acagaaagaa acccctgaac tgaactgctc tatttcctgg 13440
tggtcacaaa gagtaattct ggtttacacc tacagattga tgtcaatcta caccctgttg 13500
ataacagtgt ggccaaggac aaaaaaaagg tgctccgttt taccaattct gtaaaaaatt 13560
attggcaggg taagctcggc tagggcagga ttacatttct aggactacca tccccgaaat 13620
ttagaagata ttatatccac ataaagcata tctttcacat taatttgcaa aaatctaaaa 13680
gctttttctt agctcaagtg tgtccaagtt taccctggca gtttaaaacg atagttacaa 13740
gcagcatggg ttgtatcaga cacatttgag ggccaatttc atgtaagtga tattgggcaa 13800
gttacttcaa ctatctgtgc ctccaaggtc atactagtgt ttatttacct aaagggtacc 13860
tgttatgtaa ctttagggtg tttacattag ataatgcctg caaaatattt acttcaacgc 13920
ctaaaacata gttaagtatt caataaatac ctactattgt cactactaac ttaaaagttt 13980
agagattaag agcagaatct ggggtgagac aaacttaggt tcaaatccta gtattgttgg 14040
gtaatcttgg gcaagttact taacctctct gatttgtgta atttaaaaaa ttagttaata 14100
tacataacag ggcttagaag agtatctagc acatagcacc atttaagcat ttgttattgc 14160
taacatgcaa acaatttaag ggaaagaaat tttttaaaaa ggaagaggga tttgcaaact 14220
aaaaacaatg agtatcttat gttcaaagaa aactaacaaa cagccagctc tagcaataat 14280
taaattcact atatactggg gcaggcatca caccccaaag ctaaaagcgt ctacctaggc 14340
caggcacggt ggctcatgcc tgtaatccca gcactttggg aagcagaggc gggcagatcg 14400
cttgagctca ggagttcaag accagcctgg acaacatggc aaaacaccat ctctacaaaa 14460
aatacaaata ttaggccggg cgcagtggct cacgcctgta atcccagcac tttgggaggc 14520
caaggcgggt ggatcacctg agatcaggag ttcgagagta gcctggccaa catggtgaaa 14580
cctcgtctct attaaaaata caaaaaatta gccaggcatg gtggcaggcg cctgtaatcc 14640
cagctactca gggggatgag gtaggagaat cgcttgaacc cgggaggcag aggttgcact 14700
gagccgagat catgccactg tactccagcc cgggcaacaa gagcgaaact ccatctcaaa 14760
aaataaataa ataaataaat aaaataaagt acaaatatta gccagggatg gtggtgcgca 14820
cctgtagtcc cagctacttg ggaggctgaa gtgggagaat cccctgagcc tggggagaat 14880
cacccgagcc cgggaagtcg aggctgcagt gagcagtgat tgtgccactg cactccatcc 14940
taggtgacag agtgagaccc tgtctcaaaa aaaagaaatt ggcagaatta agtaagttga 15000
tgtttagaga tgaaaaatca acattttttc ctcagcaact gaataaaaac aacagccact 15060
accatttttt tgagtaccta tttgtagcct attttttaac tggtattact cgagagagag 15120
agagctaggt tcgagacaga gctccttctc ttaataactg tatgacctag ggtatgtctg 15180
ttagcctctc tgaggcttca aaggttcctc atctgtaaaa tggtaataat cataccattg 15240
ctacagggct gttttgaaga ctaattagga ctatgtaagt aaacatgatg atggctatta 15300
ttactgttcc ccgccagggg ccatgcaagg gttgctgatt cacatagact gtcttataat 15360
cctctcaata actccaagag gtagccagca cctcagatat acataaaatg acttaagccc 15420
agagaggtga agtaagttgc ccacagccac acaactagta aatagcccaa acaagctgga 15480
ttcccagtta gactccgtta atagcactgc tctttacctt aagtcattac aatgcctaat 15540
atgaaataga atcgcttctt tcttagggtt caagtggtta attatttaat gtattcattc 15600
aacaaaccat catcgaggac ctcttacaag ccaagtactg tgctaagtgc tagagttacg 15660
gcggtgattc ctgcccttaa aaagttttag tgggagaaac aacaggtaac caggtcattg 15720
ccaaaacaac aaaaataatc ataataaagc aggctaaagc atatttaact ggccggggtt 15780
ttgactattt tagcaagcat gatcagaacg gttgaggagg gaggccagca gcttggccgg 15840
ttcaacaaac aagaaaaaac cagtgagggt ggagctaaga taccagaggc tgattacggt 15900
taagaatgtt cttgaaggta aggaccagat tctcattttc tatatcctgg ggcatcggtc 15960
agcatggaat ctggattcta gcacatgtga atttcggctt gaaatgacct aatgcctttt 16020
ccctagttcc ttcgtgtgtc aaatacgcat ggttaccgct accagagctg tagtggggct 16080
tcaatgaggc catgagcatc tccataaaga tgaactacag tgtgtgcaaa actaaaggca 16140
aaacctggtc cccacacgcc ctcccaggtg gtcgctttcc gtgccgaggc ccctccagag 16200
gtgccccgag aacctcacca tcgcacccca aacttccagg gaagggcctc tcccgagaaa 16260
gcccccacgc ccccaccccg cgccatcatt cccgaatctg ccctcggccc ctccccgcag 16320
cacgctcgca ggcggcacat gtcaaccaaa acgccatttc caccttctct tcccacacgc 16380
agtcctcttt tcccagggct cccccgagga gggacccacc ccaaaccccg ccattccgtc 16440
ctccctgccg ccctcgcgtg acgtaaagcc gaacccggga aactggccgc ccccgcctgc 16500
ggggttccct gggcccggcc gctctagaac tagtggatcc caattgaagg cctggtctaa 16560
atgactccaa aatcaccact taattcaaga gactgatttc cctgagtcag gccccttaaa 16620
gcagctattt caatgggaca gggaaacaac cctaggatct ggattagaat cacttggggg 16680
ctgccacacc cccagggctc tgatcctgcc cttctcccac acgcacattc acatactgct 16740
gcagtgacct tccatttcta atgggttcct gggccatctg tcaggtatag ggaatggaaa 16800
aggggttggg gaggctctgc ttcagaaagt ttgtgtcagg ggctcccaga gcctccacag 16860
atagatagca ggggtcccca ccctaccatg gcagctataa atgtgatcaa catttattgg 16920
cctaggatac agcagttagc aaaatgcctg atgtagttcc cactccgtgg aggttgcagg 16980
ctagccaaga agtcatgagt tcagcaaccc ttacgcacca gtgggatgag attggaccag 17040
gccgagggta gtcttgggaa cactcagcat ttgtctgagg gccagaagag gctgcttgcc 17100
ctcagacagg aggtcagcat ctttattgta gcccatgaca cctctacacc attgctcttc 17160
tggtcttatg gaagacatct ttgggcctga taacagcgga gtctgtgtcc cacttgtcca 17220
ggctggagtg ccacatcagg cacactccag ttgcagggac agcacagaca agtttcagga 17280
aggctggtgg cctccaggag gttaacctta taaggccaga ttgtaaccta gttgaaaaac 17340
atacacatgc catgataata aaagaaccta ggcaccatta caagagaaaa aatcattttt 17400
gtagatacga gcatggattc ttgggtgggt cagacacact gggcttgtgc tctgactgca 17460
ctgtctcccc tacctgacct tgggtaaacc ataagactgc tgcatgactc agtgtccacc 17520
ccaaaaaagt accggtagat attggccaca gtagatatca gctagagtgg actctcatga 17580
caatgagggg agatgtattc cccatcttag gcacctggga ctctaccttc catcttctgc 17640
tccgtgtctc tccatcccca ggctcttcag aactcaggga gtccagaatg tcagctccca 17700
gatttcagcc ttcagaaagg aaacccatta ccgttcagtt gaacaaatgt tgtctgagcc 17760

-continued

```
ccagatctgg gctcagaggc catctaggct atgagacaag aggggaacaa agcaccgtct  17820
gcactcactc accacactca cttgctgtcc caggtcacat ccatcgggta gagaatctaa  17880
gaggctgagc tagctcccgc caccagccca gcccacccca cctggcccct tccttccttc  17940
tacaaaatat gcaccacctg tcaaagggtg ggcagtgcca ggcctgcata cagagcactg  18000
agtgtaaaag cagacatgga ccctgacctc caggagcttc caattttctt gaagagacaa  18060
atcagctggc atttcagtcc agtgtgatct gctcttggtg agcacagacc tagggagttg  18120
gggcagcttc ccagaagaac tgcagtccag gctgagggca gagaaatgag gggaatggcg  18180
aggaattggg gagcaggggg gagctcagta gagagccaag ggcgggaggt gagaagtccg  18240
tgttgggcca ggagctaccc tccggtggcc acagccgaag tcgaggatgc ctttggaact  18300
catccccact tctctctttc tgtatgtagc cgtccaagaa caagtcacct ccaagtgtag  18360
ccggatcaag gcaagccccc catctagcaa gcacttgatg ccacccagaa ctgggcttct  18420
tcagaacaat ctgagtccag gaatgatccc actcaccagg caccagagct gcgagggcat  18480
gggagtgatc tcaccaactc tggggaagcg gcaaggaatt ttcacctcca gcccccagtg  18540
tcccatcctc tcacactcag gccagactcc cctgggcaga cttgactctg tctgccagca  18600
tatgcagagc cccaaggcca ccccaccaga agtgcccctg cctgggttct gtcccagctc  18660
cctgggcacc cagtccttga gtccccacca gctcagacgg cctagtgtgc caagaatgcc  18720
cactgcgttc aacaatgctg catgggtcac agcggcagca gctgtgacca cagcagtttc  18780
ggggaaaaca cccctcagcc aagtggataa tagcgttcag cagcactcac cttctggcca  18840
ggcctgcctt cagaggccat ctgattggga ggcacaagtg cccgctgcga tgggaacaca  18900
agtgcccctg gccaacaacc ccagcttcag cctgctgggc agccagagcc tcaggcagag  18960
cccggtacag ggcccggtgc ctgtagcaaa caccaccaag ttcctccagc agggtatggc  19020
cagctttagt cccctgagcc ccatacaggg catcgagcca ccaagctatg tggctgctgc  19080
tgccaccgct gctgctgctt ctgccgttgc tgccagccag ttcccaggtc cgttcgacag  19140
aacggatatt ccccctgagc tgccacctgc cgactttttg cgccagcccc aacccccact  19200
aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcaccca  19380
ggatgctggg gcactttaaa tctgagcagg atgcccatag aaacccccat ggtgacatca  19440
ctctaggaag tggtgtcgat ccatacccgc agttgtctcc cgttacaatt tgagtggtgt  19500
tgtcagccca tgcttatccc tctctctacc tgtgacaaaa tggaaagctg gtgatttttc  19560
aagctacgtg tacatatttg aaaattttgt aaatggtttt cctaaacatt aatgacagaa  19620
gtatttatac ttcattttgt gactttgtaa ataaagcgac ggcttttgtt tcagtagagt  19680
tgtgtttact atgcattgtt ttgtgtttat tatacaatgt tacaaatatg cagaccgtgt  19740
tgtttgctcc agtgatacct tgttaagcta ggtggctgag tcgcttatgg ttttaatgca  19800
atgagcaatg tggatatgac caagagttgt tgtgcaagtt gacaaatgcc aaatagaaaa  19860
ccacttggcc atttatttct atgttcacta aaaatcctat tgccttgtgt gattcttaat  19920
ctcttttgcg aacctttcag tctccgctag ctctttccta atgagcttta cagcagaagc  19980
tgttttatcg ttaagtgccc cacagagaca ctttaccagg aggctgggag agttctccag  20040
atttgggaga ggcgcagaga cagtgtgtga gccgagccct gtctcagcaa tccacctgga  20100
ggagctagag tatcctcctc cctttaccat tcagaccgag agaaaaagcc cagcttgtgt  20160
```

-continued

```
gcaccctcgt ggggttaagg cgagctgttc ctggtttaaa gcctttcagt atttgttttg  20220
atgtaaggct ctgtggtttg ggggggaaca tctgtaaaca ttattagttg atttggggtt  20280
tgtctttgat ggtttctatc tgcaattatc gtcatgtata tttaagtgtc tgttatagaa  20340
aacccacacc cactgtcctg taaacttttc tcagtgtcca gactttctgt aatcacattt  20400
taattgccac ctcgtatttc acctctacat ttgaaatctg gcgtctgttt caagccagtg  20460
tgttttttct tcgttctgta ataaacagcc aggagaaaag tgcctctatg tttttatttt  20520
tcaagggagt attcagtacc tacaaaccca agtcaggaag cctgctagtg gctttggttc  20580
tttcagaggc tgctcgatgc cttgtgtgtc agaaagaaag attcagcagt tttgcatcat  20640
ggcaaagaag cctgttattt tggggctcag cccctcattt tatagaggat gaaacagagg  20700
gggatgggag gtcacaaaga caactgcccc gggagcaggt gtgggggaga cttgccctga  20760
gggtctagac gctctgcacc accgtcctgt ctcccttgct gaagaccaca catgcccttc  20820
tttgaccaga ccctgccacc tgataggcca ggacctggta ggcgggtacc caggtttcat  20880
ggatggaacc acatctcccc aaaagtgggg aggtagctac tgggatgcac gcctcccgcc  20940
atgtgctata ggagagcagc tgaagcaaca gttgggatca gatgtagtca caattgaatg  21000
catcatcaca tttatccctc taagtggctg ggagagttga tatcctcatc cctaaggtac  21060
aaaatgttcc aatttgatca gtggctttca ggagctgaga aaggcatgtg ctctgaggca  21120
gagctgttat gtcccgcaga gcctaaaaat gctctaagaa catgctccct gccaaaattc  21180
tcaatggctg tgacaaggga caacgatcga ccaatggggg tggaagcaga cctccgcagt  21240
ccaggggcca gagctaggac agaggggtcg gagaaagagt cattttccca acactccagc  21300
tcttggccag tcctcacaca gtcccctcct gcttcctgct gagagagata tcctcatagg  21360
tctgggtaaa gtccttcagt cagctttcat tccctgtcac caactttgtc tctgttctcc  21420
ctgcccgtct caggcagcac tcctcaggaa acctctccaa gagccagcct cactgcagcg  21480
cccactattg tccctctgcc tcaagtgtcc catccatgcc aggccccagg caggctgcag  21540
ctttccctca gggccacacc aaagcacttg ggctcagctg tgctgtcccc ctccatcact  21600
gagctcaggg gcagcagggg tggggtgcca ggaggcccat tcacccttct ctggctctgt  21660
gttggaccca cctgcccagc cactgctgct tagaacctac ccgctgggaa aatgaagccc  21720
tcccggaggg gccacctcaa cctgagagcc tcacggatca cagttgtccc cactcagctc  21780
tgccagccct cagagaccca tagataaaag ctgagcttgg ctcgcagagc tggttccatc  21840
ttccattccc agagggttca acttcctacc ccaaccacac agggaacctc aaggctgagc  21900
cagtgtgggc tgcagtgcag accagcttcc tggacacgtc ctgccacctg accccaggct  21960
ggcctcactg cccctggcac tcctgaccct atcctcattc ctcctggcag tgcgtgttct  22020
gccattccgc tttcccttag ctgtcctctc actgtactgt cagcttctcc ttttccaggt  22080
gccccccagg ggctttccac atgaccctgt caccccacag cccatccagc accaattcca  22140
gctctctgcc acccttcaaa ggagtgacag tgccctgctt cacctcccac tcacccctca  22200
acccagagca atctggctcc agtcttgcct ccttccccct aagtactcta gtcacagttc  22260
caaattcctc ctggtcataa agccaaatga agcttcctgg tcctcagcgg acttgccact  22320
tcagcagtac tggactctct cctcccagaa acctgtttcc ccttggctcc tggagcccac  22380
actctgctgg aatccttctg cctctctggc ctgtagcctg gccctctctc ccaacctgag  22440
gtccattctc tcctgctcct ccacaagatg ttgctccttc cattacttcc tccctctcaa  22500
```

-continued

```
ccaaagctcc ttcattagct ctttatcttc tggtttcttc ccctgggcag acgaatggat  22560
tcaagagcct gtggcccagc agcccagcac tccaggatct cagcacttca gcatcccagt  22620
accctagcat ctcaataccc cagcacccca gcaccatagt attccagcac cccattgtcc  22680
aagcatctca gcactccagc atcccagcac cccaacactc cagcagccca gaatctcagc  22740
accctagcac tgcagcatct caggacccca gcacttcagc atcccagcac actagtactc  22800
cagcatctcg gcaccccagc acctaggcat cccaacaccc agcaccccag cacttaagca  22860
tcccaccact acagtatctc aacactccag caccccagca ccatagtgtt ccagcacccc  22920
agcatcccaa caccccagca cttaagcatc ccaacacctc ggcatcccaa caccccagca  22980
ctgcagcatc tcagcacctt agcatcccag tgccctagca tctcaatgct ccagcacacc  23040
agtactacag tattccagca ccccagcact ccagcatctc agcactgcag cactgcagca  23100
ctccagcatc ccaaaatccc agcatcccaa caccccagca gaccagcaga ccagcatctc  23160
agcaccgcag catccaagga ctatcccagc atcccagcaa cccagcacct cagcatccca  23220
acaccccagc atttcagcat ggcaacaccc cagtacccca gcacttcagc accccagtat  23280
cccagcatct cagcgaccca gtatcacaaa acctcagcat cctagcaccc cagcacccca  23340
gcaccttagc accttagcat cccagcatct cagcgcctca gcatcttgat attctggctg  23400
aggtcagcgt ggtgtatcta gtcagggtcc taactttcac ttcgcaggga aatgctgctg  23460
gactgggtct catgttgggc tgaagctctc tagacccctt gaagacagca taaaagagct  23520
tggagacgct gggtgtcccc catggaagag ttcactctca tcctgctttg acaacagcct  23580
tctctggggt ccctcacggg cccctctttc ttactgcaag tttgtctctg agaagactgt  23640
gatgcagaag tcactcagct gcctgtggct cctgaagagc tgaaggtgga ggcctgtagg  23700
cctccctatg agaggcgcag aaaaaaccat gattgctagt ggggaggtgc tccctctaca  23760
acccactcca taatctgccc ccgcccagct ctgaggccag ccccagggga aaatgccaga  23820
tccccaggga ggtgtgtgag acctcagggg ctccctcctc ccttacagca ggctcaggcc  23880
cctgggggcc tcagggccaa ggtctgtggg taagctacta tctctcactt gtcctctagc  23940
cacaaaagcc agggagatct ggcaatggac atgaggttct gaagaagcac atatgactgg  24000
cttcctaatg cgtggttgtt cagtgattca ataaacacgc atgggccagg catggggaaa  24060
tagacaaaca tgatccccaa cctctcccag agtgaactgg gagggaggag tgttcatccc  24120
tcaggattac accagagaaa caaaccagca ggagatatat atggttttgg ggggtcaaga  24180
aagaggaaaa acctggcaag gcaagtccaa aatcatagga caggctgtca ggaagggcag  24240
cctggaacct ctcaagcagg agctgatgct gcagtccaca ggcagaattt cttcttcctc  24300
ggggaaatct cagctttgtt cttaaggcct ttcaactgat tggctgaggt ctgccccttc  24360
ccccacattc tccaggataa tcttccttac ttaaagtcaa ctattaatca cagctacaaa  24420
atcccttcac agctacacat agatcagtgt ttgattgacg aacagcccct acagcctagc  24480
caagttgaca cataaaacta accatcacag ggggacaaat gatgtaaaca catcaacaaa  24540
taaaacagta acaagttaag gtctatggaa aaaacacaga aggggcagag agaaagaaag  24600
caagaaggag agtcccagtt tgctagggct tgtgggaagt ggggagcagt tctctttagc  24660
taggatattt gggaaaggca tatctgaagg agtgatattt gagcttagat taaaagatgg  24720
gaaggagcaa gccatgcaaa gagctaggat gttccaagca gagacggaac agcaagtgca  24780
aatgtcagga ggaatagaag gaggctggtg ggtggggtcc agtgagcaag aggagggcag  24840
gcaggagagg ggatggggag gtgggcaggc ccagaccacc cagggccctg gagactatcc  24900
```

-continued

```
tgatccaaca agggaagcct tgagtcactt cagtgtccat gtggagaatg gacctcagac  24960
tgaatgaggg aggcagtaag gagggcctct acctccaggg cttcgccctg tggactgcgc  25020
atagacatct ccaactcaga aagtctgaac caaactttcc atagttcccc caagtctggg  25080
catcctccta ctcagtgaaa ggcagccatc acacctccct gccctgctcc cggatgcccc  25140
aaatcctctt ggtctccaag tccagaacct gagacttgtc cttgatgttt gtctttccct  25200
cacccttct gtattctggg aagatgggtt tttttccccc agatgaatct gtaaaacttc  25260
tgtgatcaca ataaaaattc tggcagtatt attttctgga acatgacaaa gtgattcaaa  25320
attatttatc tggaagacta caaaacaaga atagccagga aatttctaaa aagaaagaag  25380
aaggaggagg agaaagaagg aggaggaaaa ggaggagaag aagaaaagaa aaagaaccaa  25440
gaaagggttc tagctctacc aaatattaaa acatatcatg aagctattta aaacaatatg  25500
gttgtggata ctgaaaaaga tgtgaataaa gtggaaggaa aataaataga aatgcacatg  25560
gggattgaga ctgtgaaaaa ggcagcatct cacatcagtg agggatgttc aacacctggt  25620
gttgggaaaa ctggctagtc atttaaacca aacaactggg tcctctacct cactcctgac  25680
attaagatac atttagatga ttcaaagagt aagacagaaa aaataacacg tgaaaacact  25740
atcagaaaac aacgtgggcc aggtgtggtg ggtcacgcct gtaatcccag cactttggga  25800
ggccgaggca gacagatcac ctgaggtggg gagttcaaga ccagcctgac caacatggtg  25860
aaatcctgtc tctactaaaa atacaaaatt agctgagcgt ggtggcgcat gcctgtaatc  25920
ccagctactc aggaggccga ggcaggagaa tcacttgaac ctgggaggca gaggttgtgg  25980
tgagccgaga tcacgccatt gcactccagc ctgggcaaca agagtgaaaa tccatctaaa  26040
aaaaaaaaaa aaagccaagg tggatatttt tatagtatca gggtagatca agcttctcca  26100
atcatgacat gaaacccaga aaccataaaa gaaaagaatg ataaaattgc ccacgtaaag  26160
taaaaagctt gcacacagaa aaacaccata caggttacaa gatgagcagc aaaatcagag  26220
aaaaaacatt gcaattcagg acacacagag gctattgttc ctaatattta aaaataaaag  26280
tagtggattg tctacaaaaa gatgaagaca agaatttcag aaaaccaaat actgcatgtt  26340
ttcacttaca agtggaagct aaacactgag tacacgtgta cacaaagaat ggaaccatag  26400
gccaggcacc gtggctcacg cctgtaatcc cagtactttg cgaggccgaa gcgggcggat  26460
cacctgaggt gaggagttcg agaccatcct ggccaacatg gtgaaaccca gtctctacta  26520
aaaatacaaa aattagccgg gcgtggtggt gggtgcctgt aatcccagct actcgggagg  26580
ctgcggcagt agaatcgctt gaaccctgga ggtggacctt gcagtgagcc gagatcgcac  26640
cactgcactc cagcctgggc aacagagtga gactccatct caaaaaaaaa aaaaaggaat  26700
agaacaatag acactggggc ctacttgagg gaggagggtg aggatcaaaa acctgcctat  26760
caggtactat gcttattacc tgggtggtga aataatctgt acaccaaacc ccagtgacat  26820
gcaatttacc gatgtaacaa acctgcccat gtacccgctg aacctaaaat aaaagttgga  26880
aaaaaatata gaaattttct ttgtaatagc caaaaactgc aaacagccca ggtgtctatt  26940
agtagaatgc ataaacaaac tcgggcatgt tcatacaatg taaaactact catcaataaa  27000
aagtgatact tctcagcaat gaaaagaaac tagctactga taccagctac aacatggatg  27060
gatttcaagt gctttatgat gagagcaaga agccagacac aaaagtgtct atatatatat  27120
acagtatata tacgtatata tacacatata tacagtatat atatacatat acatgtatat  27180
atatactgta tatatactgt atatatatac acagtatata tatacatata tacagtgtat  27240
```

-continued

```
atatactgtg tatatataca tgtatatata ctgtgtatat atacatgtat atatactgtg  27300
tatatataca tgtatatata ctgtgtatat atacatgtat atatatgtat actgtatata  27360
tactgtatat atatatacac atatatacag tatatatata cagtatatac tgtatatata  27420
cagtatatac gtgtatatat acatatatac agtatatatg taaatataca tatatacagt  27480
atatatgtaa atatacatat atacatgtat atatatacac tatatatata catatatagt  27540
gtatatatac atatatacat gtatatattt actatatgat tccatttata taaagtgcca  27600
aaacagtcaa aaataatcta tgtggaaaaa atcaacaaag ggatcccccg ggctgcagga  27660
attcgatggc gcgccgacgt cgcatgctcc tctagactcg aggaattcgg taccccgggt  27720
tcgaaatcga taagcttgga tcggccgcaa taaaatatct ttattttcat tacatctgtg  27780
tgttggtttt ttgtgtgaat cgtaactaac atacgctctc catcaaaaca aaacgaaaca  27840
aaacaaacta gcaaaatagg ctgtccccag tgcaagtgca ggtgccagaa catttctcta  27900
tcgaggatct gcgatcgctg aattctgggg actttccact ggggactttc cactggggac  27960
tttccactgg ggactttcca ctggggactt tccactcctg cagcagtgga tattcccaga  28020
aaactttttg gatgcagttg ggatttcct ctttactgga tgtggacaat atcctcctat  28080
tattcacagg aagcaatccc tcctataaaa gggcctcaga ggaagtagtg ttcagctgtt  28140
cttggctgac ttcacatcaa agctcctata ctgacctgag acagagccat gaattccgtt  28200
tttttttttt tttttggaaa tatgagggtt tttccgcttc tgacagtgga acggaatgac  28260
agcagcacag gctggtgaat gactactttc tttataagca accaccttga gcctgaaatg  28320
gcagtcgcta gtctctattg ccttgctgtg gcctcgggat ggaaatctgc tggggaccct  28380
acagtcacct aatctctctc cttctcatcc ttctgtttca ttcagaggca gcctgccgcc  28440
cttctgggaa aagaccctgc aagatgcaag ccttcagaat ctgggatact aaccagaaga  28500
ccttttacct gagaaacaac cagctcattg ctgggtactt acaaggacca aatatcaaac  28560
tagaagaaaa gatagacatg gtgcctattg accttcatag tgtgttcttg ggcatccacg  28620
ggggcaagct gtgcctgtct tgtgccaagt ctggagatga tatcaagctc cagctggagg  28680
aagttaacat cactgatctg agcaagaaca aagaagaaga caagcgcttt accttcatcc  28740
gctctgagaa aggccccacc accagctttg agtcagctgc ctgtccagga tggttcctct  28800
gcacaacact agaggctgac cgtcctgtga gcctcaccaa cacaccggaa gagcccctta  28860
tagtcacgaa gttctacttc caggaagacc aatagtctag ctcgacatga taagatacat  28920
tgatgagttt ggacaaacca caactagaat gcagtgaaaa aaatgcttta tttgtgaaat  28980
ttgtgatgct attgctttat ttgtgaaatt tgtgatgcta ttgctttatt tgtaaccatt  29040
ataagctgca ataaacaagt taacaacaac aattgcattc attttatgtt tcaggttcag  29100
ggggaggtgt gggaggtttt ttaaagcaag taaaacctct acaaatgtgg tagatccatt  29160
taaatgttag atccggagag ctcccaacgc gttgggtcga cggcgcgcct accagtaaaa  29220
aagaaaacct attaaaaaaa caccactcga cacggcacca gctcaatcag tcacagtgta  29280
aaaaagggcc aagtgcagag cgagtatata taggactaaa aaatgacgta acggttaaag  29340
tccacaaaaa acacccagaa aaccgcacgc gaacctacgc ccagaaacga aagccaaaaa  29400
acccacaact tcctcaaatc gtcacttccg ttttcccacg ttacgtcact tcccatttta  29460
agaaaactac aattcccaac acatacaagt tactccgccc taaaacctac gtcacccgcc  29520
ccgttcccac gccccgcgcc acgtcacaaa ctccaccccc tcattatcat attggcttca  29580
atccaaaata aggtatatta ttgatgatgt tt                                29612
```

<210> SEQ ID NO 9
<211> LENGTH: 29273
<212> TYPE: DNA
<213> ORGANISM: Artificial Sequence
<220> FEATURE:
<223> OTHER INFORMATION: helper-dependent adenoviral vector containing equine Il-1Ra

<400> SEQUENCE: 9
aaacatcatc aataatatac cttattttgg attgaagcca atatgataat gaggggggtgg 60 agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
ttccgggtca aagttggcgt tttgatatca agcttatcga taccgtaaac aagtctttaa 480
ttcaagcaag actttaacaa gttaaaagga gcttatgggt aggaagtagt gttatgatgt 540
atgggcataa agggttttaa tgggatagtg aaaatgtcta taataatact taaatggctg 600
cccaatcacc tacaggattg atgtaaacat ggaaaaggtc aaaaacttgg gtcactaaaa 660
tagatgatta atggagagga tgaggttgat agttaaatgt agataagtgg tcttattctc 720
aataaaaatg tgaacataag gcgagtttct acaaagatgg acaggactca ttcatgaaac 780
agcaaaaact ggacatttgt tctaatcttt gaagagtatg aaaaattcct attttaaagg 840
taaaacagta actcacagga aataccaacc caacataaaa tcagaaacaa tagtctaaag 900
taataaaaat caaacgtttg cacgatcaaa ttatgaatga aattcactac taaaattcac 960
actgattttg tttcatccac agtgtcaatg ttgtgatgca tttcaattgt gtgacacagg 1020
cagactgtgg atcaaaagtg gtttctggtg cgacttactc tcttgagtat acctgcagtc 1080
ccctttctta agtgtgttaa aaaaaaaggg ggatttcttc aattcgccaa tactctagct 1140
ctccatgtgc tttctaggaa acaagtgtta acccacctta tttgtcaaac ctagctccaa 1200
aggacttttg actccccaca aaccgatgta gctcaagaga gggtatctgt caccagtatg 1260
tatagtgaaa aaagtatccc aagtcccaac agcaattcct aaaaggagtt tatttaaaaa 1320
accacacaca cctgtaaaat aagtatatat cctccaaggt gactagtttt aaaaaaacag 1380
tattggcttt gatgtaaagt actagtgaat atgttagaaa aatctcactg taaccaagtg 1440
aaatgaaagc aagtatggtt tgcagagatt caaagaaaat ataagaaaac ctactgttgc 1500
cactaaaaag aatcatatat taaatatact cacacaatag ctcttcagtc tgataaaatc 1560
tacagtcata ggaatggatc tatcactatt tctattcagt gctttgatgt aatccagcag 1620
gtcagcaaag aatttatagc ccccccttgag cacacagagg gctacaatgt gatggcctcc 1680
catctccttc atcacatctc gagcaagacg ttcagtccta cagaaataaa atcaggaatt 1740
taatagaaag tttcatacat taaactttat aacaaacacc tcttagtcat taaacttcca 1800
caccaacctg ggcaatatag tgagacccca tgcctgcaaa aaaaaaaaaa ttagccaggc 1860
atggtagcat gtacctgtag tcccagctac ttgagaggtg aggtgggaaa atcactttag 1920
tgcaggatgt tgaggctgga gtgaactgtg attgtgccac tgcactccag cctggacaat 1980
agagcaagac cttgtctcaa aaaaatgcat taaaaatttt ttttaaatct tccacgtatc 2040
acatcctttg ccctcatgtt tcataaggta aaaaatttga taccttcaaa aaaaccaagc 2100
ataccactat cataattttt tttaaatgca aataaaaaca agataccatt ttcacctatc 2160
agactggcag gttctgatta aatgaaattt tctggataat atacaatatt aagagagact 2220
gtagaaactg ggccagtggc tcatgcctgt aatcccagca ctttgggagg ctgggtaaca 2280
tggcgaaccc tgtttctaca aaataaaaat attagctggg agtggtggcg cacacctata 2340
gtcccagcta ctcaggaggc tgaggtggaa ggatcgcttg aacccaggag gttgagactg 2400
cagtgaactg tgatcattct gctgcactgc accccagcct gggcaacaga gaccttgtct 2460
caaaaaaaaa aaaaaaagag acaaattgtg aagagaaagg tactctcata taacatcagg 2520
agtataaaat gattcaactt cttagaggaa aatttggcaa taccaaaata ttcaataaac 2580
tctttcccct tgacccagaa attccacttg aataaagctg aacaagtacc aaacatgtaa 2640
aagaatgttt cttctagtac agtcggtaag aacaaaatag tgtctatcaa tagtggactg 2700
gttaaatcag ttatggtatc tccataagac agaatgctat gcaaccttta aaatatatta 2760
gatagctcta gacacactaa tattaaaagt gtccaataac atttaaaact atactcatac 2820
gttaaaatat aaatgtatat atgtactttt gcatatagta tacatgcata ggccagtgct 2880
tgagaagaaa tgtgtacaga aggctgaaag gagagaactt tagtcttctt gtttatggcc 2940
tccatagtta gaatatttta taacacaaat attttgatat tataatttta aaataaaaac 3000
acagaatagc cagacataca atgcaagcat tcaataccag gtaaggtttt tcactgtaat 3060
tgacttaaca gaaaattttc aagctagatg tgcataataa taaaaatctg accttgcctt 3120
catgtgattc agccccagtc cattaccctg tttaggactg agaaatgcaa gactctggct 3180
agagttcctt cttccatctc ccttcaatgt ttactttgtt ctggtcccta cagagtccca 3240
ctataccaca actgatacta agtaattagt aaggccctcc tcttttattt ttaataaaga 3300
agattttaga aagcatcagt tatttaataa gttggcctag tttatgttca aatagcaagt 3360
actcagaaca gctgctgatg tttgaaatta acacaagaaa aagtaaaaaa cctcatttta 3420
agatcttact tacctgtcca taattagtcc atgaggaata aacacccttt ccaaatcctc 3480
agcataatga ttaggtatgc aaaataaatc aaggtcataa cctggttcat catcactaat 3540
ctgaaaaaga aatatagctg tttcaatgag agcattacag gatacaaaca tttgattgga 3600
ttaagatgtt aaaaaataac cttagtctat cagagaaatt taggtgtaag atgatattag 3660
taactgttaa ctttgtaggt atgataatga attatgtaag aaaacaacag gccgggcggg 3720
ttggttcaca cgtgtaatcc cagcactttg ggaggctgag gcaggcagac tgcctgagct 3780
caggagttcg agaccagcct gggcaacacg gtgaaatccc gtctctacta aaaatacaaa 3840
aaaattagcc gggtgtggtg acacatgcct gtagtcccag ctacttggga ggctgaggca 3900
ggagaatcac ttgaacctgg gaggtgaagg ttgcagtgag ccaagatggc accacttcac 3960
tccagcctgg gaaacagagc aagactctgt ctctgagctg agatggcacc acttcactcc 4020
agcctgggaa acagagcaag actctgtctc aaaaaaaaca aaacacacaa acaaaaaaac 4080
aggctgggcg cggtggctca cgcctgtaat cccagcactt tgggaggccg aggcgggtgg 4140
atcacctgag gtcaggagtt ccagaccagc cttgtcaaca tggtgaaacc tcccccccgcc 4200
gtctctacta aaaatacaaa aattagccag gcgtggtggc aggagcctgt aatcccagct 4260
acttgggagg ctgaggcagg agaatcgctt gtacccagaa ggcagaggtt gcactgagct 4320
gagatggcac cattgcactc cagcctgggg gacaagagcg agatttcgtc tttaaaaaac 4380

-continued

```
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tattttttca ttttcaatgt catttttatt agttaattta taatacccat   6240
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
```

ctatacagca ggcagaagtc aatattgatt tgtttttaaa gaaacatgta ctactttcat 6840
aagcagaaaa aatttctatt cttgggggaa aagattatgc cagatcctct aggattaaat 6900
gctgatgcat ctgctaaacc ttcacatatc agaacatatt tactatagaa agaatgaaaa 6960
tgggacattt gtgtgtcacc tatgtgaaca ttccaaaaat attttacaac aactaagtat 7020
tttataaatt ttatgaactg aaatttagtt caagttctag gaaaatacaa accttgctag 7080
atattataaa aatgatacaa tatatattca tttcaggctc atcagaatat atctgttatc 7140
acttgacaag aatgaaaatg caccattttg tagtgcttta aaatcaggaa gatccagagt 7200
actaaaaatg acttcttcct tgaagcttac tcaccaactt cctcccagtt actcactgct 7260
tctgccacaa gcataaacta ggacccagcc agaactccct tgaaatatac acttgcaacg 7320
attactgcat ctatcaaaat ggttcagtgc ctggctacag gttctgcaga tcgactaaga 7380
atttgaaaag tcttgtttat ttcaaaggaa gcccatgtga attctgccca gagttcatcc 7440
cagatatgca gtctaagaat acagacagat cagcagagat gtattctaaa acaggaattc 7500
tggcaatata acaaattgat ttccaatcaa aacagattta cataccatac ttatgtcaag 7560
aagttgtttt gttttattgc atcctagatt ttattttttt gatttatggt ttactttaag 7620
cataaaaaat ttgtcaatac aactcttccc aaaaggcata aacaaaaatt cataaaactt 7680
gcatcacttg agatacttca ggtatgaatt cacaactttg ttacaactta ctatatatat 7740
gcacacatat atatatattt gggtatattg ggggggttct aatttaagaa atgcataatt 7800
ggctatagac agacagttgt cagaacttgg caatgggtac gtgcaggttc attataccaa 7860
gtctacttgt agttgttcaa aatgtatcat aatacaaggc cgggcgaggt cgtcacgcct 7920
gtaatcccag cattttggga ggctaaggca ggaggattgc ttgaggtcag gagtttgtga 7980
ccagcctggg caacagagca agaccctgtc tccaaaaaga aaaaaaataa tttttttacaa 8040 aataaaaaca aaatgtatca tcagacgaaa ttaaataaga ggcaattcat ttaaatgaca 8100
acttttccca gcttgacatt taacaaaaag tctaagtcct cttaattcat atttaatgat 8160
caaatatcaa atactaattt tttttttttt tttttttttg agacggagtc tcgctctgtc 8220
gcccaggctg gagtgcagtg gcgcgatcct ggctcactgc aagctccgcc tcccgggttc 8280
acgccattct cctgcctcag cctcccgagt agctgggatt acagacatgc gccaccacgc 8340
ccggctaatt ttgtattttt agtagagatg gggtttctcc atgttggtca ggctggtctt 8400
gaatttccca cctcaggtga tctgcctgcc tcagcctcac aaagcagtag ctgggactac 8460
aggcacccac caccacactt ggttaattct tttgtatttt ttttgtaaag acgggatttc 8520
accatgttag ccaggatggt ctcgatctcc tgatctcatg atccgcccgc ctcagcctcc 8580
caaagtgctg ggattacagg cgtgagccac cccgcccggc catcaaatac taattcttaa 8640
atggtaagga cccactattc agaacctgta tccttatcac taatatgcaa atatttattg 8700
aatacttact atgtcatgca tactagagag agttagataa atttgataca gctaccctca 8760
cagaacttac agtgtaatag atggcatgac atgtacatga gtaactgtga acagtgttaa 8820
attgctattt aaaaaaaaag acggctgggc gctgtggctc atgcctgtaa tcccagcact 8880
ttgggaggcc aaggcaagtt gatcgctcga ggtcaagagt tcgagaccag cctggccaac 8940
gtggtaaaac cccgtctcta ctaaaaatac aaaaaaaaaa ttagccaggc atggtggcac 9000
aggcctgtaa tcccagctac tagggaggct gagacatgga gaactgcttg aatccaggag 9060
gcagaggtta cagtgagccg agatcatacc actacactcc agcctgagtg acagagcgag 9120

-continued

```
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc tttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
```

acaaattact aataattatg cacgtcacat ctgtaataat ggccttcatg taaacatttt 11580
tgtggtttac acataaaatc tctaattaca aagctatatt atctaaaatt acagtaagca 11640
agaaaattaa tccaagctaa gacaatactt gcaacatcaa ttcatcatct gtgacaagga 11700
ctgcttaagt ctctttgtgg ttaaaaagga aaaaaaaaaa aaagacatgt tggccagatg 11760
cggtggctca cacctgtaat cccagcactt tgggaggctg aggtgggcgg atcacccctg 11820
gcctgcccaa catggtgaaa ccccgtctct actaaaaaca caaaaattag ctgggcgtgg 11880
tggcgggcgc ctgtaattcc agctactcgg gaggctgagg caggagaatt gctagaaccc 11940
aggaggcaga gattgcagtg agctgagatt gcaccattgc actacagtct gggcaacaaa 12000
agtgaaactc catcttaaaa aaaaaaagac aatgttcgtg ggtccaaaca agacttaatg 12060
gaagtgagtc taaaaatgag ctatgtgggc caggcgtagt ggctcccacc tgtaatccca 12120
gcactttggg aggccgaagc aggcagatca tgaggtcagg agatggagac catcctggcc 12180
aacacggtga aatcctgtct ctacaaaaat tagctgggcg tggtggtgcc tgcctgtaat 12240
cccagctact cagaaggctc aggcaggaga atcgcttgaa ccagggagtc ggtggctaga 12300
gtgagccgag atttgcatca ctgcactcct gcctggtgac agagcaagac tccatctcaa 12360
aaaaaacaaa caaaaataaa agataaaaat gagctatgtg aattaaaaga ggtataacaa 12420
tagataaacc atattttatt taattcctag taatgagtaa tatttccaaa cttctggaat 12480
gggcagaaat tgctagttgg catattttta ccttttatat tcagatacat taaaattctc 12540
aaaaaaaaac acctcaaagc agatgatccg ccatctcctt ggataatttg tgttaactca 12600
ggataacaga aaaccaaaat tatgagttac tgatgcaata ttcctaaatg taaaaataat 12660
taaagctaat agtagattca tcttccaatt tcatatcagt cttacaaata aactacatat 12720
ataacttgct tgccttccct tctgagggat aaagctgtta gaagaattaa aatcagcatt 12780
cttgactatt caaccaaggg agggataaat tattactcat tctagggaca tgggctcata 12840
actactacat gtgtaaggac atgaatttac ccaatattac aatttttcct tttattagtg 12900
tgtacagtgg aagaatagac atgttcactc tggacaaaaa aaaaattata cttatcagtt 12960
atcagaagca caatgctgaa gacagtagtt ccataacaat ttgaagtatg tgatcgaact 13020
agtagattat cttagtagta gtgaattatt gtaaatgtta gtaatttggc agccactggg 13080
cagaaaaata agaattgagg ctcaatattg atattaatgg tggtgattga cacataaatt 13140
ttatcaagtc tacacaatat aaaattacag aaaggtagaa gagtatacca gtacaacttc 13200
aacatatctt cactacaagg gagtaaaatg acatggccta gttactatct aatgaactgc 13260
agaaaactaa aagaaaactc caaggcaact cttctctgct gatctggttg gtccttttcc 13320
taccttttgc aatacccaga tacaaacaat ggatagaaaa caaagtagac ttgtagtatg 13380
caggtcacag tgctaaattc acagaaagaa acccctgaac tgaactgctc tatttcctgg 13440
tggtcacaaa gagtaattct ggtttacacc tacagattga tgtcaatcta caccctgttg 13500
ataacagtgt ggccaaggac aaaaaaaagg tgctccgttt taccaattct gtaaaaaatt 13560
attggcaggg taagctcggc tagggcagga ttacatttct aggactacca tccccgaaat 13620
ttagaagata ttatatccac ataaagcata tctttcacat taatttgcaa aaatctaaaa 13680
gctttttctt agctcaagtg tgtccaagtt taccctggca gtttaaaacg atagttacaa 13740
gcagcatggg ttgtatcaga cacatttgag ggccaatttc atgtaagtga tattgggcaa 13800
gttacttcaa ctatctgtgc ctccaaggtc atactagtgt ttatttacct aaagggtacc 13860

-continued

```
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
cttgagctca ggagttcaag accagcctgg acaacatggc aaaacaccat ctctacaaaa  14460
aatacaaata ttaggccggg cgcagtggct cacgcctgta atcccagcac tttgggaggc  14520
caaggcgggt ggatcacctg agatcaggag ttcgagagta gcctggccaa catggtgaaa  14580
cctcgtctct attaaaaata caaaaaatta gccaggcatg gtggcaggcg cctgtaatcc  14640
cagctactca gggggatgag gtaggagaat cgcttgaacc cgggaggcag aggttgcact  14700
gagccgagat catgccactg tactccagcc cgggcaacaa gagcgaaact ccatctcaaa  14760
aaataaataa ataaataaat aaaataaagt acaaatatta gccagggatg gtggtgcgca  14820
cctgtagtcc cagctacttg ggaggctgaa gtgggagaat cccctgagcc tggggagaat  14880
cacccgagcc cgggaagtcg aggctgcagt gagcagtgat tgtgccactg cactccatcc  14940
taggtgacag agtgagaccc tgtctcaaaa aaaagaaatt ggcagaatta agtaagttga  15000
tgtttagaga tgaaaaatca acattttttc ctcagcaact gaataaaaac aacagccact  15060
accatttttt tgagtaccta tttgtagcct attttttaac tggtattact cgagagagag  15120
agagctaggt tcgagacaga gctccttctc ttaataactg tatgacctag ggtatgtctg  15180
ttagcctctc tgaggcttca aaggttcctc atctgtaaaa tggtaataat cataccattg  15240
ctacagggct gttttgaaga ctaattagga ctatgtaagt aaacatgatg atggctatta  15300
ttactgttcc ccgccagggg ccatgcaagg gttgctgatt cacatagact gtcttataat  15360
cctctcaata actccaagag gtagccagca cctcagatat acataaaatg acttaagccc  15420
agagaggtga agtaagttgc ccacagccac acaactagta aatagcccaa acaagctgga  15480
ttcccagtta gactccgtta atagcactgc tctttacctt aagtcattac aatgcctaat  15540
atgaaataga atcgcttctt tcttagggtt caagtggtta attatttaat gtattcattc  15600
aacaaaccat catcgaggac ctcttacaag ccaagtactg tgctaagtgc tagagttacg  15660
gcggtgattc ctgcccttaa aaagttttag tgggagaaac aacaggtaac caggtcattg  15720
ccaaaacaac aaaaataatc ataataaagc aggctaaagc atatttaact ggccggggtt  15780
ttgactattt tagcaagcat gatcagaacg gttgaggagg gaggccagca gcttggccgg  15840
ttcaacaaac aagaaaaaac cagtgagggt ggagctaaga taccagaggc tgattacggt  15900
taagaatgtt cttgaaggta aggaccagat tctcattttc tatatcctgg ggcatcggtc  15960
agcatggaat ctggattcta gcacatgtga atttcggctt gaaatgacct aatgcctttt  16020
ccctagttcc ttcgtgtgtc aaatacgcat ggttaccgct accagagctg tagtggggct  16080
tcaatgaggc catgagcatc tccataaaga tgaactacag tgtgtgcaaa actaaaggca  16140
aaacctggtc cccacacgcc ctcccaggtg gtcgctttcc gtgccgaggc ccctccagag  16200
gtgccccgag aacctcacca tcgcacccca aacttccagg gaagggcctc tcccgagaaa  16260
```

gcccccacgc ccccaccccg cgccatcatt cccgaatctg ccctcggccc ctccccgcag 16320
cacgctcgca ggcggcacat gtcaaccaaa acgccatttc caccttctct tcccacacgc 16380
agtcctcttt tcccagggct cccccgagga gggacccacc ccaaaccccg ccattccgtc 16440
ctccctgccg ccctcgcgtg acgtaaagcc gaacccggga aactggccgc ccccgcctgc 16500
ggggttccct gggcccggcc gctctagaac tagtggatcc caattgaagg cctggtctaa 16560
atgactccaa aatcaccact taattcaaga gactgatttc cctgagtcag gcccccttaaa 16620
gcagctattt caatgggaca gggaaacaac cctaggatct ggattagaat cacttggggg 16680
ctgccacacc cccagggctc tgatcctgcc cttctcccac acgcacattc acatactgct 16740
gcagtgacct tccatttcta atgggttcct gggccatctg tcaggtatag ggaatggaaa 16800
aggggttggg gaggctctgc ttcagaaagt ttgtgtcagg ggctcccaga gcctccacag 16860
atagatagca ggggtcccca ccctaccatg gcagctataa atgtgatcaa catttattgg 16920
cctaggatac agcagttagc aaaatgcctg atgtagttcc cactccgtgg aggttgcagg 16980
ctagccaaga agtcatgagt tcagcaaccc ttacgcacca gtgggatgag attggaccag 17040
gccgagggta gtcttgggaa cactcagcat ttgtctgagg gccagaagag gctgcttgcc 17100
ctcagacagg aggtcagcat ctttattgta gcccatgaca cctctacacc attgctcttc 17160
tggtcttatg gaagacatct ttgggcctga taacagcgga gtctgtgtcc cacttgtcca 17220
ggctggagtg ccacatcagg cacactccag ttgcagggac agcacagaca agtttcagga 17280
aggctggtgg cctccaggag gttaacctta taaggccaga ttgtaaccta gttgaaaaac 17340
atacacatgc catgataata aaagaaccta ggcaccatta caagagaaaa aatcattttt 17400
gtagatacga gcatggattc ttgggtgggt cagacacact gggcttgtgc tctgactgca 17460
ctgtctcccc tacctgacct tgggtaaacc ataagactgc tgcatgactc agtgtccacc 17520
ccaaaaaagt accggtagat attggccaca gtagatatca gctagagtgg actctcatga 17580
caatgagggg agatgtattc cccatcttag gcacctggga ctctaccttc catcttctgc 17640
tccgtgtctc tccatcccca ggctcttcag aactcaggga gtccagaatg tcagctccca 17700
gatttcagcc ttcagaaagg aaacccatta ccgttcagtt gaacaaatgt tgtctgagcc 17760
ccagatctgg gctcagaggc catctaggct atgagacaag aggggaacaa agcaccgtct 17820
gcactcactc accacactca cttgctgtcc caggtcacat ccatcgggta gagaatctaa 17880
gaggctgagc tagctcccgc caccagccca gcccacccca cctggcccct tccttccttc 17940
tacaaaatat gcaccacctg tcaaagggtg ggcagtgcca ggcctgcata cagagcactg 18000
agtgtaaaag cagacatgga ccctgacctc caggagcttc caattttctt gaagagacaa 18060
atcagctggc atttcagtcc agtgtgatct gctcttggtg agcacagacc tagggagttg 18120
gggcagcttc ccagaagaac tgcagtccag gctgagggca gagaaatgag gggaatggcg 18180
aggaattggg gagcaggggg gagctcagta gagagccaag ggcgggaggt gagaagtccg 18240
tgttgggcca ggagctaccc tccggtggcc acagccgaag tcgaggatgc ctttggaact 18300
catccccact tctctctttc tgtatgtagc cgtccaagaa caagtcacct ccaagtgtag 18360
ccggatcaag gcaagccccc catctagcaa gcacttgatg ccacccagaa ctgggcttct 18420
tcagaacaat ctgagtccag gaatgatccc actcaccagg caccagagct gcgagggcat 18480
gggagtgatc tcaccaactc tggggaagcg gcaaggaatt ttcacctcca gcccccagtg 18540
tcccatcctc tcacactcag gccagactcc cctgggcaga cttgactctg tctgccagca 18600

-continued

```
tatgcagagc cccaaggcca ccccaccaga agtgcccctg cctgggttct gtcccagctc  18660
cctgggcacc cagtccttga gtccccacca gctcagacgg cctagtgtgc caagaatgcc  18720
cactgcgttc aacaatgctg catgggtcac agcggcagca gctgtgacca cagcagtttc  18780
ggggaaaaca cccctcagcc aagtggataa tagcgttcag cagcactcac cttctggcca  18840
ggcctgcctt cagaggccat ctgattggga ggcacaagtg cccgctgcga tgggaacaca  18900
agtgcccctg gccaacaacc ccagcttcag cctgctgggc agccagagcc tcaggcagag  18960
cccggtacag ggcccggtgc ctgtagcaaa caccaccaag ttcctccagc agggtatggc  19020
cagctttagt cccctgagcc ccatacaggg catcgagcca ccaagctatg tggctgctgc  19080
tgccaccgct gctgctgctt ctgccgttgc tgccagccag ttcccaggtc cgttcgacag  19140
aacggatatt ccccctgagc tgccacctgc cgactttttg cgccagcccc aacccccact  19200
aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcaccca  19380
ggatgctggg gcactttaaa tctgagcagg atgcccatag aaacccccat ggtgacatca  19440
ctctaggaag tggtgtcgat ccatacccgc agttgtctcc cgttacaatt tgagtggtgt  19500
tgtcagccca tgcttatccc tctctctacc tgtgacaaaa tggaaagctg gtgatttttc  19560
aagctacgtg tacatatttg aaaattttgt aaatggtttt cctaaacatt aatgacagaa  19620
gtatttatac ttcattttgt gactttgtaa ataaagcgac ggcttttgtt tcagtagagt  19680
tgtgtttact atgcattgtt ttgtgtttat tatacaatgt tacaaatatg cagaccgtgt  19740
tgtttgctcc agtgatacct tgttaagcta ggtggctgag tcgcttatgg ttttaatgca  19800
atgagcaatg tggatatgac caagagttgt tgtgcaagtt gacaaatgcc aaatagaaaa  19860
ccacttggcc atttatttct atgttcacta aaaatcctat tgccttgtgt gattcttaat  19920
ctcttttgcg aacctttcag tctccgctag ctctttccta atgagcttta cagcagaagc  19980
tgttttatcg ttaagtgccc cacagagaca ctttaccagg aggctgggag agttctccag  20040
atttgggaga ggcgcagaga cagtgtgtga gccgagccct gtctcagcaa tccacctgga  20100
ggagctagag tatcctcctc cctttaccat tcagaccgag agaaaaagcc cagcttgtgt  20160
gcaccctcgt ggggttaagg cgagctgttc ctggtttaaa gcctttcagt atttgttttg  20220
atgtaaggct ctgtggtttg ggggggaaca tctgtaaaca ttattagttg atttggggtt  20280
tgtctttgat ggtttctatc tgcaattatc gtcatgtata tttaagtgtc tgttatagaa  20340
aacccacacc cactgtcctg taaacttttc tcagtgtcca gactttctgt aatcacattt  20400
taattgccac ctcgtatttc acctctacat ttgaaatctg gcgtctgttt caagccagtg  20460
tgttttttct tcgttctgta ataaacagcc aggagaaaag tgcctctatg tttttatttt  20520
tcaagggagt attcagtacc tacaaaccca agtcaggaag cctgctagtg gctttggttc  20580
tttcagaggc tgctcgatgc cttgtgtgtc agaaagaaag attcagcagt tttgcatcat  20640
ggcaaagaag cctgttattt tggggctcag cccctcattt tatagaggat gaaacagagg  20700
gggatgggag gtcacaaaga caactgcccc gggagcaggt gtgggggaga cttgccctga  20760
gggtctagac gctctgcacc accgtcctgt ctcccttgct gaagaccaca catgcccttc  20820
tttgaccaga ccctgccacc tgataggcca ggacctggta ggcgggtacc caggtttcat  20880
ggatggaacc acatctcccc aaaagtgggg aggtagctac tgggatgcac gcctcccgcc  20940
atgtgctata ggagagcagc tgaagcaaca gttgggatca gatgtagtca caattgaatg  21000
```

```
catcatcaca tttatccctc taagtggctg ggagagttga tatcctcatc cctaaggtac  21060
aaaatgttcc aatttgatca gtggctttca ggagctgaga aaggcatgtg ctctgaggca  21120
gagctgttat gtcccgcaga gcctaaaaat gctctaagaa catgctccct gccaaaattc  21180
tcaatggctg tgacaaggga caacgatcga ccaatggggg tggaagcaga cctccgcagt  21240
ccaggggcca gagctaggac agaggggtcg gagaaagagt cattttccca acactccagc  21300
tcttggccag tcctcacaca gtcccctcct gcttcctgct gagagagata tcctcatagg  21360
tctgggtaaa gtccttcagt cagctttcat tccctgtcac caactttgtc tctgttctcc  21420
ctgcccgtct caggcagcac tcctcaggaa acctctccaa gagccagcct cactgcagcg  21480
cccactattg tccctctgcc tcaagtgtcc catccatgcc aggccccagg caggctgcag  21540
ctttccctca gggccacacc aaagcacttg ggctcagctg tgctgtcccc ctccatcact  21600
gagctcaggg gcagcagggg tggggtgcca ggaggcccat tcacccttct ctggctctgt  21660
gttggaccca cctgcccagc cactgctgct tagaacctac ccgctgggaa aatgaagccc  21720
tcccggaggg gccacctcaa cctgagagcc tcacggatca cagttgtccc cactcagctc  21780
tgccagccct cagagaccca tagataaaag ctgagcttgg ctcgcagagc tggttccatc  21840
ttccattccc agagggttca acttcctacc ccaaccacac agggaacctc aaggctgagc  21900
cagtgtgggc tgcagtgcag accagcttcc tggacacgtc ctgccacctg accccaggct  21960
ggcctcactg cccctggcac tcctgaccct atcctcattc ctcctggcag tgcgtgttct  22020
gccattccgc tttcccttag ctgtcctctc actgtactgt cagcttctcc ttttccaggt  22080
gccccccagg ggctttccac atgaccctgt caccccacag cccatccagc accaattcca  22140
gctctctgcc acccttcaaa ggagtgacag tgccctgctt cacctcccac tcacccctca  22200
acccagagca atctggctcc agtcttgcct ccttccccct aagtactcta gtcacagttc  22260
caaattcctc ctggtcataa agccaaatga agcttcctgg tcctcagcgg acttgccact  22320
tcagcagtac tggactctct cctcccagaa acctgtttcc ccttggctcc tggagcccac  22380
actctgctgg aatccttctg cctctctggc ctgtagcctg gccctctctc ccaacctgag  22440
gtccattctc tcctgctcct ccacaagatg ttgctccttc cattacttcc tccctctcaa  22500
ccaaagctcc ttcattagct ctttatcttc tggtttcttc ccctgggcag acgaatggat  22560
tcaagagcct gtggcccagc agcccagcac tccaggatct cagcacttca gcatcccagt  22620
accctagcat ctcaataccc cagcacccca gcaccatagt attccagcac cccattgtcc  22680
aagcatctca gcactccagc atcccagcac cccaacactc cagcagccca gaatctcagc  22740
accctagcac tgcagcatct caggacccca gcacttcagc atcccagcac actagtactc  22800
cagcatctcg gcaccccagc acctaggcat cccaacaccc agcaccccag cacttaagca  22860
tcccaccact acagtatctc aacactccag caccccagca ccatagtgtt ccagcacccc  22920
agcatcccaa caccccagca cttaagcatc ccaacacctc ggcatcccaa caccccagca  22980
ctgcagcatc tcagcacctt agcatcccag tgccctagca tctcaatgct ccagcacacc  23040
agtactacag tattccagca ccccagcact ccagcatctc agcactgcag cactgcagca  23100
ctccagcatc ccaaaatccc agcatcccaa caccccagca gaccagcaga ccagcatctc  23160
agcaccgcag catccaagga ctatcccagc atcccagcaa cccagcacct cagcatccca  23220
acaccccagc atttcagcat ggcaacaccc cagtacccca gcacttcagc accccagtat  23280
cccagcatct cagcgaccca gtatcacaaa acctcagcat cctagcaccc cagcacccca  23340
```

-continued

```
gcaccttagc accttagcat cccagcatct cagcgcctca gcatcttgat attctggctg  23400
aggtcagcgt ggtgtatcta gtcagggtcc taactttcac ttcgcaggga aatgctgctg  23460
gactgggtct catgttgggc tgaagctctc tagacccctt gaagacagca taaaagagct  23520
tggagacgct gggtgtcccc catggaagag ttcactctca tcctgctttg acaacagcct  23580
tctctggggt ccctcacggg cccctctttc ttactgcaag tttgtctctg agaagactgt  23640
gatgcagaag tcactcagct gcctgtggct cctgaagagc tgaaggtgga ggcctgtagg  23700
cctccctatg agaggcgcag aaaaaaccat gattgctagt ggggaggtgc tccctctaca  23760
acccactcca taatctgccc ccgcccagct ctgaggccag ccccagggga aaatgccaga  23820
tccccaggga ggtgtgtgag acctcagggg ctccctcctc ccttacagca ggctcaggcc  23880
cctgggggcc tcagggccaa ggtctgtggg taagctacta tctctcactt gtcctctagc  23940
cacaaaagcc agggagatct ggcaatggac atgaggttct gaagaagcac atatgactgg  24000
cttcctaatg cgtggttgtt cagtgattca ataaacacgc atgggccagg catggggaaa  24060
tagacaaaca tgatccccaa cctctcccag agtgaactgg gagggaggag tgttcatccc  24120
tcaggattac accagagaaa caaaccagca ggagatatat atggttttgg ggggtcaaga  24180
aagaggaaaa acctggcaag gcaagtccaa aatcatagga caggctgtca ggaagggcag  24240
cctggaacct ctcaagcagg agctgatgct gcagtccaca ggcagaattt cttcttcctc  24300
ggggaaatct cagctttgtt cttaaggcct ttcaactgat tggctgaggt ctgccccttc  24360
ccccacattc tccaggataa tcttccttac ttaaagtcaa ctattaatca cagctacaaa  24420
atcccttcac agctacacat agatcagtgt ttgattgacg aacagcccct acagcctagc  24480
caagttgaca cataaaacta accatcacag ggggacaaat gatgtaaaca catcaacaaa  24540
taaaacagta acaagttaag gtctatggaa aaaacacaga aggggcagag agaaagaaag  24600
caagaaggag agtcccagtt tgctagggct tgtgggaagt ggggagcagt tctctttagc  24660
taggatattt gggaaaggca tatctgaagg agtgatattt gagcttagat taaaagatgg  24720
gaaggagcaa gccatgcaaa gagctaggat gttccaagca gagacggaac agcaagtgca  24780
aatgtcagga ggaatagaag gaggctggtg ggtggggtcc agtgagcaag aggagggcag  24840
gcaggagagg ggatggggag gtgggcaggc ccagaccacc cagggccctg gagactatcc  24900
tgatccaaca agggaagcct tgagtcactt cagtgtccat gtggagaatg gacctcagac  24960
tgaatgaggg aggcagtaag gagggcctct acctccaggg cttcgccctg tggactgcgc  25020
atagacatct ccaactcaga aagtctgaac caaactttcc atagttcccc caagtctggg  25080
catcctccta ctcagtgaaa ggcagccatc acacctccct gccctgctcc cggatgcccc  25140
aaatcctctt ggtctccaag tccagaacct gagacttgtc cttgatgttt gtctttccct  25200
cacccttttct gtattctggg aagatgggtt tttttccccc agatgaatct gtaaaacttc  25260
tgtgatcaca ataaaaattc tggcagtatt attttctgga acatgacaaa gtgattcaaa  25320
attatttatc tggaagacta caaaacaaga atagccagga aatttctaaa aagaaagaag  25380
aaggaggagg agaaagaagg aggaggaaaa ggaggagaag aagaaaagaa aaagaaccaa  25440
gaaagggttc tagctctacc aaatattaaa acatatcatg aagctattta aaacaatatg  25500
gttgtggata ctgaaaaaga tgtgaataaa gtggaaggaa aataaataga aatgcacatg  25560
gggattgaga ctgtgaaaaa ggcagcatct cacatcagtg agggatgttc aacacctggt  25620
gttgggaaaa ctggctagtc atttaaacca aacaactggg tcctctacct cactcctgac  25680
attaagatac atttagatga ttcaaagagt aagacagaaa aaataacacg tgaaaacact  25740
```

```
atcagaaaac aacgtgggcc aggtgtggtg ggtcacgcct gtaatcccag cactttggga  25800
ggccgaggca gacagatcac ctgaggtggg gagttcaaga ccagcctgac caacatggtg  25860
aaatcctgtc tctactaaaa atacaaaatt agctgagcgt ggtggcgcat gcctgtaatc  25920
ccagctactc aggaggccga ggcaggagaa tcacttgaac ctgggaggca gaggttgtgg  25980
tgagccgaga tcacgccatt gcactccagc ctgggcaaca agagtgaaaa tccatctaaa  26040
aaaaaaaaaa aaagccaagg tggatatttt tatagtatca gggtagatca agcttctcca  26100
atcatgacat gaaacccaga aaccataaaa gaaaagaatg ataaaattgc ccacgtaaag  26160
taaaaagctt gcacacagaa aaacaccata caggttacaa gatgagcagc aaaatcagag  26220
aaaaaacatt gcaattcagg acacacagag gctattgttc ctaatattta aaaataaaag  26280
tagtggattg tctacaaaaa gatgaagaca agaatttcag aaaaccaaat actgcatgtt  26340
ttcacttaca agtggaagct aaacactgag tacacgtgta cacaaagaat ggaaccatag  26400
gccaggcacc gtggctcacg cctgtaatcc cagtactttg cgaggccgaa gcgggcggat  26460
cacctgaggt gaggagttcg agaccatcct ggccaacatg gtgaaaccca gtctctacta  26520
aaaatacaaa aattagccgg gcgtggtggt gggtgcctgt aatcccagct actcgggagg  26580
ctgcggcagt agaatcgctt gaaccctgga ggtggacctt gcagtgagcc gagatcgcac  26640
cactgcactc cagcctgggc aacagagtga gactccatct caaaaaaaaa aaaaaggaat  26700
agaacaatag acactggggc ctacttgagg gaggagggtg aggatcaaaa acctgcctat  26760
caggtactat gcttattacc tgggtggtga aataatctgt acaccaaacc ccagtgacat  26820
gcaatttacc gatgtaacaa acctgcccat gtacccgctg aacctaaaat aaaagttgga  26880
aaaaaatata gaaattttct ttgtaatagc caaaaactgc aaacagccca ggtgtctatt  26940
agtagaatgc ataaacaaac tcgggcatgt tcatacaatg taaaactact catcaataaa  27000
aagtgatact tctcagcaat gaaaagaaac tagctactga taccagctac aacatggatg  27060
gatttcaagt gctttatgat gagagcaaga agccagacac aaaagtgtct atatatatat  27120
acagtatata tacgtatata tacacatata tacagtatat atatacatat acatgtatat  27180
atatactgta tatatactgt atatatatac acagtatata tatacatata tacagtgtat  27240
atatactgtg tatatataca tgtatatata ctgtgtatat atacatgtat atatactgtg  27300
tatatataca tgtatatata ctgtgtatat atacatgtat atatatgtat actgtatata  27360
tactgtatat atatatacac atatatacag tatatatata cagtatatac tgtatatata  27420
cagtatatac gtgtatatat acatatatac agtatatatg taaatataca tatatacagt  27480
atatatgtaa atatacatat atacatgtat atatatacac tatatatata catatatagt  27540
gtatatatac atatatacat gtatatattt actatatgat tccatttata taaagtgcca  27600
aaacagtcaa aaataatcta tgtggaaaaa atcaacaaag ggatccccg ggctgcagga  27660
attcgatggc gcgccgacgt cgcatgctcc tctagactcg aggaattcgg taccccgggt  27720
tcgaaatcga taagcttgga tccggagagc tcgataacat ttaaatggat ctaccacatt  27780
tgtagaggtt ttacttgctt taaaaaacct cccacacctc cccctgaacc tgaaacataa  27840
aatgaatgca attgttgttg ttaacttgtt tattgcagct tataatggtt acaaataaag  27900
caatagcatc acaaatttca caaataaagc aatagcatca caaatttcac aaataaagca  27960
ttttttcac tgcattctag ttgtggtttg tccaaactca tcaatgtatc ttatcatgtc  28020
gagctaggat cccgcggccg cctactggtc ctcctggagg tagaacttgg tgaccatgaa  28080
```

ggactctttg ggcttgttgg tgaggctgac gggccggtct gcctcctgcg ccgtgcagag 28140
gaaccagcca gggcaggcgg cagactcgaa gctggtggtg gggccactgt ttgagcggat 28200
gaaggtgaag cgcttgttct cctccttgtt cttgctcagg tcagtgatgt taactgcctc 28260
caattggaac ctaatctcat caccagactt gacacaggcc aggcacagct tcctcccatg 28320
gagtcccagg aatagagcat caggctcaat gggcaccaca tctatcttct cttgtaattt 28380
agtatttgat tcttgcaagt atccagcaac tagttggtta ttcctcatgt agaaggtctt 28440
ctggttaaca tcccagattc tgaaggcttg catcttgcag ggtctcttcc ccaaagggtg 28500
gcaggctgtc tctgagtaga gcaagaaaag gaggagagag attaggtgtc tgacagaacg 28560
cctgcggatt tccataccgg tggatccatg gctctgtctc aggtcagtat aggagctttg 28620
atgtgaagtc agccaagaac agctgaacac tacttcctct gaggcccttt tataggaggg 28680
attgcttcct gtgaataata ggaggatatt gtccacatcc agtaaagagg aaatccccaa 28740
ctgcatccaa aaagttttct gggaatatcc actgctgcag gagtggaaag tccccagtgg 28800
aaagtcccca gtggaaagtc cccagtggaa agtccccagt ggaaagtccc cagaatttcg 28860
acggcgcgcc taccagtaaa aaagaaaacc tattaaaaaa acaccactcg acacggcacc 28920
agctcaatca gtcacagtgt aaaaaagggc caagtgcaga gcgagtatat ataggactaa 28980
aaaatgacgt aacggttaaa gtccacaaaa aacacccaga aaaccgcacg cgaacctacg 29040
cccagaaacg aaagccaaaa aacccacaac ttcctcaaat cgtcacttcc gttttcccac 29100
gttacgtcac ttcccatttt aagaaaacta caattcccaa cacatacaag ttactccgcc 29160
ctaaaaccta cgtcacccgc cccgttccca cgccccgcgc cacgtcacaa actccacccc 29220
ctcattatca tattggcttc aatccaaaat aaggtatatt attgatgatg ttt 29273

<210> SEQ ID NO 10
<211> LENGTH: 534
<212> TYPE: DNA
<213> ORGANISM: Homo sapiens

<400> SEQUENCE: 10
atggaaatct gcagaggcct ccgcagtcac ctaatcactc tcctcctctt cctgttccat 60
tcagagacga tctgccgacc ctctgggaga aaatccagca agatgcaagc cttcagaatc 120
tgggatgtta accagaagac cttctatctg aggaacaacc aactagttgc tggatacttg 180
caaggaccaa atgtcaattt agaagaaaag atagatgtgg tacccattga gcctcatgct 240
ctgttcttgg gaatccatgg agggaagatg tgcctgtcct gtgtcaagtc tggtgatgag 300
accagactcc agctggaggc agttaacatc actgacctga gcgagaacag aaagcaggac 360
aagcgcttcg ccttcatccg ctcagacagt ggccccacca ccagttttga gtctgccgcc 420
tgccccggtt ggttcctctg cacagcgatg gaagctgacc agcccgtcag cctcaccaat 480
atgcctgacg aaggcgtcat ggtcaccaaa ttctacttcc aggaggacga gtag 534

<210> SEQ ID NO 11
<211> LENGTH: 535
<212> TYPE: DNA
<213> ORGANISM: Mus musculus

<400> SEQUENCE: 11
atggaaatct gctggggacc ctacagtcac ctaatctctc tccttctcat ccttctgttt 60
cattcagagg cagcctgccg cccttctggg aaaagaccct gcaagatgca agccttcaga 120
atctgggata ctaaccagaa gaccttttac ctgagaaaca accagctcat tgctgggtac 180

```
ttacaaggac caaatatcaa actagaagaa aagatagaca tggtgcctat tgaccttcat    240

agtgtgttct tgggcatcca cgggggcaag ctgtgcctgt cttgtgccaa gtctggagat    300

gatatcaagc tccagctgga ggaagttaac atcactgatc tgagcaagaa caaagaagaa    360

gacaagcgct ttaccttcat ccgctctgag aaaggcccca ccaccagctt tgagtcagct    420

gcctgtccag gatggttcct ctgcacaaca ctagaggctg accgtcctgt gagcctcacc    480

aacacaccgg aagagcccct tatagtcacg aagttctact tccaggaaga ccaat         535
```

```
<210> SEQ ID NO 12
<211> LENGTH: 534
<212> TYPE: DNA
<213> ORGANISM: Unknown
<220> FEATURE:
<223> OTHER INFORMATION: Equus sp.

<400> SEQUENCE: 12

atggaaatcc gcaggcgttc tgtcagacac ctaatctctc tcctcctttt cttgctctac     60

tcagagacag cctgccaccc tttggggaag agaccctgca agatgcaagc cttcagaatc    120

tgggatgtta accagaagac cttctacatg aggaataacc aactagttgc tggatacttg    180

caagaatcaa atactaaatt acaagagaag atagatgtgg tgcccattga gcctgatgct    240

ctattcctgg gactccatgg gaggaagctg tgcctggcct gtgtcaagtc tggtgatgag    300

attaggttcc aattggaggc agttaacatc actgacctga gcaagaacaa ggaggagaac    360

aagcgcttca ccttcatccg ctcaaacagt ggccccacca ccagcttcga gtctgccgcc    420

tgccctggct ggttcctctg cacggcgcag gaggcagacc ggcccgtcag cctcaccaac    480

aagcccaaag agtccttcat ggtcaccaag ttctacctcc aggaggacca gtag          534
```

```
<210> SEQ ID NO 13
<211> LENGTH: 177
<212> TYPE: PRT
<213> ORGANISM: Homo sapiens

<400> SEQUENCE: 13

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160
```

```
Met Pro Asp Glu Gly Val Met Val Thr Lys Phe Tyr Phe Gln Glu Asp
                165                 170                 175

Glu


<210> SEQ ID NO 14
<211> LENGTH: 178
<212> TYPE: PRT
<213> ORGANISM: Mus musculus

<400> SEQUENCE: 14

Met Glu Ile Cys Trp Gly Pro Tyr Ser His Leu Ile Ser Leu Leu Leu
1               5                   10                  15

Ile Leu Leu Phe His Ser Glu Ala Ala Cys Arg Pro Ser Gly Lys Arg
            20                  25                  30

Pro Cys Lys Met Gln Ala Phe Arg Ile Trp Asp Thr Asn Gln Lys Thr
        35                  40                  45

Phe Tyr Leu Arg Asn Asn Gln Leu Ile Ala Gly Tyr Leu Gln Gly Pro
    50                  55                  60

Asn Ile Lys Leu Glu Glu Lys Ile Asp Met Val Pro Ile Asp Leu His
65                  70                  75                  80

Ser Val Phe Leu Gly Ile His Gly Gly Lys Leu Cys Leu Ser Cys Ala
                85                  90                  95

Lys Ser Gly Asp Asp Ile Lys Leu Gln Leu Glu Glu Val Asn Ile Thr
            100                 105                 110

Asp Leu Ser Lys Asn Lys Glu Glu Asp Lys Arg Phe Thr Phe Ile Arg
        115                 120                 125

Ser Glu Lys Gly Pro Thr Thr Ser Phe Glu Ser Ala Ala Cys Pro Gly
    130                 135                 140

Trp Phe Leu Cys Thr Thr Leu Glu Ala Asp Arg Pro Val Ser Leu Thr
145                 150                 155                 160

Asn Thr Pro Glu Glu Pro Leu Ile Val Thr Lys Phe Tyr Phe Gln Glu
                165                 170                 175

Asp Gln


<210> SEQ ID NO 15
<211> LENGTH: 177
<212> TYPE: PRT
<213> ORGANISM: Unknown
<220> FEATURE:
<223> OTHER INFORMATION: Equus sp.

<400> SEQUENCE: 15

Met Glu Ile Arg Arg Arg Ser Val Arg His Leu Ile Ser Leu Leu Leu
1               5                   10                  15

Phe Leu Leu Tyr Ser Glu Thr Ala Cys His Pro Leu Gly Lys Arg Pro
            20                  25                  30

Cys Lys Met Gln Ala Phe Arg Ile Trp Asp Val Asn Gln Lys Thr Phe
        35                  40                  45

Tyr Met Arg Asn Asn Gln Leu Val Ala Gly Tyr Leu Gln Glu Ser Asn
    50                  55                  60

Thr Lys Leu Gln Glu Lys Ile Asp Val Val Pro Ile Glu Pro Asp Ala
65                  70                  75                  80

Leu Phe Leu Gly Leu His Gly Arg Lys Leu Cys Leu Ala Cys Val Lys
                85                  90                  95

Ser Gly Asp Glu Ile Arg Phe Gln Leu Glu Ala Val Asn Ile Thr Asp
            100                 105                 110
```

```
Leu Ser Lys Asn Lys Glu Glu Asn Lys Arg Phe Thr Phe Ile Arg Ser
        115                 120                 125

Asn Ser Gly Pro Thr Thr Ser Phe Glu Ser Ala Ala Cys Pro Gly Trp
    130                 135                 140

Phe Leu Cys Thr Ala Gln Glu Ala Asp Arg Pro Val Ser Leu Thr Asn
145                 150                 155                 160

Lys Pro Lys Glu Ser Phe Met Val Thr Lys Phe Tyr Leu Gln Glu Asp
                165                 170                 175

Gln


<210> SEQ ID NO 16
<211> LENGTH: 24
<212> TYPE: DNA
<213> ORGANISM: Artificial Sequence
<220> FEATURE:
<223> OTHER INFORMATION: PRG4-F Primer

<400> SEQUENCE: 16

acttcagcta aagagacacg gagt                                              24


<210> SEQ ID NO 17
<211> LENGTH: 27
<212> TYPE: DNA
<213> ORGANISM: Artificial Sequence
<220> FEATURE:
<223> OTHER INFORMATION: PRG4-R Primer

<400> SEQUENCE: 17

gttcaggtgg ttccttggtt gtagtaa                                           27


<210> SEQ ID NO 18
<211> LENGTH: 20
<212> TYPE: DNA
<213> ORGANISM: Artificial Sequence
<220> FEATURE:
<223> OTHER INFORMATION: Sox9-F Primer

<400> SEQUENCE: 18

aagccacacg tcaagcgacc                                                   20


<210> SEQ ID NO 19
<211> LENGTH: 20
<212> TYPE: DNA
<213> ORGANISM: Artificial Sequence
<220> FEATURE:
<223> OTHER INFORMATION: Sox9-R Primer

<400> SEQUENCE: 19

gtgctgctga tgccgtaact                                                   20


<210> SEQ ID NO 20
<211> LENGTH: 26
<212> TYPE: DNA
<213> ORGANISM: Artificial Sequence
<220> FEATURE:
<223> OTHER INFORMATION: Col2a1-F Primer

<400> SEQUENCE: 20

gctcatccag ggctccaatg atgtag                                            26


<210> SEQ ID NO 21
<211> LENGTH: 23
<212> TYPE: DNA
<213> ORGANISM: Artificial Sequence
```

<220> FEATURE:
<223> OTHER INFORMATION: Col2a1-R Primer

<400> SEQUENCE: 21
cgggaggtct tctgtgatcg gta 23

<210> SEQ ID NO 22
<211> LENGTH: 21
<212> TYPE: DNA
<213> ORGANISM: Artificial Sequence
<220> FEATURE:
<223> OTHER INFORMATION: Gapdh-F Primer

<400> SEQUENCE: 22
gcaagagagg ccctatccca a 21

<210> SEQ ID NO 23
<211> LENGTH: 23
<212> TYPE: DNA
<213> ORGANISM: Artificial Sequence
<220> FEATURE:
<223> OTHER INFORMATION: Gapdh-R Primer

<400> SEQUENCE: 23
ctccctaggc ccctcctgtt att 23

<210> SEQ ID NO 24
<211> LENGTH: 24
<212> TYPE: DNA
<213> ORGANISM: Artificial Sequence
<220> FEATURE:
<223> OTHER INFORMATION: Vegf-F Primer

<400> SEQUENCE: 24
tggacttgtg ttgggaggag gatg 24

<210> SEQ ID NO 25
<211> LENGTH: 23
<212> TYPE: DNA
<213> ORGANISM: Artificial Sequence
<220> FEATURE:
<223> OTHER INFORMATION: Vegf-R Primer

<400> SEQUENCE: 25
gcctcttctt ccaccaccgt gtc 23

<210> SEQ ID NO 26
<211> LENGTH: 24
<212> TYPE: DNA
<213> ORGANISM: Artificial Sequence
<220> FEATURE:
<223> OTHER INFORMATION: Mmp13-F Primer

<400> SEQUENCE: 26
gcaatctttc tttggcttag aggt 24

<210> SEQ ID NO 27
<211> LENGTH: 22
<212> TYPE: DNA
<213> ORGANISM: Artificial Sequence
<220> FEATURE:
<223> OTHER INFORMATION: Mmp13-R Primer

<400> SEQUENCE: 27
ggtgttttgg gatgcttagg gt 22

<210> SEQ ID NO 28
<211> LENGTH: 20
<212> TYPE: DNA
<213> ORGANISM: Artificial Sequence
<220> FEATURE:
<223> OTHER INFORMATION: Col10a1-F Primer

<400> SEQUENCE: 28
aaagcttacc cagcagtagg 20

<210> SEQ ID NO 29
<211> LENGTH: 20
<212> TYPE: DNA
<213> ORGANISM: Artificial Sequence
<220> FEATURE:
<223> OTHER INFORMATION: Col10a1-R Primer

<400> SEQUENCE: 29
acgtactcag aggagtagag 20

<210> SEQ ID NO 30
<211> LENGTH: 24
<212> TYPE: DNA
<213> ORGANISM: Artificial Sequence
<220> FEATURE:
<223> OTHER INFORMATION: GAPDH_F Primer

<400> SEQUENCE: 30
ataccaggaa atgagcttga caaa 24

<210> SEQ ID NO 31
<211> LENGTH: 20
<212> TYPE: DNA
<213> ORGANISM: Artificial Sequence
<220> FEATURE:
<223> OTHER INFORMATION: GAPDH_R Primer

<400> SEQUENCE: 31
tgaaggtcgg agtcaacgga 20

<210> SEQ ID NO 32
<211> LENGTH: 26
<212> TYPE: DNA
<213> ORGANISM: Artificial Sequence
<220> FEATURE:
<223> OTHER INFORMATION: VEGF_F Primer

<400> SEQUENCE: 32
gatcggtgac agtcactagc ttatct 26

<210> SEQ ID NO 33
<211> LENGTH: 22
<212> TYPE: DNA
<213> ORGANISM: Artificial Sequence
<220> FEATURE:
<223> OTHER INFORMATION: VEGF_R Primer

<400> SEQUENCE: 33
tacacacaaa tacaagttgc ca 22

<210> SEQ ID NO 34
<211> LENGTH: 29
<212> TYPE: DNA
<213> ORGANISM: Artificial Sequence
<220> FEATURE:
<223> OTHER INFORMATION: MMP13_F Primer -continued

<400> SEQUENCE: 34
tgcccttctt cacacagaca ctaacgaaa 29

<210> SEQ ID NO 35
<211> LENGTH: 29
<212> TYPE: DNA
<213> ORGANISM: Artificial Sequence
<220> FEATURE:
<223> OTHER INFORMATION: MMP13_R Primer

<400> SEQUENCE: 35
ggccacatct actattctta ccactgctc 29

<210> SEQ ID NO 36
<211> LENGTH: 22
<212> TYPE: DNA
<213> ORGANISM: Artificial Sequence
<220> FEATURE:
<223> OTHER INFORMATION: COL10A1_F Primer

<400> SEQUENCE: 36
gcccactacc caagaccaag ac 22

<210> SEQ ID NO 37
<211> LENGTH: 21
<212> TYPE: DNA
<213> ORGANISM: Artificial Sequence
<220> FEATURE:
<223> OTHER INFORMATION: COL10A1_R Primer

<400> SEQUENCE: 37
gacccctctc acctggacga c 21

<210> SEQ ID NO 38
<211> LENGTH: 20
<212> TYPE: DNA
<213> ORGANISM: Artificial Sequence
<220> FEATURE:
<223> OTHER INFORMATION: HIF3A_F Primer

<400> SEQUENCE: 38
ggctgttccg cctacgagta 20

<210> SEQ ID NO 39
<211> LENGTH: 19
<212> TYPE: DNA
<213> ORGANISM: Artificial Sequence
<220> FEATURE:
<223> OTHER INFORMATION: HIF3A_R Primer

<400> SEQUENCE: 39
agcaaggtgg atgctcttg 19

<210> SEQ ID NO 40
<211> LENGTH: 24
<212> TYPE: DNA
<213> ORGANISM: artificial sequence
<220> FEATURE:
<223> OTHER INFORMATION: Fwd Primer

<400> SEQUENCE: 40
tctctttatg aggagttgtg gccc 24

<210> SEQ ID NO 41

-continued

```
<211> LENGTH: 24
<212> TYPE: DNA
<213> ORGANISM: artificial sequence
<220> FEATURE:
<223> OTHER INFORMATION: Reverse primer

<400> SEQUENCE: 41

cgacaacacc acggaattgt cagt                                            24
```